(12) United States Patent
von Maltzahn et al.

(10) Patent No.: US 10,894,057 B2
(45) Date of Patent: Jan. 19, 2021

(54) GLYCAN THERAPEUTIC COMPOSITIONS AND RELATED METHODS THEREOF

(71) Applicant: KALEIDO BIOSCIENCES, INC., Cambridge, MA (US)

(72) Inventors: Geoffrey A. von Maltzahn, Somerville, MA (US); Yvonne J. Yamanaka, Cambridge, MA (US); Jared Silverman, Brookline, MA (US); John Miles Milwid, Winchester, MA (US); Jacob Rosenblum Rubens, Cambridge, MA (US); John M. Geremia, Watertown, MA (US)

(73) Assignee: Kaleido Biosciences, Inc., Lexington, MA (US)

( * ) Notice: Subject to any disclaimer, the term of this patent is extended or adjusted under 35 U.S.C. 154(b) by 90 days.

(21) Appl. No.: 16/140,091

(22) Filed: Sep. 24, 2018

(65) Prior Publication Data
US 2019/0091249 A1   Mar. 28, 2019

Related U.S. Application Data

(63) Continuation of application No. 15/568,243, filed as application No. PCT/US2016/029082 on Apr. 23, 2016, now abandoned.
(Continued)

(51) Int. Cl.
*A61K 31/702* (2006.01)
*A61K 35/741* (2015.01)
(Continued)

(52) U.S. Cl.
CPC .......... *A61K 31/702* (2013.01); *A23L 33/125* (2016.08); *A23L 33/135* (2016.08); *A61K 31/716* (2013.01); *A61K 31/733* (2013.01);
*A61K 35/741* (2013.01); *A61K 45/06* (2013.01); *A61P 1/00* (2018.01); *A61P 3/02* (2018.01); *A61P 35/00* (2018.01); *A61P 35/04* (2018.01); *A61P 43/00* (2018.01); *A23V 2002/00* (2013.01)

(58) Field of Classification Search
None
See application file for complete search history.

(56) References Cited

U.S. PATENT DOCUMENTS 2,027,904 A   1/1936   Farber
2,436,967 A   3/1948   Leuk
(Continued)

FOREIGN PATENT DOCUMENTS

CN   1600146 A   3/2005
CN   1731938 S   2/2006
(Continued)

OTHER PUBLICATIONS

Adamberg et al., "Degradation of fructans and production of propionic acid by Bacteroides thetaiomicron are enhanced by the shortage of amino acids," Front Nutr (2014) vol. 1, Article 21, 10 pages.
(Continued)

*Primary Examiner* — David W Berke-Schlessel
(74) *Attorney, Agent, or Firm* — Wolf, Greenfield & Sacks, P.C.

(57) ABSTRACT

Preparations of glycan therapeutics, pharmaceutical compositions, dietary supplements and medical foods thereof are provided, and methods of using said gycan therapeutics, e.g. in cancer therapy.

23 Claims, 27 Drawing Sheets

Related U.S. Application Data

(60) Provisional application No. 62/278,333, filed on Jan. 13, 2016, provisional application No. 62/238,110, filed on Oct. 6, 2015, provisional application No. 62/238,112, filed on Oct. 6, 2015, provisional application No. 62/216,995, filed on Sep. 10, 2015, provisional application No. 62/216,997, filed on Sep. 10, 2015, provisional application No. 62/152,017, filed on Apr. 23, 2015, provisional application No. 62/152,011, filed on Apr. 23, 2015, provisional application No. 62/152,007, filed on Apr. 23, 2015.

(51) Int. Cl.
| | |
|---|---|
| *A23L 33/135* | (2016.01) |
| *A61P 35/04* | (2006.01) |
| *A23L 33/125* | (2016.01) |
| *A61P 1/00* | (2006.01) |
| *A61K 31/716* | (2006.01) |
| *A61K 31/733* | (2006.01) |
| *A61P 35/00* | (2006.01) |
| *A61K 45/06* | (2006.01) |
| *A61P 3/02* | (2006.01) |
| *A61P 43/00* | (2006.01) |

(56) References Cited

U.S. PATENT DOCUMENTS

| | | |
|---|---|---|
| 2,719,179 A | 9/1955 | Mora et al. |
| 3,766,165 A | 10/1973 | Rennhard |
| 3,876,794 A | 4/1975 | Rennhard |
| 3,973,049 A | 8/1976 | Furda et al. |
| 4,671,967 A | 6/1987 | Patel et al. |
| 4,761,401 A | 8/1988 | Couchman et al. |
| 4,927,811 A | 5/1990 | Quarles |
| 4,965,354 A | 10/1990 | Yanaki et al. |
| 5,051,500 A | 9/1991 | Elmore |
| 5,424,418 A | 6/1995 | Duflot |
| 5,556,899 A | 9/1996 | Afzali-Ardakani et al. |
| 5,558,899 A | 9/1996 | Kuzee et al. |
| 5,573,794 A | 11/1996 | Duflot |
| 5,580,762 A | 12/1996 | Karube et al. |
| 5,645,647 A | 7/1997 | Guzek et al. |
| 5,780,620 A | 7/1998 | Mandai et al. |
| 5,843,922 A | 12/1998 | Whistler et al. |
| 6,423,833 B1 | 7/2002 | Catani et al. |
| 6,475,552 B1 | 11/2002 | Shah et al. |
| 6,559,302 B1 | 5/2003 | Shah et al. |
| 6,630,586 B1 | 10/2003 | Fouache et al. |
| 6,638,916 B1 | 10/2003 | Cowden et al. |
| 6,677,142 B1 | 1/2004 | Weissmuller et al. |
| 7,608,291 B2 | 10/2009 | Baillon et al. |
| 7,608,436 B2 | 10/2009 | Harrison et al. |
| 7,615,365 B2 | 11/2009 | Caimi et al. |
| 8,057,480 B2 | 11/2011 | Dorawa et al. |
| 8,057,840 B2 | 11/2011 | Harrison et al. |
| 8,143,235 B2 | 3/2012 | Gorselink et al. |
| 8,148,505 B2 | 4/2012 | Ando et al. |
| 8,227,448 B2 | 7/2012 | Van Laere et al. |
| 8,445,460 B2 | 5/2013 | Deremaux et al. |
| 8,466,242 B2 | 6/2013 | Geremia et al. |
| 8,476,388 B2 | 7/2013 | Geremia et al. |
| 8,591,919 B2 | 11/2013 | Stahl et al. |
| 8,741,376 B2 | 6/2014 | Broekaert et al. |
| 8,835,403 B2 | 9/2014 | Geng et al. |
| 8,993,039 B2 | 3/2015 | Harrison et al. |
| 9,079,171 B2 | 7/2015 | Geremia et al. |
| 9,205,418 B2 | 12/2015 | Geremia et al. |
| 9,238,845 B2 | 1/2016 | Baynes et al. |
| 9,410,216 B2 | 8/2016 | Eyal et al. |
| 9,481,739 B2 | 11/2016 | Essers et al. |
| 9,492,473 B2 | 11/2016 | Von Maltzahn et al. |
| 9,512,239 B2 | 12/2016 | Naeye et al. |
| 9,725,776 B2 | 8/2017 | Dumesic et al. |
| 9,757,403 B2 | 9/2017 | Von Maltzahn et al. |
| 9,783,619 B2 | 10/2017 | Bureau et al. |
| 10,131,721 B2 | 11/2018 | Geremia et al. |
| 2003/0162300 A1 | 8/2003 | Kunz et al. |
| 2004/0220389 A1 | 11/2004 | Buchwald et al. |
| 2004/0235789 A1 | 11/2004 | Day et al. |
| 2005/0004070 A1 | 1/2005 | Stahl et al. |
| 2005/0075311 A1 | 4/2005 | Lane |
| 2006/0008574 A1 | 1/2006 | Begli et al. |
| 2006/0014717 A1 | 1/2006 | Angstrom et al. |
| 2006/0051812 A1 | 3/2006 | Helin |
| 2006/0127448 A1 | 6/2006 | Carlson et al. |
| 2007/0036840 A1 | 2/2007 | Tuduri et al. |
| 2007/0048432 A1 | 3/2007 | Holzgraefe et al. |
| 2007/0148728 A1 | 6/2007 | Johnson et al. |
| 2007/0249524 A1 | 10/2007 | Dieckgraefe |
| 2007/0254848 A1 | 11/2007 | Geng et al. |
| 2008/0051573 A1 | 2/2008 | Hirth et al. |
| 2009/0098240 A1 | 4/2009 | Mills et al. |
| 2010/0284972 A1 | 11/2010 | Naeye et al. |
| 2011/0052538 A1 | 3/2011 | Brown et al. |
| 2012/0034366 A1 | 2/2012 | Hoffman et al. |
| 2012/0220740 A1 | 8/2012 | Geremia et al. |
| 2013/0005684 A1 | 1/2013 | Fichert et al. |
| 2013/0028869 A1 | 1/2013 | Bruggeman et al. |
| 2013/0216693 A1 | 8/2013 | Harrison et al. |
| 2014/0060522 A1 | 3/2014 | Baynes et al. |
| 2014/0105864 A1 | 4/2014 | Di Leo |
| 2014/0187474 A1 | 7/2014 | Sonnenburg |
| 2014/0234912 A1 | 8/2014 | Dekany et al. |
| 2014/0335131 A1 | 11/2014 | Mazmanian et al. |
| 2015/0087616 A1 | 3/2015 | Ritter et al. |
| 2015/0202607 A1 | 7/2015 | Geremia et al. |
| 2015/0238948 A1 | 8/2015 | Geremia |
| 2015/0352133 A1 | 12/2015 | Jennewein |
| 2016/0007642 A1 | 1/2016 | Geremia et al. |
| 2016/0015065 A1 | 1/2016 | Sumner et al. |
| 2016/0032038 A1 | 2/2016 | Baynes et al. |
| 2016/0122447 A1 | 5/2016 | Geremia et al. |
| 2016/0366909 A1 | 12/2016 | Geremia et al. |
| 2017/0151268 A1 | 6/2017 | von Maltzahn et al. |
| 2017/0151269 A1 | 6/2017 | von Maltzahn et al. |
| 2018/0000145 A1 | 1/2018 | Geremia et al. |
| 2018/0000146 A1 | 1/2018 | Geremia |
| 2018/0037599 A1 | 2/2018 | Duflot et al. |
| 2019/0209600 A1 | 7/2019 | Gubler |
| 2020/0093845 A1 | 3/2020 | Von Maltzahn et al. |

FOREIGN PATENT DOCUMENTS

| | | |
|---|---|---|
| CN | 102892303 S | 1/2013 |
| CN | 103562401 S | 2/2014 |
| CN | 104171365 S | 12/2014 |
| EA | 011417 B1 | 2/2009 |
| EP | 0549478 A1 | 6/1993 |
| EP | 1634599 A1 | 3/2006 |
| EP | 1887017 A1 | 2/2008 |
| EP | 2138048 A1 | 12/2009 |
| EP | 2248907 A1 | 11/2010 |
| EP | 2666788 A1 | 11/2013 |
| EP | 2401925 B1 | 5/2014 |
| ES | 2304223 A1 | 9/2008 |
| JP | H06-121693 A | 5/1994 |
| JP | H10-316740 A | 12/1998 |
| JP | 200186999 A | 4/2001 |
| JP | 2003516757 A | 5/2003 |
| JP | 2004182628 A | 7/2004 |
| JP | 200881501 A | 4/2008 |
| JP | 4597630 B2 | 12/2010 |
| JP | 2011-501670 A | 1/2011 |
| JP | 2011512386 A | 4/2011 |
| JP | 2012-158526 A | 8/2012 |
| JP | 2014-513985 A | 6/2014 |
| JP | 2014205704 A | 10/2014 |
| RU | 2153503 | 7/2000 |
| RU | 2509477 C1 | 3/2014 |
| WO | WO 1998/041544 A1 | 9/1998 |
| WO | 2004026341 A1 | 4/2004 |

(56) References Cited

FOREIGN PATENT DOCUMENTS

| | | |
|---|---|---|
| WO | 2004052121 A1 | 6/2004 |
| WO | WO 2004/052121 A1 | 6/2004 |
| WO | 2005003329 A1 | 1/2005 |
| WO | 2006030100 A1 | 3/2006 |
| WO | WO 2006/030100 A1 | 3/2006 |
| WO | 2006041930 A2 | 4/2006 |
| WO | 2007010084 A2 | 1/2007 |
| WO | 2007050656 A2 | 5/2007 |
| WO | 2007117175 A1 | 10/2007 |
| WO | 2008037839 A1 | 4/2008 |
| WO | 2008156354 A1 | 12/2008 |
| WO | WO 2009/051977 A1 | 4/2009 |
| WO | 2009059283 A1 | 5/2009 |
| WO | 2009082214 A1 | 7/2009 |
| WO | 2010105207 A1 | 9/2010 |
| WO | 2010136742 A1 | 12/2010 |
| WO | WO 2010/143961 A1 | 12/2010 |
| WO | 2011008086 A1 | 1/2011 |
| WO | 2011016866 A1 | 2/2011 |
| WO | WO 2012/076321 A1 | 6/2012 |
| WO | WO 2012/156897 A1 | 11/2012 |
| WO | 2014031956 A1 | 2/2014 |
| WO | 2014043708 A1 | 3/2014 |
| WO | 2014145276 A1 | 9/2014 |
| WO | 2015153841 A1 | 10/2015 |
| WO | 2016007778 A1 | 1/2016 |
| WO | WO 2016/007778 A1 | 1/2016 |
| WO | 2016122884 A1 | 8/2016 |
| WO | 2016122885 A1 | 8/2016 |
| WO | 2016122889 A1 | 8/2016 |
| WO | WO 2016/122885 A1 | 8/2016 |
| WO | 2016172657 A2 | 10/2016 |
| WO | 2016172658 A2 | 10/2016 |
| WO | WO 2016/172657 A2 | 10/2016 |
| WO | 2016122887 A9 | 2/2017 |
| WO | 2017083520 A1 | 5/2017 |
| WO | WO 2018/106845 A1 | 6/2018 |

OTHER PUBLICATIONS

Aida et al., "Mushroom as a potential source of prebiotics: a review", Trends in Food Science & Technology, 20, pp. 567-575, 2009.
Alam et al. "Efficacy of Partially Hydrolyzed Guar Gum-Added Oral Rehydration Solution in the Treatment of Severe Cholera in Adults" Digestion (2008) vol. 78, pp. 24-29.
Beards et al., "Bacterial, SCFA and gas profiles a range of food ingredients following in vitro fermentation by human :colonic microbiota," Anaerobe (2010) vol. 16, pp. 420-425.
Belknap et al. "The effects of psyllium hydrophilic mucilloid on diarrhea in enterally fed patients" Heart & Lung (1997) vol. 26, No. 3, pp. 229-237.
Bergstrom, K. et al. Defective Intestinal Mucin type O Glycosylation Causes Spontaneous Colitis Associated cancer in Mice. Gastroenterology Apr. 5, 2016.
Bier et al., "Generally Recognized as Safe (GRAS) Determination for the Addition of Polydextrose to Infant Formula as a Prebiotic Ingredient in Combination with Galactooligosaccharides", U.S. Food and Drug Administration, GRAS Notice, dated Aug. 2007.
Cassellas et al., "Oral oligofructose-enriched inulin supplementation in acute ulcerative colitis is well tolerated and associated with lowered faecal calprotectin," Aliment Pharmacol Ther (2007) vol. 25, pp. 1061-1067.
Clemente et al. "The Impact of the Gut Microbiota on Human Health: An Integrative View" Cell (2012) vol. 148, No. 6, pp. 1258-1270.
Deng et al. "Effect of dietary fiber on intestinal barrier function of 5-Fu stressed rats" Res Exp Med (1999) vol. 199, pp. 111-119.
Duggan et al., "Protective nutrients and functional foods for the gastrointestinal tract," Am J Clin Nutr (2002) vol. 75, pp. 789-808.
Dutton et al. "The Constitution of a Synthetic Xylan" Canadian Journal of Chemistry (1962) vol. 40, No. 8, pp. 1479-1483.
Extended European Search Report for EP Application No. 15819734.3 dated Feb. 7, 2018.
Extended European Search Report for EP Application No. 16743841.5 dated Jul. 13, 2018.
Extended European Search Report for EP Application No. 16743842.3 dated Jul. 9, 2018.
Extended European Search Report for EP Application No. 16743843.1 dated Jun. 6, 2018.
Extended European Search Report for EP Application No. 17206409.9 dated Jun. 21, 2018.
Fischer et al. "The gel-forming polysaccharide of psyllium husk (Plantago ovata Forsk)" Carbohydrate Research (2004) vol. 339, pp. 2009-2017.
Fuhrer et al., "Milk sialyllactose influences colitis in mice through selective intestinal bacterial colonization," J Exp Med (2010) vol. 207, No. 13, pp. 2843-2854.
Hopkins et al., "Nondigestible Oligosaccharides Enhance Bacterial Colonization Resistance against Clostridium difficile In Vitro," App Env Micro (2003) vol. 69, No. 4, pp. 1920-1927.
International Search Report and Written Opinion for International Application No. PCT/US2016/029082 dated Oct. 14, 2016.
International Search Report and Written Opinion for International Application No. PCT/US2016/029083 dated Oct. 14, 2016.
International Search Report and Written Opinion issued in PCT/US2015/039795, dated Oct. 7, 2015.
International Search Report and Written Opinion issued in PCT/US2016/013265, dated Mar. 11, 2016.
International Search Report and Written Opinion issued in PCT/US2016/013271, dated Mar. 11, 2016.
International Search Report and Written Opinion issued in PCT/US2016/013280 dated Mar. 21, 2016.
Islek et al. "The role of Bifidobacterium lactis B94 plus inulin in the treatment of acute infectious diarrhea in children" Turk J Gastroenterol (2014) vol. 25, pp. 628-633.
Kau et al., "Human nutrition, the gut microbiome, and immune system: envisioning the future," Nat (2011) vol. 474, pp. 327-336.
Kellow et al., "Metabolic benefits of dietary prebiotics in human subjects: a systematic review of randomised controlled trials," Br J Nutr (2014) vol. 111, pp. 1147-1161.
Lewis et al. "Effect of the Prebiotic Oligofructose on Relapse of Clostridium difficile-Associated Diarrhea: A Randomized, Controlled Study" Clinical Gastroenterology and Hepatology (2005) vol. 3, pp. 442-448.
Lin et al. "Irinotecan (CPT-11) Chemotherapy Alters Intestinal Microbiota in Tumour Bearing Rats" PLoS One (2012) vol. 7, No. 7, e39764, pp. 1-8.
Louis et al. "How to Manipulate the Microbiota: Prebiotics" Microbiota of the Human Body, Advances in Experimental Medicine and Biology (2016) No. 9, pp. 119-142.
Nakamura et al. "Suppressive effect of patrially hydrolyzed guar gum on transitory diarrhea induced by ingestion of maltitol and lactitol in healthy humans" European Journal of Clinical Nutrition (2007) vol. 61, pp. 1086-1093.
Neyrink et al. "Prebiotic Effects of Wheat Arabinoxylan Related to the Increase in Bifidobacteria, Roseburia and Bacteroides/ Prevotella in Diet-Induced Obese Mice" PLoS One (2011) vol. 6, No. 6, e20944, pp. 1-12.
Prisciandaro et al. "Probiotic factors partially improve parameters of 5-fluorouracil-induced intestinal mucositis in rats" Cancer Biology & Therapy (2011) vol. 11, No. 7, pp. 671-677.
Röytiö et al. "The fermentation of polydextrose in the large intestine and its beneficial effects," Benef Microb (2014) vol. 5, No. 3, pp. 305-313.
Sanz et al. "Influence of Glycosidic Linkages and Molecular Weight on the Fermentation of Maltose-Based Oligosaccharides by Human Gut Bacteria" J. Agric. Food Chem. (2006) vol. 54, pp. 9779-9784.
Schley et al., "The immune-enhancing effects of dietary fibres and prebiotics," Br J Nutr (2002) vol. 87, Suppl 2, pp. S221-S230.
Scott et al. "Prebiotic stimulation of human colonic butyrate-producing bacteria and bifidobacteria, in vitro" FEMS Microbiology Ecology (2014) vol. 87, pp. 30-40.

(56) References Cited

OTHER PUBLICATIONS

Sharon, N. Carbohydrates as Future Anti-Adhesion Drugs for Infectious Diseases. Biochimica et Biophysica 1760(4) 527-537, Apr. 2006.

Simpson et al. "Review article: dietary fibre-microbiota interactions" Alimentary Pharmacology and Therapeutics (2015) vol. 42, 158-179.

Synytsya et al., "Glucans from fruit bodies of cultivated mushrooms *Pleurotus ostreatus* and *Pleurotus eryngii*: Structure and potential prebiotic activity" Carbohydrate Polymers, (2009) pp. 548-556.

Tomlin et al. "A comparative study of the effects on colon function caused by feeding ispaghula husk and polydextrose" Aliment Pharmacol Ther. (1988) vol. 2, No. 6, pp. 513-519.

Wu et al., "Diminution of the gut resistome after a gut microbiota-targeted dietary intervention in obese children," Nature Scientific Reports (2016) vol. 6, Article 24030, 9 pages.

Louis et al. "Diversity of human colonic butyrate-producing bacteria; inulin caused increases in Faecalbacterium prausnitzii; studied abundance of butyrate producing bacteria" Env Microbio (2010) vol. 12, No. 2, pp. 304-314.

Fasina et al. "Comparative efficacy of a yeast product and bacitracin methylene disalicylate in enhancing early growth and intestinal maturation in broiler chicks from breeder hens of different ages," Poult Sci. (2011) vol. 90, pp.1067-1073.

Courtin et al. "Effects of xylooligosaccharides (XOS), arabinoxylooligosaccharides (AXOS), and soluble arabinoxylan on gut bacteria of chickens; XOS and AXOS stimulate bifidobacteria" J Sci of Food and Agric (2008) vol. 88, pp. 2517-2522.

Smilowitz et al "Breast Milk Oligosaccharides: Structure-FUnction Relationships in the Neonate" Annu Rev Nutr. (2014) vol. 34, pp. 143-169.

Chen et al., "Comparative Effects of Cellulose and Soluble Fibers (Pectin, Konjac Glucomannan, Inulin) on Fecal Water Toxicity toward Caco-2 Cells, Fecal Bacteria Enzymes, Bile Acid, and Short-Chain Fatty Acids," J Agric Food Chem (2010) vol. 58, pp. 10277-10281.

Louis et al. "Diversity, metabolism and microbial ecology of butyrate producing bacteria from human large intestine; some mention of prebiotics affecting SCFA and taxa levels" FEMS Microbio Lett (2009) vol. 294, pp. 1-8.

Saku et al. "Effects of polydextrose on serum lipids, lipoproteins, and apolipoproteins in healthy subjects" Clin Ther (1991) vol. 13, No. 2, pp. 254-258. Abstract Only.

Salonen et al. "Impact of diet and individual variation on intestinal microbiota composition and fermentation products in obese men" ISME J (2014) vol. 8, pp. 2218-2230.

Sheu et al. "Effects of xylooligosaccharides on type 2 diabetes; looked at SCFA levels; mention XOS effect of Bifido populations" J Nutr Sci Vitaminol (2008) vol. 54, pp. 396-401.

Ninfree et al., "Effects of Dietary Protein and Energy on Growth, Feed Conversion Efficiency and Body Composition of Tilapia aurea," J Nutr (1981) vol. 111, pp. 1001-1012.

Marlett et al. "A Poorly Fermented Gel from Psyllium Seed Husk Increases Excreta Moisture and Bile Acid Excretion in Rats" The Journal of Nutrition (2002) vol. 132, pp. 2638-2643.

Holscher et al. "Studied effects of agave inulin supplementation on fecal microbiota; saw changes in abundance of actinobacteria, bifidobacteria, and desulfovibrio; also saw effects on fermentation products (SCFAs)" J Nutr (2015) 145, 2025-32.

Mora et al. "Synthetic Polysaccharides. V. Polymerization of Various Aldoses" Journal of the American Chemical Society (1960) vol. 83, pp. 3418-3421.

Courtin et al. "Dietary Inclusion of Wheat Bran Arabinoxylooligosaccharides Induces Beneficial Nutritional Effects in Chickens" Cer. Chem (2008) vol. 85, No. 5, pp. 607-613.

Louis et al. "Review on effects of diet on gut bacterial metabolism; changes in oligofructose lead to shifts in species composition of gut bacteria; inulin and FOS selectively stimulate bifido and lactobacilli; dietary fibers have effect on bacterial growth and subsequent SCFA production" J Appl. Microbio (2007) vol. 102, pp. 1197-1208.

Boler et al. "Digestive physiological outcomes related to polydextrose and soluble maize fibre consumption by healthy adult men" Br J Nutr (2011) vol. 106, pp. 1864-1871.

Wang et al. "Preparation and structural characterization of polymannose synthesized by phosphoric acid catalyzation ender microwave irradation" Carbohydrate Polymers (2015) vol. 121, pp. 355-361.

Cummings et al. "Review of carbohydrate terminology and classification; divides carbohydrates into sugars (DP 1-2), oligosaccharides (short chain) (DP 3-9), and polysaccharides (DP ? 10); brief mention of prebiotics altering the gut microbiome balance; occassional mention of linkages" Eur J Clin Nutr (2007) vol. 61 (Suppl 1), pp. S5-S18.

Wang et al. "Rapid microwave-assisted synthesis of polydextrose and identification of structure and function" Carbohydrate Polymers (2014) vol. 113, pp. 225-230.

Gomez et al. "Purification, Characterization, and Prebiotic Properties of Pectic Oligosaccharides from Orange Peel Wastes" Journal of Agricultural and Food Chemistry (2014) vol. 62, pp. 9769-9782.

Hernot et al. "In Vitro Fermentation Profiles, Gas Production Rates and Microbiota Modulation as Affected by Certain Fructans, Galactoologosaccharides, and Polydextrose" Journal of Agricultural and Food Chemistry (2009) vol. 57, pp. 1354-1361.

Koropatkin et al. "How glycan metabolism shapes the human gut microbiota" Nature Reviews Microbiology (2012) vol. 10, pp. 323-335.

Van Den Abbeele et al. "Butyrate-producing Clostridium cluster XIVa species specifically colonize mucins in an in vitro gut model" The ISME Journal (2013) vol. 7, pp. 949-961.

Guerin-Deremaux et al. "Effects of a Soluable Dietary Fibre Nutriose on Colonic Fermentation and Excretion Rates in Rats" Nutrition Research and Practice (2010) 4(6):470-476.

Dua et al. "Characterization of lacto-n-hexaose and two fucosylated derivatives from human milk by high-performance liquid chromatography and proton NMR spectroscopy" Journal of Chromatography (1985) vol. 328, pp. 259-269.

Invitation to Pay Additional Fees for Application No. PCT/US2019/047595, dated Dec. 16, 2019.

International Search Report and Written Opinion for Application No. PCT/US2019/047595, dated Feb. 12, 2020.

Invitation to Pay Additional Fees for Application No. PCT/US2019/060626, dated Feb. 19, 2020.

International Search Report and Written Opinion for Application No. PCT/US2019/060626, dated Jul. 1, 2020.

Invitation to Pay Additional Fees for Application No. PCT/US2020/032240, dated Jul. 7, 2020.

International Search Report and Written Opinion for Application No. PCT/US2020/032240, dated Sep. 21, 2020.

[No Author Listed], Generally Recognized as Safe (GRAS) Determination for the Addition of Polydextrose to Infant Formula as a Prebiotic Ingredient in Combination with Galactooligosaccharides. Aug. 2007. 115 pages.

[No Author Listed], Product label for BMD 50, Bacitracin methylene disalicylate type A medicated article antibacterial, Zoetis. Retrieved from https://dailymed.nlm.nih.gov/dailymed/fda/fdaDrugXs1.cfm?setid=fe38871c-360e-4c29-b2c6-bb54c40ff214&type=display. Revised Jun. 2020. 5 pages.

Aggrawal et al., Technical Application Note 1151. Profiling galactosyloligosaccharide-containing samples by high-performance anion-exchange chromatography with pulsed amperometric detection (HPAE-PAD). ThermoFisher Scientific. Retrieved from https://assets.thermofisher.com/TFS-Assets/CMD/Application-Notes/AN-1151-IC-Galactosyloligosaccharides-Prebiotics-AN71993-EN.pdf on Aug. 27, 2019. 2018. 8 pages.

Archer Daniels Midland Company. ADM Ingredients Catalog, pp. I-32 .2016. 36 pages.

Boler et al., Digestive physiological outcomes related to polydextrose and soluble maize fibre consumption by healthy adult men. Br J Nutr. Dec. 2011;106(12):1864-71. doi: 10.1017/S0007114511002388. Epub May 31, 2011.

Caligur, Glycobiology: glycosaminoglycans and polysaccharides. BioFiles. 2008;3(10). 2 pages.

(56) References Cited

OTHER PUBLICATIONS

Chiavaroli et al., Dietary fiber effects in chronic kidney disease: a systematic review and meta-analysis of controlled feeding trials. Eur J Clin Nutr. Jul. 2015;69(7):761-8. doi: 10.1038/ejcn.2014.237. Epub Nov. 12, 2014.

Coulier et al., In-depth characterization of prebiotic galacto-oligosaccharides by a combination of analytical techniques. J Agric Food Chem. Sep 23, 2009;57(18):8488-95. doi: 10.1021/jf902549e.

Cummings et al., Carbohydrate terminology and classification. Eur J Clin Nutr. Dec. 2007;61 Suppl 1:S5-18. doi: 10.1038/sj.ejcn. 1602936.

Duncan et al., Lactate-utilizing bacteria, isolated from human feces, that produce butyrate as a major fermentation product. Appl Environ Microbiol. Oct. 2004;70(10):5810-7. doi: 10.1128/AEM.70.10.5810-5817.2004.

Fetzer et al., Effect of acid and heat on dextrose and dextrose polymers. Ind. Eng. Chem. 1953;45(5):1075-83.

Garber, Drugging the gut microbiome. Nat Biotechnol. Mar. 2015;33(3):228-31. doi: 10.1038/nbt.3161. Erratum in: Nat Biotechnol. May 9, 2017;35(5):481.

Gietl et al., Factors involved in the in vitro fermentability of short carbohydrates in static faecal batch cultures, International Journal of Carbohydrate Chemistry. Dec. 2012;2012:197809. DOI: 10.1155/2012/197809. 10 pages.

Goulas et al., Development of a process for the production and purification of alpha- and beta-galactooligosaccharides from Bifidobacterium bifidum NCIMB 41171. Int Dairy J. Jun. 2007;17(6):648-56. DOI: 10.1016/j.idairyj.2006.08.010.

Hamaker et al., A perspective on the complexity of dietary fiber structures and their potential effect on the gut microbiota. J Mol Biol. Nov. 25, 2014;426(23):3838-50. doi: 10.1016/j.jmb.2014.07. 028. Epub aug. 1, 2014.

Holscher et al., Agave Inulin Supplementation Affects the Fecal Microbiota of Healthy Adults Participating in a Randomized, Double-Blind, Placebo-Controlled, Crossover Trial. J Nutr. Sep. 2015;145(9):2025-32. doi: 10.3945/jn.115.217331. Epub Jul. 22, 2015.

Houdijk et al., Effects of dietary oligosaccharides on the growth performance and faecal characteristics of young growing pigs. Animal Feed Sci Technol. 1998;71:35-48.

Kobata et al., Structures and application of oligosaccharides in human milk. Proc Jpn Acad Ser B Phys Biol Sci. 2010;86(7):731-47. doi: 10.2183/pjab.86.731.

Kuechel et al., Short communication: Development of a rapid laboratory method to polymerize lactose to nondigestible carbohydrates. J Dairy Sci. Apr. 2018;101(4):2862-2866. doi: 10.3168/jds. 2017-13813. Epub Feb. 7, 2018.

Louis et al., Understanding the effects of diet on bacterial metabolism in the large intestine. J Appl Microbiol. May 2007;102(5):1197-208. doi: 10.1111/j.1365-2672.2007.03322.x.

Mountzouris et al., Modeling of oligodextran production in an ultrafiltration stirred-cell membrane reactor. Enzyme Microb Technol. Jan.-Feb. 1999;24(1-2): 75-85.

Olano-Martin et al., In vitro fermentability of dextran, oligodextran and maltodextrin by human gut bacteria. Br J Nutr. Mar. 2000;83(3):247-55. doi: 10.1017/s0007114500000325.

Ouwerkerk et al., Glycobiome: bacteria and mucus at the epithelial interface. Best Pract Res Clin Gastroenterol. Feb. 2013;27(1):25-38. doi: 10.1016/j.bpg.2013.03.001.

Pfenninger et al., Structural analysis of underivatized neutral human milk oligosaccharides in the negative ion mode by nano-electrospray MS(n) (part 2: application to isomeric mixtures). J Am Soc Mass Spectrom. 2002;13(11):1341-8.

Pryde et al., The microbiology of butyrate formation in the human colon. FEMS Microbiol Lett.Dec. 17, 2002;217(2):133-9. doi: 10.1111/j.1574-6968.2002.tb11467.x.

Reichardt et al., Phylogenetic distribution of three pathways for propionate production within the human gut microbiota. ISME J. Jun. 2014;8(6):1323-35. doi: 10.1038/ismej.2014.14. Epub Feb. 20, 2014. Erratum in: ISME J. Jun. 2014;8(6):1352.

Roberfroid, Prebiotics: the concept revisited. J Nutr. Mar. 2007;137(3 Suppl 2):830S-7S. doi: 10.1093/jn/137.3.830S.

Rodriguez-Colinas et al., Galacto-oligosaccharide synthesis from lactose solution or skim milk using the β-galactosidase from Bacillus circulans. J Agric Food Chem. Jun. 27, 2012;60(25):6391-8. doi: 10.1021/jf301156v. Epub Jun. 19, 2012.

Salvador et al., Sugar composition of dietary fibre and short-chain fatty acid production during in vitro fermentation by human bacteria. Br J Nutr. Jul. 19931;70(1):189-97. doi: 10.1079/bjn19930116.

Sanz et al., Selective fermentation of gentiobiose-derived oligosaccharides by human gut bacteria and influence of molecular weight. FEMS Microbiol Ecol. Jun. 2006;56(3):383-8. doi: 10.1111/j.1574-6941.2006.00075.x.

Si et al., Quantification of cell proliferation and alpha-toxin gene expression of Clostridium perfringens in the development of necrotic enteritis in broiler chickens. Appl Environ Microbiol. Nov. 2007;73(21):7110-3. doi: 10.1128/AEM.01108-07. Epub Sep. 7, 2007.

Timbermont et al., Necrotic enteritis in broilers: an updated review on the pathogenesis. Avian Pathol. Aug. 2011;40(4):341-7. doi: 10.1080/03079457.2011.590967.

Tremaine et al., Polymerization of lactose by twin-screw extrusion to produce indigestible oligosaccharides. International Dairy Journal. 2014;36(1):74-81.

Tremaine, Twin-Screw Extrusion of Commodity Grade Dairy Ingredients to Produce Value-Added Products. Master of Science Thesis Paper. The Graduate School of the University of Minnesota. May 2012. 152 pages.

Velayudhan et al., Characterization of Dietary Energy in Swine Feed and Feed Ingredients: A Review of Recent Research Results. Asian-Australas J Anim Sci. Jan. 2015; 28(1): 1-13. doi: 10.5713/ajas.14.0001R.

Xiao et al., Chemical synthesis of polysaccharides and polysaccharide mimetics. Prog Poly Sci. 2017;74:78-116. DOI: 10.1016/j.progpolymsci.2017.07.009.

PCT/US2019/047595, Dec. 16, 2019, Invitation to Pay Additional Fees.

PCT/US2019/047595, Feb. 12, 2020, International Search Report and Written Opinion.

PCT/US2019/060626, Feb. 19, 2020, Invitation to Pay Additional Fees.

PCT/US2019/060626, Jul. 1, 2020, International Search Report and Written Opinion.

PCT/US2020/032240, Jul. 7, 2020, Invitation to Pay Additional Fees.

PCT/US2020/032240, Sep. 21, 2020, International Search Report and Written Opinion.

GLYCAN THERAPEUTIC COMPOSITIONS AND RELATED METHODS THEREOF

CLAIM OF PRIORITY

This application is a Continuation of U.S. application Ser. No. 15/568,243, filed Oct. 20, 2017, which a U.S. national phase application under 35 U.S.C. § 371 of International Application No. PCT/US2016/029082, filed Apr. 23, 2016, which claims priority to U.S. Application No. 62/278,333, filed Jan. 13, 2016; U.S. Application No. 62/238,110, filed Oct. 6, 2015; U.S. Application No. 62/238,112, filed Oct. 6, 2015; U.S. Application No. 62/216,995, filed Sep. 10, 2015; U.S. Application No. 62/216,997, filed Sep. 10, 2015; U.S. Application No. 62/152,017, filed Apr. 23, 2015; U.S. Application No. 62/152,011, filed Apr. 23, 2015; and U.S. Application No. 62/152,007, filed Apr. 23, 2015. The disclosure of each of the foregoing applications is incorporated herein by reference in its entirety.

BACKGROUND OF THE INVENTION

Maintaining or restoring human health faces a large number of challenges many of which result from the lack of effective treatment options. There is a continued need for novel therapies and treatment regimens.

SUMMARY OF THE INVENTION

Provided herein are preparations of glycan therapeutics and pharmaceutical compositions, medical foods and dietary supplements thereof, and related methods, which have been found to be effective to treat a number of diseases, disorders or pathological conditions.

In a first aspect, the invention relates to methods of treating an immune imbalance in a human subject. Provided herein is a method of treating an immune imbalance in a human subject, comprising: administering to the subject a pharmaceutical composition, a medical food or a dietary supplement comprising a glycan therapeutic preparation, in an effective amount to treat the subject. Provided herein is a method of treating an immune imbalance in a human subject, comprising: administering to the subject a first agent comprising a glycan therapeutic preparation, optionally in combination with a second agent or therapy. In one embodiment, the first agent is a pharmaceutical composition. In one embodiment, the first agent is a medical food.

In one embodiment, the first agent is a dietary supplement. In one embodiment, the second agent is an immunomodulatory agent. In one embodiment, the second agent or therapy treats a second disease, disorder or pathological condition of the subject. In one embodiment, the first agent and the second agent are administered in an effective amount to treat the immune imbalance. In one embodiment, the first agent is administered in an effective amount to treat the immune imbalance and the second agent is administered in an effective amount to treat the second disease, disorder or pathological condition of the subject. In one embodiment, the second agent is a dietary fiber. In one embodiment, the second agent is a probiotic bacterium. In one embodiment, the combination is administered to a subject who has been treated for an immune imbalance. In one embodiment, the combination is administered to a subject who has not been treated for an immune imbalance. In one embodiment, the first agent is administered to a subject that has been treated with the second agent. In one embodiment, the second agent is administered to a subject that has been treated with the first agent. In one embodiment, the first agent and the second agent are administered concurrently to a subject.

Provided herein is a method for reducing an infection and/or an inflammation in a subject having an immune imbalance, the method comprising administering to the subject a glycan therapeutic preparation in an effective amount to reduce the infection and/or an inflammation.

Provided herein is a method of modulating the composition and/or metabolic activity of the intestinal bacterial community of a subject having an immune imbalance, comprising administering to the subject a glycan therapeutic composition and, optionally, an anti- or pro-inflammatory agent in an amount effective to modulate the subject's immune system. In one embodiment, the methods further comprise administering a probiotic microorganism. In one embodiment, a short-chain fatty acid (SCFA) is modulated. In one embodiment, the SCFA is one or more of acetate, propionate, butyrate, isovalerate, valerate, hexanoate, heptanoate, and octanoate. In one embodiment, the one or more SCFA is reduced. In some embodiments, the one or more SCFA is increased. In one embodiment, administration of the composition modulates (e.g. stimulates) growth or activity of beneficial gut bacteria, e.g., Bifidobacteria. In one embodiment, administration of the glycan therapeutic preparation modulates the growth or function of one or more bacterial taxa, including Bifidobacteria, Bifidobacteriales, Bacteroidales, Clostridiales, Parabacteroides, and *Akkermansia*. In one embodiment, administration of the glycan therapeutic preparation modulates the growth or function of one or more bacterial taxa, including Blautia, *Bifidobacterium, Roseburia, Coprococcus, Lachnospiraceae, Faecalibacterium*, Parabacteroides, and Ruminococcaceae. In one embodiment, one or more host pathways are modulated, including inflammatory responses, complement, apoptosis, antigen presentation, oxidative stress, cell adhesion, cytoskeleton remodeling, Notch signaling, Wnt signaling, and/or one or more of the metabolic pathways listed in Table 19 ((super or sub pathways or level of a metabolite). In one embodiment, one or more bile acids are modulated. In one embodiment, the bile acid is a primary bile acid. In one embodiment, the bile acid is a secondary bile acid. In one embodiment, the bile acid is one or more of glycodeoxycholic acid, glycolithocholic acid, alpha-muricholic acid, beta-muricholic acid, taurocholic acid, and taurochenodeoxycholic acid. In one embodiment, the bile acid is DCA (deoxycholic acid) and/or LCA (lithocholic acid). In one embodiment, the bile acid is increased. In one embodiment, the bile acid is decreased. In one embodiment, administration of the composition results in the modulation of one or more biomarkers including Interleukin 10, Interleukin, 4, Interleukin 13, and Interleukin 35. In one embodiment, administration of the composition results in the modulation of one or more biomarkers including C-reactive protein, interleukin-6, interleukin-8, interleukin-18, insulin, blood glucose, leptin, serum amyloid A, serum amyloid P, and tumor necrosis factor-alpha. In one embodiment, one or more cytokine selected from TNF-α, IL-8, monocyte chemoattracting protein 1 (MCP-1), TGF-β, IL-12, IFN-γ, IL-4, and IL-10 is modulated. In one embodiment, administration of the composition results in a i) a reduced immune response or ii) an enhanced immune response. In one embodiment, the production or release of pro-inflammatory cytokines is decreased. In one embodiment, the production or release of pro-inflammatory cytokines is increased. In one embodiment, the production or release of anti-inflammatory cytokines is increased. In one embodiment, the production or release of anti-inflammatory cytokines is decreased.

Provided herein is a method of modulating the function and/or activity of a pathway of a subject having an immune imbalance, comprising administering to the subject a glycan therapeutic composition and, optionally as second agent. In one embodiment, a short-chain fatty acid (SCFA) is modulated. In one embodiment, the SCFA is one or more of acetate, propionate, butyrate, isovalerate, valerate, hexanoate, heptanoate, and octanoate. In one embodiment, the one or more SCFA is reduced. In some embodiments, the one or more SCFA is increased. In one embodiment, one or more pathways are modulated, including inflammatory responses, complement, apoptosis, antigen presentation, oxidative stress, cell adhesion, cytoskeleton remodeling, Notch signaling, Wnt signaling, and/or one or more of the metabolic pathways listed in Table 19 ((super or sub pathways or level of a metabolite). In one embodiment, one or more bile acids are modulated. In one embodiment, the bile acid is a primary bile acid. In one embodiment, the bile acid is a secondary bile acid. In one embodiment, the bile acid is one or more of glycodeoxycholic acid, glycolithocholic acid, alpha-muricholic acid, beta-muricholic acid, taurocholic acid, and taurochenodeoxycholic acid. In one embodiment, the bile acid is DCA (deoxycholic acid) and/or LCA (lithocholic acid). In one embodiment, the bile acid is increased. In one embodiment, the bile acid is decreased.

Provided herein is a method of treating a dysbiosis in a subject having an immune imbalance comprising administering to the subject a pharmaceutical composition comprising a glycan therapeutic preparation in an effective amount to treat the dysbiosis.

For any and all of the foregoing methods, in one embodiment, the immune imbalance is a suppression of the subject's immune system. In one embodiment, the subject exhibits a deficient immune-surveillance. In one embodiment, the subject has a pathogenic infection. In one embodiment, the subject has a cancer. In one embodiment, the immune imbalance is an aberrant activation of the subject's immune system. In one embodiment, the subject has a inflammatory disease that increase the risk of developing a cancer. In one embodiment, the subject has graft-versus-host disease. In one embodiment, the subject has an autoimmune disease. In one embodiment, the subject has an inflammatory gastrointestinal disease. In one embodiment, the immune imbalance is acute. In one embodiment, the immune imbalance is chronic. In one embodiment, the immune imbalance is local. In one embodiment, the immune imbalance is systemic. In one embodiment, the immune imbalance is accompanied by aberrant growth of a pathogenic cell. In one embodiment, the pathogenic cell is an intracellular pathogen, an extracellular pathogen, or a cancerous cell.

For any and all of the foregoing methods, in one embodiment, the glycan therapeutic preparation: i) comprises branched glycans, ii) the branched glycans comprise branched oligosaccharides, iii) the glycan therapeutic preparation has an average degree of branching (DB) of at least 0.01, iv) at least 50% of the glycans in the preparation have a degree of polymerization (DP) of at least 3 and less than 30 glycan units, v) the ratio of alpha- to beta-glycosidic bonds present in the glycans of the preparation overall is between about 1:1 to about 5:1, or vi) any combination of one, two, three, four or five of i), ii), iii), iv) and v).

For any and all of the foregoing methods, in one embodiment, the glycan therapeutic preparation: i) comprises branched glycans, ii) the branched glycans comprise branched oligosaccharides, iii) the branched oligosaccharides comprise glucose, galactose, arabinose, mannose, fructose, xylose, fucose, or rhamnose glycan units, iv) the average degree of branching (DB) of the branched glycans in the glycan therapeutic preparation is between 0.01 and 0.3, v) at least 50% of the glycans in the glycan therapeutic preparation have a degree of polymerization (DP) of at least 3 and less than 30 glycan units, vi) the average DP of the glycan therapeutic preparation is between about DP6 and about DP10, vii) the ratio of alpha- to beta-glycosidic bonds present in the glycans of the glycan therapeutic preparation is between about 1:1 to about 5:1, viii) the glycan therapeutic preparation has a final solubility limit in water of at least about 60 Brix at 23° C., or ix) any combination of one, two, three, or four, five, six, seven, or eight of i), ii), iii), iv), v), vi), vii), and viii).

For any and all of the foregoing methods, in one embodiment, the glycan therapeutic preparation: i) comprises branched glycans, ii) the branched glycans comprise one or more glycan units, iii) the branched glycans comprise at least 1% of branched glycan units, iv) the branched glycans have a degree of polymerization (DP) of between 2 and 30 glycan units, v) the branched glycans have a 1:1, 1:2, 1:3, 1:4, or 1:5 beta- to alpha-configuration, vi) the branched glycans comprise a mixture of beta and alpha linkages of one or more of (1-2), (1-3), (1-4), (1-6), (2-3), and (2-6); vii) the glycan therapeutic preparation comprises a mixture of branched glycans and unbranched glycans, viii) the glycan therapeutic preparation comprises a mixture of digestible and non-digestible glycans, or ix) any combination of one, two, three, or four, five, six, seven, or eight of i), ii), iii), iv), v), vi), vii), and viii).

In a second aspect, the invention relates to methods of treating a nutritional imbalance in a human subject. Provided herein is a method of treating a nutritional imbalance in a human subject, comprising: administering to the subject a pharmaceutical composition, a medical food or a dietary supplement comprising a glycan therapeutic preparation, in an effective amount to treat the subject.

Provided herein is a method of treating a nutritional imbalance in a human subject, comprising: administering to the subject a first agent comprising a glycan therapeutic preparation, optionally in combination with a second agent or therapy. In one embodiment, the first agent is a pharmaceutical composition. In one embodiment, the first agent is a medical food. In one embodiment, the first agent is a dietary supplement. In one embodiment, the second agent is metabolism modulating agent. In one embodiment, the second agent or therapy treats a second disease, disorder or pathological condition of the subject. In one embodiment, the first agent and the second agent are administered in an effective amount to treat the nutritional imbalance. In one embodiment, the first agent is administered in an effective amount to treat the nutritional imbalance and the second agent is administered in an effective amount to treat the second disease, disorder or pathological condition of the subject. In one embodiment, the second agent is a dietary fiber. In one embodiment, the second agent is a probiotic bacterium. In one embodiment, the combination is administered to a subject who has been treated for a nutritional imbalance. In one embodiment, the combination is administered to a subject who has not been treated for a nutritional imbalance. In one embodiment, the first agent is administered to a subject that has been treated with the second agent. In one embodiment, the second agent is administered to a subject that has been treated with the first agent. In one embodiment, the first agent and the second agent are administered concurrently to a subject.

Provided herein is a method for reducing an inflammation in a subject having a nutritional imbalance, the method comprising administering to the subject a glycan therapeutic preparation in an effective amount to reduce the inflammation.

Provided herein is a method of modulating the composition and/or metabolic activity of the intestinal bacterial community of a subject having a nutritional imbalance, comprising administering to the subject a glycan therapeutic composition and an anti- or pro-inflammatory agent in an amount effective to modulate the subject's immune system. In one embodiment, the methods further comprise administering a probiotic microorganism. In one embodiment, a short-chain fatty acid (SCFA) is modulated. In one embodiment, the SCFA is one or more of acetate, propionate, butyrate, isovalerate, valerate, hexanoate, heptanoate, and octanoate. In one embodiment, the one or more SCFA is reduced. In some embodiments, the one or more SCFA is increased. In one embodiment, administration of the composition modulates (e.g. stimulates) growth or activity of beneficial gut bacteria, e.g., Bifidobacteria. In one embodiment, administration of the glycan therapeutic preparation modulates the growth or function of one or more bacterial taxa, including Bifidobacteria, Bifidobacteriales, Bacteroidales, Clostridiales, Parabacteroides, and *Akkermansia*. In one embodiment, administration of the glycan therapeutic preparation modulates the growth or function of one or more bacterial taxa, including Blautia, *Bifidobacterium, Roseburia, Coprococcus, Lachnospiraceae, Faecalibacterium*, Parabacteroides, and Ruminococcaceae. In one embodiment, one or more host pathways are modulated, including inflammatory responses, complement, apoptosis, antigen presentation, oxidative stress, cell adhesion, cytoskeleton remodeling, Notch signaling, Wnt signaling, and/or one or more of the metabolic pathways listed in Table 19 ((super or sub pathways or level of a metabolite). In one embodiment, one or more bile acids are modulated. In one embodiment, the bile acid is a primary bile acid. In one embodiment, the bile acid is a secondary bile acid. In one embodiment, the bile acid is one or more of glycodeoxycholic acid, glycolithocholic acid, alpha-muricholic acid, beta-muricholic acid, taurocholic acid, and taurochenodeoxycholic acid. In one embodiment, the bile acid is DCA (deoxycholic acid) and/or LCA (lithocholic acid). In one embodiment, the bile acid is increased. In one embodiment, the bile acid is decreased. In one embodiment, administration of the composition results in the modulation of one or more biomarkers including Interleukin 10, Interleukin, 4, Interleukin 13, and Interleukin 35. In one embodiment, administration of the composition results in the modulation of one or more biomarkers including C-reactive protein, interleukin-6, interleukin-8, interleukin-18, insulin, blood glucose, leptin, serum amyloid A, serum amyloid P, and tumor necrosis factor-alpha. In one embodiment, one or more cytokine selected from TNF-α, IL-8, monocyte chemoattracting protein 1 (MCP-1), TGF-β, IL-12, IFN-γ, IL-4, and IL-10 is modulated. In one embodiment, administration of the composition results in a i) a reduced immune response or ii) an enhanced immune response. In one embodiment, the production or release of pro-inflammatory cytokines is decreased. In one embodiment, the production or release of pro-inflammatory cytokines is increased. In one embodiment, the production or release of anti-inflammatory cytokines is increased. In one embodiment, the production or release of anti-inflammatory cytokines is decreased.

Provided herein is a method of modulating the function and/or activity of a pathway of a subject having an nutritional imbalance, comprising administering to the subject a glycan therapeutic composition and, optionally as second agent. In one embodiment, a short-chain fatty acid (SCFA) is modulated. In one embodiment, the SCFA is one or more of acetate, propionate, butyrate, isovalerate, valerate, hexanoate, heptanoate, and octanoate. In one embodiment, the one or more SCFA is reduced. In some embodiments, the one or more SCFA is increased. In one embodiment, one or more pathways are modulated, including inflammatory responses, complement, apoptosis, antigen presentation, oxidative stress, cell adhesion, cytoskeleton remodeling, Notch signaling, Wnt signaling, and/or one or more of the metabolic pathways listed in Table 19 ((super or sub pathways or level of a metabolite). In one embodiment, one or more bile acids are modulated. In one embodiment, the bile acid is a primary bile acid. In one embodiment, the bile acid is a secondary bile acid. In one embodiment, the bile acid is one or more of glycodeoxycholic acid, glycolithocholic acid, alpha-muricholic acid, beta-muricholic acid, taurocholic acid, and taurochenodeoxycholic acid. In one embodiment, the bile acid is DCA (deoxycholic acid) and/or LCA (lithocholic acid). In one embodiment, the bile acid is increased. In one embodiment, the bile acid is decreased.

Provided herein is a method of treating a dysbiosis in a subject having a nutritional imbalance comprising administering to the subject a pharmaceutical composition comprising a glycan therapeutic preparation in an effective amount to treat the dysbiosis.

For any and all of the foregoing methods, in one embodiment, the nutritional imbalance is acute. In one embodiment, the nutritional imbalance is chronic. In one embodiment, the subject has a metabolic disease or syndrome. In one embodiment, the subject has a wasting syndrome. In one embodiment, the wasting syndrome is cachexia. In one embodiment, the subject has cancer. In one embodiment, the cancer is a gastrointestinal cancer. In one embodiment, the cancer is a non-gastrointestinal cancer.

For any and all of the foregoing methods, in one embodiment, the glycan therapeutic preparation: i) comprises branched glycans, ii) the branched glycans comprise branched oligosaccharides, iii) the glycan therapeutic preparation has an average degree of branching (DB) of at least 0.01, iv) at least 50% of the glycans in the preparation have a degree of polymerization (DP) of at least 3 and less than 30 glycan units, v) the ratio of alpha- to beta-glycosidic bonds present in the glycans of the preparation overall is between about 1:1 to about 5:1, or vi) any combination of one, two, three, four or five of i), ii), iii), iv) and v).

For any and all of the foregoing methods, in one embodiment, the glycan therapeutic preparation: i) comprises branched glycans, ii) the branched glycans comprise branched oligosaccharides, iii) the branched oligosaccharides comprise glucose, galactose, arabinose, mannose, fructose, xylose, fucose, or rhamnose glycan units, iv) the average degree of branching (DB) of the branched glycans in the glycan therapeutic preparation is between 0.01 and 0.3, v) at least 50% of the glycans in the glycan therapeutic preparation have a degree of polymerization (DP) of at least 3 and less than 30 glycan units, vi) the average DP of the glycan therapeutic preparation is between about DP6 and about DP10, vii) the ratio of alpha- to beta-glycosidic bonds present in the glycans of the glycan therapeutic preparation is between about 1:1 to about 5:1, viii) the glycan therapeutic preparation has a final solubility limit in water of at least about 60 Brix at 23° C., or ix) any combination of one, two, three, or four, five, six, seven, or eight of i), ii), iii), iv), v), vi), vii), and viii).

For any and all of the foregoing methods, in one embodiment, the glycan therapeutic preparation: i) comprises branched glycans, ii) the branched glycans comprise one or more glycan units, iii) the branched glycans comprise at least 1% of branched glycan units, iv) the branched glycans have a degree of polymerization (DP) of between 2 and 30 glycan units, v) the branched glycans have a 1:1, 1:2, 1:3, 1:4, or 1:5 beta- to alpha-configuration, vi) the branched glycans comprise a mixture of beta and alpha linkages of one or more of (1-2), (1-3), (1-4), (1-6), (2-3), and (2-6); vii) the glycan therapeutic preparation comprises a mixture of branched glycans and unbranched glycans, viii) the glycan therapeutic preparation comprises a mixture of digestible and non-digestible glycans, or ix) any combination of one, two, three, or four, five, six, seven, or eight of i), ii), iii), iv), v), vi), vii), and viii).

In a third aspect, the invention relates to methods of treating cancer in a human subject. Provided herein is a method of treating cancer in a human subject, comprising: administering to the subject a pharmaceutical composition, a medical food or a dietary supplement comprising a glycan therapeutic preparation, in an effective amount to treat the subject.

Provided herein is a method of treating cancer in a human subject, comprising: administering to the subject a first agent comprising a glycan therapeutic preparation, optionally in combination with a second agent or therapy.

In one embodiment, the first agent is a pharmaceutical composition. In one embodiment, the first agent is a medical food. In one embodiment, the first agent is a dietary supplement. In one embodiment, the second agent is a checkpoint modulator, a cancer vaccine, an anti-cancer biologic, or a chemotherapeutic agent. In one embodiment, the immune checkpoint inhibitor is an antibody, a fusion protein, or a small molecule. In one embodiment, the cancer vaccine is a tumor cell vaccine, an antigen vaccine, a dendritic cell vaccine, a DNA vaccine, or a vector based vaccine. In one embodiment, the anti-cancer biologic is a cytokine or an antibody. In one embodiment, the chemotherapeutic agent is an alkylating agent, an antimetabolite, a folic acid analog, a pyrimidine analog, a purine analog, a *vinca* alkaloid, an epipodopyyllo toxin, an antibiotic, L-asparaginase, a topoisomerase inhibitor, an interferon, a platinum coordination complex, anthracenedione substituted urea, a methyl hydrazine derivative, an adrenocortical suppressant, an adrenocorticosteroid, a progestin, an estrogen, an anti-estrogen, an androgen, an anti-androgen, or a gonadotropin-releasing hormone analog. In one embodiment, the second therapy is adoptive T cell therapy, NK cell therapy, or a non drug treatment. In one embodiment, the non-drug treatment is radiation therapy, cryotherapy, hyperthermia or surgical excision of tumor tissue. In one embodiment, the adoptive T cell therapy comprises administering autologous and/or allogeneic T-cells. In one embodiment, the second agent is a dietary fiber. In one embodiment, the second agent is a probiotic bacterium. In one embodiment, the combination is administered to a subject who has been treated with an anti-cancer therapy. In one embodiment, the combination is administered to a subject who has not been treated with an anti-cancer therapy. In one embodiment, the first agent is administered to a subject that has been treated with the second agent. In one embodiment, the second agent is administered to a subject that has been treated with the first agent. In one embodiment, the first agent and the second agent are administered concurrently to a subject.

Provided herein is a method of modulating the composition and/or metabolic activity of the intestinal bacterial community of a subject having cancer, comprising administering to the subject a glycan therapeutic composition and an anti- or pro-inflammatory agent in an amount effective to modulate the subject's immune system. In one embodiment, the methods further comprise administering an anti-cancer agent. In one embodiment, the methods further comprise administering a probiotic microorganism. In one embodiment, a short-chain fatty acid (SCFA) is modulated. In one embodiment, the SCFA is one or more of acetate, propionate, butyrate, isovalerate, valerate, hexanoate, heptanoate, and octanoate. In one embodiment, the one or more SCFA is reduced. In some embodiments, the one or more SCFA is increased. In one embodiment, administration of the composition results in induction of apoptosis of cancer and precancerous cells in the subject. In one embodiment, administration of the composition modulates (e.g. stimulates) growth or activity of beneficial gut bacteria, e.g., Bifidobacteria. In one embodiment, administration of the glycan therapeutic preparation modulates the growth or function of one or more bacterial taxa, including Bifidobacteria, Bifidobacteriales, Bacteroidales, Clostridiales, Parabacteroides, and *Akkermansia*. In one embodiment, administration of the glycan therapeutic preparation modulates the growth or function of one or more bacterial taxa, including Blautia, *Bifidobacterium, Roseburia, Coprococcus, Lachnospiraceae, Faecalibacterium*, Parabacteroides, and Ruminococcaceae. In one embodiment, one or more host pathways are modulated, including inflammatory responses, complement, apoptosis, antigen presentation, oxidative stress, cell adhesion, cytoskeleton remodeling, Notch signaling, Wnt signaling, and/or one or more of the metabolic pathways listed in Table 19 ((super or sub pathways or level of a metabolite). In one embodiment, one or more bile acids are modulated. In one embodiment, the bile acid is a primary bile acid. In one embodiment, the bile acid is a secondary bile acid. In one embodiment, the bile acid is one or more of glycodeoxycholic acid, glycolithocholic acid, alpha-muricholic acid, beta-muricholic acid, taurocholic acid, and taurochenodeoxycholic acid. In one embodiment, the bile acid is DCA (deoxycholic acid) and/or LCA (lithocholic acid). In one embodiment, the bile acid is increased. In one embodiment, the bile acid is decreased. In one embodiment, administration of the composition results in the modulation of one or more biomarkers including Interleukin 10, Interleukin, 4, Interleukin 13, and Interleukin 35. In one embodiment, administration of the composition results in the modulation of one or more biomarkers including C-reactive protein, interleukin-6, interleukin-8, interleukin-18, insulin, blood glucose, leptin, serum amyloid A, serum amyloid P, and tumor necrosis factor-alpha. In one embodiment, one or more cytokine selected from TNF-$\alpha$, IL-8, monocyte chemoattracting protein 1 (MCP-1), TGF-$\beta$, IL-12, IFN-$\gamma$, IL-4, and IL-10 is modulated. In one embodiment, administration of the composition results in a i) a reduction of intestinal cancer, and/or ii) an enhanced immune response. In one embodiment, the production or release of pro-inflammatory cytokines is decreased. In one embodiment, the production or release of anti-inflammatory cytokines is increased.

Provided herein is a method of modulating the function and/or activity of a pathway of a subject having an immune imbalance, comprising administering to the subject a glycan therapeutic composition and, optionally as second agent. In one embodiment, a short-chain fatty acid (SCFA) is modulated. In one embodiment, the SCFA is one or more of acetate, propionate, butyrate, isovalerate, valerate, hexanoate, heptanoate, and octanoate. In one embodiment, the one or more SCFA is reduced. In some embodiments, the one or more SCFA is increased. In one embodiment, one or more pathways are modulated, including inflammatory responses, complement, apoptosis, antigen presentation, oxidative stress, cell adhesion, cytoskeleton remodeling, Notch signaling, Wnt signaling, and/or one or more of the metabolic pathways listed in Table 19 ((super or sub pathways or level of a metabolite). In one embodiment, one or more bile acids are modulated. In one embodiment, the bile acid is a primary bile acid. In one embodiment, the bile acid is a secondary bile acid. In one embodiment, the bile acid is one or more of glycodeoxycholic acid, glycolithocholic acid, alpha-muricholic acid, beta-muricholic acid, taurocholic acid, and taurochenodeoxycholic acid. In one embodiment, the bile acid is DCA (deoxycholic acid) and/or LCA (lithocholic acid). In one embodiment, the bile acid is increased. In one embodiment, the bile acid is decreased.

Provided herein is a method of treating a dysbiosis in a subject having cancer comprising administering to the subject a pharmaceutical composition comprising a glycan therapeutic preparation in an effective amount to treat the dysbiosis. In one embodiment, the subject undergoes an anti-cancer therapy. In one embodiment, the cancer therapy. In one embodiment, the cancer therapy is a non-drug therapy. In one embodiment, the subject undergoes pain management therapy for cancer pain. In one embodiment, the pain management therapy comprises administering opioids. In one embodiment, the subject exhibits constipation. In one embodiment, the constipation is acute. In one embodiment, the constipation is chronic. In one embodiment, the subject exhibits diarrhea. In one embodiment, the diarrhea is acute. In one embodiment, the diarrhea is chronic.

Provided herein is a method for reducing an infection and/or an inflammation in a subject having cancer, the method comprising administering to the subject a glycan therapeutic preparation in an effective amount to reduce the infection and/or an inflammation.

Provided herein is a method for inducing apoptosis of a cancer or a precancerous cell in the subject having cancer, the method comprising administering to the subject a glycan therapeutic preparation in an effective amount to induce apoptosis of the cancer or precancerous cell.

In one embodiment, the cancer is colon cancer or liver cancer. In one embodiment, the glycan therapeutic preparation is administered in combination with another agent or therapy. In one embodiment, the other agent or therapy is selected from radiation and chemotherapy and antibiotic therapy. In one embodiment, the other agent is selected from a probiotic, a prebiotic dietary fiber, an antibacterial agent, an anti-inflammatory agent, or an anti-cancer agent. In one embodiment, one or more genes or gene products selected from Jun, Myc, Fos, Adamts1, ATF3, DDit4, Egr1, Sox9, IL1a, Gadd45b, and Gadd45 g are modulated.

Provided herein is a method of reducing the risk of cancer in a subject comprising administering to the subject a glycan therapeutic preparation in an effective amount to promote a healthy microbiota in the subject, thereby reducing the cancer risk in the subject.

In one embodiment, the cancer is selected from breast cancer, ovarian cancer, osteosarcoma, cervical cancer, lung cancer, bladder cancer, pancreatic cancer, prostate cancer, or melanoma. In one embodiment, the glycan therapeutic preparation is administered in combination with another agent or therapy. In one embodiment, the other agent or therapy is selected from radiation and chemotherapy and antibiotic therapy. In one embodiment, the other agent is selected from a probiotic, a prebiotic dietary fiber, an antibacterial agent, an anti-inflammatory agent, or an anti-cancer agent. In one embodiment, the healthy microbiota comprises microbial strains selected from *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacilli, Christensenella minuta*, or a *Christensenellaceae* species, *Streptococcus thermophilus, Enterococcus* and *Bacillus* species, *E. coli*, and *Sacharomyces boulardii*.

Provided herein is a method of modulating the composition of the intestinal bacterial community of a subject having cancer, comprising administering to the subject a glycan therapeutic preparation and an anti-cancer agent, in an amount effective to stimulate the growth of beneficial bacteria in the digestive system.

Provided herein is a method of modulating the metabolic activity of the intestinal bacterial community of a subject having cancer, comprising administering to the subject a glycan therapeutic composition and an anti-cancer agent, in an amount effective to modulate the metabolic activity of beneficial bacteria in the digestive system. In one embodiment, the metabolic activity is one or more of those listed in Table 19 ((super or sub pathways or level of a metabolite). In one embodiment, the methods further comprise administering an anti-inflammatory agent. In one embodiment, the methods further comprise administering a probiotic microorganism. In one embodiment, the beneficial bacteria are selected from one or more of: *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacilli, Christensenella minuta*, and *Christensenellaceae*. In one embodiment, the beneficial bacteria include *bifidobacterium*. In one embodiment, a beneficial gut bacterial microbiota is disturbed. In one embodiment, the cancer is colon or liver cancer.

In one embodiment, the expression of an oncogene is repressed. In one embodiment, the oncogene is one of: jun, myc and fos. In one embodiment, the glycan therapeutic composition is labeled as a medical food. In one embodiment, the method further comprises changes in the diet of the subject. In one embodiment, the change is one or more of: i) increasing dietary fiber intake, ii) eliminating gastrointestinal stimulants, iii) administering anticholinergic medications before meals. In one embodiment, the method further comprises one or more of: i) taking anxiety reducing measures, ii) regular exercise, iii) counseling for anxiety or depression. In one embodiment, the method further comprises identifying risk factors for developing a GI-related disease, to diagnose a GI-related disease, to evaluate the prognosis or severity of said disease, to evaluate the success of a treatment regimen, or any combination thereof, and wherein the GI related disease is cancer. In one embodiment, identifying the risk factors comprises acquiring the metabolite profile of a subject's tissue sample or microbial culture from the subject's tissue. In one embodiment, the metabolite for the purposes of diagnosis, prognostic risk assessment, or treatment assessment includes short chain fatty acids, bile acids, and lactate and those listed in Table 2. In one embodiment, the bile acid is a primary bile acid. In one embodiment, the bile acid is a secondary bile acid. In one embodiment, the bile acid is one or more of glycodeoxycholic acid, glycolithocholic acid, alpha-muricholic acid, beta-muricholic acid, taurocholic acid, and taurochenodeoxycholic acid. In one embodiment, the bile acid is DCA (deoxycholic acid) and/or LCA (lithocholic acid). In one embodiment, the bile acid is increased. In one embodiment, the bile acid is decreased.

For any and all of the foregoing methods, in one embodiment, the cancer is a primary or non-metastatic tumor. In one embodiment, the cancer is a metastatic or a metastasized tumor. In one embodiment, the cancer is a solid cancer. In one embodiment, the cancer is a liquid cancer. In one embodiment, the cancer is an immunogenic cancer. In one embodiment, the immunogenic cancer comprises one or more of the following characteristics: (a) tumor infiltrating lymphocytes (TIL), (b) somatic mutations, (c) neoantigens, (d) tertiary lymphoid structures; (e) high expression of inflammatory gene expression, or (f) immune cells exhibiting immunosuppressive phenotype. In one embodiment, the cancer is a gastrointestinal cancer. In one embodiment, the gastrointestinal cancer is colorectal cancer, pancreatic cancer, gastric cancer, oesophageal cancer, hepatocellular cancer, cholangiocellular cancer, oral cancer, or lip cancer. In one embodiment, the cancer is a non-gastrointestinal cancer. In one embodiment, the non-gastrointestinal cancer is a urogenital cancer, a gynecological cancer, a lung cancer, a head and neck cancer, a CNS cancer, a malignant mesothelioma; a breast cancer, a skin cancer, a thyroid cancer; a bone and soft tissue sarcoma; or a hematologic neoplasia. In one embodiment, the urogenital cancer is a hormone sensitive prostate cancer, a hormone refractory prostate cancer, a renal cell cancer, a bladder cancer, or a penile cancer. In one embodiment, the gynecological cancer is an ovarian cancer, a cervical cancer, an endometrial cancer. In one embodiment, the lung cancer is a small-cell lung cancer or a non-small-cell lung cancer. In one embodiment, the head and neck cancer is a squamous cell cancer. In one embodiment, the CNS cancer is a malignant glioma, an astrocytomas, a retinoblastoma or a brain metastasis. In one embodiment, the breast cancer is a hormone refractory metastatic breast cancer. In one embodiment, the skin cancer is a malignant melanoma, a basal and squamous cell skin cancer, a Merkel cell carcinoma, a lymphoma of the skin, or Kaposi Sarcoma. In one embodiment, the hematologic neoplasia is a multiple myeloma, an acute myelogenous leukemia, a chronic myelogenous leukemia, a myelodysplastic syndrome, an acute lymphoblastic leukemia, or Hodgkin's lymphoma.

For any and all of the foregoing methods, in one embodiment, the glycan therapeutic preparation: i) comprises branched glycans, ii) the branched glycans comprise branched oligosaccharides, iii) the glycan therapeutic preparation has an average degree of branching (DB) of at least 0.01, iv) at least 50% of the glycans in the preparation have a degree of polymerization (DP) of at least 3 and less than 30 glycan units, v) the ratio of alpha- to beta-glycosidic bonds present in the glycans of the preparation overall is between about 1:1 to about 5:1, or vi) any combination of one, two, three, four or five of i), ii), iii), iv) and v).

For any and all of the foregoing methods, in one embodiment, the glycan therapeutic preparation: i) comprises branched glycans, ii) the branched glycans comprise branched oligosaccharides, iii) the branched oligosaccharides comprise glucose, galactose, arabinose, mannose, fructose, xylose, fucose, or rhamnose glycan units, iv) the average degree of branching (DB) of the branched glycans in the glycan therapeutic preparation is between 0.01 and 0.3, v) at least 50% of the glycans in the glycan therapeutic preparation have a degree of polymerization (DP) of at least 3 and less than 30 glycan units, vi) the average DP of the glycan therapeutic preparation is between about DP6 and about DP10, vii) the ratio of alpha- to beta-glycosidic bonds present in the glycans of the glycan therapeutic preparation is between about 1:1 to about 5:1, viii) the glycan therapeutic preparation has a final solubility limit in water of at least about 60 Brix at 23° C., or ix) any combination of one, two, three, or four, five, six, seven, or eight of i), ii), iii), iv), v), vi), vii), and viii).

For any and all of the foregoing methods, in one embodiment, the glycan therapeutic preparation: i) comprises branched glycans, ii) the branched glycans comprise one or more glycan units, iii) the branched glycans comprise at least 1% of branched glycan units, iv) the branched glycans have a degree of polymerization (DP) of between 2 and 30 glycan units, v) the branched glycans have a 1:1, 1:2, 1:3, 1:4, or 1:5 beta- to alpha-configuration, vi) the branched glycans comprise a mixture of beta and alpha linkages of one or more of (1-2), (1-3), (1-4), (1-6), (2-3), and (2-6); vii) the glycan therapeutic preparation comprises a mixture of branched glycans and unbranched glycans, viii) the glycan therapeutic preparation comprises a mixture of digestible and non-digestible glycans, or ix) any combination of one, two, three, or four, five, six, seven, or eight of i), ii), iii), iv), v), vi), vii), and viii) . . . .

In a fourth aspect, the invention relates to methods of treating subjects with a glycan therapeutic preparation that also receive a second treatment or therapy and methods of selecting subjects for treatment. Provided herein is a method of treating a subject comprising: a) administering a pharmaceutical composition comprising a glycan therapeutic preparation to a subject who has been treated with a second treatment or therapy, b) administering a second treatment or therapy to a subject who has been treated with a pharmaceutical composition comprising a glycan therapeutic preparation, or c) administering a pharmaceutical composition comprising a glycan therapeutic preparation and administering a second treatment or therapy to a subject.

In one embodiment, the treatment or therapy is an anti-cancer treatment or therapy. In one embodiment, the treatment or therapy is a treatment for nutritional imbalance. In one embodiment, the treatment or therapy is a treatment for immune imbalance.

Provided herein is a method of selecting a subject for a treatment, comprising: (a) identifying a subject who has a disease, disorder or pathological condition, and (b) selecting the identified subject for treatment with a glycan therapeutic preparation.

In one embodiment, the disease, disorder or pathological condition is cancer. In one embodiment, the disease, disorder or pathological condition is nutritional imbalance. In one embodiment, the disease, disorder or pathological condition is immune imbalance. In one embodiment, the step of selecting is carried out on the basis that the glycan therapeutic preparation will provide therapeutic benefit to the subject. In one embodiment, the step of selecting is carried out on the basis that the subject will or is expected to benefit from administration of the glycan therapeutic preparation. In one embodiment, the subject is treatment naïve. In one embodiment, the subject has received anti-cancer treatment or therapy. In one embodiment, the subject has received treatment for nutritional imbalance. In one embodiment, the subject has received treatment for immune imbalance. In one embodiment, the method further comprises assessing the subject's gastrointestinal microbiota. In one embodiment, the assessment is carried out before, during and/or after the treatment. In one embodiment, treatment with a glycan therapeutic preparation modulates the abundance of a bacterial taxa. In one embodiment, the glycan therapeutic preparation is administered in an amount and for a time effective to result in shifted or modulated bacterial taxa in the subject's gastrointestinal microbiota. In one embodiment, the taxa are one or more of Bifidobacteria, Bacteroides and *Akkermansia*. In one embodiment, the taxa are of one or more of Bifidobacteria, Bifidobacteriales, Bacteroidales, Clostridiales, Parabacteroides, and *Akkermansia*. In one embodiment, the taxa are one or more of Blautia, *Bifidobacterium, Roseburia, Coprococcus, Lachnospiraceae, Faecalibacterium*, Parabacteroides, and Ruminococcaceae. In one embodiment, the treatment results in increased levels of Th17 or Th1 cells in the subject. In one embodiment, the method further comprises identifying risk factors for developing a cancer or second disease or disorder, to diagnose a cancer or second disease or disorder, to evaluate the prognosis or severity of the a cancer or second disease or disorder, to evaluate the success of a treatment regimen, or any combination thereof. In one embodiment, identifying the risk factors comprises acquiring the metabolite profile of a subject's tissue sample or microbial culture from the subject's tissue. In one embodiment, the metabolite for the purposes of diagnosis, prognostic risk assessment, or treatment assessment includes short chain fatty acids, bile acids, and lactate and the metabolites listed in Table 2. In one embodiment, the bile acid is a primary bile acid. In one embodiment, the bile acid is a secondary bile acid. In one embodiment, the bile acid is one or more of glycodeoxycholic acid, glycolithocholic acid, alpha-muricholic acid, beta-muricholic acid, taurocholic acid, and taurochenodeoxycholic acid. In one embodiment, the bile acid is DCA (deoxycholic acid) and/or LCA (lithocholic acid). In one embodiment, the bile acid is increased. In one embodiment, the bile acid is decreased. In one embodiment, the method further comprises changes in the diet of the subject. In one embodiment, the change is one or more of: i) increasing dietary fiber intake, ii) eliminating gastrointestinal stimulants, iii) administering anticholinergic medications before meals. In one embodiment, the method further comprises one or more of: i) taking anxiety reducing measures, ii) regular exercise, iii) counseling for anxiety or depression.

For any and all of the foregoing methods, in one embodiment, the glycan therapeutic preparation: i) comprises branched glycans, ii) the branched glycans comprise branched oligosaccharides, iii) the glycan therapeutic preparation has an average degree of branching (DB) of at least 0.01, iv) at least 50% of the glycans in the preparation have a degree of polymerization (DP) of at least 3 and less than 30 glycan units, v) the ratio of alpha- to beta-glycosidic bonds present in the glycans of the preparation overall is between about 1:1 to about 5:1, or vi) any combination of one, two, three, four or five of i), ii), iii), iv) and v).

For any and all of the foregoing methods, in one embodiment, the glycan therapeutic preparation: i) comprises branched glycans, ii) the branched glycans comprise branched oligosaccharides, iii) the branched oligosaccharides comprise glucose, galactose, arabinose, mannose, fructose, xylose, fucose, or rhamnose glycan units, iv) the average degree of branching (DB) of the branched glycans in the glycan therapeutic preparation is between 0.01 and 0.3, v) at least 50% of the glycans in the glycan therapeutic preparation have a degree of polymerization (DP) of at least 3 and less than 30 glycan units, vi) the average DP of the glycan therapeutic preparation is between about DP6 and about DP10, vii) the ratio of alpha- to beta-glycosidic bonds present in the glycans of the glycan therapeutic preparation is between about 1:1 to about 5:1, viii) the glycan therapeutic preparation has a final solubility limit in water of at least about 60 Brix at 23° C., or ix) any combination of one, two, three, or four, five, six, seven, or eight of i), ii), iii), iv), v), vi), vii), and viii).

For any and all of the foregoing methods, in one embodiment, the glycan therapeutic preparation: i) comprises branched glycans, ii) the branched glycans comprise one or more glycan units, iii) the branched glycans comprise at least 1% of branched glycan units, iv) the branched glycans have a degree of polymerization (DP) of between 2 and 30 glycan units, v) the branched glycans have a 1:1, 1:2, 1:3, 1:4, or 1:5 beta- to alpha-configuration, vi) the branched glycans comprise a mixture of beta and alpha linkages of one or more of (1-2), (1-3), (1-4), (1-6), (2-3), and (2-6); vii) the glycan therapeutic preparation comprises a mixture of branched glycans and unbranched glycans, viii) the glycan therapeutic preparation comprises a mixture of digestible and non-digestible glycans, or ix) any combination of one, two, three, or four, five, six, seven, or eight of i), ii), iii), iv), v), vi), vii), and viii).

In a fifth aspect, the invention relates to methods of treating symptoms of a treatment or therapy, such as, e.g., toxicity symptoms in a human subject. Provided herein is a method of reducing a symptom of a treatment or therapy, in a subject, comprising a) administering a pharmaceutical composition comprising a glycan therapeutic preparation to a subject who has received the treatment or therapy; b) administering the treatment or therapy to a subject who has been treated with a pharmaceutical composition comprising a glycan therapeutic preparation; or c) administering a pharmaceutical composition comprising a glycan therapeutic preparation and administering the treatment or therapy to a subject, thereby reducing a symptom of the treatment or therapy in the subject.

In one embodiment, the treatment or therapy is an anti-cancer treatment or therapy. In one embodiment, the treatment or therapy is a treatment for nutritional imbalance. In one embodiment, the treatment or therapy is a treatment for immune imbalance. In one embodiment, the symptom is a side-effect of the treatment or therapy. In one embodiment, the onset of the symptom is prior to administration of the glycan therapeutic preparation. In one embodiment, the glycan therapeutic preparation is administered after onset of the symptom. In one embodiment, the symptom of the treatment or therapy is unwanted. In one embodiment, the symptom is a gastrointestinal symptom. In one embodiment, the symptom is a digestive abnormality. In one embodiment, the gastrointestinal symptom is one or more of abdominal pain, cramping, nausea, vomiting, upset stomach, gas, bloating, flatulence, diarrhea, constipation, heartburn, mucositis, and weight-gain, weight loss. In one embodiment, the symptom is a non-gastrointestinal symptom. In one embodiment, the non-gastrointestinal symptom is one or more of anxiety, fear, depression, mental fog, dermatitis, chest pain, shortness of breath. In one embodiment, the symptom is concurrent with or the result of an anti-cancer treatment or therapy. In one embodiment, the symptom is concurrent with or the result of a treatment for nutritional imbalance. In one embodiment, the symptom is concurrent with or the result of a treatment for immune imbalance. In one embodiment, the symptom is one or more of radiation injury pain, surgical pain, phantom pain, acute pain, chronic or persistent pain, breakthrough pain, peripheral neuropathy, stomatitis, mucositis, nausea, vomiting, diarrhea, constipation, urinary incontinence, fatigue, anemia, lymphedema, infection, anxiety, fear, depression, fertility defect, and increased risk of developing a second cancer. In one embodiment, the symptom is malnutrition or cachexia. In one embodiment, the symptom is mucositis. In one embodiment, the mucositisis is oral mucositis. In one embodiment, the mucositis is associated with chemotherapy treatment or radiation therapy. In one embodiment, the symptom is dose-limiting for the drug treatment or therapy, thereby preventing the subject from being treated with the maximal efficacious dose of a drug.

Provided herein is a method of reducing toxicity of a drug treatment in a subject in need thereof comprising: a) administering a pharmaceutical composition comprising a glycan therapeutic preparation to a subject who has received the drug treatment; b) administering the drug treatment to a subject who has been treated with a pharmaceutical composition comprising a glycan therapeutic preparation; or c) administering a pharmaceutical composition comprising a glycan therapeutic preparation and administering the drug treatment to a subject, in an effective amount to treat the subject.

In one embodiment, the drug treatment comprises administering an immunomodulatory drug. In one embodiment, the drug treatment comprises administering a metabolism modulatory drug. In one embodiment, the drug treatment comprises administering an anti-cancer drug. In one embodiment, the anti-cancer drug is irinotecan or 5-fluorouracil. In one embodiment, the toxicity is a dose-limiting toxicity, thereby preventing the subject from being treated with the maximal efficacious dose of a drug. In one embodiment, tolerance of the subject to drug treatment is increased to a dose exceeding a sub-efficacious dose. In one embodiment, tolerance of the subject to drug treatment is increased to a dose equal to or exceeding the maximal efficacious dose of a drug in the subject. In one embodiment, the methods further comprise administering a pharmaceutical composition comprising a glycan therapeutic preparation to a subject who has received a first treatment, and optionally, providing a second treatment, e.g., wherein the second treatment comprises administration of the drug or therapy at a higher dosage, at more frequent intervals, at a higher total of individual administrations, providing a higher Cmax, providing a higher trough level, etc., than the prior treatment. In one embodiment, the methods further comprise providing a subsequent treatment to a subject who has received a pharmaceutical composition comprising a glycan therapeutic preparation and received the first treatment, wherein the second treatment comprises administration of the drug or therapy at a higher dosage, at more frequent intervals, at a higher total of individual administrations, providing a higher Cmax, providing a higher trough level, etc., than the prior treatment. In one embodiment, the methods further comprise evaluating one or more of: the suitability of the subject for glycan treatment, the responsiveness of the subject to glycan treatment, and/or the progression of the glycan treatment in the subject, comprising: a) acquiring a value for a parameter related to the level of a biomarker modulated by a glycan therapeutic preparation, and b) responsive to the value, classifying the subject, selecting a treatment for the subject, or administering the treatment to the subject, thereby evaluating the subject. In one embodiment, one or more biomarkers selected from: i) changes in gastrointestinal microbiota, ii) changes in metabolites of the gastric environment, iii) production of organic acids, iv) modulation of the immune system, v) modulation of inflammatory biomarkers, vi) modulation of immunoglobulins vii) increased absorption of minerals in the colon, viii) modulation of lipid metabolism, ix) lowering of cholesterol, x) modulation of host homeostasis. In one embodiment, the modulation is of one or more metabolic pathways listed in Table 19 ((super or sub pathways or level of a metabolite).

Provided herein is a method of treating symptoms associated with gastrointestinal distress, comprising administering to a subject undergoing an anti-cancer therapy a glycan therapeutic composition comprising a mixture of branched glycans in an effective amount to treat one or more symptom associated with gastrointestinal distress.

In one embodiment, the methods further comprise administering an anti-inflammatory agent. In one embodiment, the methods further comprise administering a probiotic microorganism. In one embodiment, a beneficial gut bacterial microbiota is disturbed. In one embodiment, the anti-cancer therapy is radiation or chemotherapy. In one embodiment, the symptom is constipation or diarrhea. In one embodiment, the symptom is gas, heartburn, stomach upset, bloating, flatulence, diarrhea, abdominal pain, cramping, nausea, or vomiting. In one embodiment, administration of the composition results in a decrease in i) diarrhea, ii) a decrease in constipation, iii) a reduction in toxic catabolites. In one embodiment, a reduction or elimination of symptoms persists after treatment of the condition has concluded. In one embodiment, administration of the composition results in an improvement of bowel regularity. In one embodiment, the reduction in the at least one of the one or more symptoms of the gastrointestinal disorder following treatment is about a 10%, 20%, 30%, 40%, 50%, 60%, 70%, 80%, 90%, 95%, or 100% decrease in a subject reported severity of the at least one of the one or more symptoms of the gastrointestinal disorder. In one embodiment, the reduction in at least one of the one or more symptoms of the gastrointestinal disorder persists for at least about a day, a week, a month, 3 months, 6 months, 9 months, or a year after treatment.

For any and all of the foregoing methods, in one embodiment, the glycan therapeutic preparation: i) comprises branched glycans, ii) the branched glycans comprise branched oligosaccharides, iii) the glycan therapeutic preparation has an average degree of branching (DB) of at least 0.01, iv) at least 50% of the glycans in the preparation have a degree of polymerization (DP) of at least 3 and less than 30 glycan units, v) the ratio of alpha- to beta-glycosidic bonds present in the glycans of the preparation overall is between about 1:1 to about 5:1, or vi) any combination of one, two, three, four or five of i), ii), iii), iv) and v).

For any and all of the foregoing methods, in one embodiment, the glycan therapeutic preparation: i) comprises branched glycans, ii) the branched glycans comprise branched oligosaccharides, iii) the branched oligosaccharides comprise glucose, galactose, arabinose, mannose, fructose, xylose, fucose, or rhamnose glycan units, iv) the average degree of branching (DB) of the branched glycans in the glycan therapeutic preparation is between 0.01 and 0.3, v) at least 50% of the glycans in the glycan therapeutic preparation have a degree of polymerization (DP) of at least 3 and less than 30 glycan units, vi) the average DP of the glycan therapeutic preparation is between about DP6 and about DP10, vii) the ratio of alpha- to beta-glycosidic bonds present in the glycans of the glycan therapeutic preparation is between about 1:1 to about 5:1, viii) the glycan therapeutic preparation has a final solubility limit in water of at least about 60 Brix at 23° C., or ix) any combination of one, two, three, or four, five, six, seven, or eight of i), ii), iii), iv), v), vi), vii), and viii).

For any and all of the foregoing methods, in one embodiment, the glycan therapeutic preparation: i) comprises branched glycans, ii) the branched glycans comprise one or more glycan units, iii) the branched glycans comprise at least 1% of branched glycan units, iv) the branched glycans have a degree of polymerization (DP) of between 2 and 30 glycan units, v) the branched glycans have a 1:1, 1:2, 1:3, 1:4, or 1:5 beta- to alpha-configuration, vi) the branched glycans comprise a mixture of beta and alpha linkages of one or more of (1-2), (1-3), (1-4), (1-6), (2-3), and (2-6); vii) the glycan therapeutic preparation comprises a mixture of branched glycans and unbranched glycans, viii) the glycan therapeutic preparation comprises a mixture of digestible and non-digestible glycans, or ix) any combination of one, two, three, or four, five, six, seven, or eight of i), ii), iii), iv), v), vi), vii), and viii).

For any and all of the foregoing aspects, and for any method described herein that includes administering a glycan therapeutic preparation, the glycan therapeutic preparation may comprise one or more homo-glycans selected from xyl100, rha100, ara100, gal100, glu100, fuc100, fru100, and man100. For any method described herein that includes administering a glycan therapeutic preparation, the glycan therapeutic preparation may comprise one or more hetero-glycans selected from ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 and glu90gly10. For any method described herein that includes administering a glycan therapeutic preparation, the glycan therapeutic preparation may comprise one or more hetero-glycans selected from xyl75glu12gal12, xyl33glu33gal33, glu33gal33fuc33, man52glu29gal19, and glu33gal33neu33. For any method described herein that includes administering a glycan therapeutic preparation, the glycan therapeutic preparation may comprise one or more homo or hetero-glycans selected from xyl100, rha100, ara100, gal100, glu100, man100, fuc100, fru100, ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 and glu90gly10, xyl75glu12gal12, xyl33glu33gal33, glu33gal33fuc33, man52glu29gal19, and glu33gal33neu33. For any method described herein that includes administering a glycan therapeutic preparation, the glycan therapeutic preparation may comprise one or more homo or hetero-glycans selected from ara50gal50, glu33gal33fuc33, glu50gal50, gal100, glu100, xyl100, ara100, ara60xyl40, glu80man20, glu60man40, man52glu29gal19, man100. For any method described herein that includes administering a glycan therapeutic preparation, the glycan therapeutic preparation may comprise one or more homo-glycans selected from man100, xyl100, or glu100. For any method described herein that includes administering a glycan therapeutic preparation, the glycan therapeutic preparation may comprise man100. For any method described herein that includes administering a glycan therapeutic preparation, the glycan therapeutic preparation may comprise xyl100. For any method described herein that includes administering a glycan therapeutic preparation, the glycan therapeutic preparation may comprise glu100. For any method described herein that includes administering a glycan therapeutic preparation, the glycan therapeutic preparation may comprise one or more hetero-glycans selected from glu50gal50, glu80man20, glu33gal33fuc33, man52glu29gal19. For any method described herein that includes administering a glycan therapeutic preparation, the glycan therapeutic preparation may comprise comprise glu50gal50. For any method described herein that includes administering a glycan therapeutic preparation, the glycan therapeutic preparation may comprise glu80man20. For any method described herein that includes administering a glycan therapeutic preparation, the glycan therapeutic preparation may comprise glu33gal33fuc33. For any method described herein that includes administering a glycan therapeutic preparation, the glycan therapeutic preparation may comprise man52glu29gal19.

For any and all of the foregoing aspects, and for any method in which beneficial bacteria are modulated the beneficial bacteria include bacteria of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus*, and *Streptococcus*, and/or one or more of the species *Akkermansia municiphilia, minuta, Clostridium coccoides, Clostridium leptum, Clostridium scindens, Dialister invisus, Eubacterium rectal, Eubacterium eligens, Faecalibacterium prausnitzii, Streptococcus salivarius*, and *Streptococcus thermophilus*, and the taxa listed in Tables 1, 3, and 4.

In a sixth aspect, the invention relates to kits for treating cancer. Provided herein is a kit for treating cancer in a human subject, comprising: a package comprising (i) a first pharmaceutical composition comprising a glycan therapeutic preparation, (ii) optionally, a second anti-neoplastic or anti-cancer pharmaceutical composition, and (iii) instructions for using the first and/or the second pharmaceutical compositions for treating cancer in a human patient.

In one embodiment, the glycan therapeutic preparation: i) comprises branched glycans, ii) the branched glycans comprise branched oligosaccharides, iii) the glycan therapeutic preparation has an average degree of branching (DB) of at least 0.01, iv) at least 50% of the glycans in the preparation have a degree of polymerization (DP) of at least 3 and less than 30 glycan units, v) the ratio of alpha- to beta-glycosidic bonds present in the glycans of the preparation overall is between about 1:1 to about 5:1, or vi) any combination of one, two, three, four or five of i), ii), iii), iv) and v).

In one embodiment, the glycan therapeutic preparation: i) comprises branched glycans, ii) the branched glycans comprise branched oligosaccharides, iii) the branched oligosaccharides comprise glucose, galactose, arabinose, mannose, fructose, xylose, fucose, or rhamnose glycan units, iv) the average degree of branching (DB) of the branched glycans in the glycan therapeutic preparation is between 0.01 and 0.3, v) at least 50% of the glycans in the glycan therapeutic preparation have a degree of polymerization (DP) of at least 3 and less than 30 glycan units, vi) the average DP of the glycan therapeutic preparation is between about DP6 and about DP10, vii) the ratio of alpha- to beta-glycosidic bonds present in the glycans of the glycan therapeutic preparation is between about 1:1 to about 5:1, viii) the glycan therapeutic preparation has a final solubility limit in water of at least about 60 Brix at 23° C., or ix) any combination of one, two, three, or four, five, six, seven, or eight of i), ii), iii), iv), v), vi), vii), and viii).

In one embodiment, the glycan therapeutic preparation: i) comprises branched glycans, ii) the branched glycans comprise one or more glycan units, iii) the branched glycans comprise at least 1% of branched glycan units, iv) the branched glycans have a degree of polymerization (DP) of between 2 and 30 glycan units, v) the branched glycans have a 1:1, 1:2, 1:3, 1:4, or 1:5 beta- to alpha-configuration, vi) the branched glycans comprise a mixture of beta and alpha linkages of one or more of (1-2), (1-3), (1-4), (1-6), (2-3), and (2-6); vii) the glycan therapeutic preparation comprises a mixture of branched glycans and unbranched glycans, viii) the glycan therapeutic preparation comprises a mixture of digestible and non-digestible glycans, or ix) any combination of one, two, three, or four, five, six, seven, or eight of i), ii), iii), iv), v), vi), vii), and viii).

In a seventh aspect, the invention relates to dosage forms for the treatment of a disease, disorder or condition. Provided herein is a unit dosage form effective to treat a disease, disorder, or pathological condition comprising a glycan therapeutic preparation formulated for oral, enteral, rectal, intravenous, or intratumoral administration.

In one embodiment, the disease, disorder, or pathological condition is cancer. In one embodiment, the disease, disorder, or pathological condition is a nutritional imbalance. In one embodiment, the disease, disorder, or pathological condition is an immune imbalance. In one embodiment, the unit dosage form is formulated as a pharmaceutical composition. In one embodiment, the unit dosage form is formulated as a medical food. In one embodiment, the unit dosage form is formulated as a dietary supplement. In one embodiment, the dosage form is formulated for oral consumption by a subject. In one embodiment, the dosage form is formulated to dissolve in an aqueous solution and is orally administered as a beverage, syrup, solution, or suspension. In one embodiment, the dosage form is formulated for enteral administration. In one embodiment, the administration is nasogastric, nasojejunal, oral gastric, or oral jejuna. In one embodiment, the dosage form is formulated for rectal administration. In one embodiment, the administration is enema, suppository, or colonoscopy. In one embodiment, the dosage form is formulated as a delayed release or time controlled system. In one embodiment, the dosage form is formulated to release the therapeutic glycan preparation in a specific region of the GI tract. In one embodiment, the specific region of the GI tract comprises the stomach, small intestine, large intestine, or colon. In one embodiment, the composition modulates the abundance of a bacterial genus present in the GI tract. In one embodiment, the bacterial taxa is bifidobacteria, bacteroides, akkamensia. In one embodiment, the bacterial taxa is Bifidobacteria, Bifidobacteriales, Bacteroidales, Clostridiales, Parabacteroides, and *Akkermansia*. In one embodiment, the bacterial taxa is Blautia, *Bifidobacterium, Roseburia, Coprococcus, Lachnospiraceae, Faecalibacterium*, Parabacteroides, and Ruminococcaceae. In one embodiment, the composition modulates the abundance of a bacterial genus present in one or both of the small intestine or large intestine. In one embodiment, the composition modulates the abundance of a bacterial genus predominant in the small intestine selected from the group of genus *Achromobacter, Agrobacterium, Blautia, Burkholderia, Coprococcus, Cryocola, Enterococcus, Eubacterium, Holdemania, Lactococcus, Mycobacterium, Pseudoramibacter, Ralstonia, Sphingomonas, Streptococcus*, and *Turicibacter*. In one embodiment, the composition modulates the abundance of a bacterial genus predominant in the large intestine selected from the group of genus *Anaerotruncus, Akkermansia, Bacteroides, Bilophila, Butyricimonas, Odoribacter, Parabacteroides, Phascolarctobacterium, Prevotella*, and *Ruminococcus*.

In one embodiment, the glycan therapeutic preparation: i) comprises branched glycans, ii) the branched glycans comprise branched oligosaccharides, iii) the glycan therapeutic preparation has an average degree of branching (DB) of at least 0.01, iv) at least 50% of the glycans in the preparation have a degree of polymerization (DP) of at least 3 and less than 30 glycan units, v) the ratio of alpha- to beta-glycosidic bonds present in the glycans of the preparation overall is between about 1:1 to about 5:1, or vi) any combination of one, two, three, four or five of i), ii), iii), iv) and v).

In one embodiment, the glycan therapeutic preparation: i) comprises branched glycans, ii) the branched glycans comprise branched oligosaccharides, iii) the branched oligosaccharides comprise glucose, galactose, arabinose, mannose, fructose, xylose, fucose, or rhamnose glycan units, iv) the average degree of branching (DB) of the branched glycans in the glycan therapeutic preparation is between 0.01 and 0.3, v) at least 50% of the glycans in the glycan therapeutic preparation have a degree of polymerization (DP) of at least 3 and less than 30 glycan units, vi) the average DP of the glycan therapeutic preparation is between about DP6 and about DP10, vii) the ratio of alpha- to beta-glycosidic bonds present in the glycans of the glycan therapeutic preparation is between about 1:1 to about 5:1, viii) the glycan therapeutic preparation has a final solubility limit in water of at least about 60 Brix at 23° C., or ix) any combination of one, two, three, or four, five, six, seven, or eight of i), ii), iii), iv), v), vi), vii), and viii).

In one embodiment, the glycan therapeutic preparation: i) comprises branched glycans, ii) the branched glycans comprise one or more glycan units, iii) the branched glycans comprise at least 1% of branched glycan units, iv) the branched glycans have a degree of polymerization (DP) of between 2 and 30 glycan units, v) the branched glycans have a 1:1, 1:2, 1:3, 1:4, or 1:5 beta- to alpha-configuration, vi) the branched glycans comprise a mixture of beta and alpha linkages of one or more of (1-2), (1-3), (1-4), (1-6), (2-3), and (2-6); vii) the glycan therapeutic preparation comprises a mixture of branched glycans and unbranched glycans, viii) the glycan therapeutic preparation comprises a mixture of digestible and non-digestible glycans, or ix) any combination of one, two, three, or four, five, six, seven, or eight of i), ii), iii), iv), v), vi), vii), and viii).

In an eighths aspect, the invention relates to a composition comprising glycan therapeutic preparations. Provided herein is a composition comprising: a) a digestible glycan therapeutic preparation and a substantially non-digestible saccharide or dietary fiber, b) a substantially non-digestible glycan therapeutic preparation and a digestible saccharide or dietary fiber, c) a substantially non-digestible glycan therapeutic preparation and a substantially non-digestible saccharide or dietary fiber, or d) a digestible glycan therapeutic preparation and a digestible saccharide or dietary fiber, and any one of (a), (b), (c), (d) optionally comprising a probiotic bacterium.

In one embodiment, the composition is formulated as a pharmaceutical composition. In one embodiment, the composition further comprises a pharmaceutically acceptable excipient or carrier. In one embodiment, the composition is formulated as a medical food. In one embodiment, the composition is labeled a medical food. In one embodiment, the composition is formulated as a dietary supplement. In one embodiment, the composition is labeled a dietary supplement. In one embodiment, the composition further comprises an essential nutrient. In one embodiment, the composition is effective to treat an immune imbalance. In one embodiment, the composition is effective to treat a nutritional imbalance. In one embodiment, the composition is effective to treat a cancer. In one embodiment, the glycan therapeutic preparation is selectively digested by gut microbiota constituents. In one embodiment, selective digestion results in modulation of the composition and/or activity of the gut microbiota. In one embodiment, the growth of one or more of *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacilli, Christensenella*

*minuta*, and *Christensenellaceae* is selectively stimulated. In one embodiment, the glycan therapeutic preparation is substantially non-digestible by humans in the absence of specific bacteria in the gut, wherein the specific bacteria are capable of utilizing the glycan therapeutic as a carbon source. In one embodiment, the glycan therapeutic is resistant to gastric acidity. In one embodiment, the glycan therapeutic is resistant to hydrolysis by a mammalian enzyme. In one embodiment, the mammalian enzyme is human amylase. In one embodiment, the glycan therapeutic is resistant to gastrointestinal absorption.

Provided herein is a composition for use in any of the methods described herein.

Provided herein is a dosage form comprising the composition.

For any and all of the foregoing, in one embodiment, the glycan therapeutic preparation: i) comprises branched glycans, ii) the branched glycans comprise branched oligosaccharides, iii) the glycan therapeutic preparation has an average degree of branching (DB) of at least 0.01, iv) at least 50% of the glycans in the preparation have a degree of polymerization (DP) of at least 3 and less than 30 glycan units, v) the ratio of alpha- to beta-glycosidic bonds present in the glycans of the preparation overall is between about 1:1 to about 5:1, or vi) any combination of one, two, three, four or five of i), ii), iii), iv) and v).

For any and all of the foregoing, in one embodiment, the glycan therapeutic preparation: i) comprises branched glycans, ii) the branched glycans comprise branched oligosaccharides, iii) the branched oligosaccharides comprise glucose, galactose, arabinose, mannose, fructose, xylose, fucose, or rhamnose glycan units, iv) the average degree of branching (DB) of the branched glycans in the glycan therapeutic preparation is between 0.01 and 0.3, v) at least 50% of the glycans in the glycan therapeutic preparation have a degree of polymerization (DP) of at least 3 and less than 30 glycan units, vi) the average DP of the glycan therapeutic preparation is between about DP6 and about DP10, vii) the ratio of alpha- to beta-glycosidic bonds present in the glycans of the glycan therapeutic preparation is between about 1:1 to about 5:1, viii) the glycan therapeutic preparation has a final solubility limit in water of at least about 60 Brix at 23° C., or ix) any combination of one, two, three, or four, five, six, seven, or eight of i), ii), iii), iv), v), vi), vii), and viii).

For any and all of the foregoing, in one embodiment, the glycan therapeutic preparation: i) comprises branched glycans, ii) the branched glycans comprise one or more glycan units, iii) the branched glycans comprise at least 1% of branched glycan units, iv) the branched glycans have a degree of polymerization (DP) of between 2 and 30 glycan units, v) the branched glycans have a 1:1, 1:2, 1:3, 1:4, or 1:5 beta- to alpha-configuration, vi) the branched glycans comprise a mixture of beta and alpha linkages of one or more of (1-2), (1-3), (1-4), (1-6), (2-3), and (2-6); vii) the glycan therapeutic preparation comprises a mixture of branched glycans and unbranched glycans, viii) the glycan therapeutic preparation comprises a mixture of digestible and non-digestible glycans, or ix) any combination of one, two, three, or four, five, six, seven, or eight of i), ii), iii), iv), v), vi), vii), and viii).

For any and all of the foregoing aspects, and for any pharmaceutical composition, medical food, dietary supplement, dosage form, or kit comprising a glycan therapeutic preparation described herein, the glycan therapeutic preparation may comprise one or more homo-glycans selected from xyl100, rha100, ara100, gal100, glu100, fuc100, fru100, and man100. For any pharmaceutical composition, medical food, dietary supplement, dosage form, or kit comprising a glycan therapeutic preparation described herein, the glycan therapeutic preparation may comprise one or more hetero-glycans selected from ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 and glu90gly10. For any pharmaceutical composition, medical food, dietary supplement, dosage form, or kit comprising a glycan therapeutic preparation described herein, the glycan therapeutic preparation may comprise one or more hetero-glycans selected from xyl75glu12gal12, xyl33glu33gal33, glu33gal33fuc33, man52glu29gal19, and glu33gal33neu33. For any pharmaceutical composition, medical food, dietary supplement, dosage form, or kit comprising a glycan therapeutic preparation described herein, the glycan therapeutic preparation may comprise one or more homo or hetero-glycans selected from xyl100, rha100, ara100, gal100, glu100, man100, fuc100, fru100, ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 and glu90gly10, xyl75glu12gal12, xyl33glu33gal33, glu33gal33fuc33, man52glu29gal19, and glu33gal33neu33. For any pharmaceutical composition, medical food, dietary supplement, dosage form, or kit comprising a glycan therapeutic preparation described herein, the glycan therapeutic preparation may comprise one or more homo or hetero-glycans selected from ara50gal50, glu33gal33fuc33, glu50gal50, gal100, glu100, xyl100, ara100, ara60xyl40, glu80man20, glu60man40, man52glu29gal19, man100. For any pharmaceutical composition, medical food, dietary supplement, dosage form, or kit comprising a glycan therapeutic preparation described herein, the glycan therapeutic preparation may comprise one or more homo-glycans selected from man100, xyl100, or glu100. For any pharmaceutical composition, medical food, dietary supplement, dosage form, or kit comprising a glycan therapeutic preparation described herein, the glycan therapeutic preparation may comprise man100. For any pharmaceutical composition, medical food, dietary supplement, dosage form, or kit comprising a glycan therapeutic preparation described herein, the glycan therapeutic preparation may comprise xyl100. For any pharmaceutical composition, medical food, dietary supplement, dosage form, or kit comprising a glycan therapeutic preparation described herein, the glycan therapeutic preparation may comprise glu100. For any pharmaceutical composition, medical food, dietary supplement, dosage form, or kit comprising a glycan therapeutic preparation described herein, the glycan therapeutic preparation may comprise one or more hetero-glycans selected from glu50gal50, glu80man20, glu33gal33fuc33, man52glu29gal19. For any pharmaceutical composition, medical food, dietary supplement, dosage form, or kit comprising a glycan therapeutic preparation described herein, the glycan therapeutic preparation may comprise glu50gal50. For any pharmaceutical composition, medical food, dietary supplement, dosage form, or kit comprising a glycan therapeutic preparation described herein, the glycan therapeutic preparation may comprise glu80man20. For any pharmaceutical composition, medical food, dietary supplement, dosage form, or kit comprising a glycan therapeutic preparation described herein, the glycan therapeutic preparation may comprise glu33gal33fuc33. For any pharmaceutical composition, medical food, dietary supplement, dosage form, or kit comprising a glycan therapeutic preparation described herein, the glycan therapeutic preparation may comprise man52glu29gal19.

For any and all of the foregoing aspects, and for any pharmaceutical composition, medical food, dietary supplement, dosage form, or kit comprising a probiotic bacteria, and any method that includes administering a probiotic bacteria, the a probiotic bacteria may comprise bacteria of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus,* and *Streptococcus,* and/or one or more of the species *Akkermansia municiphilia, minuta, Clostridium coccoides, Clostridium leptum, Clostridium scindens, Dialister invisus, Eubacterium rectal, Eubacterium eligens, Faecalibacterium prausnitzii, Streptococcus salivarius,* and *Streptococcus thermophilus,* and the taxa listed in Tables 1, 3, and 4.

For any and all of the foregoing aspects, and for any pharmaceutical composition, medical food, dietary supplement, dosage form, or kit comprising an anti-cancer agent or drug, and any method that includes administering a cancer agent, the cancer agent may comprise, e.g., checkpoint inhibitors (such as, e.g., anti-PD-1, anti-PD-L1, anti-CTLA4, anti-TIM-3, anti-LAG-3); vaccines (such as, e.g., autologous cancer vaccines, allogeneic cancer vaccines, neoantigen cancer vaccines, shared antigen cancer vaccines (e.g. NY-ESO-1)); targeted kinase inhibitors (such as, e.g., Imatinib mesylate, Ibrutinib, Neratinib, Palpociclib, Erlotinib, Lapatinib); antibodies (such as, e.g., Bevacizumab, Trastuzumab, Rituximab, Cetuximab); chemotherapeutics (such as, e.g., irinotecan, 5-flurouracil, lenalidomide, capecitabine, docetaxel), antibody-drug conjugates (e.g. ado-trastuzumab emtansine), and any other anti-cancer drug mentioned elsewhere herein. In one embodiment, the anti-cancer agent is PD-L1. In one embodiment, the anti-cancer is 5-FU and/or irinotecan.

For any and all of the foregoing aspects, and for any pharmaceutical composition, medical food, dietary supplement, dosage form, or kit comprising an immunomodulatory agent or drug (e.g., pro- or anti-inflammatory), and any method that includes administering an immunomodulatory agent (e.g., pro- or anti-inflammatory), the immunomodulatory agent may comprise, e.g., pro-inflammatory agents (e.g. pro-inflammatory cytokines), anti-inflammatory agents (e.g. anti-inflammatory cytokines, NSAIDs, anti-allergy agents), steroids, hormones, interleukins, vaccines/antigens, anti-microbial agents (e.g. anti-virals) and anti-neoplastic agents.

For any and all of the foregoing aspects, and for any pharmaceutical composition, medical food, dietary supplement, dosage form, or kit comprising a metabolism modulating agent or drug, and any method that includes administering an metabolism modulating agent, the metabolism modulating agent may comprise, e.g., insulin, metformin, lorcaserin, somatropin, miglitol, sitagliptin, simvastatin, progestagens, corticosteroids, hormones, and interleukins.

In any and all of the foregoing aspects, in some embodiments, the invention features compounds and compositions (e.g., pharmaceutical compositions, medical foods, or dietary supplements) for use in, e.g., treating an immune imbalance in a subject; reducing an infection and/or an inflammation in a subject having an immune imbalance; modulating the composition and/or metabolic activity of the intestinal bacterial community of a subject having an immune imbalance; treating a dysbiosis in a subject having an immune imbalance; treating a nutritional imbalance in a subject; modulating the composition and/or metabolic activity of the intestinal bacterial community of a subject having a nutritional imbalance; treating a dysbiosis in a subject having a nutritional imbalance; treating cancer in a subject; modulating the composition and/or metabolic activity of the intestinal bacterial community of a subject having cancer; treating a dysbiosis in a subject having cancer; reducing an infection and/or an inflammation in a subject having cancer; inducing apoptosis of a cancer or a precancerous cell in a subject having cancer; reducing the risk of cancer in a subject; modulating the composition of the intestinal bacterial community of a subject having cancer; modulating the metabolic activity of the intestinal bacterial community of a subject having cancer; reducing a symptom of a treatment or therapy in a subject; reducing toxicity of a drug treatment or therapy in a subject; treating symptoms associated with gastrointestinal distress; modulating the function and/or activity of a pathway of a subject having an immune imbalance; modulating the function and/or activity of a pathway of a subject having a nutritional imbalance; and/or modulating the function and/or activity of a pathway of a subject having cancer.

BRIEF DESCRIPTION OF THE FIGURES

FIG. 8A: Bacterial phyla, percent (%) relative abundance in 1% fecal slurry exposed to no added carbon, xyl100, man52glu29gal19, glu100, and FOS; FIG. 8B: Bifidobacteriales % relative abundance in 1% fecal slurry exposed to no added carbon, xyl100, man52glu29gal19, glu100, and FOS; FIG. 8C: Bifidobacteria % relative abundance in 1% fecal slurry exposed to no added carbon, xyl100, man52glu29gal19, glu100, and FOS; FIG. 8D: Bacteroidales % relative abundance in 1% fecal slurry exposed to no added carbon, xyl100, man52glu29gal19, glu100, and FOS; FIG. 8E: Clostridiales % relative abundance in 1% fecal slurry exposed to no added carbon, xyl100, man52glu29gal19, glu100, and FOS.

DETAILED DESCRIPTION OF THE INVENTION

Figure 1:
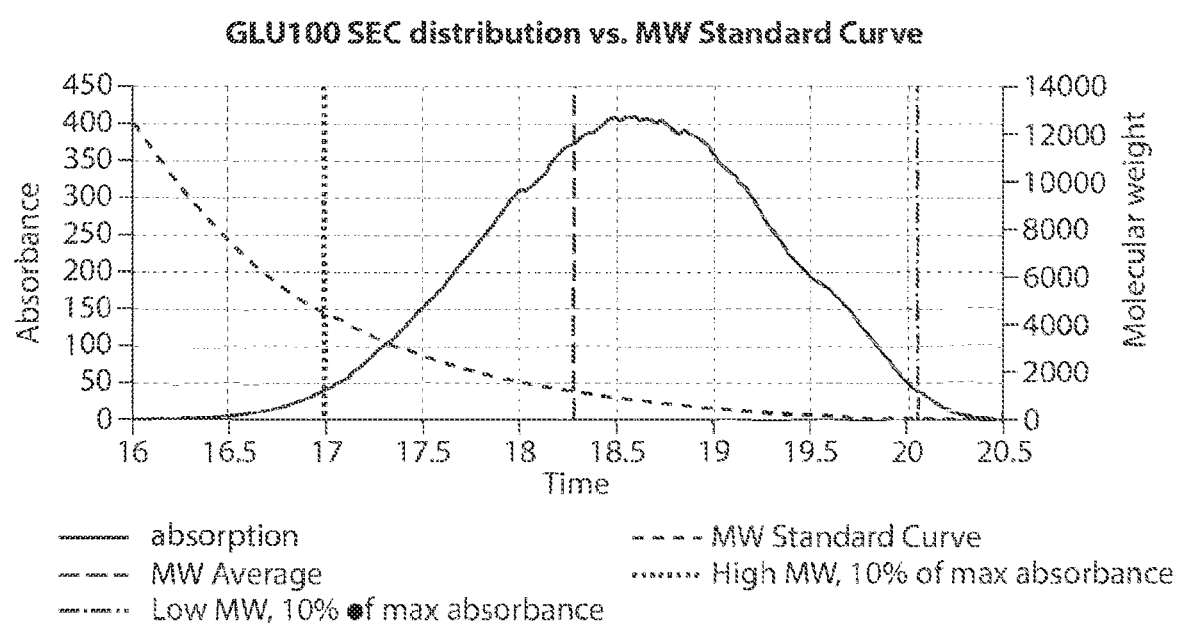
FIG. 1: A representative SEC curve between 16 and 20.5 minutes of a glu100 sample showing the average MW and the MW at 10% of maximum absorption on both the leading and trailing edges of the curve.

Described herein are preparations of glycan therapeutics and pharmaceutical compositions, medical foods and dietary supplements thereof, and related methods, which have been found to be effective to treat a number of diseases, disorders or pathological conditions.

Definitions

As used herein, the term "abundance" as it relates to a microbial taxa refers to the presence of one microbial taxa as compared to another microbial taxa in a defined microbial niche, such as the GI tract, or in the entire host organism (e.g. a human or a laboratory animal model of disease).

"Acquire" or "acquiring" as the terms are used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing a synthetic or analytical method or protocol) to obtain the value or physical entity. "Indirectly acquiring" refers to receiving the value or physical entity from another party or source (e.g., a third party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., an NMR spectrometer to obtain an NMR spectrum.

As used herein, "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments so long as they exhibit the desired activity.

As used herein, the term "cancer" refers to a cell (or cells) that has an aberrant capacity for autonomous growth or replication and an abnormal state or condition (e.g. of a tissue or organ) characterized by proliferative cell growth. "Cancer" as used herein includes any solid or liquid, benign or malignant, non-invasive or invasive cancer or tumor, including hyperplasias, neoplasms, carcinoma, sarcoma, or a hematopoietic neoplastic disorder (e.g., a leukemia) and pre-cancerous or premalignant lesions.

As used herein, "colonization" of a host organism refers to the non-transitory residence of a bacterium or other microbial organism in a niche.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In other embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

"Diversity of a microbial community" or "microbial diversity" as used herein refers to the diversity found in the microbiota of a within a given niche or host subject. Diversity can relate to the number of distinct microbial taxa and/or richness of the microbial taxa within the niche or host and can be expressed, e.g. using the Shannon Diversity index (Shannon entropy), alpha-beta diversity, total number of observed OTUs, or Chao1 index, as described herein. In some embodiments, a microbiome regulator described herein modulates diversity within a microbial community, which may be expressed using Shannon entropy as a measure. For example, the more unequal the abundances of the bacterial taxa, the larger the weighted geometric mean of the $p_i$ values in Shannon's formula, and the smaller the corresponding Shannon entropy. If practically all abundance is concentrated to one taxa, and the other taxa are very rare (even if there are many of them), Shannon entropy approaches zero. When there is only one taxa Shannon entropy exactly equals zero.

As used herein, a "dosage regimen", "dosing regimen", or "treatment regimen" is a modality of drug administration that achieves a therapeutic objective. A dosage regimen includes definition of one, two, three, or four of: a route of administration, a unit dose, a frequency of dosage, or a length of treatment.

As used herein, a "dysbiosis" refers to the state of the microbiota under conditions of host disease, predisposition to host disease, or other unwanted condition or symptom of the host. In an embodiment, dysbiosis refers to the state of the microbiota under conditions of disease. Dysbiosis can be contrasted with eubiosis, which refers to the state of the microbiota under healthy conditions of the host. The state of the microbiota may include the characteristics relating to either the structure or function of the microbiota. In an embodiment, a dysbiosis includes an imbalance in the state of the microbiota, wherein the normal diversity or relative abundance of a microbial taxa is affected, e.g., relative to a second bacterial taxa or relative to the abundance of said taxa under conditions of health. In an embodiment, a dysbiosis comprises an imbalance in the function of the microbiota, e.g., a change in level of gene expression, level of a gene product, or metabolic output (e.g., an immune function such as immune surveillance it the inflammation response). In some embodiments, a dysbiosis is an an undesired, e.g., unhealthy, state associated with unwanted symptoms in the host and that no longer promotes health. A "dysbiosis of the gastrointestinal microbiota" refers to an imbalanced state of the microbiota of the GI tract (e.g., in the stomach, small intestine, or large intestine).

As used herein, "ecological niche" or simply "niche" refers to the ecological space in which an organism or group of organisms occupies (such as the GI tract or one or more subsection of the GI-tract, such as, e.g., the stomach, the large and small intestine, the rectum, etc.). In some embodiments, niche specifically refers to a space that microorganisms occupy. Niche may describe how an organism or population of organisms responds to the distribution of resources, physical parameters (e.g., host tissue space) and competitors (e.g., by growing when resources are abundant, and when predators, parasites and pathogens are scarce) and how it in turn alters those same factors (e.g., limiting access to resources by other organisms, acting as a food source for predators and a consumer of prey).

An "effective amount" and "therapeutically effective amount" as used herein refers to an amount of a pharmaceutical composition or a drug agent that is sufficient to provide a desired effect. In some embodiments, a physician or other health professional decides the appropriate amount and dosage regimen. An effective amount also refers to an amount of a pharmaceutical composition or a drug agent that prevents the development or relapse of a medical condition.

As used herein, a "glycan therapeutic preparation" (also referred to as a "preparation of glycan therapeutics", "glycan preparation" or "glycan therapeutic") is a preparation comprising glycans (sometimes referred to as glycan species) that exhibits a therapeutic effect. A glycan therapeutic comprises a synthetic mixture of a plurality of mono-, di-, oligomeric and/or polymeric glycan species (e.g. oligo- and/or polysaccharides, referred to as "oligosaccharides"), wherein the oligomeric and/or polymeric glycan species comprise glycan units that are linked by glycosidic bonds. In some embodiments, a glycan therapeutic may be formulated into a pharmaceutical composition, a medical food or dietary supplement for human use. In some embodiments, a glycan therapeutic may be formulated in any suitable dosage form including a kit. In some embodiments, preparations of glycan therapeutics do not contain one or more naturally occurring oligo- or polysaccharide, including: glucooligosaccharide, mannanoligosaccharide, inulin, lychnose, maltotretraose, nigerotetraose, nystose, sesemose, stachyose, isomaltotriose, nigerotriose, maltotriose, melezitose, maltotriulose, raffinose, kestose, fructooligosaccharide, 2'-fucosyllactose, galactooligosaccharide, glycosyl, idraparinux, isomaltooligosaccharide, maltodextrin, xylooligosaccharide, agar, agarose, alginic acid, alguronic acid, alpha glucan, amylopectin, amylose, arabioxylan, beta-glucan, callose, capsulan, carrageenan, cellodextrin, cellulin, cellulose, chitin, chitin nanofibril, chitin-glucan complex, chitosan, chrysolaminarin, curdlan, cyclodextrin, alpha-cyl-codextrin, dextran, dextrin, dialdehyde starch, ficoll, fructan, fucoidan, galactoglucomannan, galactomannan, galactosamineogalactan, gellan gum, glucan, glucomannan, glucoronoxyland, glycocalyx, glycogen, hemicellulose, hypromellose, icodextrin, kefiran, laminarin, lentinan, levan polysaccharide, lichenin, mannan, mucilage, natural gum, paramylon, pectic acid, pectin, pentastarch, phytoglycogen, pleuran, poligeenan, polydextrose, porphyran, pullulan, schizophyllan, sepharose, sinistrin, sizofiran, sugammadex, welan gum, xantham gum, xylan, xyloglucan, zymosan, and the like. In some embodiments, a glycan exists as a salt, e.g., a pharmaceutically acceptable salt.

A "glycan unit" as used herein refers to the individual unit of a glycan species disclosed herein, e.g., the building blocks from which the glycan species is made. In an embodiment, a glycan unit is a monomer. In an embodiment, a glycan unit is a dimer. In an embodiment a glycan unit is a monosaccharide. In an embodiment, a glycan unit is a disaccharide. In some embodiments, the glycan unit is a carbohydrate and may be selected from a sugar alcohol, a short-chain fatty acid, a sugar acid, an imino sugar, a deoxy sugar, and an amino sugar. In some embodiments, the glycan unit is erythrose, threose, erythrulose, arabinose, lyxose, ribose, xylose, ribulose, xylulose, allose, altrose, galactose, glucose, gulose, idose, mannose, talose, fructose, psicose, sorbose, tagatose, fucose, fuculose, rhamnose, mannoheptulose, sedoheptulose, and the like. In some embodiments, the glycan unit is glucose, galactose, arabinose, mannose, fructose, xylose, fucose, or rhamnose. In embodiments, a glycan comprises distinct glycan units, e.g., a first and a second monosaccharide, or a first and a second disaccharide, or a monosaccharide and a disaccharide. In embodiments, a glycan comprises distinct glycan units, e.g., a first, a second, a third, a fourth, and/or a fifth distinct glycan unit.

As used herein, an "isolated" or "purified" glycan therapeutic preparation (also sometimes referred to as "polished") is substantially pure and free of contaminants, e.g. pathogens or otherwise unwanted biological material, or toxic or otherwise unwanted organic or inorganic compounds. In some embodiments, pure or isolated compounds, compositions or preparations may contain traces of solvents and/or salts (such as less than 10%, 9%, 8%, 7%, 6%, 5%, 4%, 3%, 2%, 1%, less than 0.5% or 0.1% by w/w, w/v, v/v or molar %). Purified compounds are or preparations contain at least about 60% (by w/w, w/v, v/v or molar %), at least about 75%, at least about 90%, at least about 95%, at least about 97%, at least about 98%, or at least about 99% by w/w, w/v, v/v or molar % the compound(s) of interest. For example, a purified (substantially pure) or isolated preparation of glycan therapeutics is one that is at least 80%, 85%, 90%, 91%, 92%, 93%, 94%, 95%, 98%, 99%, 99.5%, 99.8%, 99.9% or 100% of the glycan therapeutic by w/w, w/v, v/v or molar % (i.e. not including any solvent, such as e.g. water, in which the glycan therapeutic preparation may be dissolved) and separated from the components that accompany it, e.g. during manufacture, extraction/purification and/or processing (e.g. such that the glycan therapeutic is substantially free from undesired compounds). Purity may be measured by any appropriate standard method, for example, by column chromatography (e.g., size-exclusion chromatography (SEC)), thin layer chromatography (TLC), gas chromatography (GC), high-performance liquid chromatography (HPLC) or nuclear magnatic resonance (NMR) spectroscopy. Purified or purity may also define a degree of sterility that is safe for administration to a human subject, e.g., lacking viable infectious or toxic agents.

As used herein, "microbiome" refers to the genetic content of the communities of microbes that live in and on a subject (e.g. a human subject), both sustainably and transiently, including eukaryotes, archaea, bacteria, and viruses (including bacterial viruses (e.g., phage)), wherein "genetic content" includes genomic DNA, RNA such as ribosomal RNA and messenger RNA, the epigenome, plasmids, and all other types of genetic information. In some embodiments, microbiome specifically refers to genetic content of the communities of microorganisms in a niche.

"Microbiota" as used herein refers to the community of microorganisms that occur (sustainably or transiently) in and on a subject (e.g. a human subject), including eukaryotes, archaea, bacteria, and viruses (including bacterial viruses, e.g. phage). In some embodiments, microbiota specifically refers to the microbial community in a niche.

"Modulate the microbiota" or "modulating the microbiota" as used herein refers to changing the state of the microbiota. Changing the state of the microbiota may include changing the structure and/or function of the microbiota. A change in the structure of the microbiota is, e.g., a change in the relative composition of a taxa, e.g., in one or more region of the GI tract such as the cecum, ascending colon, transverse colon, descending colon, sigmoid colon, and/or rectum. In an embodiment, a change in the structure of the microbiota comprises a change in the abundance of a taxa, e.g., relative to another taxa or relative to what would be observed in the absence of the modulation. Modulation of the microbiota may also, or in addition, include a change in a function of the microbiota, such as a change in microbiota gene expression, level of a gene product (e.g., RNA or protein), or metabolic output of the microbiota. Functions of the microbiota may also include host pathogen protection, host nutrition, host metabolism and host immune modulation. Modulation of the structure or function of the microbiota may additionally induce a change in one or more functional pathway of the host (e.g., a change in gene expression, level of a gene product, and/or metabolic output of a host cell or host process) as a result of a change in the microbiota or its function.

As used herein, the term "oligosaccharide" refers to a molecule consisting of multiple (i.e., two or more) individual glycan units linked covalently. Each glycan unit may be linked through a glycosidic bond (e.g., a 1->2 glycosidic bond, a 1->3 glycosidic bond, a 1->4 glycosidic bond, a 1->5 glycosidic bond or a 1->6 glycosidic bond) present in either the alpha or beta configuration. As used herein, the term "pathogenic" (e.g. "pathogenic bacteria") refers to a substance, microorganism or condition that has the capability to cause a disease. In certain contexts, pathogens also include microbes (e.g. bacteria) that are associated with a disease or condition but for which a causative relationship (e.g., a direct causative relationship) has not been established or has yet to be established.

As used herein, a "pharmaceutical composition" or "pharmaceutical preparation" is a composition or preparation having pharmacological activity or other direct effect in the mitigation, treatment, or prevention of disease, and/or a finished dosage form or formulation thereof and is for human use. A pharmaceutical composition or pharmaceutical preparation is typically produced under good manufacturing practices (GMP) conditions. Pharmaceutical compositions or preparations may be sterile or non-sterile. If non-sterile, such pharmaceutical compositions meet the microbiological specifications and criteria for non-sterile pharmaceutical products as described in the U.S. Pharmacopeia (USP) or European Pharmacopoeia (EP). Pharmaceutical compositions may further comprise or may be co-administered with additional active agents, such as, e.g. additional therapeutic agents. Pharmaceutical compositions may also comprise pharmaceutically acceptable excipients, solvents, carriers, fillers, or any combination thereof.

The term "phenotype" refers to a set of observable characteristics of an individual entity. For example, an individual subject may have a phenotype of "healthy" or "diseased." A phenotype may describe the state of an entity, wherein all entities within a phenotype share the same set of characteristics that describe the phenotype. The phenotype of an individual results in part, or in whole, from the interaction of the entities genome and/or microbiome with the environment. As used herein, the term "polysaccharide" refers to a polymeric molecule consisting of multiple individual glycan units linked covalently. In some embodiments, a polysaccharide comprises at least 10 or more glycan units (e.g., at least 10, at least 15, at least 20, at least 25, or at least 50, at least 100, at least 250, at least 500, or at least 1000 glycan units). Each glycan unit may be linked through a glycosidic bond (e.g., a 1->2 glycosidic bond, a 1->3 glycosidic bond, a 1->4 glycosidic bond, a 1->5 glycosidic bond and a 1->6 glycosidic bond) present in either the alpha or beta configuration. In some embodiments, a polysaccharide is a homogenous polymer comprising identical repeating units. In other embodiments, a polysaccharide is a heterogeneous polymer comprised of varied repeating units. Polysaccharides may further be characterized by a degree of branching (DB, branching points per residue) or a degree of polymerization (DP). As used herein, the term "subject" or "patient" generally refers to any human subject. The term does not denote a particular age or gender. Subjects may include pregnant women. Subjects may include a newborn (a preterm newborn, a full term newborn), an infant up to one year of age, young children (e.g., 1 yr to 12 yrs), teenagers, (e.g., 13-19 yrs), adults (e.g., 20-64 yrs), and elderly adults (65 yrs and older). A subject does not include an agricultural animal, e.g., farm animals or livestock, e.g., cattle, horses, sheep, swine, chickens, etc. In general, a subject comprises a host and its corresponding microbiota.

A "substantial decrease" as used herein is a decrease of 5%, 10%, 20%, 30%, 40%, 50%, 60%, 70%, 80%, 90%, 95%, 97%, 98%, 99%, 99.9%, or 100%.

A "substantial increase" as used herein is an increase of 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, or more than 1000%.

"Synthetic" as used herein refers to a man-made compound or preparation, such as a glycan therapeutic preparation, that is not naturally occurring. In one embodiment, the polymeric catalyst described herein is used to synthesize the glycans of the preparation under suitable reaction conditions, e.g. by a polymerization reaction that creates oligomers and polymers from individual glycan units that are added to the reaction. In some embodiments, the polymeric catalyst acts as a hydrolysis agent and can break glycosidic bonds. In other embodiments, the polymer catalyst can form glycosidic bonds. Synthetic glycan therapeutic preparations may also include glycan therapeutics that are not isolated from a natural oligo- or polysaccharide source. It is to be understood that while the glycan therapeutic preparation is not isolated from a natural oligo- or polysaccharide source, the glycan units making up the glycan therapeutic can be and often are isolated from natural oligo- or polysaccharide sources, including those listed herein, or are synthesized de novo.

The terms "treating" and "treatment" as used herein refer to the administration of an agent or composition to a subject (e.g., a symptomatic subject afflicted with an adverse condition, disorder, or disease) so as to affect a reduction in severity and/or frequency of a symptom, eliminate a symptom and/or its underlying cause, and/or facilitate improvement or remediation of damage, and/or preventing an adverse condition, disorder, or disease in an asymptomatic subject who is susceptible to a particular adverse condition, disorder, or disease, or who is suspected of developing or at risk of developing the condition, disorder, or disease.

Generation of Glycan Therapeutic Preparations

Preparations comprising a plurality of glycans such as, e.g., oligosaccharide mixtures can be generated using a non-enzymatic catalyst, e.g., the polymeric catalyst described in U.S. Pat. No. 8,466,242, "POLYMERIC ACID CATALYSTS AND USES THEREOF" or by other suitable methods. Methods to prepare the polymeric and solid-supported catalysts described herein can be found in WO 2014/031956, "POLYMERIC AND SOLID-SUPPORTED CATALYSTS, AND METHODS OF DIGESTING CELLULOSIC MATERIALS USING SUCH CATALYSTS." The glycans generated, e.g., by using the catalyst, for example as described in WO 2016/007778, "OLIGOSACCHARIDE COMPOSITIONS AND METHODS FOR PRODUCING THEREOF" can be structurally much more diverse glycans than those produced by enzymatic reactions. All patent applications are incorporated herein by reference.

Provided are also methods for generating the preparations of glycans (e.g. oligosaccharides) described herein, for example by: a) providing one or more mono- or disaccharide glycan unit, or a combination thereof, b) contacting the mono- or disaccharides with any of the polymeric catalysts described herein and a suitable solvent (such as, e.g. water or a non-aqueous solvent) for a period of time sufficient to produce a polymerized species population (with a desired average degree of polymerization); and c) isolating and/or recovering at least a portion of the polymerized glycan preparation.

In some embodiments, preparations of glycans (e.g. oligosaccharides) are polymolecular. In some embodiments, preparations of glycans (e.g. oligosaccharides) are polymolecular and polydisperse. For example, the glycan therapeutic preparations comprise a mixture of distinct oligosaccharide species (e.g. of different degree of polymerization and degree of branching and different alpha-to-beta glycosidic bond ratios). In some embodiments, the glycan therapeutic preparations comprise a plurality of distinct species (e.g. oligosaccharides) and may consist of $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or more species in various proportions to each other. Herein described are the average properties of the glycan therapeutic preparations, such as degree of polymerization, degree of branching, alpha- and beta-glycosidic bond ratios, etc.

Figure 6A:
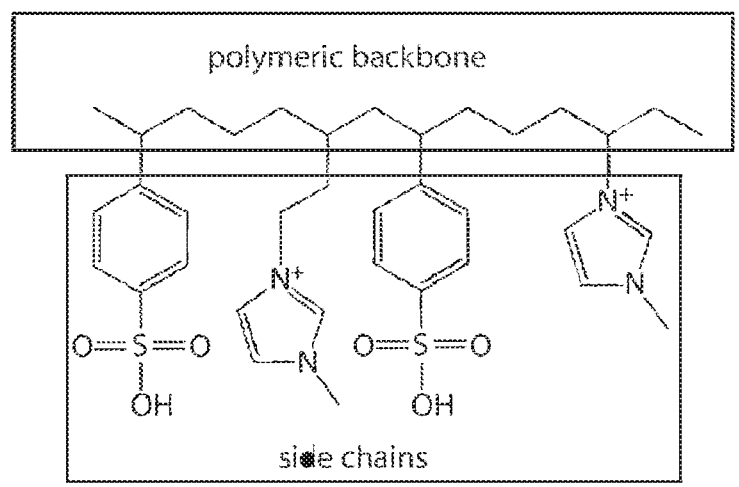
FIGS. 6A-6B. A portion of an exemplary catalyst with a polymeric backbone and side chains is illustrated in FIG. 6A. A portion of an exemplary catalyst, in which a side chain with the acidic group is connected to the polymeric backbone by a linker and in which a side chain with the cationic group is connected directly to the polymeric backbone is illustrated in FIG. 6B.
Figure 6B:
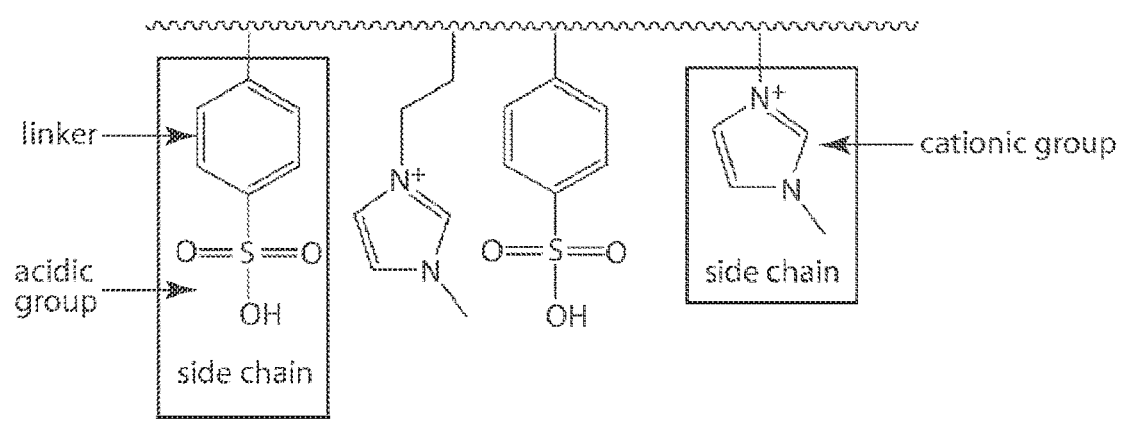

In certain embodiments, the starting material (comprising the glycan units) is contacted with a polymer catalyst under conditions that promote the formation of one or more glycosidic bond between glycan units, thereby producing a preparation of glycans. In one embodiment, the glycan unit is a monosaccharide. In one embodiment, the glycan unit is a disaccharide. Suitable polymer catalysts comprise acidic monomers and ionic monomers that are connected to form a polymeric backbone, wherein each acidic monomer has at least one Bronsted-Lowry acid, and each ionic monomer independently has at least one nitrogen-containing cationic group or phosphorous-containing cationic group. In some embodiments, each acidic monomer of the polymer catalyst may have one Bronsted-Lowry acid, and optionally the Bronsted-Lowry acids are distinct. In some embodiments, each ionic monomer of the polymer catalyst has one nitrogen-containing cationic group or phosphorous-containing cationic group. In some embodiments, at least one ionic monomer of the polymer catalyst has two nitrogen-containing cationic groups or phosphorous-containing cationic groups. A schematic outlining the general functional groups is shown in FIGS. 6a and 6b.

Generally, the polymeric catalyst and the glycan units are introduced into an interior chamber of a reactor, either concurrently or sequentially. Glycan (e.g. oligosaccharides) synthesis can be performed in a batch process or a continuous process. For example, in one embodiment, glycan synthesis is performed in a batch process, where the contents of the reactor are continuously mixed or blended, and all or a substantial amount of the products of the reaction are removed (e.g. isolated and/or recovered). In one variation, glycan synthesis is performed in a batch process, where the contents of the reactor are initially intermingled or mixed but no further physical mixing is performed. In another variation, glycan synthesis is performed in a batch process, wherein once further mixing of the contents, or periodic mixing of the contents of the reactor, is performed (e.g., at one or more times per hour), all or a substantial amount of the products of the reaction are removed (e.g. isolated and/or recovered) after a certain period of time.

In other embodiments, glycan (e.g. oligosaccharide) synthesis is performed in a continuous process, where the contents flow through the reactor with an average continuous flow rate but with no explicit mixing. After introduction of the polymeric catalyst and glycan units into the reactor, the contents of the reactor are continuously or periodically mixed or blended, and after a period of time, less than all of the products of the reaction are removed (e.g. isolated and/or recovered). In one variation, glycan synthesis is performed in a continuous process, where the mixture containing the catalyst and glycan units is not actively mixed. Additionally, mixing of catalyst and the glycan units may occur as a result of the redistribution of polymeric catalysts settling by gravity, or the non-active mixing that occurs as the material flows through a continuous reactor.

In some embodiments of the method, the starting material for the polymerization reaction is one or more glycan unit selected from one or more monosaccharides, one or more disaccharides, or a combination thereof. In some embodiments of the method, the starting material for the polymerization reaction is one or more glycan unit selected from a furanose sugar and a pyranose sugar. In some embodiments of the method, the starting material for the polymerization reaction is one or more glycan unit selected from a tetrose, a pentose, a hexose, or a heptose. In some embodiments of the method, the starting material for the polymerization reaction is one or more glycan unit selected from a glucose, a galactose, an arabinose, a mannose, a fructose, a xylose, a fucose, and a rhamnose, all optionally in either their L- or D-form, in alpha or beta configuration (for dimers), and/or a deoxy-form, where applicable, and any combination thereof. In some embodiments, the glycan units are substituted or derivatized with one or more of an acetate ester, sulfate half-ester, phosphate ester, or a pyruvyl cyclic acetal group, or have been otherwise derivatized at, e.g., at one or more hydroxyl groups.

The glycan units used in the methods described herein may include one or more sugars. In some embodiments, the one or more sugars are selected from monosaccharides, disaccharides, and trisaccharides, or any mixtures thereof. In some embodiments, the one or more sugars are monosaccharides, such as one or more C5 or C6 monosaccharides. In some embodiments, the one or more sugars are C5 monosaccharides. In other embodiments, the one or more sugars are C6 monosaccharides.

In some embodiments, the starting material for the polymerization reaction is one or more glycan unit selected from monosaccharides and other carbohydrates including glycolaldehyde, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, fucose, fuculose, rhamnose, mannoheptulose, sedoheptulose, neuraminic acid, N-acetylneuraminic acid, N-acetylgalactosamine, N-acetylglucosamine, fructosamine, galactosamine, glucosamine, sorbitol, glycerol, erythritol, threitol, arabitol, xylitol, mannitol, sorbitol, galactitol, fucitol, and lactic acid.

In some embodiments, the starting material for the polymerization reaction is one or more glycan unit selected from a monosaccharide. In some embodiments, the monosaccharide is glucose, galactose, fructose, fucose, mannose, arabinose, rhamnose, and xylose. In one embodiment, the glycan unit is not glucose. In one embodiment, the glycan unit is not galactose. In one embodiment, the glycan unit is not fructose. In one embodiment, the glycan unit is not fucose. In one embodiment, the glycan unit is not mannose. In one embodiment, the glycan unit is not arabinose. In one embodiment, the glycan unit is not rhamnose. In one embodiment, the glycan unit is not xylose.

In some embodiments, the starting material for the polymerization reaction is one or more glycan unit selected from disaccharides and other carbohydrates including acarviosin, N-acetyllactosamine, allolactose, cellobiose, chitobiose, glactose-alpha-1,3-galactose, gentiobiose, isomalt, isomaltose, isomaltulose, kojibiose, lactitol, lactobionic acid, lactose, lactulose, laminaribiose, maltitol, maltose, mannobiose, melibiose, melibiulose, neohesperidose, nigerose, robinose, rutinose, sambubiose, sophorose, sucralose, sucrose, sucrose acetate isobutyrate, sucrose octaacetate, trehalose, turanose, vicianose, and xylobiose.

In some embodiments, the starting material for the polymerization reaction is one or more glycan unit selected from an amino sugar, a deoxy sugar, an imino sugar, a sugar acid, a short-chain fatty acid, and a sugar alcohol.

Suitable glycan units include amino sugars, such as, e.g. acarbose, N-acetylemannosamine, N-acetylmuramic acid, N-acetylneuraminic acid, N-acetyletalosaminuronic acid, arabinopyranosyl-N-methyl-N-nitrosourea, D-fructose-L-histidine, N-glycolyneuraminic acid, ketosamine, kidamycin, mannosamine, 1B-methylseleno-N-acetyl-D-galactosamine, muramic acid, muramyl dipeptide, phosphoribosylamine, PUGNAc, sialyl-Lewis A, sialyl-Lewis X, validamycin, voglibose, N-acetylgalactosamine, N-acetylglucosamine, aspartylglucosamine, bacillithiol, daunosamine, desosamine, fructosamine, galactosamine, glucosamine, meglumine, and perosamine.

Suitable glycan units include deoxy sugars, such as, e.g. 1-5-ahydroglucitol, cladinose, colitose, 2-deoxy-D-glucose, 3-deoxyglucasone, deoxyribose, dideoxynucleotide, digitalose, fludeooxyglucose, sarmentose, and sulfoquinovose.

Suitable glycan units include imino sugars, such as, e.g. castanospermine, 1-deoxynojirimycin, iminosugar, miglitol, miglustat, and swainsonine.

Suitable glycan units include sugar acids, such as, e.g. N-acetylneuraminic acid, N-acetyltalosamnuronic acid, aldaric acid, aldonic acid, 3-deoxy-D-manno-oct-2-ulosonic acid, glucuronic acid, glucosaminuronic acid, glyceric acid, N-glycolylneuraminic acid, iduronic acid, isosaccharinic acid, pangamic acid, sialic acid, threonic acid, ulosonic acid, uronic acid, xylonic acid, gluconic acid, ascorbic acid, ketodeoxyoctulosonic acid, galacturonic acid, galactosaminuronic acid, mannuronic acid, mannosaminuronic acid, tartaric acid, mucic acid, saccharic acid, lactic acid, oxalic acid, succinic acid, hexanoic acid, fumaric acid, maleic acid, butyric acid, citric acid, glucosaminic acid, malic acid, succinamic acid, sebacic acid, and capric acid.

Suitable glycan units include short-chain fatty acids, such as, e.g., formic acid, acetic acid, propionic acid, butryic acid, isobutyric acid, valeric acid, and isovaleric acid.

Suitable glycan units include sugar alcohols, such as, e.g., methanol, ethylene glycol, glycerol, erythritol, threitol, arabitol, ribitol, xylitol, mannitol, sorbitol, galactitol, iditol, volemitol, fucitol, inositol, maltotritol, maltotetraitol, and polyglycitol.

In some embodiments, the glycan unit may exist as a salt (e.g., a pharmaceutically acceptable salt), such as, e.g., a hydrochlorate, hydroiodate, hydrobromate, phosphate, sulfate, methanesulfate, acetate, formate, tartrate, malate, citrate, succinate, lactate, gluconate, pyruvate, fumarate, propionate, aspartate, glutamate, benzoate, ascorbate salt.

The glycan units used in the methods described herein may be obtained from any commercially known sources, or produced according to any methods known in the art.

Reaction Conditions

In some embodiments, the glycan units and catalyst (e.g., polymeric catalyst or solid-supported catalyst) are allowed to react for at least 1 hour, at least 2 hours, at least 3 hours, at least 4 hours, at least 6 hours, at least 8 hours, at least 16 hours, at least 24 hours, at least 36 hours, or at least 48 hours; or between 1-24 hours, between 2-12 hours, between 3-6 hours, between 1-96 hours, between 12-72 hours, or between 12-48 hours.

In some embodiments, the degree of polymerization (DP) of the glycan preparation produced according to the methods described herein can be regulated by the reaction time. For example, in some embodiments, the degree of polymerization of the glycan preparation is increased by increasing the reaction time, while in other embodiments, the degree of polymerization of the glycan preparation is decreased by decreasing the reaction time.

Reaction Temperature

In some embodiments, the reaction temperature is maintained in the range of about 25° C. to about 150° C. In certain embodiments, the temperature is from about 30° C. to about 125° C., about 60° C. to about 120° C., about 80° C. to about 115° C., about 90° C. to about 110° C., about 95° C. to about 105° C., or about 100° C. to 110° C.

Amount of Glycan Units

The amount of the glycan unit used in the methods described herein relative to the amount solvent used may affect the rate of reaction and yield. The amount of the glycan unit used may be characterized by the dry solids content. In certain embodiments, dry solids content refers to the total solids of a slurry as a percentage on a dry weight basis. In some embodiments, the dry solids content of the glycan unit is between about 5 wt % to about 95 wt %, between about 10 wt % to about 80 wt %, between about 15 wt %, to about 75 wt %, or between about 15 wt %, to about 50 wt %.

Amount of Catalyst

The amount of the catalyst used in the methods described herein may depend on several factors including, for example, the selection of the type(s) of glycan unit, the concentration of the glycan unit, and the reaction conditions (e.g., temperature, time, and pH). In some embodiments, the weight ratio of the catalyst to the glycan unit(s) is about 0.01 g/g to about 50 g/g, about 0.01 g/g to about 5 g/g, about 0.05 g/g to about 1.0 g/g, about 0.05 g/g to about 0.5 g/g, about 0.05 g/g to about 0.2 g/g, or about 0.1 g/g to about 0.2 g/g.

Solvent

In certain embodiments, synthesis of the glycans (e.g. oligosaccharides) using the polymeric catalyst is carried out in an aqueous environment. One suitable aqueous solvent is water. Generally, water with lower concentrations of ionic species is preferable, as such ionic species may reduce the effectiveness of the polymeric catalyst. In some embodiments where the aqueous solvent is water, the water has less than 10% of ionic species (e.g., salts of sodium, phosphorous, ammonium, magnesium). In some embodiments where the aqueous solvent is water, the water has a resistivity of at least 0.1 megaohm-centimeters, of at least 1 megaohm-centimeters, of at least 2 megaohm-centimeters, of at least 5 megaohm-centimeters, or of at least 10 megaohm-centimeters.

Water Content

In some embodiments, water is produced with each glycosidic bond formed between the one or more glycan units (dehydration reaction). In certain embodiments, the methods described herein may further include monitoring the amount of water present in the reaction mixture and/or the ratio of water to glycan unit or catalyst over a period of time. In some embodiments, the method further includes removing at least a portion of water produced in the reaction mixture (e.g., by removing at least about any of 10%, 20%, 30%, 40%, 50%, 60%, 70%, 80%, 90%, 95%, 97%, 99%, or 100%, such as by vacuum filtration). It should be understood, however, that the amount of water to glycan unit may be adjusted based on the reaction conditions and specific catalyst used.

Any method known in the art may be used to remove water in the reaction mixture, including, for example, by vacuum filtration, vacuum distillation, heating, and/or evaporation. In some embodiments, the method comprises including water in the reaction mixture.

In some aspects, provided herein are methods of producing a glycan preparation, by: combining a glycan unit and a catalyst having acidic and ionic moieties to form a reaction mixture, wherein water is produced in the reaction mixture; and removing at least a portion of the water produced in the reaction mixture. In certain variations, at least a portion of water is removed to maintain a water content in the reaction mixture of less than 99%, less than 90%, less than 80%, less than 70%, less than 60%, less than 50%, less than 40%, less than 30%, less than 20%, less than 10%, less than 5%, or less than 1% by weight.

In some embodiments, the degree of polymerization of the glycan preparation produced can be regulated by adjusting or controlling the concentration of water present in the reaction mixture. For example, in some embodiments, the degree of polymerization of the glycan preparation is increased by decreasing the water concentration, while in other embodiments, the degree of polymerization of the glycan preparation is decreased by increasing the water concentration. In some embodiments, the water content of the reaction is adjusted during the reaction to regulate the degree of polymerization of the glycan preparation produced.

For example, a majority, e.g. about 55%, 60%, 65%, 70%, 75%, 80%, 85%, 90%, 95%, or about 97% of the glycan therapeutic preparation has a DP of between 2 and 25, between 3 and 25, between 4 and 25, between 5 and 25, between 6 and 25, between 7 and 25, between 8 and 25, between 9 and 25, between 10 and 25, between 2 and 30, between 3 and 30, between 4 and 30, between 5 and 30, between 6 and 30, between 7 and 30, between 8 and 30, between 9 and 30, or between 10 and 30.

In one example, to a round bottom flask equipped with an overhead stirrer and a jacketed short-path condenser one or more glycan units may be added along with 1-50% (1-10%, 1-20%, 1-30%, 1-40%, 1-60%, 1-70%) by dry weight of one or more of the catalysts described herein. Water or another compatible solvent (0.1-5 equiv, 1-5 equiv, 1-4 equiv, 0.1-4 equiv) may be added to the dry mixture and the slurry can be combined at slow speed (e.g. 10-100 rpm, 50-200 rpm, 100-200 rpm) using a paddle sized to match the contours of the selected round bottom flask as closely as possible. The mixture is heated to 70-180° C. (70-160° C., 75-165° C., 80-160° C.) under 10-1000 mbar vacuum pressure. The reaction may be stirred for 30 minutes to 6 hours, constantly removing water from the reaction. Reaction progress can be monitored by HPLC.

The yield of conversion for the one or more glycan units in the methods described herein can be determined by any suitable method known in the art, including, for example, high performance liquid chromatography (HPLC). In some embodiments, the yield of conversion to a glycan therapeutic preparation with DP>1 after combining the one or more glycan units with the catalyst (e.g., at 2, 3, 4, 8, 12, 24, or 48 hours after combining the one or more glycan units with the catalyst) is greater than about 50% (e.g., greater than about 55%, 60%, 65%, 70%, 75%, 80%, 85%, 90%, 95%, or 98%). In some embodiments, the yield of conversion to a glycan therapeutic preparation with >DP2 after combining the one or more glycan units with the catalyst (e.g., at 2, 3, 4, 8, 12, 24, or 48 hours after combining the one or more glycan units with the catalyst) is greater than 30% (e.g., greater than 35%, 40%, 45%, 50%, 55%. 60%, 65%, 70%, 75%, 80%, 85%, 90%, 95%, or 98%). In some embodiments, the yield of conversion to a glycan therapeutic preparation with >DP3 after combining the one or more glycan units with the catalyst (e.g., at 2, 3, 4, 8, 12, 24, or 48 hours after combining the one or more glycan units with the catalyst) is greater than 30% (e.g., greater than 35%, 40%, 45%, 50%, 55%. 60%, 65%, 70%, 75%, 80%, 85%, 90%, 95%, or 98%).

In some embodiments, the glycan therapeutic preparation has a degree of polymerization (DP) distribution after combining the one or more glycan units with the polymeric catalyst (e.g., at 2, 3, 4, 8, 12, 24, or 48 hours after combining the one or more glycan units with the catalyst) is: DP2=0%-40%, such as less than 40%, less than 30%, less than 20%, less than 10%, less than 5%, or less than 2%; or 10%-30% or 15%-25%; DP3=0%-20%, such as less than 15%, less than 10%, less than 5%; or 5%-15%; and DP4+ =greater than 15%, greater than 20%, greater than 30%, greater than 40%, greater than 50%; or 15%-75%, 20%-40% or 25%-35%.

The solid mass obtained by the process can be dissolved in a volume of water sufficient to create a solution of approximately 50 Brix (grams sugar per 100 g solution). Once dissolution is complete, the solid catalyst can be removed by filtration. The solution comprising therapeutic glycans can be concentrated to about 50-75 Brix, e.g., by rotary evaporation. In some embodiments, the solution comprising therapeutic glycans can be concentrated to about 50-60 Brix, 60-70 Brix, 70-80 Brix, 55-65 Brix, 65-75 Brix, or 75-85 Brix. In some embodiments, the solution comprising therapeutic glycans can be concentrated to about 50, 55, 60, 65, 70, 75, 80, or about 85 Brix. Optionally, an organic solvent can be used and water immiscible solvents can be removed by biphasic extraction and water miscible solvents can be removed, e.g., by rotary evaporation concomitant to the concentration step.

Additional Processing Steps

Optionally, the glycan preparation produced may undergo additional processing steps. Additional processing steps may include, for example, purification steps. Purification steps may include, for example, separation, dilution, concentration, filtration, desalting or ion-exchange, chromatographic separation, or decolorization, or any combination thereof.

Decolorization

In some embodiments, the methods described herein further include a decolorization step. The glycan preparation produced may undergo a decolorization step using any method known in the art, including, for example, treatment with an absorbent, activated carbon, chromatography (e.g., using ion exchange resin), hydrogenation, and/or filtration (e.g., microfiltration).

In certain embodiments, the glycan preparations produced are contacted with a color-absorbing material at a particular temperature, at a particular concentration, and/or for a particular duration of time. In some embodiments, the mass of the color absorbing species contacted with the glycan preparation is less than 50% of the mass of the glycan preparation, less than 35% of the mass of the glycan preparation, less than 20% of the mass of the glycan preparation, less than 10% of the mass of the glycan preparation, less than 5% of the mass of the glycan preparation, less than 2% of the mass of the glycan preparation, or less than 1% of the mass of the glycan preparation.

In some embodiments, the glycan preparations are contacted with a color absorbing material. In certain embodiments, the glycan preparations are contacted with a color absorbing material for less than 10 hours, less than 5 hours, less than 1 hour, or less than 30 minutes. In a particular embodiment, the glycan preparations are contacted with a color absorbing material for 1 hour.

In certain embodiments, the glycan preparations are contacted with a color absorbing material at a temperature from about 20 to 100 degrees Celsius, about 30 to 80 degrees Celsius, about 40 to 80 degrees Celsius, or about 40 to 65 degrees Celsius. In a particular embodiment, the glycan preparations are contacted with a color absorbing material at a temperature of about 50 degrees Celsius.

In certain embodiments, the color absorbing material is activated carbon. In one embodiment, the color absorbing material is powdered activated carbon. In other embodiments, the color absorbing material is an ion exchange resin. In one embodiment, the color absorbing material is a strong base cationic exchange resin in a chloride form. In another embodiment, the color absorbing material is cross-linked polystyrene. In yet another embodiment, the color absorbing material is cross-linked polyacrylate. In certain embodiments, the color absorbing material is Amberlite FPA91, Amberlite FPA98, Dowex 22, Dowex Marathon MSA, or Dowex Optipore SD-2.

Ion-Exchange/De-Salting (Demineralization)

In some embodiments, the glycan preparations are contacted with a material to remove salts, minerals, and/or other ionic species. In certain embodiments, the glycan preparations are flowed through an anionic/cationic exchange column pair. In one embodiment, the anionic exchange column contains a weak base exchange resin in a hydroxide form and the cationic exchange column contains a strong acid exchange resin in a protonated form.

Separation and Concentration

In some embodiments, the methods described herein further include isolating the glycan preparation produced. In certain variations, isolating the glycan preparation comprises separating at least a portion of the glycan preparation from at least a portion of the catalyst, using any method known in the art, including, for example, centrifugation, filtration (e.g., vacuum filtration, membrane filtration), and gravity settling. In some embodiments, isolating the glycan preparation comprises separating at least a portion of the glycan preparation from at least a portion of any unreacted glycan units, using any method known in the art, including, for example, filtration (e.g., membrane filtration), chromatography (e.g., chromatographic fractionation), differential solubility, and centrifugation (e.g., differential centrifugation).

In some embodiments, the methods further include a concentration step. For example, the isolated glycan preparations undergo evaporation (e.g., vacuum evaporation) to produce a concentrated glycan preparation. In other embodiments, the isolated glycan preparations undergo a spray drying step to produce a powdered glycan preparation. In certain embodiments, the isolated glycan preparations undergo both an evaporation step and a spray drying step.

Fractionation

In some embodiments, glycan therapeutic preparations (e.g. oligosaccharides) are created that are polydisperse, exhibiting a range of degrees of polymerization. In some embodiments, the methods described herein further include a fractionation step. Glycan species (e.g., oligosaccharides) may be separated by molecular weight using any method known in the art, including, for example, high-performance liquid chromatography, adsorption/desorption (e.g. low-pressure activated carbon chromatography), or filtration (for example, ultrafiltration or diafiltration). In certain embodiments, glycan species are separated into pools representing 60%, 65%, 70%, 75%, 80%, 85%, 90%, 95%, 97%, 98%, or greater than 98% short (about DP1-2), medium (about DP3-10), long (about DP11-18), or very long (about DP>18) species.

In certain embodiments, glycan species are fractionated by adsorption onto a carbonaceous material and subsequent desorption of fractions by washing the material with mixtures of an organic solvent in water at a concentration of 1%, 5%, 10%, 20%, 50%, or 100%. In one embodiment, the adsorption material is activated charcoal. In another embodiment, the adsorption material is a mixture of activated charcoal and a bulking agent such as diatomaceous earth or Celite 545 in 5%, 10%, 20%, 30%, 40%, or 50% portion by volume or weight.

In further embodiments, glycan species are separated by passage through a high-performance liquid chromatography system. In certain variations, glycan species are separated by ion-affinity chromatography, hydrophilic interaction chromatography, or size-exclusion chromatography including gel-permeation and gel-filtration.

In other embodiments, low molecular weight materials are removed by filtration methods. In certain variations, low molecular weight materials may be removed by dialysis, ultrafiltration, diafiltration, or tangential flow filtration. In certain embodiments, the filtration is performed in static dialysis tube apparatus. In other embodiments, the filtration is performed in a dynamic flow filtration system. In other embodiments, the filtration is performed in centrifugal force-driven filtration cartridges.

Characteristics of Glycan Therapeutic Preparations

The glycan therapeutics described herein may comprise oligosaccharides and/or polysaccharides (referred to herein as "oligosaccharides"). In some embodiments, the glycan therapeutics comprise homo-oligo- or polymers (e.g., homo-glycans), wherein all the glycan units in the oligomer or polymer are of the same type. Glycan therapeutics comprising homopolymers can include monosaccharides bonded together via a single or multiple glycosidic bond types.

In some embodiments, the glycan therapeutics comprise hetero-oligo- or polymers (e.g., heteroglycans), wherein more than one type of glycan unit is present. Glycan therapeutics comprising heteropolymers can include distinct types of monosaccharides bonded together via a single or multiple glycosidic bond types.

In some embodiments, hydrolysis may be used to generate the constituent glycan units that are suitable to produce the glycans described herein. In one embodiment, the glycan unit is a monosaccharide. Monosaccharides may exist in many different forms, for example, conformers, cyclic forms, acyclic forms, stereoisomers, tautomers, anomers, and isomers.

Degree of Polymerization

In some embodiments, about 55%, 60%, 65%, 70%, 75%, 80%, 85%, 90%, 95%, or about 97% of the glycan therapeutic preparation has a DP of at least 5 and less than 30 glycan units. In some embodiments, about 55%, 60%, 65%, 70%, 75%, 80%, 85%, 90%, 95%, or about 97% of the glycan therapeutic preparation has a DP of at least 3 and less than 30 glycan units. In some embodiments, about 55%, 60%, 65%, 70%, 75%, 80%, 85%, 90%, 95%, or about 97% of the glycan therapeutic preparation has a DP of at least 3 and less than 25 glycan units. In some embodiments, about 55%, 60%, 65%, 70%, 75%, 80%, 85%, 90%, 95%, or about 97% of the glycan therapeutic preparation has a DP of at least 8 and less than 30 glycan units. In some embodiments, about 55%, 60%, 65%, 70%, 75%, 80%, 85%, 90%, 95%, or about 97% of the glycan therapeutic preparation has a DP of at least 10 and less than 30 glycan units. In some embodiments, about 55%, 60%, 65%, 70%, 75%, 80%, 85%, 90%, 95%, or about 97% of the glycan therapeutic preparation has a DP of between 3, 4, 5, 6, 7, 8 and 10, 11, 12, 13, 14, 15, 16, 17, 18, 19, 20 glycan units. In some embodiments, about 55%, 60%, 65%, 70%, 75%, 80%, 85%, 90%, 95%, or about 97% of the glycan therapeutic preparation has a DP of between 10, 11, 12, 13, 14, 15, 16, 17, 18, 19 and 20, 21, 22, 23, 24, 25, 26, 27, 28, 29, 30 glycan units. In some embodiments, about 55%, 60%, 65%, 70%, 75%, 80%, 85%, 90%, 95%, or about 97% of the glycan therapeutic preparation has a DP of between 3, 4, 5, 6, 7, 8, 9, 10 and 20, 21, 22, 23, 24, 25, 26, 27, 28 glycan units.

In one embodiment, the glycan therapeutic preparation has a degree of polymerization (DP) of at least 3 and less than 30 glycan units. In one embodiment, the glycan therapeutic preparation has a degree of polymerization (DP) of at least 5 and less than 30 glycan units. In one embodiment, the glycan therapeutic preparation has a degree of polymerization (DP) of at least 3 and less than 25 glycan units.

In one embodiment, about 55%, 60%, 65%, 70%, 75%, 80%, 85%, 90%, 95%, or about 97% of the glycan therapeutic preparation has a DP of at least 2. In one embodiment, about 55%, 60%, 65%, 70%, 75%, 80%, 85%, 90%, 95%, or about 97% of the glycan therapeutic preparation has a DP of at least 3.

In some embodiments, glycan therapeutic preparations are provided, wherein at least 5%, 10%, 15%, 20%, 25%, 30%, 35%, 40%, 45%, 50%, 55%, 60%, 65%, 70%, 75%, 80%, 85%, 90%, 95%, 97%, 98%, 99%, 99.8%, or at least 99.9% or even 100% of the glycan therapeutic preparation has a degree of polymerization (DP) of at least 2, 3, 4, 5, 6, 7, 8, 9, 10, 11, or at least 12 glycan units and less than 75, 70, 65, 60, 55, 50, 45, 40, 35, 30, 25, 20, 19, 18, 17, 16, or less than 15 glycan units.

In some embodiments, glycan therapeutic preparations are provided, wherein at least 5%, 10%, 15%, 20%, 25%, 30%, 35%, 40%, 45%, 50%, 55%, 60%, 65%, 70%, 75%, 80%, 85%, 90%, 95%, 97%, 98%, 99%, 99.8%, or at least 99.9% or even 100% of the glycan therapeutic preparation has a degree of polymerization (DP) of at least 3 and less than 30 glycan units, at least 5 and less than 30 glycan units, or at least 8 and less than 30 glycan units.

In some embodiments, about 55%, 60%, 65%, 70%, 75%, 80%, 85%, 90%, 95%, or about 97% of the glycan therapeutic preparation has an average degree of polymerization (DP) of about DP5, DP6, DP7, DP8, DP9, DP10, DP11, DP12, DP13, DP14, or DP15.

In some embodiments, glycan therapeutic preparations are provided wherein at least 50%, 60%, 70%, or 80% of the glycan therapeutic preparation has a degree of polymerization of at least 3 and less than 30 glycan units, or of at least 5 and less than 25 glycan units. In some embodiments, the average DP of the glycan therapeutic preparation is between about DP7 and DP9 or between about DP6 and DP10. In some embodiments, these glycan therapeutic preparations comprise an alpha- to beta-glycosidic bond ratio from 0.8:1 to 5:1 or from 1:1 to 4:1. In some embodiments, the fractionated preparations have an average degree of branching of between about 0.01 and about 0.2 or between about 0.05 and 0.1.

In one embodiment, a polydisperse, fractionated glycan therapeutic preparation is provided comprising at least 85%, 90%, or at least 95% medium-length species with a DP of about 3-10. In one embodiment, a polydisperse, fractionated glycan therapeutic preparation is provided comprising at least 85%, 90%, or at least 95% long-length species with a DP of about 11-18. In one embodiment, a polydisperse, fractionated glycan therapeutic preparation is provided comprising at least 85%, 90%, or at least 95% very long-length species with a DP of about 18-30. In some embodiments, the medium, long and very long fractionated preparations comprise an alpha- to beta-glycosidic bond ratio from 0.8:1 to 5:1 or from 1:1 to 4:1. In some embodiments, the fractionated preparations have an average degree of branching of between about 0.01 and about 0.2 or between about 0.05 and 0.1.

In some embodiments, about 55%, 60%, 65%, 70%, 75%, 80%, 85%, 90%, 95%, or about 97% of the glycan therapeutic preparation has an average molecular weight of about 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800 g/mol and less than 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, and 5000 g/mol.

Degree of Branching

In some embodiments, the glycan preparations (e.g. oligosaccharides) range in structure from linear to highly branched. Unbranched glycans may contain only alpha linkages or only beta linkages. Unbranched glycans may contain at least one alpha and at least one beta linkage. Branched glycans may contain at least one glycan unit being linked via an alpha or a beta glycosidic bond so as to form a branch. The branching rate or degree of branching (DB) may vary, such that about every $2^{nd}$, $3^{rd}$, $4^{th}$, $5^{th}$, $6^{th}$, $7^{th}$, $8^{th}$, $9^{th}$, $10^{th}$, $15^{th}$, $20^{th}$, $25^{th}$, $30^{th}$, $35^{th}$, $40^{th}$, $45^{th}$, $50^{th}$, $60^{th}$, or $70^{th}$ unit comprises at least one branching point. For example, animal glycogen contains a branching point approximately every 10 units.

In some embodiments, preparations of glycan therapeutics are provided, wherein the preparation comprises a mixture of branched glycans, wherein the average degree of branching (DB, branching points per residue) is 0, 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 0.95, 0.99, 1, or 2. In some embodiments, preparations of glycan therapeutics are provided, wherein the average degree of branching is at least 0.01, 0.05, 0.1, 0.2, 0.3, or at least 0.4. In some embodiments, preparations of glycan therapeutics are provided, wherein the average degree of branching is between about 0.01 and 0.1, 0.01 and 0.2, 0.01 and 0.3, 0.01 and 0.4, or 0.01 and 0.5. In some embodiments, preparations of glycan therapeutics are provided, wherein the average degree of branching is between about 0.05 and 0.1, 0.05 and 0.2, 0.05 and 0.3, 0.05 and 0.4, or 0.05 and 0.5. In some embodiments, preparations of glycan therapeutics are provided, wherein the average degree of branching is between about 0.1 and 0.2, 0.1 and 0.3, 0.1 and 0.4, or 0.1 and 0.5. In some embodiments, preparations of glycan therapeutics are provided, wherein the average degree of branching is not 0. In some embodiments, preparations of glycan therapeutics are provided, wherein the average degree of branching is not between at least 0.1 and less than 0.4 or at least 0.2 and less than 0.4. In some embodiments, the preparations of glycan therapeutics comprise linear glycans. In some embodiments, the preparations of glycan therapeutics comprise glycans that exhibit a branched or branch-on-branch structure, e.g., branched glycans (such as, e.g., branched oligosaccharides and/or branched polysaccharides).

In some embodiments, preparations of glycan therapeutics are provided wherein the average degree of branching (DB) is not 0, but is at least 0.01, 0.05, 0.1, or at least 0.2, or ranges between about 0.01 and about 0.2 or between about 0.05 and 0.1.

Glycosidic Linkages

The linkage or bonds between two glycan units can be expressed, for example, as 1,4, 1->4, or (1-4), used interchangeably and are referred to herein as glycosidic linkages or bonds for compounds comprising one or more sugars (e.g. monosaccharides, disaccharides and the like). Monosaccharides can be in the cyclic form (e.g. pyranose or furanose form). For example, lactose is a disaccharide composed of cyclic forms of galactose and glucose joined by a beta (1-4) linkage where the acetal oxygen bridge is in the beta orientation.

Linkages or bonds between the individual glycan units found in preparations of glycan therapeutics may include one or more (e.g., two or more, three or more, four or more, five or more, six or more, etc.) of alpha 1->2, alpha 1->3, alpha 1->4, alpha 1->6, alpha 2->1, alpha 2->3, alpha 2->4, alpha 2->6, beta 1->2, beta 1->3, beta 1->4, beta 1->6, beta 2->1, beta 2->3, beta 2->4, and beta 2->6.

In some embodiments, the glycan therapeutic preparation comprises both alpha- and beta-glycosidic bonds selected from the group consisting of 1->2 glycosidic bond, a 1->3 glycosidic bond, a 1->4 glycosidic bond, a 1->5 glycosidic bond and a 1->6 glycosidic bond. In some embodiments, the glycan therapeutic preparation comprises at least two or at least three alpha and beta 1->2 glycosidic bonds, alpha and beta 1->3 glycosidic bonds, alpha and beta 1->4 glycosidic bonds, alpha and beta 1->5 glycosidic bonds, and/or alpha and beta 1->6 glycosidic bonds.

In some embodiments, the glycan therapeutic preparations comprise only alpha linkages. In some embodiments, the glycan therapeutics comprise only beta linkages. In some embodiments, the glycan therapeutics comprise mixtures of alpha and beta linkages.

In some embodiments, the alpha:beta glycosidic bond ratio in a preparation is about 0.1:1, 0.2:1, 0.3:1, 0.4:1, 0.5:1, 0.6:1, 0.7:1, 0.8:1, 0.9:1, 1:1, 1.2:1, 1.5:1, 1.7:1, 2:1, 2.2:1, 2.5:1, 2.7:1, 3:1, 4:1, 5:1, 6:1, 7:1, 8:1, 9:1, or about 10:1.

In some embodiments, the glycan therapeutic preparations comprise and alpha:beta glycosidic bond ratio in a preparation of about 0.8:1, 1:1, 2:1, 3:1, 4:1 or 5:1, or it ranges from about 0.8:1 to about 5:1 or from about 1:1 to about 4:1.

In some embodiments, the preparations of glycan therapeutics (e.g. oligosaccharides) comprises substantially all alpha- or beta configured glycan units, optionally comprising about 1%, 2%, 3%, 4% 5%, 6%, 7%, 8%, 9%, 10%, 11%, 12%, 13%, 14%, 15%, 16%, 17%, 18%, 19%, or 20% of the respective other configuration.

In some embodiments, the preparations of glycan therapeutics comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% glycans with alpha glycosidic bonds. In some embodiments, the preparations of glycan therapeutics comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% glycans with beta glycosidic bonds. In some embodiments, preparations of glycan therapeutics are provided, wherein at least 10%, 15%, 20%, 25%, 30%, 35%, 40%, 45%, 50%, 55%, 60%, 65%, 70%, 75%, 80%, or at least 85% of glycans with glycosidic bonds that are alpha glycosidic bonds, at least 10%, 15%, 20%, 25%, 30%, 35%, 40%, 45%, 50%, 55%, 60%, 65%, 70%, 75%, 80%, or at least 85% of glycans with glycosidic bonds that are beta glycosidic bonds, and wherein the percentage of alpha and beta glycosidic bonds does not exceed 100%.

In some embodiments, preparations of glycan therapeutics are provided, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% of glycan glycosidic bonds are one or more of: 1->2 glycosidic bonds, 1->3 glycosidic bonds, 1->4 glycosidic bonds, and 1->6 glycosidic bonds. In some embodiments, preparations of glycan therapeutics are provided, wherein at least 1%, 2%, 3%, 4%, 5%, 6%, 7%, 8%, 9%, 10%, 15%, at least 20%, or 25% each of glycan glycosidic bonds are 1->2, 1->3, 1->4, and 1->6 glycosidic bonds. Optionally, the preparations of glycan therapeutics further comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, or at least 85% of glycan glycosidic bonds that are selected from the group consisting of: alpha 2->1, alpha 2->3, alpha 2->4, alpha 2->6, beta 2->1, beta 2->3, beta 2->4, and beta 2->6, glycosidic bonds.

In some embodiments, the preparations of glycan therapeutics comprise glycans with at least two glycosidic bonds selected from the group consisting of alpha 1->2 and alpha 1->3, alpha 1->2 and alpha 1->4, alpha 1->2 and alpha 1->6, alpha 1->2 and beta 1->2, alpha 1->2 and beta 1->3, alpha 1->2 and beta 1->4, alpha 1->2 and beta 1->6, alpha 1->3 and alpha 1->4, alpha 1->3 and alpha 1->6, alpha 1->3 and beta 1->2, alpha 1->3 and beta 1->3, alpha 1->3 and beta 1->4, alpha 1->3 and beta 1->6, alpha 1->4 and alpha 1->6, alpha 1->4 and beta 1->2, alpha 1->4 and beta 1->3, alpha 1->4 and beta 1->4, alpha 1->4 and beta 1->6, alpha 1->6 and beta 1->2, alpha 1->6 and beta 1->3, alpha 1->6 and beta 1->4, alpha 1->6 and beta 1->6, beta 1->2 and beta 1->3, beta 1->2 and beta 1->4, beta 1->2 and beta 1->6, beta 1->3 and beta 1->4, beta 1->3 and beta 1->6, and beta 1->4 and beta 1->6.

For preparations comparing branched glycan therapeutics (e.g. those with a DB of 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 0.95, 0.99, 1, or 2) comprising a side chain, which can be the same or a different side chain, the side chain may be attached via one or more beta and alpha linkages, such as (1-2), (1-3), (1-4), (1-6), (2-3), (2-6) or other suitable linkages to the main chain.

Glycan Units

In some embodiments, preparations of glycan therapeutics are provided, wherein at least one glycan unit is a sugar in L-form. In some embodiments, preparations of glycans are provided, wherein at least one glycan unit is a sugar in D-form. In some embodiments, preparations of glycans are provided, wherein the glycan units are sugars in L- or D-form as they naturally occur or are more common (e.g. D-glucose, D-xylose, L-arabinose).

In some embodiments, the preparation of glycan therapeutics (e.g. oligosaccharides) comprises a desired mixture of L- and D-forms of glycan units, e.g. of a desired ratio, such as: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150 L- to D-forms or D- to L-forms.

In some embodiments, the preparation of glycan therapeutics comprises glycans with substantially all L- or D-forms of glycan units, optionally comprising about 1%, 2%, 3%, 4% 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the respective other form.

In some embodiments, preparations of glycan therapeutics are provided, wherein at least one glycan unit is a diose, triose, tetrose, a pentose, a hexose, or a heptose. Optionally, the glycan units involved in the formation of the glycans are varied. Examples of monosaccharide glycan units include hexoses, such as glucose, galactose, and fructose, and pentoses, such as xylose. The monosaccharide glycan units may exist in an acyclic (open-chain) form. Open-chain monosaccharides with same molecular graph may exist as two or more stereoisomers. The monosaccharides may also exist in a cyclic form through a nucleophilic addition reaction between the carbonyl group and one of the hydroxyls of the same molecule. The reaction creates a ring of carbon atoms closed by one bridging oxygen atom. In these cyclic forms, the ring usually has 5 (furanoses) or 6 atoms (pyranoses).

In some embodiments, the preparation of glycan therapeutics (e.g. oligosaccharides) comprises a desired mixture of different monosaccharide glycan units, such as a mixture of a diose, a triose, tetrose, pentose, hexose, or heptose, including any mixtures of two or more pentoses (e.g., arabinose and xylose) and mixtures of two or more hexoses (e.g., glucose and galactose), in any desired ratio, e.g. for any two glycan units: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150, etc., for any three glycan units: 1:1:1, 1:2:1, 1:3:1, 1:4:1, 1:5:1, 1:6:1, 1:7:1, 1:8:1, 1:9:1, 1:10:1, 1:12:1, 1:14:1, 1:16:1, 1:18:1, 1:20:1, 1:1:2, 1:2:2, 1:3:2, 1:4:2, 1:5:2, 1:6:2, 1:7:2, 1:8:2, 1:9:2, 1:10:2, 1:1:3, 1:2:3, 1:3:3, 1:4:3, 1:5:3, 1:6:3, 1:7:3, 1:8:3, 1:9:3, 1:10:3, 1:1:4, 1:2:4, 1:3:4, 1:4:4, 1:5:4, 1:6:4, 1:7:4, 1:8:4, 1:9:4, 1:10:4, 1:1:5, 1:2:5, 1:3:5, 1:4:5, 1:5:5, 1:6:5, 1:7:5, 1:8:5, 1:9:5, 1:10:5, etc., for any four glycan units: 1:1:1:1, 1:2:2:1, 1:3:2:1, 1:4:2:1, 1:5:2:1, 1:6:2:1, 1:7:2:1, 1:8:2:1, 1:9:2:1, 1:10:2:1, 1:1:1:2, 1:2:2:2, 1:3:2:2, 1:4:2:2, 1:5:2:2, 1:6:2:2, 1:7:2:2, 1:8:2:2, 1:9:2:2, 1:10:2:2, etc., for any five glycan units: 1:1:1:1:1, 1:2:2:1:1, etc., for any six glycan units: 1:1:1:1:1:1, 1:1:1:1:1:2, etc., for any seven glycan units: 1:1:1:1:1:1:1, 1:1:1:1:1:1:2, etc., and so on.

In some embodiments, the preparation of glycan therapeutics comprises a desired mixture of two, three, four or five different glycan units, such as a mixture of, e.g., i) one or more glycan units selected from monosaccharides, selected from glucose, galactose, arabinose, mannose, fructose, xylose, fucose, and rhamnose; ii) one or more glycan units selected from disaccharides selected from acarviosin, n-acetyllactosamine, allolactose, cellobiose, chitobiose, galactose-alpha-1,3-galactose, gentiobiose, isomalt, isomaltose, isomaltulose, kojibiose, lactitol, lactobionic acid, lactose, lactulose, laminaribiose, maltitol, maltose, mannobiose, melibiose, melibiulose, neohesperidose, nigerose, robinose, rutinose, sambubiose, sophorose, sucralose, sucrose, sucrose acetate isobutyrate, sucrose octaacetate, trehalose, turanose, vicianose, and xylobiose; iii) one or more glycan units selected from amino sugars selected from acarbose, N-acetylemannosamine, N-acetylmuramic acid, N-acetylnueraminic acid, N-acetyletalosaminuronic acid, arabinopyranosyl-N-methyl-N-nitrosourea, D-fructose-L-histidine, N-glycolyneuraminic acid, ketosamine, kidamycin, mannosamine, 1B-methylseleno-N-acetyl-D-galactosamine, muramic acid, muramyl dipeptide, phosphoribosylamine, PUGNAc, sialyl-Lewis A, sialyl-Lewis X, validamycin, voglibose, N-acetylgalactosamine, N-acetylglucosamine, aspartylglucosamine, bacillithiol, daunosamine, desosamine, fructosamine, galactosamine, glucosamine, meglumine, and perosamine; iv) one or more glycan units selected from deoxy sugars selected from 1-5-ahydroglucitol, cladinose, colitose, 2-deoxy-D-glucose, 3-deoxyglucasone, deoxyribose, dideoxynucleotide, digitalose, fludeooxyglucose, sarmentose, and sulfoquinovose; v) one or more glycan units selected from imino sugars selected from castanospermine, 1-deoxynojirimycin, iminosugar, miglitol, miglustat, and swainsonine; one or more glycan units selected from sugar acids selected from N-acetylneuraminic acid, N-acetyltalosamnuronic acid, aldaric acid, aldonic acid, 3-deoxy-D-manno-oct-2-ulosonic acid, glucuronic acid, glucosaminuronic acid, glyceric acid, N-glycolylneuraminic acid, iduronic acid, isosaccharinic acid, pangamic acid, sialic acid, threonic acid, ulosonic acid, uronic acid, xylonic acid, gluconic acid, ascorbic acid, ketodeoxyoctulosonic acid, galacturonic acid, galactosaminuronic acid, mannuronic acid, mannosaminuronic acid, tartaric acid, mucic acid, saccharic acid, lactic acid, oxalic acid, succinic acid, hexanoic acid, fumaric acid, maleic acid, butyric acid, citric acid, glucosaminic acid, malic acid, succinamic acid, sebacic acid, and capric acid; vi) one or more glycan units selected from short-chain fatty acids selected from formic acid, acetic acid, propionic acid, butryic acid, isobutyric acid, valeric acid, and isovaleric acid; and vii) one or more glycan units selected from sugar alcohols selected from methanol, ethylene glycol, glycerol, erythritol, threitol, arabitol, ribitol, xylitol, mannitol, sorbitol, galactitol, iditol, volemitol, fucitol, inositol, maltotritol, maltotetraitol, and polyglycitol.

In some embodiments, the preparation of glycan therapeutics comprises a glycan unit or plurality of glycan units present in a salt form (e.g., a pharmaceutically acceptable salt form), such as, e.g., a hydrochlorate, hydroiodate, hydrobromate, phosphate, sulfate, methanesulfate, acetate, formate, tartrate, malate, citrate, succinate, lactate, gluconate, pyruvate, fumarate, propionate, aspartate, glutamate, benzoate, ascorbate salt.

Exemplary glycans are described by a three-letter code representing the monomeric sugar component followed by a number out of one hundred reflecting the percentage of the material that monomer constitutes. Thus, 'glu100' is ascribed to a glycan generated from a 100% D-glucose (glycan unit) input and 'glu50gal50' is ascribed to a glycan generated from 50% D-glucose and 50% D-galactose (glycan units) input or, alternatively from a lactose dimer (glycan unit) input. As used herein: xyl=D-xylose; ara=L-arabinose; gal=D-galactose; glu=D-glucose; rha=L-rhamnose; fuc=L-fucose; man=D-mannose; sor=D-sorbitol; gly=D-glycerol; neu=NAc-neuraminic acid.

In some embodiments, the preparation of glycan therapeutics comprises one glycan unit A selected from i) to vii) above, wherein glycan unit A comprises 100% of the glycan unit input. For example, in some embodiments, the glycan therapeutic preparation is selected from the homo-glycans xyl100, rha100, ara100, gal100, glu100, and man100. In some embodiments, the glycan therapeutic preparation is selected from the homo-glycans fuc100 and fru100. In some embodiments, the glycan therapeutic preparation comprises man100.

In some embodiments, the preparation of glycan therapeutics comprises a mixture of two glycan units A and B selected independently from i) to vii) above, wherein A and B may be selected from the same or a different group i) to vii) and wherein A and B may be selected in any desired ratio (e.g. anywhere from 1-99% A and 99-1% B, not exceeding 100%).

For example, in some embodiments, the glycan therapeutic preparation is selected from the hetero-glycans ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 and glu90gly10.

In some embodiments, the preparation of glycan therapeutics comprises a mixture of three glycan units A, B and C selected independently from i) to vii) above, wherein A, B and C may be selected from the same or a different group i) to vii) and wherein A, B and C may be selected in any desired ratio (e.g. anywhere from 1-99% A, 1-99% B, 1-99% C, not exceeding 100%).

For example, in some embodiments, the glycan therapeutic preparation is selected from the hetero-glycans xyl75glu12gal12, xyl33glu33gal33, glu33gal33fuc33, man52glu29gal19, and the hybrid glycan glu33gal33neu33.

In some embodiments, the preparation of glycan therapeutics comprises a mixture of four glycan units A, B, C and D selected independently from i) to vii) above, wherein A, B, C and D may be selected from the same or a different group i) to vii) and wherein A, B, C and D may be selected in any desired ratio (e.g. anywhere from 1-99% A, 1-99% B, 1-99% C, 1-99% D, not exceeding 100%).

In some embodiments, the preparation of glycan therapeutics comprises a mixture of five glycan units A, B, C, D and E selected independently from i) to vii) above, wherein A, B, C, D and E may be selected from the same or a different group i) to vii) and wherein A, B, C, D and E may be selected in any desired ratio (e.g. anywhere from 1-99% A, 1-99% B, 1-99% C, 1-99% D, 1-99% E, not exceeding 100%).

In some embodiments, preparations of glycan therapeutics are provided, wherein at least one glycan unit is selected from the group consisting of a glucose, a galactose, an arabinose, a mannose, a fructose, a xylose, a fucose, and a rhamnose. In one embodiment, the glycan unit is not glucose. In one embodiment, the glycan unit is not galactose. In one embodiment, the glycan unit is not fructose. In one embodiment, the glycan unit is not fucose. In one embodiment, the glycan unit is not mannose. In one embodiment, the glycan unit is not arabinose. In one embodiment, the glycan unit is not rhamnose. In one embodiment, the glycan unit is not xylose.

In some embodiments, the preparation of glycan therapeutics comprises a desired mixture of two different monosaccharide glycan units, such as a mixture of, e.g., glucose and galactose, glucose and arabinose, glucose and mannose, glucose and fructose, glucose and xylose, glucose and fucose, glucose and rhamnose, galactose and arabinose, galactose and mannose, galactose and fructose, galactose and xylose, galactose and fucose, and galactose and rhamnose, arabinose and mannose, arabinose and fructose, arabinose and xylose, arabinose and fucose, and arabinose and rhamnose, mannose and fructose, mannose and xylose, mannose and fucose, and mannose and rhamnose, fructose and xylose, fructose and fucose, and fructose and rhamnose, xylose and fucose, xylose and rhamnose, and fucose and rhamnose, etc., e.g. a in a ratio of 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, or 1:100 or the reverse ratio thereof.

In some embodiments, the preparation of glycan therapeutics (e.g. oligosaccharides) comprises a desired mixture of three different monosaccharide glycan units, such as a mixture of, e.g. for glucose-containing glycan-therapeutic preparations, glucose, galactose and arabinose; glucose, galactose and mannose; glucose, galactose and fructose; glucose, galactose and xylose; glucose, galactose and fucose, glucose, galactose and rhamnose; glucose, arabinose, and mannose; glucose, arabinose and fructose; glucose, arabinose and xylose; glucose, arabinose and fucose; glucose, arabinose and rhamnose; glucose, mannose and fructose; glucose, mannose and xylose; glucose, mannose and fucose; glucose, mannose rhamnose; glucose, fructose and xylose; glucose, fructose and fucose; glucose, fructose and rhamnose; glucose, fucose and rhamnose, etc., e.g. a in a ratio of 1:1:1, 1:2:1, 1:3:1, 1:4:1, 1:5:1, 1:6:1, 1:7:1, 1:8:1, 1:9:1, 1:10:1, 1:12:1, 1:14:1, 1:16:1, 1:18:1, 1:20:1, 1:1:2, 1:2:2, 1:3:2, 1:4:2, 1:5:2, 1:6:2, 1:7:2, 1:8:2, 1:9:2, 1:10:2, 1:1:3, 1:2:3, 1:3:3, 1:4:3, 1:5:3, 1:6:3, 1:7:3, 1:8:3, 1:9:3, 1:10:3, 1:1:4, 1:2:4, 1:3:4, 1:4:4, 1:5:4, 1:6:4, 1:7:4, 1:8:4, 1:9:4, 1:10:4, 1:1:5, 1:2:5, 1:3:5, 1:4:5, 1:5:5, 1:6:5, 1:7:5, 1:8:5, 1:9:5, 1:10:5, etc.

In some embodiments, preparations of glycan therapeutics are provided, wherein at least one glycan unit is a furanose sugar. In some embodiments, preparations of glycans are provided, wherein at least one glycan unit is a pyranose sugar. In some embodiments, glycan therapeutics comprise mixtures of furanose and pyranose sugars. In some embodiments, the furanose: pyranose sugar ratio in a preparation is about 0.1:1, 0.2:1, 0.3:1, 0.4:1, 0.5:1, 0.6:1, 0.7:1, 0.8:1, 0.9:1, 1:1, 1.2:1, 1.5:1, 1.7:1, 2:1, 2.2:1, 2.5:1, 2.7:1, 3:1, 4:1, 5:1, 6:1, 7:1, 8:1, 9:1, or about 10:1.

In some embodiments, the preparation of glycan therapeutics (e.g. oligosaccharides) comprises a desired mixture of furanose and pyranose sugars, e.g. of a desired ratio, such as: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150 furanose to and pyranose or pyranose to furanose.

In some embodiments, the preparation of glycan therapeutics comprises substantially all furanose or pyranose sugar, optionally comprising 1%, 2%, 3%, 4% 5%, 6%, 7%, 8%, 9%, 10%, 11%, 12%, 13%, 14%, 15%, 16%, 17%, 18%, 19%, or 20% of the respective other sugar.

In some embodiments, the preparation of glycan therapeutics comprises substantially all pyranose sugar and no more than about 0.1%, 02%, 0.5%, 1%, 2%, 3%, 4%, or no more than 5% of monomeric glycan units in the preparation in furanose form. In some embodiments, no more than 3%, 2% or no more than 1% of monomeric glycan units in the preparation are in furanose form.

In some embodiments, the preparation of glycan therapeutics does not comprise N-acetylgalactosamine or N-acetylglucosamine. In some embodiments, the preparation of glycans does not comprise sialic acid. In some embodiments, the preparation of glycan therapeutics does not comprise a lipid and fatty acid. In some embodiments, the preparation of glycan therapeutics does not comprise an amino acid.

In some embodiments, the preparation of glycan therapeutics does not comprise a detectable repeating unit. In some embodiments, the preparation of glycan therapeutics does not comprise a statistically significant amount of a repeating unit. In some embodiments, the repeating unit has a DP of at least 2, 3, 4, 5, or at least 6 glycan units. For example, hyaluronan is a glycosaminoglycan with a repeating disaccharide unit consisting of two glucose derivatives, glucuronate (glucuronic acid) and N-acetylglucosamine. The glycosidic linkages are beta (1->3) and beta (1->4). Cellulose is a polymer made with repeated glucose units linked together by beta-linkages. The presence and amount of repeating units can be determined, e.g. using by total hydrolysis (e.g. to determine the proportion of glycan units), methylation analysis (e.g. to determine the distribution of bond types), and HSQC (e.g. to determine the distribution of alpha- and beta-glycosides). Statistical methods to determine significance are known by one of skill in the art.

If desired, the monosaccharide or oligosaccharide glycan units of the glycans are further substituted or derivatized, e.g., hydroxyl groups can be etherified or esterified. For example, the glycans (e.g. oligosaccharide) can contain modified saccharide units, such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). The degree of substitution (DS, average number of hydroxyl groups per glycosyl unit) can be 1, 2, or 3, or another suitable DS. In some embodiments, 1%, 2%, 3%, 4% 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 80%, 85%, 90%, 95%, 96%, 97%, 98%, 99%, or 100% of glycan units are substituted or derivatized. In some embodiments, the degree of substitution varies between subunits, e.g., a certain percentage is not derivatized, exhibits a DS of 1, exhibits a DS of 2, or exhibits a DS of 3. Any desired mixture can be generated, e.g. 0-99% of subunits are not derivatized, 0-99% of subunits exhibit a DS of 1, 0-99% of subunits exhibit a DS of 2, and 0-99% of subunits exhibit a DS of 3, with the total making up 100%. The degree of substitution can be controlled by adjusting the average number of moles of substituent added to a glycosyl moiety (molar substitution (MS)). The distribution of substituents along the length of the glycan oligo- and polysaccharide chain can be controlled by adjusting the reaction conditions, reagent type, and extent of substitution. In some embodiments, the monomeric subunits are substituted with one or more of an acetate ester, sulfate half-ester, phosphate ester, or a pyruvyl cyclic acetal group.

Solubility

In some embodiments, the glycan therapeutic preparations are highly branched, e.g. have an average DB of at least 0.01, 0.05, or 0.1. In some embodiments, the glycan therapeutic preparations have an average DB of about 0.01 to about 0.05, 0.01 to 0.1, 0.05 to 0.1, or about 0.1 to about 0.2. In some embodiments, the glycan therapeutic preparations comprising branched oligosaccharide are highly soluble. In some embodiments, glycan therapeutic preparations can be concentrated to at least to 55 Brix, 65 Brix, 60 Brix, 65 Brix, 70 Brix, 75 Brix, 80 Brix, or at least 85 Brix without obvious solidification or crystallization at 23° C. (final solubility limit). In some embodiments, glycan therapeutic preparations can be concentrated to about 50-60 Brix, 60-70 Brix, 70-80 Brix, 55-65 Brix, 65-75 Brix, or to about 75-85 Brix. In some embodiments, glycan therapeutic preparations can be concentrated to about 50, 55, 60, 65, 70, 75, 80, or about 85 Brix without obvious solidification or crystallization at 23° C. (final solubility limit).

In some embodiments, glycan therapeutic preparations are concentrated to at least about 0.5 g/ml, 1 g/ml, 1.5 g/ml, 2 g/ml, 2.5 g/ml, 3 g/ml, 3.5 g/ml or at least 4 g/ml without obvious solidification or crystallization at 23° C. (final solubility limit).

In some embodiments, the glycan therapeutic preparations (e.g. oligosaccharides) are branched, e.g. have an average DB of at least 0.01, 0.05, or 0.1 and has a final solubility limit in water of at least about 70 Brix, 75 Brix, 80 Brix, or at least about 85 Brix at 23° C. or is at least about 1 g/ml, 2 g/ml or at least about 3 g/ml.

In some embodiments, the preparation of glycan therapeutics has a final solubility limit of at least 0.001 g/L, 0.005 g/L, 0.01 g/L, 0.05 g/L, 0.1 g/L, 0.2 g/L, 0.3 g/L, 0.4 g/L, 0.5 g/L, 0.6 g/L, 0.7 g/L, 0.8 g/L, 0.9 g/L, 1 g/L, 5 g/L, 10 g/L, 20 g/L, 30 g/L, 40 g/L, 50 g/L, 100 g/L, 200 g/L, 300 g/L, 400 g/L, 500 g/L, 600 g/L, 700 g/L, 800 g/L, 900 g/L, 1000 g/L in deionized water, or in a suitable buffer such as, e.g., phosphate-buffered saline, pH 7.4 or similar physiological pH and at 20° C. In some embodiments, the preparation of glycan therapeutics is greater than 50%, greater than 60%, greater than 70%, greater than 80%, greater than 90%, greater than 95%, greater than 96%, greater than 97%, greater than 98%, greater than 99%, or greater than 99.5% soluble with no precipitation observed at a concentration of greater than 0.001 g/L, 0.005 g/L, 0.01 g/L, 0.05 g/L, 0.1 g/L, 0.2 g/L, 0.3 g/L, 0.4 g/L, 0.5 g/L, 0.6 g/L, 0.7 g/L, 0.8 g/L, 0.9 g/L, 1 g/L, 5 g/L, 10 g/L, 20 g/L, 30 g/L, 40 g/L, 50 g/L, 100 g/L, 200 g/L, 300 g/L, 400 g/L, 500 g/L, 600 g/L, 700 g/L, 800 g/L, 900 g/L, 1000 g/L in deionized water, or in a suitable buffer such as, e.g., phosphate-buffered saline, pH 7.4 or similar physiological pH and at 20° C.

Sweetness

In some embodiments, the preparation of glycan therapeutics has a desired degree of sweetness. For example, sucrose (table sugar) is the prototype of a sweet substance. Sucrose in solution has a sweetness perception rating of 1, and other substances are rated relative to this (e.g., fructose, is rated at 1.7 times the sweetness of sucrose). In some embodiments, the sweetness of the preparation of glycan therapeutics ranges from 0.1 to 500,000 relative to sucrose. In some embodiments, the relative sweetness is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 90, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10000, 25000, 50000, 75000, 100000, 150000, 200000, 250000, 300000, 350000, 40000, 450000, 500000, or more than 500,000 relative to sucrose (with sucrose scored as one). In some embodiments, the preparation of glycan therapeutics is mildly sweet, or both sweet and bitter.

In some embodiments, the preparation of glycan therapeutics, e.g. a preparation that is substantially DP2+ or DP3+(e.g. at least 80%, 90%, or at least 95%, or a fractionated preparation of DP2+ or DP3+), is substantially imperceptible as sweet and the relative sweetness is about 0, 0.0001, 0.001, 0.005, 0.01, 0.05, 0.1, 0.2, 0.3, 0.4, 0.5, 0.6, 0.7, 0.8, or about 0.9 relative to sucrose (with sucrose scored as one).

Identification and Characterization of Glycan Therapeutic Preparations

If desired, the glycan therapeutic preparations can be characterized by any method known in the art and by the methods described herein.

The molar percentage of species with a degree of polymerization (DP) of n (denoted here as DP(n)) in a population is determined by high performance liquid chromatography (HPLC), e.g., on an Agilent 1260 BioInert series instrument equipped with a refractive index (RI) detector and a variety of columns familiar to those skilled in the art using water as the mobile phase. The columns are selected from chemistries including HILIC, metal coordination, and aqueous size-exclusion chromatography that best isolate the species of interest. Molar % DP(n) is determined by the formula:

% DP($n$)=100*AUC[DP($n$)]/AUC[DP(total)], where AUC is defined as the area under the curve for the species of interest as determined by calibration to known standards. The molar percentage of glycosidic bond isomers (% alpha and beta) are determined by nuclear magnetic resonance (NMR) spectroscopy using a variety of 2D techniques familiar to those skilled in the art. Alpha- and beta-isomers may be distinguished, e.g., by their distinct shift on the NMR spectrum and the molar percentage is determined by the formula:

% (glycosidic isomer $n$) of glycosidic bonds=100*AUC [shift (isomer $n$)]/AUC [shift (isomer alpha+isomer beta)], where AUC is defined as the area under the curve at a specific shift value known to represent the desired isomer n. The molar percentage of regiochemical isomers is determined in an analogous fashion using the formula:

% (regioisomer $n$) of regioisomers=100*AUC [shift (regioisomer $n$)]/AUC [shift (all regioisomers)].

The relative percentage of monomeric sugars making up the oligomeric population is determined, e.g., by total acidic digestion of the oligomeric sample followed by conversion to the alditol acetate followed by gas chromatographic (GC) analysis of the resultant monomeric solutions compared against GC of known standards. The molar percentage of monomer(n), where n can be any sugar, is determined by the formula:

% (sugar $n$)=100*AUC [sugar $n$]/AUC [total of all monomeric sugars].

In some embodiments, the solubility of the preparation of glycan therapeutics can be controlled, e.g. by selecting the charge, structure (e.g. DP, degree of branching), and/or derivatization of the glycan units.

For glycan therapeutic preparations, the monomeric building blocks (e.g. the monosaccharide or glycan unit composition), the anomeric configuration of side chains, the presence and location of substituent groups, degree of polymerization/molecular weight and the linkage pattern can be identified by standard methods known in the art, such as, e.g. methylation analysis, reductive cleavage, hydrolysis, GC-MS (gas chromatography-mass spectrometry), MALDI-MS (Matrix-assisted laser desorption/ionization-mass spectrometry), ESI-MS (Electrospray ionization-mass spectrometry), HPLC (High-Performance Liquid chromatography with ultraviolet or refractive index detection), HPAEC-PAD (High-Performance Anion-Exchange chromatography with Pulsed Amperometric Detection), CE (capillary electrophoresis), IR (infra red)/Raman spectroscopy, and NMR (Nuclear magnetic resonance) spectroscopy techniques. For polymers of crystalline consistency, the crystal structure can be solved using, e.g., solid-state NMR, FT-IR (Fourier transform infrared spectroscopy), and WAXS (wide-angle X-ray scattering). The DP, DP distribution, and polydispersity can be determined by, e.g., viscosimetry and SEC (SEC-HPLC, high performance size-exclusion chromatography). Alien groups, end groups and substituents can be identified, e.g., using SEC with labeling, aqueous analytics, MALDI-MS, FT-IR, and NMR. To identify the monomeric components of the glycans methods such as, e.g. acid-catalyzed hydrolysis, HPLC (high performance liquid chromatography) or GLC (gas-liquid chromatography) (after conversion to alditol acetates) may be used. To determine the linkages present in the glycans, in one example, the polysaccharide is methylated with methyl iodide and strong base in DMSO, hydrolysis is performed, a reduction to partially methylated alditols is achieved, an acetylation to methylated alditol acetates is performed, and the analysis is carried out by GLC/MS (gas-liquid chromatography coupled with mass spectrometry). In some embodiments, to determine the polysaccharide sequence a partial depolymerization is carried out using an acid or enzymes to determine the structures. Possible structures of the polysaccharide are compared to those of the hydrolytic oligomers, and it is determined which one of the possible structures could produce the oligomers. To identify the anomeric configuration, in one example, the intact polysaccharide or a preparation of oligosaccharides are subjected to enzymatic analysis, e.g. they are contacted with an enzyme that is specific for a particular type of linkage, e.g., β-galactosidase, or a-glucosidase, etc., and NMR may be used to analyze the products.

For example, the distribution of (or average) degree of polymerization (DP) of a glycan therapeutic preparation may be measured by injecting a sample with a concentration of, e.g., 10-100 mg/mL onto an Agilent 1260 BioPure HPLC (or similar) equipped with a 7.8×300 mm BioRad Aminex HPX-42A column (or similar) and RI detector as described, e.g., in Gomez et al. (Purification, Characterization, and Prebiotic Properties of Pectic Oligosaccharides from Orange Peel Wastes, J Agric Food Chem, 2014, 62:9769). Alternatively, a sample with a concentration may be injected into a Dionex ICS5000 HPLC (or similar) equipped with a 4×250 mm Dionex CarboPac PA1 column (or similar) and PAD detector as described, e.g., in Holck et al., (Feruloylated and nonferuloylated arabino-oligosaccharides from sugar beet pectin selectively stimulate the growth of *bifidobacterium* spp. in human fecal in vitro fermentations, Journal of Agricultural and Food Chemistry, 2011, 59(12), 6511-6519). Integration of the resulting spectrum compared against a standard solution of oligomers allows determination of the average DP.

Distribution of molecular weights can be measured, e.g., by MALDI mass spectrometry. Oligosaccharide concentration can be measured with a Mettler-Toledo sugar refractometer (or similar) with the final value adjusted against a standardized curve to account for refractive differences between monomers and oligomers.

Distribution of glycoside regiochemistry can be characterized, e.g., by a variety of 2D-NMR techniques including COSY, HMBC, HSQC, DEPT, and TOCSY analysis using standard pulse sequences and a Bruker 500 MHz spectrometer. Peaks can be assigned by correlation to the spectra of naturally occurring polysaccharides with known regiochemistry.

In some embodiments, the relative peak assignment of a sample is dependent on a number of factors including the concentration and purity of the sample, the identity and quality of the solvent (e.g., the isotopically labeled solvent), and the pulse sequence utilized. As such, in embodiments, the relative peak assignment of, for example, a glycan comprising glucose may vary (e.g., by about 0.01 ppm, about 0.02 ppm, or about 0.05 ppm) when the NMR spectrum is obtained in similar conditions due to said factors. In these instances as used herein, the terms "corresponding peak" or "corresponding peaks" refer to NMR peaks associated with the same sample but that vary (e.g., by about 0.01 ppm, about 0.02 ppm, or about 0.05 ppm) due to factors including, for example, the concentration and purity of the sample, the identity and quality of the isotopically labeled solvent, and the pulse sequence utilized.

Monomeric compositions of oligomers may be measured, e.g., by the complete hydrolysis method in which a known amount of oligomer is dissolved into a strong acid at elevated temperature and allowed sufficient time for total hydrolysis to occur. The concentration of individual monomers may then be measured by the HPLC or GC methods described herein and known in the art to achieve relative abundance measurements as in Holck et al. Absolute amounts can be measured by spiking the HPLC sample with a known amount of detector active standard selected to prevent overlap with any of the critical signals.

The degree of branching in any given population may be measured by the methylation analysis method established, e.g., by Hakomori (J. Biochem. (Tokyo), 1964, 55, 205). With these data, identification of potential repeat units may be established by combining data from the total hydrolysis, average DP, and methylation analysis and comparing them against the DEPT NMR spectrum. Correlation of the number of anomeric carbon signals to these data indicates if a regular repeat unit is required to satisfy the collected data as demonstrated, e.g., in Harding, et al. (Carbohydr. Res. 2005, 340, 1107).

Preparation of glycan therapeutics (e.g. those comprising monosaccharide or disaccharide glycan units such as glucose, galactose, fucose, xylose, arabinose, rhamnose, and mannose) may be identified using one, two, three, or four of the following parameters: a) the presence of 2, 3, 4, 5, 6, 7 or more (e.g. at least 4 or 5) diagnostic anomeric NMR peaks each representing a different glycosidic bond type, b) an alpha- to beta-bond ratio between about 0.8 to 1 and about 5 to 1 (e.g. between about 1:1 and 4:1, commonly favoring the alpha bond type), c) at least 2 or at least 3 different glycoside regiochemistries from the list of 1,2-; 1,3-; 1,4-; and 1,6-substituted and at least 2 or at least 3 different glycoside regiochemistries from list of 1,2,3-; 1,2,4-; 1,2,6-; 1,3,4-; 1,3,6-; and 1,4,6-substituted, and d) a DP distribution in which at least 50%, 60%, 70% or at least 80% of the individual species have a DP of at least 2, at least 3, between 3 and 30 or between 5 and 25. In some embodiments, glycan therapeutic preparations have average properties (e.g., DP, DB, alpha:beta glycosidic bond ratio) that are distinct from naturally occurring preparations of oligosaccharides. These structural features may be analyzed and optionally quantified by any suitable method known in the art and those described herein. The glycan therapeutic preparations described herein have at least one, two, three, four, or at least five of the following characteristics:

(i) a distribution of molecular weights ranging, e.g. from about DP3 to about DP30 or from about DP5 to about DP25 that may be identified by quantitative mass spectrometry measurements, SEC-HPLC, IAC-HPLC, or IEC-HPLC;

(ii) a significant proportion of both alpha and beta bonds, with bond ratios, e.g., ranging from 0.8:1, 1:1, 2:1, 3:1, 4:1, to 5:1 (generally favoring the alpha stereochemistry) that may be identified by a variety of NMR techniques including the HSQC pulse sequence which allows explicit discrimination and quantitation of signals from alpha and beta glycosides. The presence of both alpha- and beta-glycosidic bonds in the observed ratios (see Table 6, showing the presence of a large proportion of both alpha and beta bonds across the single and multi-sugar glycans tested) in glycan therapeutic preparation of some embodiments, is distinct from preparations of naturally occurring oligo- or polysaccharides which generally favor one primary glycosidic stereochemistry and optionally comprise only a relatively small portion of the opposing stereochemistry;

(iii) presence of at least one, two, three or four glycoside regiochemistries that may be identified either by a fingerprint NMR process or by the permethylation branching identification developed by Hakomori, et al. In some embodiments, glycan therapeutic preparations have at least 0.1%, 0.2%, 0.5%, 1%, 2%, 3%, 4%, 5%, 6%, 7%, 8%, 9%, or at least 10% of one, two, three or four of the 1,2-; 1,3-; 1,4-, and 1,6-glycoside bond types. In some embodiments, glycan therapeutic preparations have at least 0.1%, 0.2%, 0.5%, 1%, 2%, 3%, 4%, 5%, 6%, 7%, 8%, 9%, or at least 10% of two of the 1,2-; 1,3-; 1,4-, and 1,6-glycoside bond types. In some embodiments, glycan therapeutic preparations have at least 0.1%, 0.2%, 0.5%, 1%, 2%, 3%, 4%, 5%, 6%, 7%, 8%, 9%, or at least 10% of three of the 1,2-; 1,3-; 1,4-, and 1,6-glycoside bond types. In some embodiments, glycan therapeutic preparations have at least 0.1%, 0.2%, 0.5%, 1%, 2%, 3%, 4%, 5%, 6%, 7%, 8%, 9%, or at least 10% of all four of the 1,2-; 1,3-; 1,4-, and 1,6-glycoside bond types. In some embodiments, the glycan therapeutic preparation additionally comprises at least 0.1%, 0.2%, 0.5%, 1%, 2%, 3%, 4% or at least 5% of branched bond types. In some embodiments, the glycan therapeutic preparation comprises at least 0.1%, 0.2%, 0.5%, 1%, 2%, 3%, 4% or at least 5% of at least one, two, or at least three branched bond types including 1,3,6-; 1,4,6-; or 1,2,4-glycosides. In some embodiments, the glycan therapeutic preparation comprises at least two branched bond types of 1,3,6-; 1,4,6-; or 1,2,4-glycosides. In some embodiments, the glycan therapeutic preparation comprises at least 0.1%, 0.2%, 0.5%, 1%, 2%, 3%, 4% or at least 5% of three branched bond types of 1,3,6-; 1,4,6-; or 1,2,4-glycosides. Sugars that do not have a hydroxyl group at a given position X will not will not have the 1,X-bond type, e.g. fucose (6-dehydroxy-galactose) will not have 1,6-glycosidic bonds but will have 1,2-; 1,3-; and 1,4-glycosidic bonds. In some embodiments, the glycan therapeutic preparation comprises at least 0.1%, 02%, 0.5%, 1%, 2%, or at least 3% of monomeric glycan units in furanose form. The presence of a large number of glycoside regiochemistries and branching (see FIG. 4 for 3 exemplary glycans) in glycan therapeutic preparation of some embodiments, is distinct from preparations of naturally occurring oligo- or polysaccharides which generally favor specific bond architectures. Although all of these regiochemistries are known to occur in oligosaccharides of natural sources, preparations of naturally sourced oligosaccharide do not comprise the number and complexity of regiochemistries that are exhibited by glycan therapeutic preparations of some embodiments.

Figure 5:
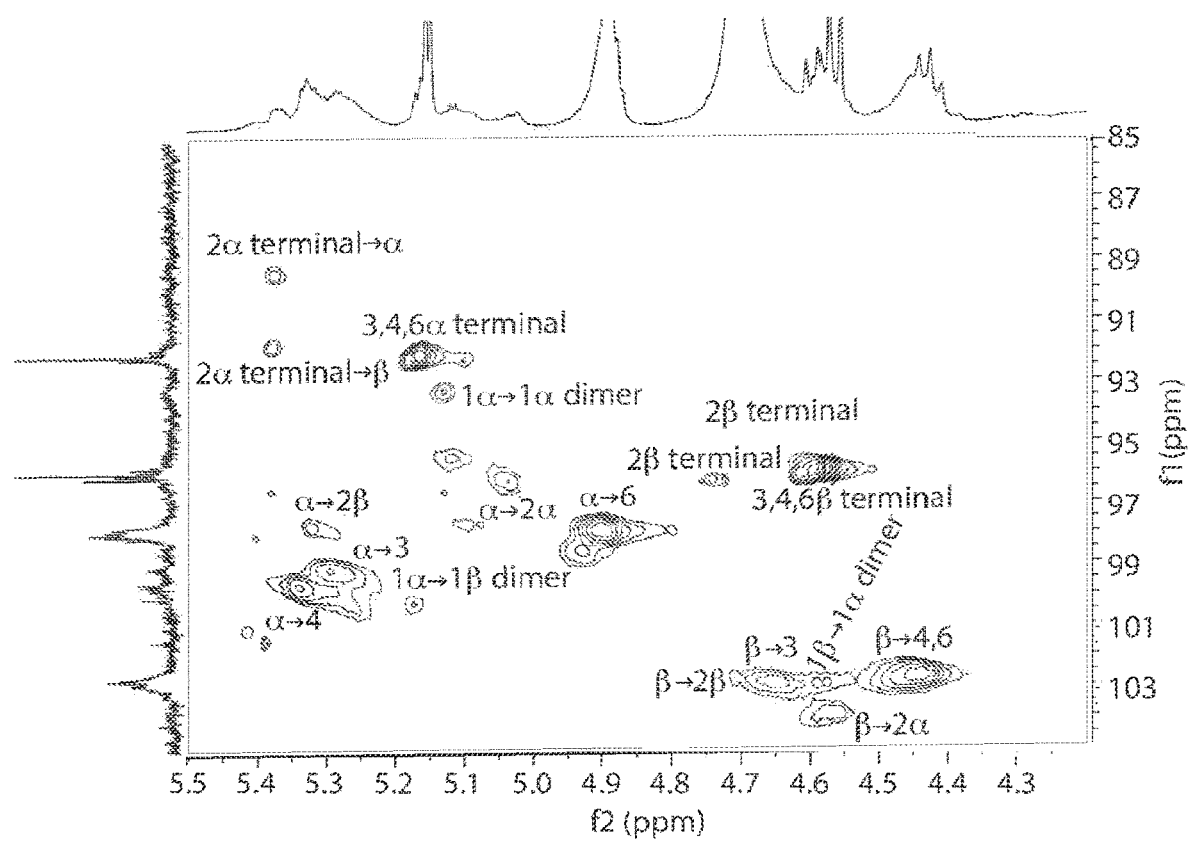
FIG. 5. A representative partial assignment of the peaks in the anomeric region of a glu100 sample $^1$H-$^{13}$C HSQC spectrum showing the separation between alpha and beta isomers in the $^1$H axis, with alpha isomers downfield ($^1$H>4.8 ppm in this case) and beta isomers upfield ($^1$H<4.8 ppm in this case). In addition, terminal and internal sugars can be distinguished in the $^{13}$C axis with terminal sugars upfield ($^{13}$C<94 ppm for alpha and $^{13}$C<100 ppm for beta in this case) and internal sugars downfield ($^{13}$C>94 ppm for alpha and $^{13}$C>100 ppm for beta in this case).

(iv) a distribution of glycosidic bonds that represents at least 50%, 60%, 70%, 80% or at least 90% of all possible combinations of regio- and stereochemistries. Individually, the regiochemical distribution can be determined by branching analysis and the stereochemical distribution can be determined by NMR. The HSQC-NMR. In some embodiments, the glycan therapeutic preparations exhibit a diversity of peaks in the anomeric region that are associated with a multiplicative combination of both regiochemistry and stereochemistry. In some embodiments, the glycan therapeutic preparation comprises at least two or at least three of alpha-1,2-; alpha-1,3-; alpha-1,4-; and alpha-1,6-glycosides and at least two, or at least three of beta-1,2-; beta-1,3-; beta-1,4-; and beta-1,6-glycosides. In some embodiments, the glycan therapeutic preparation comprises all four of alpha-1,2-; alpha-1,3-; alpha-1,4-; and alpha-1,6-glycosides and all four of beta-1,2-; beta-1,3-; beta-1,4-; and beta-1,6-glycosides. As an exemplar, HSQC of a glu100 preparation shows that the preparation contains all alpha-1,2-; alpha-1,3-; alpha-1,4-; and alpha-1,6-glycosides as well as all beta-1,2-; beta-1,3-; beta-1,4-; and beta-1,6-glycosides. Sugars that do not have a hydroxyl group at a given position X will not will not have the 1,X-bond type, e.g. fucose (6-dehydroxy-galactose) will not have 1,6-glycosidic bonds but will have 1,2-; 1,3-; and 1,4-glycosidic bonds;

(v) a unique HSQC "fingerprint" that is the result of the additive nature of the HSQC pulse sequence. For any given glycan, the HSQC spectra allow the identification of peaks that are unique to specific regio- and stereochemical bond arrangement. For example, FIG. 5 shows a partial assignment of the spectra of a glu100 preparation demonstrating how these peaks may be used to identify specific glycosidic regio- and stereochemistries. Component glycan units (e.g. sugars) within a glycan demonstrate spin-isolation in the HSQC pulse sequence and the HSQC spectrum of any glycan consisting of multiple sugars is the sum of peaks of its individual sugars. Glycan unit constituents (e.g. monomers) can be identified by an HSQC spectrum that shows 4, 5, 6 or more of the peaks listed in Table 7 for each of its component glycan units (e.g. sugars). The spectra in FIGS. 3 a-c exemplify this by comparing the spectra of preparations of glu100, gal100, and glu50gal50.

Pharmaceutical Compositions, Medical Foods, Supplements, and Unit Dosage Forms

Provided herein are pharmaceutical compositions comprising glycan therapeutic preparations. Further provided herein are medical foods comprising glycan therapeutic preparations. Still further provided herein are dietary supplements comprising glycan therapeutic preparations. Optionally, the pharmaceutical compositions, medical foods and dietary supplements comprising glycan therapeutic preparations further comprise a second (or third, fourth, etc.) therapeutic agent or active compound. In one embodiment, the agent or compound is a prebiotic substance, such as a dietary fiber. In one embodiment, the agent or compound is a probiotic bacterium. In one embodiment, the agent or compound is a micronutrient, such as a vitamin, mineral or polyphenol compound. In one embodiment, the agent or compound is a therapeutic drug, such as, e.g., an anti-cancer drug, a pain management drug, a drug that manages treatment side-effects, a drug that manages metabolism, an anti-inflammatory drug, or an anti-microbial agent.

In some embodiments, the pharmaceutical compositions and medical foods and dietary supplements comprising glycan therapeutic preparations do not contain a prebiotic substance. In some embodiments, the pharmaceutical compositions and medical foods and dietary supplements comprising glycan therapeutic preparations do not contain a probiotic bacterium.

In some embodiments, the pharmaceutical compositions or medical foods and dietary supplements comprise a glycan therapeutic preparation of xyl100, rha100, ara100, gal100, glu100, fuc100, fru100 or man100.

In some embodiments, the pharmaceutical compositions or medical foods and dietary supplements comprise a glycan therapeutic preparation of ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 or glu90gly10.

In some embodiments, the pharmaceutical compositions or medical foods and dietary supplements comprise a glycan therapeutic preparation of xyl75glu12gal12, xyl33glu33gal33, glu33gal33fuc33, man52glu29gal19, and the hybrid glycan glu33gal33neu33.

In some embodiments, the pharmaceutical compositions or medical foods and dietary supplements comprise a glycan therapeutic preparation of glu100, ara100, xyl100, glu50gal50, man52glu29gal19, or glu33gal33fuc33.

In some embodiments, the pharmaceutical compositions or medical foods and dietary supplements comprise a glycan therapeutic preparation of glu100 and man52glu29gal19.

In some embodiments, the pharmaceutical compositions or medical foods and dietary supplements comprise a glycan therapeutic preparation of man100.

In some embodiments, the pharmaceutical compositions or medical foods and dietary supplements comprise a glycan therapeutic preparation of xyl100.

In some embodiments, pharmaceutical compositions and medical foods and dietary supplements comprising glycan therapeutic preparations (and kits comprising same) comprise one or more micronutrient. In some embodiments, the micronutrient is selected from the group consisting of a trace mineral, choline, a vitamin, and a polyphenol.

In some embodiments, the micronutrient is a trace metal. Trace minerals suitable as a micronutrient include boron, cobalt, chromium, calcium, copper, fluoride, iodine, iron, magnesium, manganese, molybdenum, selenium, and zinc.

In some embodiments, the micronutrient is a vitamin. Vitamins suitable as a micronutrient include Vitamin B complex, Vitamin B1 (thiamin), Vitamin B2 (riboflavin), Vitamin B3 (niacin), Vitamin B5 (pantothenic acid), Vitamin B6 group (pyridoxine, pyridoxal, pyridoxamine), Vitamin B7 (biotin), Vitamin B8 (ergadenylic acid), Vitamin B9 (folic acid), Vitamin B12 (cyanocobalamin), Choline, Vitamin A (retinol), Vitamin C (ascorbic acid), Vitamin D, Vitamin E (tocopherol), Vitamin K, carotenoids (alpha carotene, beta carotene, cryptoxanthin, lutein, lycopene) and zeaxanthin.

In some embodiments, the micronutrient is a polyphenol. Polyphenols are chemical compounds or molecules that are characterized by having at least one aromatic ring with one or more hydroxyl groups. In some embodiments, the polyphenol is a synthetic polyphenol or a naturally occurring polyphenol. In some embodiments, the polyphenol is a naturally occurring polyphenol and is derived from plant source material.

In some embodiments, the polyphenol is a flavonoid or catechin. In some embodiments, the flavonoid or catechin is selected from anthocyanins, chalcones, dihydrochalcones, dihydroflavonols, flavanols, flavanones, flavones, flavonols and isoflavonoids. In some embodiments, the polyphenol is a lignan.

In some embodiments, the polyphenol is selected from alkylmethoxyphenols, alkylphenols, curcuminoids, furanocoumarins, hydroxybenzaldehydes, hydroxybenzoketones, hydroxycinnamaldehydes, hydroxycoumarins, hydroxyphenylpropenes, methoxyphenols, naphtoquinones, phenolic terpenes, and tyrosols. In some embodiments, the polyphenol is a tannin or tannic acid.

In some embodiments, the polyphenol is selected from hydroxybenzoic acids, hydroxycinnamic acids, hydroxyphenylacetic acids, hydroxyphenylpropanoic acids, and hydroxyphenylpentanoic acids. In some embodiments, the polyphenol is a stilbene.

In some embodiments, the pharmaceutical compositions and medical foods and dietary supplements comprising glycan therapeutic preparations described herein further comprise a prebiotic substance or preparation thereof.

Prebiotics include various galactans and carbohydrate based gums, such as *psyllium*, guar, carrageen, gellan, lactulose, and konjac. In some embodiments, the prebiotic is one or more of galactooligosaccharides (GOS), lactulose, raffinose, stachyose, lactosucrose, fructo-oligosaccharides (FOS, e.g. oligofructose or oligofructan), inulin, isomalto-oligosaccharide, xylo-oligosaccharides (XOS), paratinose oligosaccharide, isomaltose oligosaccharides (IMOS), trans-galactosylated oligosaccharides (e.g. transgalacto-oligosaccharides), transgalactosylate disaccharides, soybean oligosaccharides (e.g. soyoligosaccharides), chitosan oligosaccharide (chioses), gentiooligosaccharides, soy- and pectin-oligosaccharides, glucooligosaccharides, pecticoligosaccharides, palatinose polycondensates, difructose anhydride III, sorbitol, maltitol, lactitol, polyols, polydextrose, linear and branched dextrans, pullalan, hemicelluloses, reduced paratinose, cellulose, beta-glucose, beta-galactose, beta-fructose, verbascose, galactinol, xylan, inulin, chitosan, beta-glucan, guar gum, gum arabic, pectin, high sodium alginate, and lambda carrageenan, or mixtures thereof.

In some embodiments, the pharmaceutical compositions and medical foods and dietary supplements comprising glycan therapeutic preparations further comprise a probiotic bacterium or preparation thereof, e.g., derived from bacterial cultures that are generally recognized as safe (GRAS) or known commensal or probiotic microbes.

Examples of suitable probiotics include organisms classified as genera *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacillus, Bacillus, Enterococcus, Escherichia, Streptococcus, Saccharomyces, Streptomyces*, and family *Christensenellaceae*. Non-exclusive examples of probiotic bacteria that can be used in the methods and compositions described herein include *L. acidophilus, Lactobacillus* species, such as *L. crispatus, L. casei, L. rhamnosus, L. reuteri, L. fermentum, L. plantarum, L. sporogenes*, and *L. bulgaricus*, as well as *Bifidobacterium* species, such as *B. lactis, B. animalis, B. bifidum, B. longum, B. adolescentis*, and *B. infantis*. Yeasts, such as *Saccharomyces boulardii*, are also suitable as probiotics for administration to the gut, e.g. via oral dosage forms or foods. For example, yogurt is a product which already contains bacteria species, such as *Lactobacillus bulgaricus* and *Streptococcus thermophilus*.

Beneficial bacteria may include one or more of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus*, and *Streptococcus*, and/or one or more of the species *Akkermansia* municiphilia, minuta, *Clostridium coccoides, Clostridium leptum, Clostridium scindens, Dialister invisus, Eubacterium rectal, Eubacterium eligens, Faecalibacterium prausnitzii, Streptococcus salivarius*, and *Streptococcus thermophilus*. In some embodiments, the probiotic or commensal bacteria include one or more of the bacteria listed in Tables 1, 3, and 4.

Beneficial bacteria for the modulation of the gastrointestinal microbiota may include bacteria that produce organic acids (e.g. SCFAs) or that produce cytotoxic or cytostatic agents (to inhibit pathogenic growth), such as, e.g., hydrogen peroxide ($H_2O_2$) and bacteriocins. Bacteriocins are small antimicrobial peptides which can kill both closely-related bacteria, or exhibit a broader spectrum of activity (e.g., nisin).

The prebiotic substances and probiotic strains that may be combined with glycan therapeutics described herein to produce a composition may be isolated at any level of purity by standard methods and purification can be achieved by conventional means known to those skilled in the art, such as distillation, recrystallization and chromatography. If desired, the cultivated bacteria may be used in the composition. The bacteria may be separated from the culture broth by any method including, without limitations, centrifugation, filtration or decantation. The cells separated from the fermentation broth are optionally washed by water, saline (0.9% NaCl) or with any suitable buffer. The wet cell mass obtained may be dried by any suitable method, e.g., by lyophilization.

In some embodiments, the probiotic bacteria are lyophilized vegetative cells. In some embodiments, preparations of spores from sporulating probiotic bacteria are used.

In one embodiment, the pharmaceutical compositions, medical foods, or dietary supplements comprise a glycan therapeutic preparation and probiotics whose viability has been partially attenuated (e.g. a mixture comprising 10%, 20%, 30%, 40%, 50% or more non-viable bacteria), or probiotics consisting primarily of non-viable microbes (e.g. 95%, 96%, 97%, 98%, 99%, 99.9% or 100%). The compositions may further comprise microbial membranes and/or cell walls that have been isolated and purified from microbes or microbial vesicles. If desired, the probiotic organism(s) can be incorporated into the pharmaceutical glycan therapeutic composition as a culture in water or another liquid or semisolid medium in which the probiotic remains viable. In another technique, a freeze-dried powder containing the probiotic organism may be incorporated into a particulate material or liquid or semisolid material comprising the glycan preparation by mixing or blending.

In some embodiments, the pharmaceutical compositions and medical foods and dietary supplements comprising glycan therapeutic preparations further comprise a second therapeutic agent or preparation thereof, such as a drug.

For example, the second therapeutic agent is an anti-cancer drug. Examples of anti-cancer drugs include: checkpoint inhibitors (such as, e.g., anti-PD-1, anti-PD-L1, anti-CTLA4, anti-TIM-3, anti-LAG-3); vaccines (such as, e.g., autologous cancer vaccines, allogeneic cancer vaccines, neoantigen cancer vaccines, shared antigen cancer vaccines (e.g. NY-ESO-1)); targeted kinase inhibitors (such as, e.g., Imatinib mesylate, Ibrutinib, Neratinib, Palpociclib, Erlotinib, Lapatinib); antibodies (such as, e.g., Bevacizumab, Trastuzumab, Rituximab, Cetuximab); chemotherapeutics (such as, e.g., irinotecan, 5-flurouracil, lenalidomide, capecitabine, docetaxel), antibody-drug conjugates (e.g. ado-trastuzumab emtansine), and any other anti-cancer drug mentioned elsewhere herein.

For example, the second therapeutic agent is a pain-management drug. In some embodiments, the pain-management drug is an opioid, such as, e.g., codeine, fentanyl, hydrocodone, hydrocodone/acetaminophen, hydromorphone, meperidine, methadone, morphine, oxycodone, oxycodone and acetaminophen, or oxycodone and naloxone. In other embodiments, the pain-management drug is a non-opioid, such as, e.g., acetaminophen or nonsteroidal anti-inflammatory drugs (NSAIDs), such as aspirin and ibuprofen.

For example, the second therapeutic agent is an antidepressant, such as, e.g., amitriptyline, imipramine, doxepin and trazodone.

For example, the second therapeutic agent is an antiepileptic, such as, e.g., gabapentin.

For example, the second therapeutic agent is a steroid, such as, e.g. prednisone or dexamethasone.

In some embodiments, the second therapeutic agent is a drug for managing a GI tract motility disorder, such as, e.g., acute diarrhea, chronic diarrhea, acute constipation, or chronic constipation. Drugs for GI motility disorders include opioids, antibiotics, bile acid sequestrants and heavy metal containing compounds (bismuth subsalicylate). Drugs to manage diarrhea include, but are not limited to liperamide, diphenoxylate with atropine, Cholestyramine, and bismuth subsalicylate. Drugs to manage constipation include, but are not limited to magnesium citrate, magnesium hydroxide, magnesium sulfate/potassium sulfate/sodium sulfate, sodium biphosphate/sodium phosphate, lactulose, sennosides, bisacodyl, polyethylene glycol (e.g., PEG3350), docusate, polycarbophil, *psyllium*, methylcellulose, and mineral oil.

In some embodiments, the therapeutic agent is an anti-inflammatory agent, such as, e.g., an NSAID, including ibuprofen, naproxen sodium, aspirin, celecoxib, sulindac, oxaprozin, salsalate, diflunisal, piroxicam, indomethacin, etodolac, meloxicam, nabumetone, ketorolac tromethamine, naproxen/esomeprazole, or diclofenac.

In some embodiments, the second therapeutic agent is an antimicrobial agent, such as an antibiotic, an antifungal agent, or an antiviral. Antibiotics include aminoglycosides, such as amikacin, gentamicin, kanamycin, neomycin, streptomycin, and tobramycin; cephalosporins, such as cefamandole, cefazolin, cephalexin, cephaloglycin, cephaloridine, cephalothin, cephapirin, and cephradine; macrolides, such as erythromycin and troleandomycin; penicillins, such as penicillin G, amoxicillin, ampicillin, carbenicillin, cloxacillin, dicloxacillin, methicillin, nafcillin, oxacillin, phenethicillin, and ticarcillin; polypeptide antibiotics, such as bacitracin, colistimethate, colistin, polymyxin B; tetracyclines, such as chlortetracycline, demeclocycline, doxycycline, methacycline, minocycline, tetracycline, and oxytetracycline; and miscellaneous antibiotics such as chloramphenicol, clindamycin, cycloserine, lincomycin, rifampin, spectinomycin, vancomycin, viomycin and metronidazole.

The glycan therapeutic preparations described herein and the therapeutic agent or active compound may be commingled or mixed in a single pharmaceutical composition or medical food or dietary supplement. In other embodiments, they may be contained in separate containers (and/or in various suitable unit dosage forms) but packaged together in one or more kits. In some embodiments, the preparations or compositions are not packaged or placed together.

In some embodiments, a pharmaceutical composition comprises between 0.1% and 100% glycan therapeutic preparation by w/w, w/v, v/v or molar %. In another embodiment, a pharmaceutical composition comprises about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% of glycan therapeutic preparation by w/w, w/v, v/v or molar %. In one embodiment, a pharmaceutical composition comprises about 1-90%, about 10-90%, about 20-90%, about 30-90%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 90-96%, about 93-96%, about 93-95%, about 94-98%, about 93-99%, or about 90-100% of glycan therapeutic preparation by w/w, w/v, v/v or molar %.

Optionally, the pharmaceutical compositions and medical foods and dietary supplements comprising glycan therapeutic preparations comprise one or more excipients or carriers, including diluents, binders, disintegrants, dispersants, lubricants, glidants, stabilizers, surfactants, flavoring agents, and colorants. The pharmaceutical composition can comprise from about 1% to about 90% of the one or more excipients or carriers by w/w, w/v, v/v or molar %. For example, the pharmaceutical composition can comprise about 1-90%, 1-75%, 1-60%, 1-55%, 1-50%, 1-45%, 1-40%, 1-25%, 1-15%, 1-10%, 10-90%, 10-75%, 10-60%, 10-55%, 10-50%, 10-45%, 10-40%, 10-25%, 10-15%, 15-90%, 15-75%, 15-60%, 15-55%, 15-50%, 15-45%, 15-40%, 15-25%, 25-90%, 25-75%, 25-60%, 25-55%, 25-50%, 25-45%, 25-40%, 40-90%, 40-75%, 40-60%, 40-55%, 40-50%, 40-45%, 45-90%, 45-75%, 45-60%, 45-55%, 45-50%, 50-90%, 50-75%, 50-60%, 50-55%, 55-90%, 55-75%, 55-60%, 60-90%, 60-75%, 75-90% of the one or more excipients or carriers by w/w, w/v, v/v or molar %.

Pharmaceutical carriers or vehicles suitable for administration of the pharmaceutical glycan therapeutic compositions provided herein include all such carriers known to those skilled in the art to be suitable for the particular mode of administration. In addition, the compositions can one or more components that do not impair the desired action, or with components that supplement the desired action, or have another action.

Dosage Forms

The glycan therapeutic preparations described herein may be formulated into any suitable dosage form, e.g. for oral or enteral administration or formulated for injection. The dosage forms described herein can be manufactured using processes that are known to those of skill in the art. The dosage form may be suitable for any route of administration, including orally or parenterally, such as intravenously, intramuscularly, subcutaneously, intraorbitally, intracapsularly, intraperitoneally, intrarectally, intracisternally, intratumorally, intravasally, intradermally or by passive or facilitated absorption through the skin.

The dosage form may be a packet, such as any individual container that contains a pharmaceutical glycan therapeutic composition in the form of, e.g., a liquid (wash/rinse), a gel, a cream, an ointment, a powder, a tablet, a pill, a capsule, a depository, a single-use applicator or medical device (e.g. a syringe). For example, provided is also an article of manufacture, such as a container comprising a unit dosage form of the pharmaceutical glycan therapeutic composition, and a label containing instructions for use of such glycan therapeutic.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds and/or other agents (e.g., prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

In one embodiment, a provided glycan therapeutic composition includes a softgel formulation. A softgel can contain a gelatin based shell that surrounds a liquid fill. The shell can be made of gelatin, plasticizer (e.g., glycerin and/or sorbitol), modifier, water, color, antioxidant, or flavor. The shell can be made with starch or carrageenan. The outer layer can be enteric coated. In one embodiment, a softgel formulation can include a water or oil soluble fill solution, or suspension of a composition covered by a layer of gelatin.

Formulations for oral use may also be presented in a liquid dosage from. Liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydoxybenzoate or sorbic acid, and, if desired, conventional flavoring or coloring agents. In some embodiments, liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form may comprise an effective amount of a glycan therapeutic and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for administration. Examples of such vehicles and additives can be found in Remington's Pharmaceutical Sciences, 22nd edition (2012).

The pharmaceutical compositions provided herein can be in unit-dosage forms or multiple-dosage forms. A unit-dosage form, as used herein, refers to physically discrete unit suitable for administration to human in need thereof. In an embodiment, the unit-dosage form is provided in a package. Each unit-dose can contain a predetermined quantity of an active ingredient(s) sufficient to produce the desired therapeutic effect, in association with other pharmaceutical carriers or excipients. Examples of unit-dosage forms include ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include vials, bottles of tablets or capsules, or bottles of pints or gallons. In another embodiment the multiple dosage forms comprise different pharmaceutically active agents. For example a multiple dosage form can be provided which comprises a first dosage element comprising a composition comprising a glycan therapeutic and a second dosage element comprising a second active compound or therapeutic agent (e.g. an anti-cancer drug). The dosage elements can be in a modified release form. In this example, a pair of dosage elements can make a single unit dosage. In one embodiment, a kit is provided comprising multiple unit dosages, wherein each unit comprises a first dosage element comprising a composition comprising a glycan therapeutic and a second dosage element comprising a second active compound or therapeutic agent (e.g., a pharmaceutical agent, a probiotic, a prebiotic, a micronutrient, etc. or a combination thereof).

In some embodiments, the unit-dosage form comprises between about 0.001 mg to about 10 g of the glycan therapeutic. For example, the unit-dosage form may comprise about 0.001 mg to about 9.5 g, about 0.005 mg to about 9 g, about 0.01 mg to about 8.5 g, about 0.05 mg to about 8 g, about 0.075 mg to about 7.5 g, about 0.1 mg to about 7 g, about 0.25 mg to about 6.5 g, about 0.5 mg to about 6 g, about 0.75 mg to about 5.5 g, about 1 mg to about 5 g, about 2.5 mg to about 4.5 g, about 5 mg to about 4 g, about 7.5 mg to about 3.5 g, about 10 mg to about 3 g, about 12.5 mg to about 2.5 g, about 15 mg to about 2 g, about 17.5 mg to about 1.5 g, about 20 mg to about 1 g, about 25 mg to about 750 mg, about 50 mg to about 500 g, or about 75 mg to about 250 mg of the glycan therapeutic.

In certain embodiments, the unit-dosage form may comprise about 1 g to about 5 g, about 1 g to about 10 g, about 1 g to about 15 g, about 1 g to about 20 g, about 1 g to about 25 g, about 1 g to about 30 g, about 5 g to about 10 g, about 5 g to about 15 g, about 5 g to about 20 g, about 5 g to about 25 g, about 5 g to about 30 g, about 10 g to about 20 g, or about 10 g to about 30 g of the glycan therapeutic.

In certain embodiments, the unit-dosage form comprises about 0.001 mg to about 100 mg, about 0.005 mg to about 75 mg, about 0.01 mg to about 50 mg, about 0.05 mg to about 25 mg, about 0.1 mg to about 10 mg, about 0.5 mg to about 7.5 mg, or about 1 mg to about 5 mg of the glycan therapeutic. In other embodiments, the unit-dosage form comprises about 1 mg to about 100 mg, about 2.5 mg to about 75 mg, about 5 mg to about 50 mg, or about 10 mg to about 25 mg of the glycan therapeutic. In other embodiments, the unit-dosage form comprises about 100 mg to about 10 g, about 250 mg to about 7.5 g, about 500 mg to about 5 g, about 750 mg to about 2.5 g, or about 1 g to about 2 g of the glycan therapeutic.

In other embodiments, the unit-dosage form comprises between about 0.001 mL to about 1000 mL of the glycan therapeutic. For example, the unit-dosage form may comprise about 0.001 mL to about 950 mL, about 0.005 mL to about 900 mL, about 0.01 mL to about 850 mL, about 0.05 mL to about 800 mL, about 0.075 mL to about 750 mL, about 0.1 mL to about 700 mL, about 0.25 mL to about 650 mL, about 0.5 mL to about 600 mL, about 0.75 mL to about 550 mL, about 1 mL to about 500 mL, about 2.5 mL to about 450 mL, about 5 mL to about 400 mL, about 7.5 mL to about 350 mL, about 10 mL to about 300 mL, about 12.5 mL to about 250 mL, about 15 mL to about 200 mL, about 17.5 mL to about 150 mL, about 20 mL to about 100 mL, or about 25 mL to about 75 mL of the glycan therapeutic.

In certain embodiments, the unit-dosage form comprises about 0.001 mL to about 10 mL, about 0.005 mL to about 7.5 mL, about 0.01 mL to about 5 mL, about 0.05 mL to about 2.5 mL, about 0.1 mL to about 1 mL, about 0.25 mL to about 1 mL, or about 0.5 mL to about 1 mL of the glycan therapeutic. In other embodiments, the unit-dosage form comprises about 0.01 mL to about 10 mL, about 0.025 mL to about 7.5 mL, about 0.05 mL to about 5 mL, or about 0.1 mL to about 2.5 mL of the glycan therapeutic. In other embodiments, the unit-dosage form comprises about 0.1 mL to about 10 mL, about 0.25 mL to about 7.5 mL, about 0.5 mL to about 5 mL, about 0.5 mL to about 2.5 mL, or about 0.5 mL to about 1 mL of the glycan therapeutic.

In some embodiments, the unit-dosage form, e.g., a tablet, capsule (e.g., a hard capsule, push-fit capsule, or soft capsule), or softgel, has a body length of between about 0.1 inches to about 1.5 inches (e.g., about 0.5 inches and about 1 inch), or about 5 mm to about 50 mm (e.g., about 10 mm to about 25 mm). In some embodiments, the unit-dosage form. e.g., a tablet, capsule (e.g., a hard capsule, push-fit capsule, or soft capsule), or softgel, has an external diameter of about 0.05 inches to about 1 inch (e.g., about 0.1 inches to about 0.5 inches), or about 1 mm to about 25 mm (e.g., about 5 mm to about 10 mm).

Each unit-dosage form of the glycan therapeutic may have a caloric value of between about 0.01 kcal and about 1000 kcal. For example, the unit-dosage form may have a caloric value of about 0.01 kcal to about 900 kcal, about 0.05 kcal to about 800 kcal, about 0.1 kcal to about 700 kcal, about 0.25 kcal to about 600 kcal, about 0.5 kcal to about 500 kcal, about 0.75 kcal to about 400 kcal, about 1 kcal to 300 kcal, about 5 kcal to about 200 kcal, or about 10 kcal to about 100 kcal. In certain embodiments, the unit-dosage form of the glycan therapeutic has a caloric value of between 10 kcal to about 500 kcal. In other embodiments, the unit-dosage form of the glycan therapeutic has a caloric value of between 50 kcal to about 500 kcal.

In still other embodiments, the unit-dosage form may have a caloric value of about 0.001 kcal to about 100 kcal, about 0.005 kcal to about 90 kcal, about 0.01 kcal to about 80 kcal, about 0.025 kcal to about 70 kcal, about 0.05 kcal to about 60 kcal, about 0.075 kcal to about 50 kcal, about 0.1 kcal to 40 kcal, about 0.25 kcal to about 30 kcal, about 0.5 kcal to about 25 kcal, about 0.25 kcal to about 20 kcal, or about 0.1 kcal to about 10 kcal.

The unit-dosage form of the glycan therapeutic may be formulated to dissolve in an aqueous solution (e.g., water, milk, juice, and the like) and is orally administered as a beverage, syrup, solution, or suspension. For example, the unit-form dosage of the glycan therapeutic may comprise a cube, packet, lozenge, pill, tablet, capsule, candy, powder, elixir, or concentrated syrup formulated for dissolving into an aqueous solution prior to oral administration. In other embodiments, the unit-dosage form of the glycan therapeutic may comprise a cube, packet, lozenge, pill, tablet, capsule, candy, powder, elixir, or concentrated syrup formulated to dissolve in vivo, e.g., in the mouth, stomach, intestine, or colon of the subject upon oral administration.

The dosage forms described herein can be manufactured using processes that are known to those of skill in the art. For example, for the manufacture of tablets, an effective amount of a glycan therapeutic preparation can be dispersed uniformly in one or more excipients or additives, for example, using high shear granulation, low shear granulation, fluid bed granulation, or by blending for direct compression. Excipients and additives include diluents, binders, disintegrants, dispersants, lubricants, glidants, stabilizers, surfactants, antiadherents, sorbents, sweeteners, and colorants, or a combination thereof. Diluents or fillers can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, alginic acid, dextrin, casein, methyl cellulose, waxes, natural and synthetic gums, e.g., acacia, tragacanth, sodium alginate, gum arabic, xantan gum, and synthetic polymers such as polymethacrylates, polyvinyl alcohols, hydroxypropylcellulose, and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses (e.g., carboxymethylcelluloses (e.g., carboxymethylcellulose (CMC), CMC-Na, CMC-Ca)), starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. Exemplary sweeteners may include *stevia* extract, aspartame, sucrose, alitame, saccharin, and the like. If desired, the tablets can also comprise nontoxic auxiliary substances such as pH buffering agents, preservatives, e.g., antioxidants, wetting or emulsifying agents, solubilizing agents, coating agents, flavoring agents (e.g., mint, cherry, anise, peach, apricot, licorice, raspberry, vanilla), and the like. Additional excipients and additives may include aluminum acetate, benzyl alcohol, butyl paraben, butylated hydroxy toluene, calcium disodium EDTA, calcium hydrogen phosphate dihydrate, dibasic calcium phosphate, tribasic calcium phosphate, candelilla wax, carnuba wax, castor oil hydrogenated, cetylpyridine chloride, citric acid, colloidal silicone dioxide, copolyvidone, corn starch, cysteine HCl, dimethicone, disodium hydrogen phosphate, erythrosine sodium, ethyl cellulose, gelatin, glycerin, glyceryl monooleate, glyceryl monostearate, glycine, HPMC pthalate, hydroxypropylcellulose, hydroxyl propyl methyl cellulose, hypromellose, iron oxide red or ferric oxide, iron oxide yellow, iron oxide or ferric oxide, magnesium carbonate, magnesium oxide, magnesium stearate, methionine, methacrylic acid copolymer, methyl paraben, silicified microcrystalline cellulose, mineral oil, phosphoric acid, plain calcium phosphate, anhydrous calcium phosphate, polaxamer 407, polaxamer 188, plain polaxamer, polyethylene oxide, polyoxy 140 stearate, polysorbate 80, potassium bicarbonate, potassium sorbate, potato starch, povidone, propylene glycol, propylene paraben, propyl paraben, retinyl palmitate, saccharin sodium, selenium, silica, silica gel, fumed silica, sodium benzoate, sodium carbonate, sodium citrate dihydrate, sodium crossmellose, sodium lauryl sulfate, sodium metabisulfite, sodium propionate, sodium starch, sodium starch glycolate, sodium stearyl fumarate, sorbic acid, sorbitol, sorbitan monooleate, pregelatinized starch, succinic acid, triacetin, triethyl citrate, vegetable stearin, vitamin A, vitamin E, vitamin C, or a combination thereof. The amounts of these excipients and additives can be properly selected based on their relation to other components and properties of the preparation and production method.

Immediate-release formulations of an effective amount of a glycan therapeutic composition can comprise one or more combinations of excipients that allow for a rapid release of a pharmaceutically active agent (such as from 1 minute to 1 hour after administration). Controlled-release formulations (also referred to as sustained release (SR), extended-release (ER, XR, or XL), time-release or timed-release, controlled-release (CR), or continuous-release) refer to the release of a glycan therapeutic composition from a dosage form at a particular desired point in time after the dosage form is administered to a subject.

In one embodiment a controlled release dosage form begins its release and continues that release over an extended period of time. Release can occur beginning almost immediately or can be sustained. Release can be constant, can increase or decrease over time, can be pulsed, can be continuous or intermittent, and the like. In one embodiment, a controlled release dosage refers to the release of an agent from a composition or dosage form in which the agent is released according to a desired profile over an extended period of time. In one aspect, controlled-release refers to delayed release of an agent from a composition or dosage form in which the agent is released according to a desired profile in which the release occurs after a period of time.

In some embodiments, the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a glycan therapeutic). The acid sources can be any which are safe for human consumption and can generally include food acids, acid and hydrite antacids such as, for example: citric, tartaric, amalic, fumeric, adipic, and succinics. Carbonate sources include dry solid carbonate and bicarbonate salt such as sodium bicarbonate, sodium carbonate, potassium bicarbonate and potassium carbonate, magnesium carbonate and the like. Reactants which evolve oxygen or other gasses and which are safe for human consumption are also included. In one embodiment citric acid and sodium bicarbonate are used.

In another embodiment, the dosage form can be in a candy form (e.g., matrix), such as a lollipop or lozenge. In one embodiment an effective amount of a glycan therapeutic is dispersed within a candy matrix. In one embodiment the candy matrix comprises one or more sugars (such as dextrose or sucrose). In another embodiment the candy matrix is a sugar-free matrix. The choice of a particular candy matrix is subject to wide variation. Conventional sweeteners (e.g., sucrose), sugar alcohols suitable for use with diabetic patients (e.g., sorbitol or mannitol), or other sweeteners (e.g., sweeteners described herein) may be employed. The candy base can be very soft and fast dissolving, or can be hard and slower dissolving. Various forms will have advantages in different situations.

A candy mass composition comprising an effective amount of the glycan therapeutic can be orally administered to a subject in need thereof so that an effective amount of the glycan therapeutic will be released into the subject's mouth as the candy mass dissolves and is swallowed. A subject in need thereof includes a human adult or child.

The dosage forms described herein can also take the form of pharmaceutical particles manufactured by a variety of methods, including high-pressure homogenization, wet or dry ball milling, or small particle precipitation. Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In one embodiment, the pharmaceutical particles have a final size of 3-1000 microns, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 microns. In another embodiment the pharmaceutical particles have a final size of 10-500 microns. In another embodiment the pharmaceutical particles have a final size of 50-600 microns. In another embodiment the pharmaceutical particles have a final size of 100-800 microns.

In another embodiment, an oral dosage form is provided comprising a glycan therapeutic composition, wherein the oral dosage form is a syrup. The syrup can comprise about 1%, 5%, 10%, 15%, 20%, 25%, 30%, 35%, 40%, 45%, 50%, 55%, 60%, 65%, 70%, 75%, 80%, or 85% solid. The syrup can comprise about 15%, 20%, 25%, 30%, 35%, 40%, 45%, or 50% liquid, for example, water. The solid can comprise a glycan therapeutic composition. The solid can be, for example, about 1-96%, 10-96%, 20-96%, 30-96%, 40-96%, 50-96%, 60-96%, 70-96%, 80-96%, or 90-96% glycan therapeutic composition. In another embodiment, a glycan therapeutic composition is formulated as a viscous fluid.

In one embodiment, the composition comprises a foaming component, a neutralizing component, or a water-insoluble dietary fiber. A foaming component can be at least one member selected from the group consisting of sodium hydrogencarbonate, sodium carbonate, and calcium carbonate. In one embodiment a neutralizing component can be at least one member selected from the group consisting of citric acid, L-tartaric acid, fumaric acid, L-ascorbic acid, DL-malic acid, acetic acid, lactic acid, and anhydrous citric acid. In one embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

In some embodiments, the dosage forms are formulated to release the pharmaceutical compositions comprising glycan therapeutic preparations in a specific region(s) of the GI tract, such as the small or the large intestine. In some embodiments, the dosage forms are formulated to release the pharmaceutical compositions comprising therapeutic glycan preparations in a specific region(s) of the GI tract, such as the cecum, ascending colon, transverse colon, descending colon, sigmoid colon, and/or rectum.

Solid formulations for oral use may comprise an enteric coating, which may control the location at which a glycan therapeutic composition is absorbed in the digestive system. For example, an enteric coating can be designed such that a glycan therapeutic composition does not dissolve in the stomach but rather travels to the small or the large intestine, cecum, ascending colon, transverse colon, descending colon, sigmoid colon, and/or rectum, where it dissolves. An enteric coating can be stable at low pH (such as in the stomach) and can dissolve at higher pH (for example, in the small or large intestine or colon). Material that can be used in enteric coatings includes, for example, alginic acid, cellulose acetate phthalate, plastics, waxes, shellac, and fatty acids (e.g., stearic acid, palmitic acid).

In some embodiments, the dosage form for the pharmaceutical glycan therapeutic compositions described herein is an enzyme-responsive delivery system. For example, trypsin responsive polymers can be made using hydrogels that are crosslinked by peptides that are degraded by trypsin. Trypsin is active in the small intestine. Trypsin-responsive delivery systems can be used to target delivery of the pharmaceutical glycan therapeutic compositions to the small intestine. In another example, enzyme-digestible hydrogels consisting of poly(vinyl pyrrolidone) crosslinked with albumin are degraded in the presence of pepsin.

In some embodiments, the dosage form for the pharmaceutical glycan therapeutic compositions described herein is a delivery device that enables prolonged retention at a specific site in the GI tract. For example, a gastroretentive delivery system enables prolonged release of the pharmaceutical glycan therapeutic compositions to the stomach. Gastroretentive delivery may be used for the pharmaceutical glycan therapeutic compositions that modulate bacteria in the stomach or in the upper small intestine.

In some embodiments, the dosage form for the pharmaceutical glycan therapeutic compositions described herein is a mucoadhesive delivery system that adheres to the mucosal surfaces of the stomach. They are typically composed of polymers with numerous hydrogen-bonding groups, e.g., cross-linked polyacrylic acids, sodium carboxymethyl cellulose, sodium alginate, carrageenan, Carbopol 934P, or thiolated polycarbophil.

In some embodiments, the dosage form for the pharmaceutical glycan therapeutic compositions described herein is an expanding delivery system that rapidly increases in size in the stomach, which slows its passage through the pylorus. Such systems include systems that unfold in the stomach. For example, geometric shapes such as tetrahedrons, rings, disks, etc. can be packed into a gelatin capsule. When the capsule dissolves, the shape unfolds. The systems can be composed of one or more erodible polymer (e.g., hydroxypropyl cellulose), one or more nonerodible polymer (e.g., polyolefins, polyamides, polyurethanes). The glycan therapeutic may then be dispersed within the polymer matrix. The retention times can be fine-tuned by the polymer blend. Alternatively, devices made out of elastic polymers that are stable in the acidic pH of the stomach but dissolve in the neutral/alkaline conditions further along the GI tract can be used. Such polymer formulations can prevent intestinal obstruction when the device exits the stomach. Supramolecular polymer gels crosslinked by hydrogen bonds between carboxyl groups may also be used, e.g. composed of poly(acryloyl 6-aminocaproic acid) (PA6ACA) and poly (methacrylic acid-co-ethyl acrylate) (EUDRAGIT L 100-55). Other systems include swellable excipients, such as collagen sponges. For example, a hydrogel matrix (e.g. a swellable core: polyvinyl pyrrolidone XL, Carbopol 934P, calcium carbonate) swells 2-50 times in the stomach. Superporous hydrogel composites swell to hundreds of times their original volume in a few minutes. Some systems exploit gas generation to achieve expansion, e.g. carbon dioxide-generating, expandable systems that are surrounded by a hydrophilic membrane.

In some embodiments, the dosage form for the pharmaceutical glycan therapeutic compositions described herein is a density-controlled delivery system. These systems are designed to either float or sink in gastric fluids which delays their emptying from the stomach. For example, high-density systems enable the device to settle to the bottom of the stomach, below the pylorus, and thus avoid stomach emptying. Other systems are low-density/floating systems. Such devices may, e.g., comprise entrapped air in hollow chambers or may incorporate low-density materials like fats, oils, or foam powder. Low density may be achieved through swelling, e.g. hydrocolloid containing capsules dissolve upon contacting gastric fluid and the hydrocolloids swell to form a mucous body. Alternative polymers include: chitosans, sodium alginate, and glycerol monooleate matrix. Low density may be achieved through gas generation. For example, tablets loaded with carbonate and optionally citric acid generate carbon dioxide after contact with acidic aqueous media. The carbon dioxide generated is entrapped within the gelling hydrocolloid causing the system to float. Hydrocolloids include hydroxypropyl methylcellulose and Carbopol 934P.

In some embodiments, the dosage form for the pharmaceutical glycan therapeutic compositions described herein employs a design to retain a device in the small or large intestine. The location-specific nature of the device is provided by a specific triggering method, e.g. pH, enzyme, etc. These include systems designed for mucoadhesion and also microneedle pills. Microneedle pills comprise a drug reservoir spiked with microneedles that is encapsulated in a pH-responsive coating. When the pill reaches the desired location in the GI tract and the coating dissolves, the microneedles enable the pill to become stuck to the lining of the GI tract. In other embodiments, the microneedle pills comprise a capsule that consists of two chemical compartments filled with citric acid and sodium bicarbonate, respectively. As the pill dissolves in the digestive system, barriers between the two substances erode, allowing them to mix and create a chemical reaction that pushes micro-needles of saccharides through the outer layer of the capsule and into the lining of the small intestine. The saccharide needles can be filled with drugs that are delivered into nearby blood vessels as the saccharide is absorbed.

In some embodiments, the dosage form for the pharmaceutical glycan therapeutic compositions described herein employs a pH sensitive polymer coating. For example, pH-dependent polymers (bi- or tri-phasic) can be insoluble at low pH levels (e.g. acid resistance in the stomach, pH 1-2) and become increasingly soluble as pH rises, e.g. to about 5.5-6.2 in the duodenum, to about pH 5.7 in the ascending colon, to about pH 6.4 in the cecum, to about pH 6.6 in the transverse colon, to about pH 7.0 in the descending colon, to about 7.2-7.5 in the ileum, or to about pH 7.5 in the distal small intestine. In one example, TARGIT™ technology may be used for site-specific delivery of the pharmaceutical glycan therapeutic compositions in the gastrointestinal (GI) tract. The system employs pH-sensitive coatings onto injection-moulded starch capsules to target the terminal ileum and colon.

In some embodiments, the dosage form for the pharmaceutical glycan therapeutic compositions described herein is a delayed release system or time controlled release system. Such systems usually employ enteric coatings that may be combined with pH sensitive and time release functions. For example, ETP (enteric coated time-release press coated) tablets may be used that are composed of three components: a glycan therapeutic-containing core tablet (rapid release function), a press-coated, swellable hydrophobic polymer layer (e.g. hydroxypropyl cellulose layer (HPC), and a time release function. The duration of lag phase can be controlled either by weight or composition of polymer layer and an enteric coating layer (acid resistance function).

In some embodiments, the dosage form for the pharmaceutical glycan therapeutic compositions described herein employs Eudragit® enteric coatings of tablets and capsules. Other suitable synthetic polymers include: Shellac, ethyl cellulose, cellulose acetate phthalate, hydroxypropylmethyl cellulose, polyvinyl acetate phthalate and poly glutamic acid coatings, such as poly-γ-glutamic acid (γ-PGA). These coatings combine both mucoadhesive and pH-dependent release strategies. To enhance colon targeted delivery Eudragits® are methacrylic co-polymers with varying side group compositions that alter the pH at which they are soluble. For example, for Eudragit®-coated systems no significant drug release occurs in the stomach (e.g. at pH 1.4) and in the small intestine (e.g. at pH 6.3), while significant drug release can be seen at pH 7.8 in the ileocaecal region.

In some embodiments, the dosage form for the pharmaceutical glycan therapeutic compositions described herein is a microbial-triggered system, such as a polysaccharide based delivery system. Polysaccharide based delivery systems contain biodegradable and mucoadhesive polymer coatings, including coatings of chitosan and pectin. Other suitable natural polymers include, e.g., guar gum, inulin, cyclodextrin, dextran, amylase, chondrotin sulphate, and locust bean gum. These delivery systems can be used to target the glycan therapeutic to the small or the large intestine, cecum, ascending colon, transverse colon, descending colon, sigmoid colon. Coatings with naturally occurring polysaccharides like guar gum, xanthan gum, chitosan, alginates, etc. are degraded by resident gut microbes, e.g. microbes comprising enzymes such as, xylosidase, arabinosidase, galactosidase, glucosidases, etc. In some embodiments, the microbes and associated enzyme activities are predominatly located in a specific region of the GI tract (e.g., Jain A. et al., Perspectives of Biodegradable Natural Polysaccharides for Site-Specific Drug Delivery to the Colon, J Pharm Pharmaceut Sci 10(1):86-128, 2007). For example, CODES™ technology may be used to deliver the pharmaceutical glycan therapeutic compositions. This system combines the polysaccharide coating with a pH-sensitive coating. In some embodiments, the system consists of a core tablet coated with three layers of polymer coatings: The outer coating is composed of Eudragit L. This coating gets dissolved in the duodenum and exposes the next coating. The next coating is composed of Eudragit E. This layer allows the release of lactulose present in the inner core. The lactulose gets metabolized into short chain fatty acids that lower the surrounding pH where the Eudragit E layer dissolves. The dissolving of Eudragit E results in the exposure of the glycan therapeutic. The bacteria present in the colon are responsible for the degradation of polysaccharides that are released from the core tablet. The degradation of polysaccharides may result in organic acids formation that lowers the pH of the contents surrounding the tablet.

In some embodiments, the dosage form for the pharmaceutical glycan therapeutic compositions described herein is a pressure-controlled delivery system. The system employs the fact that higher pressures are encountered in the colon than in the small intestine. For example, for ethylcellulose systems that are insoluble in water, the release of glycan therapeutics occurs following disintegration of a water-insoluble polymer capsule as a result of pressure in the lumen of the colon. The release profile may be adjusted by varying the thickness of the ethylcellulose, the capsule size and/or density of the capsule.

In some embodiments, the dosage form for the pharmaceutical glycan therapeutic compositions described herein is a pulsatile colon targeted delivery system. For example, the system can be a pulsincap system. The capsule which is employed comprises a plug that is placed in the capsule that controls the release of the glycan therapeutic. A swellable hydrogel (e.g. hydroxyl propyl methyl cellulose (HPMC), poly methyl methacrylate or polyvinyl acetate) seals the drug content. When the capsule gets in contact with a fluid the plug is pushed off from the capsule and the glycan therapeutic is released. The release profile can be controlled by varying the length and/or point of intersection of the plug with the capsule body. Another system is a port system. The capsule body is enclosed in a semi-permeable membrane. The insoluble plug consists of an osmotically active agent and the glycan therapeutic. When the capsule gets in contact with a fluid the semi-permeable membrane permits inflow of the fluid which increases pressure in the capsule body. This leads to an expelling of the plug and release of the glycan therapeutic.

In some embodiments, the dosage form for the pharmaceutical glycan therapeutic compositions described herein is an osmotically controlled colon targeted delivery system. An exemplary system, OROS-CT, consists of osmotic units (up to 5 or 6 push pull units) encapsulated in a hard gelatin capsule. The push pull units are bilayered with outer enteric impermeable membrane and inner semi-permeable membrane. The internal, central part of the push pull consists of the drug layer and push layer. The glycan therapeutic is released through the semi-permeable membrane. The capsule body enclosing the push pull units is dissolved immediately after administration. In the GI tract the enteric impermeable membrane prevents water absorption. The enteric coating is dissolved in small intestine (higher pH, >7), water enters the unit through the semi-permeable membrane causing push layer to swell and force out the glycan therapeutic.

In some embodiments, the dosage form for the pharmaceutical glycan therapeutic compositions described herein is "smart pill" which can be used to release the glycan therapeutic just before reaching the ileocecal valve.

In some embodiments, the dosage form for the pharmaceutical glycan therapeutic compositions described herein is a rectally administered formulation. For example, enemas introduce a pharmaceutical glycan therapeutic composition in liquid formulation into the rectum. The volume administered is typically less than 10 mL. Suppositories introduce a pharmaceutical glycan therapeutic composition into the rectum. Suppositories are solid dosage forms that melt or dissolve when inserted into the rectum, releasing the glycan therapeutics. Typical excipients for suppository formulations include cocoa butter, polyethylene glycols, and agar.

Further provided herein are methods of making a unit-dosage form described herein, comprising providing a glycan therapeutic; formulating the glycan therapeutic into a unit-dosage form, packaging the unit-dosage form, labelling the packaged unit-dosage form, and/or selling or offering for sale the packaged and labeled unit-dosage form.

The unit-dosage forms described herein may also be processed. In one embodiment, the processing comprises one or more of: processing the dosage form into a pharmaceutical composition, e.g., formulating, combining with a second component, e.g., an excipient or buffer or a second active compound or therapeutic agent; portioning into smaller or larger aliquots; disposing into a container, e.g., a gas or liquid tight container; packaging; associating with a label; shipping or moving to a different location. In one embodiment, the processing comprises one or more of: classifying, selecting, accepting or discarding, releasing or withholding, processing into a pharmaceutical composition, shipping, moving to a different location, formulating, labeling, packaging, releasing into commerce, or selling or offering for sale, depending on whether the predetermined threshold is met. In some embodiments, the processed dosage forms comprise a glycan therapeutic described herein.

Medical Foods

Any glycan therapeutic preparation described herein may be formulated as a medical food. A medical food is defined in section 5(b)(3) of the Orphan Drug Act (21 U.S.C. 360ee(b)(3)). Medical food is formulated to be consumed (oral intake) or administered enterally (e.g. feeding/nasogastric tube) under medical supervision, e.g. by a physician. It is intended for the specific dietary management of a disease or condition, such as, e.g. cancer. Medical foods as used herein do not include food that is merely recommended by a physician as part of an overall diet to manage the symptoms or reduce the risk of a disease or condition. Medical foods comprising a preparation of glycan therapeutics are administered to a subject who has a cancer or tumor under medical supervision (which may be active and ongoing) and usually, the subject receives instructions on the use of the medical food. Medical foods may comprise, in addition to a glycan therapeutic described herein, one or more food additives, color additives, GRAS excipients and other agents or substances suitable for medical foods. Medical food preparations may be nutritionally complete or incomplete formulas.

Dietary Supplements

Any glycan therapeutic preparation described herein may be formulated as a dietary supplement. Dietary supplements are regulated under the Dietary Supplement Health and Education Act (DSHEA) of 1994. A dietary supplement is a product taken by mouth that contains a "dietary ingredient" intended to supplement the diet. The "dietary ingredients" in these products may include, in addition to a glycan therapeutic described herein, one or more of: vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms, such as a bar, but if they are, information on their label must not represent the product as a conventional food or a sole item of a meal or diet. DSHEA requires that every supplement be labeled a dietary supplement and not as a general food.

Kits

Kits are also contemplated. For example, a kit can comprise unit dosage forms of the pharmaceutical glycan therapeutic composition, and a package insert containing instructions for use of the glycan therapeutic in treatment of a disease, disorder or pathological condition, such as, e.g., cancer. The kits include a pharmaceutical glycan therapeutic composition in suitable packaging for use by a subject in need thereof. Any of the compositions described herein can be packaged in the form of a kit. A kit can contain an amount of a pharmaceutical glycan therapeutic composition (optionally additionally comprising a prebiotic substance, a probiotic bacterium, a micronutrient, and/or a second therapeutic agent, such as a drug) sufficient for an entire course of treatment, or for a portion of a course of treatment. Doses of a pharmaceutical glycan therapeutic composition can be individually packaged, or the pharmaceutical glycan therapeutic composition can be provided in bulk, or combinations thereof. Thus, in one embodiment, a kit provides, in suitable packaging, individual doses of a glycan therapeutic composition that correspond to dosing points in a treatment regimen, wherein the doses are packaged in one or more packets.

In one embodiment, the pharmaceutical glycan therapeutic composition can be provided in bulk in a single container, or in two, three, four, five, or more than five containers. For example, each container may contain enough of a pharmaceutical glycan therapeutic composition for a particular week of a treatment program that runs for a month. If more than one bulk container is provided, the bulk containers can be suitably packaged together to provide sufficient pharmaceutical glycan therapeutic composition for all or a portion of a treatment period. The container or containers can be labeled with a label indicating information useful to the subject in need thereof or the physician performing the treatment protocol, such as, e.g. dosing schedules.

The pharmaceutical glycan therapeutic composition can be packaged with other suitable substances, e.g., a second active compound or therapeutic agent or a buffer/carrier. The other substance or substances can be packaged separately from the pharmaceutical glycan therapeutic composition, or mixed with the pharmaceutical glycan therapeutic composition, or combinations thereof. Thus, in one embodiment, kits include a dosage form containing all the ingredients intended to be used in a course of treatment or a portion of a course of treatment, e.g., a pharmaceutical glycan therapeutic composition and optionally a second active compound or therapeutic agent or a buffer/carrier. In one embodiment, a pharmaceutical glycan therapeutic composition is packaged in one package or set of packages, and additional components, such as probiotic bacteria, prebiotics, and therapeutic agents (e.g., drugs, such as anti-cancer drugs) are packaged separately from the pharmaceutical glycan therapeutic composition.

Provided herein are kits for treating cancer in a patient comprising a package comprising (a) a pharmaceutical composition or medical food or dietary supplement comprising a glycan therapeutic preparation described herein, and (b) instructions for using the pharmaceutical composition for treating cancer (e.g., a cancer described herein) in a patient. In some embodiments, the kit also includes a second agent which is a pharmaceutical composition, e.g., a chemotherapeutic drug or other anti-cancer drug described herein. In other examples, the kit also contains a probiotic.

Kits can further include written materials, such as instructions, expected results, testimonials, explanations, warnings, clinical data, information for health professionals, and the like. In one embodiment, the kits contain a label or other information indicating that the kit is only for use under the direction of a health professional. The container can further include scoops, syringes, bottles, cups, applicators or other measuring or serving devices.

Administration to a Subject

The glycan therapeutic preparations, pharmaceutical compositions and therapeutic agents described herein can be administered to a subject in need thereof by various routes (e.g., systemically or locally) including, for example, orally or parenterally, such as intravenously, intramuscularly, subcutaneously, intraorbitally, intracapsularly, intraperitoneally, intrarectally, intracisternally, intratumorally, intravasally, intradermally or by passive or facilitated absorption through the skin. The therapeutic agents can be administered locally to the site of a pathologic condition, for example, intravenously or intra-arterially into a blood vessel supplying a tumor. In some embodiments, the glycan therapeutic composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy).

Active compounds and pharmaceutical agents, e.g., prebiotic substances, probiotic bacteria or drugs, may be administered separately, e.g., prior to, concurrent with or after administration of the glycan therapeutics and not as a part of the pharmaceutical composition or medical food or dietary supplement (e.g. as a co-formulation) of glycan therapeutics. In some embodiments, pharmaceutical compositions or medical foods comprising preparations of glycan therapeutics are administered in combination with a recommended or prescribed diet, e.g. a diet that is rich in probiotic and/or prebiotic-containing foods, such as it may be determined by a physician or other healthcare professional. Suitable sources of soluble and insoluble fibers are commercially available. Prebiotics can be found in certain foods, e.g.

chicory root, Jerusalem artichoke, Dandelion greens, garlic, leek, onion, asparagus, wheat bran, wheat flour, banana, milk, yogurt, sorghum, burdock, broccoli, Brussels sprouts, cabbage, cauliflower, collard greens, kale, radish and rutabaga, and miso.

In some embodiments, the composition and metabolic activity of the intestinal bacterial community may be modified. Modification of the composition and metabolic activity of the intestinal bacterial community may be performed through the administration of i) a glycan therapeutic alone (such as in the absence of exogenously administered bacteria), ii) a glycan therapeutic and one or more beneficial microorganisms (probiotics), or iii) a combination of a glycan therapeutic, a probiotics, and another agent, such as, e.g. a prebiotic (e.g. a dietary fiber), or a therapeutic agent, such as, e.g. an antibacterial agent (e.g. antibiotic), an anti-inflammatory agent, an anti-cancer agent, and the like.

In some embodiments, glycan therapeutics (e.g. oligosaccharides) have a desired degree of digestibility.

Digestibility depends on many factors, including, e.g. the degree of polymerization, the degree of branching, the type of glycosidic linkages, position of the linkages, anomeric configuration (e.g. L- or D-configuration, alpha/beta configuration) of the glycan unit. For example, furanosides are generally more susceptible to hydrolysis than pyranosides. Deoxy sugars are generally more acid labile than non-deoxy sugars. Uronic acids are generally less susceptible to hydrolysis than non-uronic monosaccharides.

Digestibility is a parameter that can be ascertained for the glycan therapeutics described herein. In some embodiments, glycan therapeutics disclosed herein are screened to assess their digestibility. Digestibility of glycan therapeutics can be assessed by any suitable method known in the art (e.g. by simulated gastric digestion half-life). In some embodiments, digestibility is assessed by a physiologically relevant in vitro digestion reaction, e.g. simulated gastric digestion and simulated intestinal digestion. To test glycan therapeutic's digestibility, they can be sequentially exposed to a simulated gastric fluid (SGF) for a desired period (e.g. the length of time it takes 90% of a meal to pass from the stomach to the small intestine) and then transferred to various GI-microbial cultures or samples. Samples at different stages of the digestion (e.g., 2, 5, 15, 30, 60 and 120 min) can be analyzed by standard glycan techniques known in the art and described herein. By monitoring the amount of intact glycan therapeutics observed over time, the half-life of digestion can be calculated. Suitable assays can be used to assess comparative digestibility (i.e., against a benchmark glycan such as, e.g. a prebiotic) or to assess absolute digestibility. In some embodiments, the digestibility (expressed as half-life) is 30 minutes or less, 20 minutes or less, 15 minutes or less, 10 minutes or less, 5 minutes or less, 4 minutes or less, 3 minutes or less, 2 minutes or less or 1 minute or less. In some embodiments, the digestibility (expressed as half-life) is 30 minutes or more, 45 minutes or more, 1 hour or more, 2 hours or more, 3 hours or more, 4 hours or more, 5 hours or more, or 10 hours or more.

In some embodiments, the glycan therapeutic is digested at a constant rate and/or at a controlled rate. In such embodiments, the rate of digestion of the glycan therapeutic may not be optimized for the highest possible rate of digestion. In such embodiments the rate of absorption of the glycan therapeutic following ingestion by a mammal may be slower and the total time period over which absorption occurs following ingestion may be longer than for glycan therapeutic of similar glycan unit composition that are digested at a faster initial rate. In some embodiments the glycan therapeutic is completely or substantially completely digested. In some embodiments the glycan therapeutic is substantially not digested or not digested.

If so desired, the glycan therapeutic composition comprises non-digestible oligo- or polysaccharides. In some embodiments, the glycan therapeutic is indigestible or incompletely digestible by human digestive systems. Glycan therapeutics are, in some embodiments, selectively digested by gut microbiota constituents that allows specific changes, both in the composition and/or activity in the commensal gut microbiota. In some embodiments, provided herein are glycan therapeutics that are non-digestible or incompletely digestible by humans in the absence of specific microbes in the gut. In these embodiments, only specific bacteria are capable of utilizing the glycan therapeutic as a carbon source.

In some embodiments, provided herein are glycan therapeutics that are non-digestible and stimulate the growth or activity of bacteria in the digestive system that are beneficial to the health of the body. In some embodiments, the glycan therapeutic is resistant to gastric acidity. In some embodiments, the glycan therapeutic is resistant to hydrolysis by mammalian enzymes. In some embodiments, the glycan therapeutic is resistant to gastrointestinal absorption. In some embodiments, the glycan therapeutic is a substrate for fermentation by the intestinal microbiota. In some embodiments, the glycan therapeutic is a selective substrate for one or a limited number of potentially beneficial bacteria in the colon, stimulating their growth and/or metabolic activity. In some embodiments, the glycan therapeutic is capable of altering the composition of intestinal microbiota to a composition richer in specific bacteria. In some embodiments, the glycan therapeutic selectively stimulates the growth and/or selective activity of intestinal bacteria associated with health and well-being.

In some embodiments, the glycan therapeutic capable of selectively stimulating the growth of beneficial bacteria including *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacilli, Christensenella minuta*, or a *Christensenellaceae* in the large intestine. In some embodiments, the glycan therapeutic is digested by the gut microbiota, resulting, e.g., in the release of hydrogen and carbon dioxide gas and short-chain fatty acids such as butyrate, if desired. A glycan therapeutic preparation, in some embodiments, promotes the selective growth of beneficial colonic bacteria, including multiple species and strains of Bifidobacteria and *Lactobacilli*. Bifidobacteria carry out non hydrogen-producing lactose fermentation reactions in addition to inhibiting hydrogen producing bacteria, such as *Escherichia coli.*

In some embodiments, provided herein are glycan therapeutics that affect the composition and/or activity of the intestinal microbiota. For example, administration of the glycan therapeutic to a subject may result in an increased prebiotic index. The prebiotic index (PI) relates to the sum of: (Bifidobacteria/total bacteria)+(*Lactobacilli*/total bacteria)−(*Bacteroides*/total bacteria)−(Clostridia/total bacteria), (see Palframan et al, 2003, Lett Appl Microbiol 37:281-284). Administration of a glycan therapeutic to a subject may result in an increase in: *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacilli, Christensenella minuta*, or a *Christensenellaceae.*

In some embodiments, glycan therapeutics are provided that comprise beta glycosidic linkages. In some embodiments, the beta glycosidic linkages make the glycans substantially non-digestible and/or unabsorbable to a human host in the stomach and small intestine. However, certain probiotic and commensal microbes are able to metabolize the glycans.

In some embodiments, glycan therapeutics are provided that comprise alpha glycosidic linkages. In some embodiments, the alpha glycosidic linkages are not hydrolyzed by human salivary amylase, but can be metabolized by *Bifidobacterium bifidum* and *Clostridium butyricum*.

In some embodiments, the therapeutic glycan is indigestible. Digestibility may differ between different enzymes or sets of enzymes, e.g. a therapeutic glycan may be digestible for certain microbes expressing certain enzymes, but may be indigestible to a mammal lacking the required enzyme(s) in the absence of hosting the microbes.

In some embodiments, the glycan therapeutic is an oligosaccharide that is optionally non-digestible by a human digestive system, contains at least one beta-glycosidic bond and/or at least one alpha-glycosidic bond that can be digested by a bacterium. In one embodiment the bacterium is a probiotic or an endogenous commensal bacterium such as, e.g. a *Lactobacilli* or a *Bifidobacteria*.

In some embodiments, the glycan therapeutics pass through the small intestine and into the large intestine (colon) mostly intact.

In some embodiment, the glycan therapeutic comprises less than 1%, 2%, 3%, 4%, 5%, 6%, 7%, 8%, 9%, 10%, 12%, 14%, 16%, 18%, 20%, 30%, 40%, 50%, 60%, 70%, 75%, 80%, 85%, 90%, 95%, 97%, 98%, or less than 99% of bonds that are hydrolyzable by a mammalian amylase enzyme. One type of hydrolyzable bonds are recognized by a mammalian amylase enzyme. Other types of hydrolyzable bonds (e.g. alpha 1,4; alpha 1,6, alpha 1,2; and alpha 1,6 glycosidic linkages) are recognized by specific microbial enzymes (e.g. alpha-glucosidase, cyclomaltodextrinase, neopullunanase, glucanotransferase, trehalohydrolase, and the like). Bonds may also be hydrolyzable by hydrolases (e.g. Amylases, Cellulases, Mannanases, Pectinases, Pullulanases, Xylanases and the like), oxireductases (Catalases, Glucose oxidases, and the like), transferases (Fructosyltransferases, Glucosyltransferases), lyases, isomerases (Glucose isomerases), ligases, and the like. In some embodiments, glycosidic bonds are catalyzed by an enzyme and the rate of catalysis can be measure by any suitable means known in the art and the rate can be compared to that of another enzyme.

In some embodiments, the glycan therapeutic exhibits a slow rate of fermentability by the microbiota. In some embodiments, the glycan therapeutic has a high degree of branching to resist digestion. In some embodiments, the glycan therapeutic has a DP of 10 or more, 12 or more, 14 or more, 16 or more, 18 or more, 20 or more, 25 or more, 30 or more to slow its digestibility. In some embodiments, the branching of the glycan therapeutic protects against digestion by human enzymes. In some embodiments, the size of the glycan therapeutic lessens the fermentation speed (digestibility speed by bacteria), e.g., in the colon. In some embodiments, the glycan therapeutic characteristics promote indigestibility by human glycosidases and promote selective digestion by the microbiota.

In some embodiments, provided herein are glycan therapeutics that can be digested by the microbiota (e.g. by carbohydrate fermentation) without certain side effects or with a substantial reduction of symptoms of fermentation, such as increased gas formation that may cause flatulence, discomfort, and/or bloating.

In one embodiment, the glycan therapeutic composition comprises one or more mono-, oligo-, and/or polysaccharides which are non-digestible by a human digestive system. In another embodiment, the glycan therapeutic composition consists essentially of a mono-, oligo-, and/or polysaccharide which is non-digestible by a human digestive system.

In another embodiment, the glycan therapeutic composition comprises a mixture of non-digestible oligosaccharides. In another embodiment, the glycan therapeutic composition comprises one or more digestible saccharides and one or more non-digestible oligosaccharides. In some embodiments, the glycan therapeutic composition comprises at least one non-digestible saccharide and optionally contains one or more digestible mono-saccharides, oligo- or polysaccharides. In one embodiment the glycan therapeutic composition comprises a mixture of one or more non-digestible oligosaccharides, non-digestible polysaccharides, free monosaccharides, non-digestible saccharides, starch, or non-starch polysaccharides.

Exemplary natural non-digestible saccharides are fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides.

Natural saccharides that are not digestible by humans include transgalactooligosaccharides, galacto-oligosaccharides, lactulose, raffinose, stachyose, lactosucrose, fructo-oligosaccharides, isomalto-oligosaccharides, xylo-oligosaccharides, paratinose oligosaccharides, difructose anhydride III, sorbitol, maltitol, lactitol, reduced paratinose, cellulose, beta-glucose, beta-galactose, beta-fructose, verbascose, galactinol, and beta-glucan, guar gum, pectin, high sodium alginate, and lambda carrageenan. Other natural saccharides include inulin, fructo-oligosaccharide (FOS), lactulose, galacto-oligosaccharide (GOS), raffinose, or stachyose.

Digestible monosaccharides or oligosaccharides are carbohydrates that can be digested by the human digestive system, and include, e.g., lactose, galactose, or glucose.

In one embodiment, a glycan therapeutic composition is a mixture of non-digestible oligosaccharides and lactose, glucose or galactose.

In another embodiment, a prebiotic composition comprises a glycan therapeutic composition wherein the glycan therapeutic composition comprises about 1-90%, about 1-80%, about 1-70%, about 1-60%, about 1-50%, about 1-40%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 92-100%, about 93-99%, about 94-98%, about 92-96%, about 93-96%, or about 93-95% glycan therapeutic by weight with the remainder comprising digestible saccharides. In some embodiments, the digestible saccharides are less than about 10% (such as about 9, 8, 7, 6, 5, 4, 3, 2, or less than 1%). In one embodiment, a glycan therapeutic composition can comprise about 1-5% digestible saccharides, such as lactose, glucose or galactose. In one embodiment the digestible saccharides are byproducts of the glycan therapeutic synthesis process.

In one embodiment, a glycan therapeutic composition comprises about 1-90%, about 1-80%, about 1-70%, about 1-60%, about 1-50%, about 1-40%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 90-96%, about 93-96%, about 93-95%, about 94-98%, about 93-99%, or about 92-100% glycan therapeutic by weight and no digestible saccharides.

In one embodiment, the glycan therapeutic composition comprises one or more non-digestible or essentially non-digestible (by a human) prebiotics. This non-digestibility is because humans lack the enzymes to break down some or all of the prebiotic oligosaccharide as it travels through the digestive tract. When a prebiotic reaches the small intestine and colon, bacteria (e.g., Bifidobacteria and *Lactobacilli*) encoding an enzyme or enzymes capable of digesting the prebiotic can break down the prebiotic into simple sugars that the bacteria can use. Suitable prebiotics can include one or more of a carbohydrate, carbohydrate monomer, carbohydrate oligomer, or carbohydrate polymer. In one embodiment, the prebiotics are non-digestible saccharides, which include non-digestible monosaccharides, non-digestible oligosaccharides, or non-digestible polysaccharides. In one embodiment, the glycan therapeutic composition comprises one or more of GOS, lactulose, raffinose, stachyose, lactosucrose, FOS (e.g. oligofructose or oligofructan), inulin, isomalto-oligosaccharide, xylo-oligosaccharide, paratinose oligosaccharide, transgalactosylated oligosaccharides (e.g. transgalacto-oligosaccharides), transgalactosylate disaccharides, soybean oligosaccharides (e.g. soyoligosaccharides), gentiooligosaccharides, glucooligosaccharides, pecticoligosaccharides, palatinose polycondensates, difructose anhydride III, sorbitol, maltitol, lactitol, polyols, polydextrose, reduced paratinose, cellulose, beta-glucose, beta-galactose, beta-fructose, verbascose, galactinol, and beta-glucan, guar gum, pectin, high, sodium alginate, and lambda carrageenan, or mixtures thereof. Other prebiotics include fructo-oligosaccharides (FOS), galactooligosaccharides (GOS), Xylo-oligosaccharides (XOS), chitosan oligosaccharide (chioses), isomaltose oligosaccharides (IMOS), gum arabic, soy- and pectin-oligosaccharides, pectin, xylan, inulin, chitosan, and/or beta-glucan. Other prebiotics include various galactans and carbohydrate based gums, such as *psyllium*, guar, carrageen, gellan, and konjac. Other prebiotics include dietary fibers, such as, for example, resistant maltodextrin, fiber dextrin, polydextrose, inulin, IMOS, the linear and branched dextrans, pullalan, hemicellulose, and combinations thereof. Dietary fiber may consist of non-starch polysaccharides such as cellulose and many other plant components such as dextrins, inulin, lignin, chitins, pectins, beta-glucans, fructo-oligosaccharides, resistant starches, soluble corn (gluco) fiber, polydextrose, and gums such as guar, locust bean, xanthan or pullulan gum. Other fiber sources include oligo- or polysaccharides, selected from the group consisting of resistant maltodextrin, polydextrose, soluble corn (gluco) fiber, fiber dextrin, pullulan, resistant starch, inulin, fructo-oligosaccharides, galacto-oligosaccharides, hemicellulose and fructose oligomer syrup or lactulose or any other prebiotic compounds (including prebiotic disaccharides such as lactulose and tagatose among others). In some embodiments, both soluble and insoluble fibers are used. For example, the weight ratio of soluble fiber to insoluble fiber may be about 1:4 to about 4:1; or about 1:1 to about 2:1.

If desired, one can target the site of fermentation from proximal, mid, to distal colon by changing the ratio of the different compounds in the compositions described herein. Consequently, a beneficial effect may be exerted on the intestinal microbiota ecology of the subject across the length of the entire colon.

Additional substances can be given in conjunction with a glycan therapeutic composition. These substances can enhance the action of the increasing doses of glycan therapeutic by, e.g., encouraging the growth of bacteria in the gut that alleviate symptoms of GI diseases, increasing adhesion of probiotic or beneficial commensal bacteria, or allowing doses of probiotic bacteria to more readily pass through the stomach without being destroyed. These substances can be given prior to treatment with glycan therapeutic, during treatment with glycan therapeutic, after treatment with glycan therapeutic, or any combination thereof. If administered during glycan therapeutic treatment, they can be administered with the dose of glycan therapeutic being given, or before or after the dose of glycan therapeutic, or any combination thereof.

Methods of Treating

Provided herein are methods of treating a disease, disorder or pathological condition comprising administering to a subject in need thereof a glycan therapeutic preparation. Also provided herein are methods of treating cancer with a pharmaceutical composition comprising a glycan therapeutic preparation described herein. Further provided herein are methods of treating cancer with a medical food comprising a glycan therapeutic preparation described herein. Yet further provided herein are methods of treating cancer with a dietary supplement comprising a glycan therapeutic preparation described herein.

Provided herein are methods of treating cancer in a human subject in need thereof. The method includes identifying a human subject in need of treatment for a tumor or cancer, and administering to the subject a pharmaceutical composition or medical food or dietary supplement comprising a glycan therapeutic preparation described herein.

In some embodiments, the glycan therapeutic preparation is formulated as a pharmaceutical composition. In other embodiments, the glycan therapeutic preparation is formulated as a medical food. In other embodiments, the glycan therapeutic preparation is formulated as a dietary supplement.

In some embodiments, the cancer may be any solid or liquid cancer and includes benign or malignant, non-invasive or invasive tumors, hyperplasias, and premalignant lesions, including gastrointestinal cancer (such as non-metastatic or metastatic colorectal cancer, pancreatic cancer, gastric cancer, oesophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g. head and neck squamous cell cancer); CNS cancer including malignant glioma, astrocytomas, retinoblastomas and brain metastases; malignant mesothelioma; non-metastatic or metastatic breast cancer (e.g. hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and haematologic neoplasias (such as multiple myeloma, acute myelogenous leukemia, chronic myelogenous leukemia, myelodysplastic syndrome, acute lymphoblastic leukemia, Hodgkin's lymphoma).

In some embodiments, the cancer is acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In some embodiments, the subject has metastatic cancer. In other embodiments, the subject has non-metastatic cancer. In some embodiments, the subject has a benign tumor. In some embodiments, the subject has a premalignant lesion or a pre-cancerous condition. Examples of premalignant lesions or pre-cancerous conditions include: actinic keratosis, Barrett's esophagus, atrophic gastritis, ductal carcinoma in situ, dyskeratosis congenital, sideropenic dysphagia, lichen planus, oral submucous fibrosis, solar elastosis, cervical dysplasia, leukoplakia, and erythroplakia.

In some embodiments, the cancer is a highly immunogenic cancer, e.g., the cancer has (e.g., as determined by analysis of a cancer biopsy) one or more of the following characteristics: (a) tumor infiltrating lymphocytes (TIL), e.g., 1 TIL per 1000 tumor cells; (b) mutations, e.g., 0.1 or more somatic mutations per megabase of tumor genomic DNA; (c) neoantigens, e.g., 1 or more neoantigen with one or more endogenous T cell receptor and/or one or more idiotype clone that recognizes a processed and presented moiety of the neoantigen; (d) tertiary lymphoid structures; (e) high expression of inflammatory gene expression, e.g., 2-fold increased expression of cytokines above baseline expression in non-cancerous tissue; and (f) immune cells exhibiting immunosuppressive phenotype, e.g. dendritic cells lacking cytokine expression. In some embodiments, the cancer is melanoma, lung cancer, bladder cancer, colorectal cancer, esophageal cancer, cervical cancer, head and neck cancer, stomach cancer, uterine cancer, liver cancer, kidney cancer, ovarian cancer, prostate cancer, myeloma, B cell lymphoma, or glioma. Methods of assessing these characteristics of the cancer are known (see, e.g., Clin Cancer Res. 2000 May; 6(5):1875-81; Nature. 2013 Aug. 22; 500(7463): 415-21. doi: 10.1038/nature12477. Epub 2013 Aug. 14; Nature. 2014 Nov. 27; 515(7528):577-81. doi: 10.1038/nature13988; Trends Immunol. 2014 November; 35(11): 571-80. doi: 10.1016/j.it.2014.09.006. Epub 2014 Oct. 22;

Front Immunol. 2013 Dec. 11; 4:438. doi: 10.3389/ fimmu.2013.00438; Eur J Cancer. 2009 January; 45(2):228- 47. doi: 10.1016/j.ejca.2008.10.026.

In some embodiments, the cancer is a primary tumor, in some embodiments, the cancer is a metastasized tumor. In some embodiments, the cancer patient has: had one or more tumors resected, received chemotherapy or other pharmacological treatment for the cancer, received radiation therapy, and/or received other therapy for the cancer.

In one embodiment, the method of treating a cancer in a subject includes a) administering a pharmaceutical composition comprising a glycan therapeutic preparation to a subject who has been treated with an anti-cancer therapy, b) administering an anti-cancer therapy to a subject who has been treated with a pharmaceutical composition comprising a glycan therapeutic preparation; or c) administering a pharmaceutical composition comprising a glycan therapeutic preparation and administering an anti-cancer therapy to a subject.

In one embodiment, the method includes administering pharmaceutical composition comprising a glycan therapeutic preparation to a subject who has been treated with an anti-cancer therapy and the treatment with the anti-cancer therapy was initiated, or completed, within 1, 2, 3, 4, 5, 6, 7, 8, 9, 10, 14, 21, 28 days of initiation, or completion, of the glycan therapeutic administration.

In one embodiment, the method includes administering an anti-cancer therapy to a subject who has been treated with a pharmaceutical composition comprising a glycan therapeutic preparation and the treatment with the glycan therapeutic preparation was initiated, or completed, within 1, 2, 3, 4, 5, 6, 7, 8, 9, 10, 14, 21, 28 days of initiation, or completion, of the administration of the anti-cancer therapy.

In one embodiment, the method includes administering a pharmaceutical composition comprising a glycan therapeutic preparation and administering an anti-cancer therapy to a subject and the glycan therapeutic preparation and the anti-cancer therapy are provided within 1, 2, 3, 4, 5, 6, 7, 8, 9, 10, 15, 20, 25, 30, 35, 40, 45, 50, 55, 60 minutes, hours, days, weeks of one another. In some embodiments, the first and second therapeutic agents (e.g. a pharmaceutical glycan therapeutic preparation and a second active compound or pharmaceutical agent) are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

In some embodiments, the pharmaceutical composition is administered in an amount and for a time effective to result in one of (or more, e.g., 2 or more, 3 or more, 4 or more of): (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, (i) increased cancer progression free survival of subject.

In some embodiments, the method of treatment optionally results in one or more of: i) enhancement of the subject's immune function, ii) improvement of the subject's gut health, iii) induction of production of epithelial enzymes, iv) induction of the synthesis of vitamins in the intestines of the subject, v) reduction in the levels of toxins in the subject's GI tract, vi) induction of apoptosis of cancer and precancerous cells in the subject, vii) improvement of the overall gastrointestinal and colonic health of the subject, viii) reduction in bloating, abdominal distention or gas production, and/or ix) improvement of bowel regularity.

In some embodiments, methods are provided to modulate GI fluid turnover. In some embodiments, methods are provided to balance (or rebalance) GI fluid homeostasis. In some embodiments, methods are provided to modulate electrolyte balance. Fluid loss can lead to electrolyte loss (Na, K, Mg, Cl). The methods include administering to a subject in need to GI fluid modulation a glycan therapeutic described herein in an amount effective to substantially (re-)balance the fluid turnover. For example, diarrhea and constipation are conditions associated with a fluid imbalance. Osmotic diarrhea can be caused, e.g., by laxatives and sugar intolerance. Secretory diarrhea can be caused, e.g., by malabsorption syndromes, drugs (e.g., quinidine, quinine, colchicine, anthraquinone cathartics, castor oil, prostaglandins), and endocrine tumors that produce substances that increase secretion, e.g., vipomas (vasoactive intestinal peptide), gastrinomas (gastrin), mastocytosis (histamine), medullary carcinoma of the thyroid (calcitonin and prostaglandins), and carcinoid tumors (histamine, serotonin, and polypeptides). Some of these mediators (e.g., prostaglandins, serotonin, and related compounds) also accelerate intestinal transit, colonic transit, or both.

In some embodiments, the pharmaceutical glycan therapeutic composition is administered in an amount and for a time effective to result in shifted or modulated state of the subject's gastrointestinal microbiota. In one embodiment, the the pharmaceutical glycan therapeutic composition is administered in an amount and for a time effective to result in shifted or modulated bacterial taxa (one or more, two or more, three or more, etc.). In one embodiment, the pharmaceutical glycan therapeutic composition is administered in an amount and for a time effective to result in shifted or modulated microbial function (e.g., a metabolic function). In one embodiment, the pharmaceutical glycan therapeutic composition is administered in an amount and for a time effective to result in a shift or modulation of the microbiome (genome), transcriptome, metabolome, or proteome of the microbiota.

In some embodiments, administration of the pharmaceutical glycan therapeutic compositions improves the overall health of the host and/or the health of a specific niche, such as the GI tract, e.g. by modulating (e.g. increasing or decreasing) the growth or abundance of one or more members of the microbial community in the niche (such as resident commensal bacteria and/or acquired pathogens or pathobionts).

In some embodiments, administration of the glycan therapeutics described herein improves the overall health of the gastrointestinal tract by influencing members of the microbial community. The glycan therapeutics described herein, e.g., activate signaling pathways within the intestinal mucosa, inhibit pathogen binding to mucosal surfaces, and/ or attenuate inflammation of the intestinal mucosa. In some embodiments, administration of the glycan therapeutics results in the treatment or prevention of an inflammatory disease, including intestinal inflammation.

In one embodiment, the treatment results in increased levels of bacteria adherent to gastrointestinal epithelial cells. For example, the treatment results in increased levels of *Citrobacter rodentium*, EHEC O157:H7, *Candida albicans, Clostridium bolteae* 90B3*Clostridium* cf. *saccharolyticum* K10, *Clostridium symbiosum* WAL-14673, *Clostridium*

*hathewayi* 12489931, *Ruminococcus obeum* A2-162, *Ruminococcus gnavus* AGR2154, Butyrate-producing bacterium SSC/2, *Clostridium* sp. ASF356, *Coprobacillus* sp. D6 cont1.1, *Eubacterium* sp. 3_1_31, Erysipelotrichaceae bacterium 21_3, *Subdoligranulum* sp. 4_3_54A2FAA, *Ruminococcus bromii* L2-63, Firmicutes bacterium ASF500, *Bacteroides dorei* 5_1_36/D4 supercont2.3, *Bifidobacterium animalis* subsp. *lactis* ATCC 27673, or *Bifidobacterium breve* UCC2003.

In some embodiments, the glycan therapeutics described herein promote the metabolism and growth of beneficial components of the gut microbiota, such as, e.g., *Bacteroides, Clostridium, Fusobacterium, Eubacterium, Ruminococcus, Peptococcus, Peptostreptococcus, Akkermansia, Faecalibacterium, Roseburia, Prevotella, Bifidobacterium, Lactobacilli,* or *Christensenella*. As such, the glycan therapeutics may be beneficial in the treatment of diseases associated with disturbed gut microbiota. As examples, colon and liver cancers may be associated with disturbed gut microbiota.

In one embodiment, the glycan therapeutics described herein increase the levels of Bifidobacteria. In one embodiment, the glycan therapeutics described herein increase the levels of *Bacteroides*. In one embodiment, the glycan therapeutics described herein increase the levels of *Akkermansia*. In one embodiment, the treatment results in an increase in the proportion of Bifidobacteria, *Bacteroides*, and/or *Akkermansia* relative to another bacterial species.

In some embodiments, methods to protect against pathogenic infection are provided, comprising administering to a subject a glycan therapeutic preparation described herein. Under certain conditions, pathogenic species are capable of causing disease by producing infection or increasing cancer risk for the host. A healthy human microbiota reduces the risk of disease upon ingestion and may comprise *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacilli, Christensenella minuta,* or a *Christensenellaceae* species, *Streptococcus thermophilus, Enterococcus* and *Bacillus* species, *E. coli,* and yeasts such as Sacharomyces *boulardii*. A healthy bacterial community protects the host, e.g., by providing an increased barrier to translocation of bacteria across the gut mucosa, by competitive exclusion of potential pathogens, and by growth inhibition of bacterial pathogens.

In another embodiment, the treatment with a glycan therapeutic described herein results in an increase in the concentration of one or more microbial metabolite in the GI tract (which may be measured, e.g., in the stool). In one embodiment, the treatment with a glycan therapeutic described herein results in a change (e.g., an improvement) in gut permeability.

The glycan therapeutics described herein when administered to a subject in an effective amount may modulate the production of one or more microbial metabolites. The glycan therapeutics when administered to a subject in an effective amount may modulate the production of one or more microbial metabolites listed in Table 2. In some embodiments, glycan therapeutics when administered to a subject in an effective amount may modulate (e.g. increase or decrease) one or more of the following microbial metabolites: formic acid, acetic acid, propionic acid, butyric acid, isobutyric acid, valeric acid, isovaleric acid, ascorbic acid, lactic acid, tryptophan, serotonin, and/or indole. In some embodiments, glycan therapeutics when administered to a subject in an effective amount may modulate (e.g. increase or decrease) one or more of the following microbial metabolites: succinic acid, trimethylamine (TMA), TMAO (trimethylamine N-oxide), deoxy cholic acid, ethyphenyl sulfate, acetaldehyde, hydrogen peroxide, and/or butanedione. In some embodiments, a substantial increase or decrease in a metabolite may be detected.

In some embodiments, glycan therapeutics described herein when administered to a subject in an effective amount may modulate (e.g. increase) one or more of the following microbial metabolites: formic acid, acetic acid, propionic acid, butyric acid, isobutyric acid, valeric acid, isovaleric acid, acorbic acid, tryptophan, serotonin, and/or indole. In some embodiments, glycan therapeutics described herein when administered to a subject in an effective amount may modulate (e.g. decrease) one or more of the following microbial metabolites: Succinic acid, TMAO, deoxy cholic acid, ethyphenyl sulfate, acetaldehyde, and/or butanedione. In some embodiments, glycan therapeutics described herein when administered to a subject in an effective amount may modulate (e.g. decrease) one or more of the following microbial metabolites: formic acid, acetic acid, propionic acid, butyric acid, isobutyric acid, valeric acid, isovaleric acid, acorbic acid, tryptophan, serotonin, and/or indole. In some embodiments, glycan therapeutics described herein when administered to a subject in an effective amount may modulate (e.g. increase) one or more of the following microbial metabolites: Succinic acid, TMAO, deoxy cholic acid, ethyphenyl sulfate, acetaldehyde, and/or butanedione.

In some embodiments, the glycan therapeutic is digested by the gut microbiota resulting, e.g., in the release of short-chain fatty acids such as butyrate, acetate, and propionate, which may act immunomodulatory (e.g. anti-inflammatory) and other metabolites (e.g. bile acids, and lactate) that may confer beneficial health effects on the host.

Some methods described herein include the administration of glycan therapeutics to modulate the host's immune functions and/or intestinal epithelial cell functions. The glycan therapeutics may upregulate the immune function, e.g. to improve the ability of the host to fight cancers, while downregulation of immune function may treat inflammation (such as, e.g., intestinal inflammation). Modulated beneficial bacteria may stimulate intestinal epithelial cell responses, including restitution of damaged epithelial barrier, production of antibacterial substances and cell-protective proteins, and blocking of cytokine-induced intestinal epithelial cell apoptosis.

In some embodiments, method of modulating a functional pathway of the microbiota of the gastrointestinal tract are provided. The methods include administering to the human subject a pharmaceutical composition comprising a glycan therapeutic preparation in an amount effective to modulate the functional pathway. In some embodiments, the functional pathway modulates the production of anti-microbial agent, a secondary bile acid, a short-chain fatty acid, a siderophore or a metabolite listed in Table 2 by the microbiota.

Bacteria can elicit both pro- and anti-inflammatory responses from host (mammalian) cells. In one embodiment, glycan therapeutics are used to alter the bacterial population or its function to elicit a desired host response. The host response may be modulated a) via secreted or shed bacterial products (e.g., short-chain fatty acids), b) stimulation of the production of antimicrobial peptides (AMPs), c) modulation (increasing or decreasing the production of) inflammatory and immunomodulatory cytokines including: interleukin-1α (IL-1α), IL-1β, IL-2, IL-4, IL-6, IL-8, IL-10, IL-12, IL-13, IL-17A, IL-17F, IL-22, IL-23, tumor necrosis factor (TNF), chemokine (C-C motif) ligand 5 (CCL5, also known as RANTES), transforming growth factor beta (TGF-β), interferon gamma (IFN-γ), or d) modulation of other innate or adaptive immune responses.

The glycan therapeutics when administered to a subject in an effective amount may modulate one or more host pathways. In some embodiments, an inflammatory state, e.g. of the GI tract is modulated by administration of a glycan therapeutic. In some embodiments, production of short-chain fatty acids (SCFAs) may be modulated. For example, SCFAs produced by the gut microbiota may serve as energy sources for colonic epithelial cells and in some embodiments contribute to the maintenance of gut barrier function. In some instances, increased gut barrier function limits plasma endotoxin levels and prevents systemic inflammation (Cani et al., Changes in gut microbiota control inflammation in obese mice through a mechanism involving GLP-2-driven improvement of gut permeability, Gut, 2009, 58:1091). In some embodiments, SCFAs promote gut barrier function by affecting mucin production and gastrointestinal peptide LL-37. SCFAs modulate a number of human immunological factors. In some embodiments, SCFAs modulate inflammation by suppressing NF-kB and the production of inflammatory cytokines such as IL-6 and TNF-α (Kim C H et al. 2014. Gut Microbiota-Derived Short-Chain Fatty Acids, T Cells, and Inflammation. Immune Network 14(6):277-288). In one embodiment, treatment with a glycan therapeutic described herein modulates (e.g., increases) that SCFA propionate. In some embodiments, propionate increases expression of Foxp3, a T cell regulatory factor, and/or IL-10, an anti-inflammatory cytokine, in colonic regulatory T cells. In some embodiments, SCFAs promote the generation of (e.g., colonic) regulatory T (Treg) cells and/or CD4+ T cells thereby limiting inflammatory responses (Arpaia et al., Metabolites produced by commensal bacteria promote peripheral regulatory T-cell generation, Nature, 2013, 504: 451; Smith P M et al. 2013. The microbial metabolites, short chain fatty acids, regulate colonic Treg cell homeostasis. Science; 341(6145)).

In some embodiments, glycan therapeutics are administered to modulate short chain fatty acid (SCFA) production of commensal bacteria including members of the families Ruminocaccaceae and Lachnospiraceae (Vital M, Howe A C, Tiedje J M. 2014. Revealing the bacterial butyrate synthesis pathways by analyzing (meta)genomic data. mBio 5(2):e00889-14. doi:10.1128/mBio.00889-14). In some embodiments, glycan therapeutics when administered in an effective amount modulate bacterial species that produce SCFAs, such as, e.g., those of the Ruminocaccaceae family and/or Lachnospiraceae family. In some embodiments, the glycan therapeutics modulate host immunity and inflammation.

In some embodiments, glycan therapeutics are administered to induce systemic effects, e.g. of SCFAs and other microbially produced immunomodulatory molecules or metabolites to modulate the inflammatory state of distal sites.

In some embodiments, the treatment with the glycan therapeutics described herein results in increased levels of Th17 or Th1 cells in the subject. In some embodiments, the treatment with the glycan therapeutics described herein results in increased levels of cytotoxic T-cells or natural killer cells in the subject. In some embodiments, the treatment with the glycan therapeutics described herein promote the growth of immune cells of the subject. In some embodiments, the treatment with the glycan therapeutics described herein promotes the differentiation of immune cells of the subject. In some embodiments, the treatment with the glycan therapeutics described herein results in increased tumor surveillance. In some embodiments, the treatment with the glycan therapeutics described herein results in increased anti-tumor activity of the host's immune system.

In some embodiments, the glycan therapeutics promote the growth of beneficial taxa (e.g., *Bacteroides* and *Bifidobacteria*). In some embodiments, promoting growth of certain taxa modulates (e.g. upregulates) the immune response of the host.

In some embodiments, the treatment with the glycan therapeutics described herein results an increase in tumor-infiltrating bacteria, e.g., in the GI tract that may infiltrate gastrointestinal tumors. In some embodiments, the treatment with the glycan therapeutics described herein results an increase of bacteria that produce toxins and/or small-molecules that decrease the growth of cancers or increase cell death of cancer cells, e.g., that of gastrointestinal cancers. In some embodiments, the treatment with the glycan therapeutics described herein results in the production of microbial metabolites that are toxic to the tumor or repress oncogene expression or oncogenic metabolism.

In some embodiments, methods of selecting a subject for a treatment (e.g., for treatment with a pharmaceutical composition, medical food or dietary supplement) are provided. The methods include: (a) identifying a subject who has a tumor or cancer (e.g., a tumor or cancer described herein), and (b) selecting the identified subject for treatment with a glycan therapeutic preparation described herein. In some embodiments, the subject is further selected for treatment with a second anti-cancer drug or therapy (e.g., a second anti-cancer drug or therapy described herein).

In some embodiments, methods of selecting a subject for a treatment include selecting a subject that is treatment naïve. In some embodiments, the subject is treatment naïve with respect to an anti-cancer therapy, such as, e.g., chemotherapy, radiation therapy or surgical removal of the tumor. In some embodiments, the subject is treatment naïve with respect to an immune suppressive therapy. In some embodiments, the subject is treatment naïve with respect to an antimicrobial therapy.

In some embodiments, methods of selecting a subject for a treatment include selecting the glycan therapeutic preparation on the basis that it will provide therapeutic benefit to the subject. In some embodiments, methods of selecting a subject for a treatment include selecting the subject on the basis that the subject will or is expected to benefit from administration of the glycan therapeutic preparation.

In some embodiments, the selection methods include assessing the subject's gastrointestinal microbiota, e.g., before, during and/or after the treatment. In one embodiment, the subject's gastrointestinal microbiota is assessed before starting treatment. In some embodiments, the results of the assessment are used to select the subject for treatment. Alternatively or in addition, assessment is used to identify a dosage or dosage regimen for the treatment.

In some embodiments, subjects are identified and selected that respond to a glycan therapeutic for initial and/or continued treatment. Responders may be identified using one or more suitable parameter as determined by a physician or other healthcare provider. The parameters include one or more of: a) a physiological treatment effect (e.g. reduction of a fever, increased well-being, increased energy, etc.), b) a desired change in a (host) biomarker (e.g. a cancer marker, an inflammatory marker, etc.), c) a microbial taxa shift (e.g., in relative abundance, change in diversity, etc.), d) a functional shift of the microbiota (e.g. a shift in metabolic output, microbial signaling, microbial gene expression, microbial protein expression), e) absence or presence of a desired bacterial taxa (in the host microbiota), etc. In some embodiments, non-responders are identified and selected. In one embodiment, treatment methods include rendering the non-responder responsive to the treatment. In some embodiments, this may include administering to the non-responder one or more bacterial taxa (e.g. one or more commensals) that are responsive to glycan (and/or second agent) treatment.

In some embodiments, methods of evaluating a subject, e.g., to evaluate suitability for glycan treatment, responsiveness to glycan treatment, or glycan treatment progression, are provided. Optionally, the glycan treatment is in combination with another treatment or therapy (e.g., a drug treatment, such as an anti-cancer drug). Changes in a variety of suitable biomarkers may be assessed. In some embodiments, changes in the microbiota are assessed or corresponding values are acquired. In some embodiments, changes in microbial metabolism (e.g. metabolite input and/or output) are assessed or corresponding values are acquired. In some embodiments, changes in the microbiome (e.g. changes on the genome or transcriptome level) are assessed or corresponding values are acquired. In some embodiments, changes in the microbial proteome are assessed or corresponding values are acquired. In some embodiments, changes in the host (e.g., metabolic, inflammatory, cardiovascular, etc.) are assessed or corresponding values are acquired. In some embodiments, changes in the host proteome (e.g. protein synthesis), metabolome, transcriptome (e.g. gene transcription/expression), cell signaling, etc. are assessed or corresponding values are acquired. In some embodiments, the methods include a) acquiring a value for a parameter related to the level of a biomarker modulated by a glycan therapeutic preparation (and/or the drug or therapy in a combination treatment); b) responsive to the value, classifying the subject, selecting a treatment for the subject, or administering the treatment to the subject, thereby evaluating a subject.

Treatment responsiveness and/or progression may be assessed or evaluated using one or more biomarker. Suitable biomarkers may be determined by a physician and may include: i) changes in gastrointestinal microbiota and the overall metabolism of the gastric environment, such as the production of organic acids (e.g., SCFAs), ii) modulation of the immune system, assessing inflammatory and immune globulins iii) increase the absorption of minerals in the colon, such as calcium, zinc or magnesium iv) regulation of lipid metabolism, lowering cholesterol, v) induction of other important processes for host homeostasis (see, reviews by Pool-Zobel B L. Inulin-type fructans and reduction in colon cancer risk: review of experimental and human data. 2005. British Journal of Nutrition 93 Suppl 1:S73-90; and Liong M T. Roles of Probiotics and Prebiotics in Colon Cancer Prevention: Postulated Mechanisms and In-vivo Evidence. 2008. International Journal of Molecular Sciences 9(5):854-63).

The glycan therapeutic treatment may result in increases or decreases of one or more biomarkers that can be determined by methods known in the art. An investigator can determine at which point or points during treatment the biomarker(s) should be measured, e.g. prior to treatment, at various intervals during treatment and/or after treatment. Any suitable sample, e.g. a gastrointestinal-specific sample such as, e.g. a tissue sample or biopsy, a swab, a gastrointestinal secretion (such as feces/a stool sample), etc. may be drawn from the subject and the sample may be analyzed by suitable methods known in the art. In some embodiments, a substantial increase or decrease in a biomarker may be detected to assess treatment progression.

In some embodiments, treatment with the glycan therapeutic results in the release of short-chain fatty acids such as butyrate, acetate, and propionate and other metabolites (e.g. bile acids, and lactate) by the microbiota that may affect one or more biological pathways of the host subject (e.g. have an immunomodulatory effect on the host).

To evaluate the effect of administered pharmaceutical glycan therapeutic compositions on SCFA production in the gut, fecal samples can be collected. SCFA levels, particularly acetate, propionate, and butyrate may be quantified. SCFAs, creatines, and hydroxy-SCFAs can be quantified by alkalinizing stool samples, obtaining fingerprints of the metabolic composition of the sample using, e.g., 1D 1H NMR spectrometer, and analyzing with supervised multivariate statistical methods. Inulin may serve as a positive control.

In some embodiments, microbial metabolite profiles of patient samples or microbes cultures from subject samples are used to identify risk factors for developing a disease, disorder or condition, such as, e.g., cancer. Exemplary metabolites for the purposes of diagnosis, prognostic risk assessment, or treatment assessment purposes include those listed in Table 2. In some embodiments, microbial metabolite profiles are taken at different time points during a subject's disease and treatment in order to evaluate the subject's disease state including recovery or relapse events, e.g., that of a tumor. In some embodiments, metabolite profiles are acquired to inform subsequent treatment.

Provided herein are methods of treating cancer in a human subject in need thereof with a combination therapy. The method includes administering to the human subject a first agent which is a pharmaceutical composition or medical food or dietary supplement comprising a glycan therapeutic preparation described herein in combination with a second agent.

In some embodiments, the glycan therapeutics described herein may be used in combination with other anti-proliferative, anti-neoplastic or anti-tumor drugs or treatments. Such drugs or treatments include chemotherapeutic drugs, e.g., cytotoxic drugs (e.g., alkylating agents, antimetabolites, anti-tumor antibiotics, topoisomerase inhibitors, mitotic inhibitors, corticosteroids); cancer growth blockers such as tyrosine kinase inhibitors and proteasome inhibitors; other chemical drugs such as L-asparaginase and bortezomib (Velcade®). Hormone therapies (or anti-hormone therapies) may be used, e.g., for hormone-sensitive cancers.

In some embodiments, the glycan therapeutics described herein may be used in combination with other anti-proliferative, anti-neoplastic or anti-tumor drugs or treatments that include an anti-cancer drug, such as, e.g., checkpoint inhibitors (such as, e.g., anti-PD-1, anti-PD-L1, anti-CTLA4, anti-TIM-3, anti-LAG-3); vaccines (such as, e.g., autologous cancer vaccines, allogeneic cancer vaccines, neoantigen cancer vaccines, shared antigen cancer vaccines (e.g. NY-ESO-1)); targeted kinase inhibitors (such as, e.g., Imatinib mesylate, Ibrutinib, Neratinib, Palpociclib, Erlotinib, Lapatinib); antibodies (such as, e.g., Bevacizumab, Trastuzumab, Rituximab, Cetuximab); chemotherapeutics (such as, e.g., irinotecan, 5-flurouracil, lenalidomide, capecitabine, docetaxel), antibody-drug conjugates (e.g. ado-trastuzumab emtansine).

Immunotherapies are another class of anti-cancer agent that may be used in the combination with glycan therapeutics. Immunotherapies include checkpoint inhibitors (see, e.g., PMID: 26598056, PMID: 26680224); T cell therapy (e.g., CAR-T cell therapy) (see, e.g., PMID: 26611350), Natural Killer (NK) cell immunomodulation (see, e.g., PMID: 26697006); and cancer vaccines (PMID: 26579225).

The glycan therapeutics described herein may be used in combination with non-drug therapies for cancer such as surgery, radiotherapy, or cryotherapy. Treatment methods may include glycan therapeutics described herein in combination with 2 or more other therapies or drugs. For example, breast cancer may be treated with a combination of glycan therapeutics described herein and surgery or radiotherapy and a chemotherapeutic cocktail or biologic (e.g., an anti-HER2 antibody).

The glycan therapeutics described herein may be used in combination with one or more of: a pain-management drug an antidepressant, an antiepileptic, a steroid, a drug for managing a GI tract motility disorder, an anti-inflammatory agent, and an antimicrobial agent, described elsewhere herein.

In one embodiment, the second agent is a therapeutic agent which is an immune checkpoint modulator. The checkpoint modulator may be an inhibitory or agonist form of the following: antibody (e.g., a monospecific antibody such as a monoclonal antibody (mAb), e.g., a humanized or fully human mAb); a fusion protein, e.g., an Fc-receptor fusion protein; or a small molecule. The check point modulator may modulate a checkpoint protein or a ligand of a checkpoint protein. In one embodiment, the checkpoint modulator is an inhibitor (e.g., an inhibitory antibody or small molecule inhibitor) of CTLA-4 (e.g., an anti-CTLA4 antibody such as ipilimumab/Yervoy or tremelimumab). In other embodiments, the checkpoint modulator is an inhibitor (e.g., an inhibitory antibody or small molecule inhibitor) of PD-1 (e.g., nivolumab/Opdivo®; pembrolizumab/Keytruda®; pidilizumab/CT-011). In other embodiments, the checkpoint modulator is an inhibitor (e.g., an inhibitory antibody or small molecule inhibitor) of PDL1 (e.g., MPDL3280A/ RG7446; MEDI4736; MSB0010718C; BMS 936559). In yet other embodiments, the checkpoint modulator is an inhibitor (e.g., an inhibitory antibody or Fc fusion or small molecule inhibitor) of PDL2 (e.g., a PDL2/Ig fusion protein such as AMP 224). In other embodiments, the checkpoint modulator modulates (e.g., an antibody modulator or small molecule modulator) B7-H3 (e.g., MGA271), B7-H4, BTLA, HVEM, TIM3, GALS, LAG3, VISTA, KIR, 2B4, CD160, CGEN-15049, CHK 1, CHK2, A2aR, B-7 family ligands, or a combination thereof.

In one embodiment, the second agent is a therapeutic agent which is an adoptive T cell (CAR-T cell) or NK cell for anti-cancer therapy. In one embodiment, the adoptive T cell therapy comprises administering to a subject autologous and/or allogeneic T-cells. In another embodiment, the autologous and/or allogeneic T-cells are targeted against tumor antigens (e.g., CD19, CD20, CD22, AFP, CEA, CA-125, MUC-1, ETA, MAGE, CA15-3, CA27-29, CA19-9, CD34, CD117, PSA, MART-1 etc.). In one embodiment, the adoptive NK cell therapy comprises administering to a subject autologous and/or allogeneic NK cells.

In one embodiment, the second agent is a therapeutic agent which is a cancer vaccine (e.g., a tumor cell vaccine, an antigen vaccine, a dendritic cell vaccine, a DNA vaccine, or vector based vaccine). The therapeutic cancer vaccine may be a dendritic cell vaccine, e.g., a dendritic cell vaccine composed of autologous dendritic cells and/or allogeneic dendritic cells. In certain embodiments, the autologous or allogeneic dendritic cells are loaded with cancer antigens prior to administration to the subject. In certain embodiments, the autologous or allogeneic dendritic cells are loaded with cancer antigens through direct administration to the tumor. The therapeutic cancer vaccine may be a peptide vaccine, e.g. synthetic peptides formulated to elicit an anti-cancer response from the host immune system. In certain embodiments, the peptides encode tumor antigens. In certain embodiments, the tumor antigens encoded by the peptides are neoantigens.

In one embodiment, the second agent is a therapeutic agent which is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodophyllotoxins, antibiotics, L-asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol®, paclitaxel (Bristol-Myers Squibb Oncology, Princeton, N.J.), ABraxane®. Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more (e.g., three, four, five, etc.) chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In one embodiment, the second agent is a therapeutic agent which is a biologic such a cytokine (e.g., interferon or an interleukin (e.g., IL-2)). In other embodiments, the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen promoting cancer growth or maintainance. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (Ibritumomab tiuxetan); Humira (Adalimumab); Xolair (Omalizumab); Bexxar (Tositumomab-I-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

In one embodiment, the second agent is an immunomodulatory drug, e.g., ABREVA (docosanol), Acyclovir, Agenerase (amprenavir), Albenza (albendazole), Aldara (imiquimod), Alinia (nitazoxanide), Allegra-D, Altabax (retapamulin), Amevive (alefacept), Aphthasol, Aptivus (tipranavir), Aptivus (tipranavir), Arcapta (indacaterol maleate inhalation powder), Astepro (azelastine hydrochloride nasal spray), Avelox I.V. (moxifloxacin hydrochloride), AzaSite (azithromycin), Baraclude (entecavir), Benlysta (belimumab), Bepreve (bepotastine besilate ophthalmic solution), Berinert (C1 Esterase Inhibitor (Human)), Besivance (besifloxacin ophthalmic suspension), Biaxin XL (clarithromycin extended-release tablets), Cancidas, Carrington patch, Cayston (aztreonam for inhalation solution), Cedax (ceftibuten), Cefazolin and Dextrose USP, CellCept, Cervarix [Human Papillomavirus Bivalent (Types 16 and 18) Vaccine, Recombinant, Children's Motrin Cold, Cinryze (C1 Inhibitor (Human)), Clarinex, Clarithromycin (Biaxin), Clemastine fumarate syrup, Cleocin (clindamycin phosphate), Coartem (artemether/lumefantrine), Combivir, Complera (emtricitabine/rilpivirine/tenofovir disoproxil fumarate), Condylox Gel 0.5% (pokofilox), Cosentyx (secukinumab), Crixivan (Indinavir sulfate), Daliresp (roflumilast), Daptacel, Descovy (emtricitabine and tenofovir alafenamide), Dificid (fidaxomicin), Doribax (doripenem), Dynabac, Edurant (rilpivirine), Egrifta (tesamorelin for injection), Entyvio (vedolizumab), Envarsus XR (tacrolimus extended-release), Epivir (lamivudine), Eraxis (anidulafungin), Evotaz (atazanavir and cobicistat), Evoxac, Extina (ketoconazole), Famvir (famciclovir), Famvir (famciclovir), Firazyr (icatibant), Flagyl ER, Flonase Nasal Spray, Flublok (seasonal influenza vaccine), Flucelvax, Influenza Virus Vaccine, FluMist (Influenza Virus Vaccine), Fluzone Preservative-free, Fortovase, Fulyzaq (crofelemer), Fuzeon (enfuvirtide), Gardasil (quadrivalent human papillomavirus (types 6, 11, 16, 18) recombinant vaccine), Gastrocrom Oral Concentrate (cromolyn sodium), Genvoya (elvitegravir, cobicistat, emtricitabine, and tenofovir alafenamide), Gralise (gabapentin), Grastek (Timothy Grass Pollen Allergen Extract), Havrix, Hepsera (adefovir dipivoxil), Hiberix (*Haemophilus* b Conjugate Vaccine; Tetanus Toxoid Conjugate), Horizant (gabapentin enacarbil), HyQvia [Immune Globulin Infusion 10% (Human) with Recombinant Human Hyaluronidase], Ilaris (canakinumab), Incivek (telaprevir), Incruse Ellipta (umeclidinium inhalation powder), INFANRIX (Diphtheria and Tetanus Toxoids and Acellular Pertussis Vaccine Adsorbed), INFERGEN (interferon alfacon-1), Intelence (etravirine), Intron A (Interferon alfa-2b, recombinant), Intron A (interferon alfa-2b, recombinant), Invirase (saquinavir), Isentress (raltegravir), Ixiaro (Japanese Encephalitis Vaccine, Inactivated, Adsorbed), Kalbitor (ecallantide), Kaletra Capsules and Oral Solution, Ketek (telithromycin), Kineret, anakinra, Lamisil (terbinafine hydrochloride) Solution, 1%, Lamisil (terbinafine hydrochloride) Tablets, Leukine (sargramostim), Lexiva (fosamprenavir calcium), Lotrisone (clotrimazole/betamethasone diprorionate) lotion, Lovenox (enoxaparin sodium) Injection, Makena (hydroxyprogesterone caproate injection), Malarone (atovaquone; proguanil hydrochloride) Tablet, Menveo (meningitis vaccine), Moxatag (amoxicillin), Myalept (metreleptin for injection), Norvir (ritonavir), Noxafil (posaconazole), Nulojix (belatacept), Odefsey (emtricitabine, rilpivirine, and tenofovir alafenamide), Oral Cytovene, Oralair (Sweet Vernal, Orchard, Perennial Rye, Timothy and Kentucky Blue Grass Mixed Pollens Allergen Extract), Oravig (miconazole), Otezla (apremilast), Panretin Gel, Pediarix Vaccine, Peg-Intron (peginterferon alfa-2b), Pegasys (peginterferon alfa-2a), Plegridy (peginterferon beta-1a), Prevnar 13 (Pneumococcal 13-valent Conjugate Vaccine), Prezcobix (darunavir and cobicistat), Prezista (darunavir), Qnasl (beclomethasone dipropionate) nasal aerosol, Qutenza (capsaicin), Ragwitek (Short Ragweed Pollen Allergen Extract), Rapamune (sirolimus) oral solution, Rapamune (sirolimus) Tablets, Rayos (prednisone) delayed-release tablets, Rebetol (ribavirin), REBETRON™ Combination Therapy, Relenza, Rescriptor Tablets (delavirdine mesylate tablets), RespiGam (Respiratory Syncitial Virus Immune Globulin Intravenous), Restasis (cyclosporine ophthalmic emulsion), Reyataz (atazanavir sulfate), Rid Mousse, Rotarix (Rotavirus Vaccine, Live, Oral), Rotateq (rotavirus vaccine, live oral pentavalent), Selzentry (maraviroc), Simponi (golimumab), Simulect, Sitavig (acyclovir) buccal tablets, Spectracef, SPORANOX (itraconazole), Stribild (elvitegravir, cobicistat, emtricitabine, tenofovir disoproxil fumarate), Stromectol (ivermectin), Sustiva, Sylvant (siltuximab), Synercid I.V., Taltz (ixekizumab), Tamiflu capsule, Taxol, Tecfidera (dimethyl fumarate), Teflaro (ceftaroline fosamil), Timentin, Tindamax, tinidazole, Tivicay (dolutegravir), Tri-Nasal Spray (triamcinolone acetonide spray), Triumeq (abacavir, dolutegravir, and lamivudine), Trivagizole 3 (clotrimazole) Vaginal Cream, Trizivir (abacavir sulfate; lamivudine; zidovudine AZT) Tablet, Trovan, Tudorza Pressair (aclidinium bromide inhalation powder), Twinrix, Tygacil (tigecycline), Tysabri (natalizumab), Tyzeka (telbivudine), Valcyte (valganciclovir HCl), Valtrex (valacyclovir HCl), VariZIG, Varicella Zoster Immune Globulin (Human), Veramyst (fluticasone furoate), Veregen (kunecatechins), Vfend (voriconazole), Vibativ (telavancin), Victrelis (boceprevir), Videx (didanosine), VIRACEPT (nelfinavir mesylate), Viramune (nevirapine), Viread (tenofovir disoproxil fumarate), Viread (tenofovir disoproxil fumarate), Viroptic, Vistide (cidofovir), Vitrasert Implant, Xifaxan (rifaximin), Xigris (drotrecogin alfa [activated]), Xyzal (levocetirizine dihydrochloride), Zerit (stavudine), Zirgan (ganciclovir ophthalmic gel), Zithromax (azithromycin), Zortress (everolimus), Zymaxid (gatifloxacin ophthalmic solution), Zyrtec (cetirizine HCl).

In one embodiment, the second agent is metabolism-modulating or cachexia-modulating drug, e.g. Accretropin (somatropin rDNA Original), ACTOplus met (pioglitazone hydrochloride and metformin hydrochloride), ACTOS, Afrezza (insulin human) Inhalation Powder, Amaryl (Glimepiride), Avandamet (rosiglitazone maleate and metformin HCl), Avandia (rosiglitazone maleate), Belviq (lorcaserin hydrochloride), Bydureon (exenatide extended-release for injectable suspension), Byetta (exenatide), Cernevit, Cycloset, bromocriptine mesylate, Desmopressin Acetate (DDAVP), Farxiga (dapagliflozin) Genotropin (somatropin) injection, Genotropin (somatropin) lyophilized powder, Geref (sermorelin acetate for injection), Glipizide Tablets, Glucagon, Glyburide Tablets, Glyset (miglitol), Humalog (insulin lispro), Increlex (mecasermin), Invokana (canagliflozin), Januvia (sitagliptin phosphate), Jardiance (empagliflozin), Jentadueto (linagliptin plus metformin hydrochloride), Juvisync (sitagliptin and simvastatin), Lantus (insulin glargine [rDNA origin] injection), Metaglip (glipizide/metformin HCl), Nesina (alogliptin), NovoLog (insulin aspart), Novolog Mix 70/30, Nutropin (somatropin-rDNA origin), Onglyza (saxagliptin), Prandin, Precose (acarbose), Symlin (pramlintide), Synjardy (empagliflozin and metformin hydrochloride), Tanzeum (albiglutide), Tradjenta (linagliptin), Tresiba (insulin degludec injection), Trulicity (dulaglutide), Victoza (liraglutide), Xigduo XR (dapagliflozin+metformin hydrochloride), Progestagens: megestrol acetate/Medroxyprogesterone acetate, Corticosteroids, Omega-3 fatty acids-EPA, Cannabinoids (dronabinol), Bortezomib, Thalidomide, Ghrelin, COX-2 inhibitors, Insulin, BCAA, Oxandrolone, Melanocortin antagonists, β2 agonists (formoterol), Anti-myostatin peptibody, Anti-IL-6, SARMs, Oxandrolone, Olanzapine, anti-IL-6 antibodies, Anamorelin, AndroGel transdermal, Testopel implant, Testim transdermal, testosterone cypionate intramuscular, Androderm transdermal, Axiron transdermal, Fortesta transdermal, megestrol oral, Megace oral, Depo-Testosterone intramuscular, Megace ES oral, testosterone enanthate intramuscular, testosterone transdermal, Striant buccal, Humatrope injection, Nutropin AQ subcutaneous, Omnitrope subcutaneous, Natesto nasal, Saizen subcutaneous, Genotropin Miniquick subcutaneous, Android oral, Aveed intramuscular, somatropin injection, testosterone implant, Genotropin subcutaneous, Norditropin FlexPro subcutaneous, methyltestosterone oral, testosterone undecanoate intramuscular, Vogelxo transdermal, somatropin subcutaneous, Testred oral, Methitest oral, testosterone buccal, testosterone nasal, Testone CIK intramuscular, Serostim subcutaneous, Zorbtive subcutaneous, Saizen subcutaneous, Nutropin AQ Nuspin subcutaneous, Zomacton subcutaneous.

In one embodiment, the second agent is a therapeutic agent which is a non-drug treatment. For example, the second therapeutic agent is radiation therapy, cryotherapy, hyperthermia and/or surgical excision of tumor tissue.

In some embodiments, the subject is treated with a glycan therapeutic described herein in combination with two or more other pharmaceutical agents, e.g., two or more (e.g., 3 or more, 4 or more) chemotherapeutic agents, or a combination of different classes of therapeutic agents described herein. For example, a cancer subject may be treated with a glycan therapeutic described herein in combination with radiation therapy, a chemotherapeutic cocktail of 2, 3, 4 or more drugs, and optionally also in combination with a checkpoint inhibitor or a cell therapy (e.g., T cell therapy).

If determined useful by a treating physician or other healthcare provider, the pharmaceutical glycan therapeutic compositions described herein can be administered in combination with various other standard of care therapies. In some embodiments, the combination of administration of the glycan therapeutic and the standard-of-care therapy agent (e.g., an anti-cancer drug) has additive or synergistic treatment effects. The pharmaceutical glycan therapeutic compositions may be administered prior to, concurrent with, or post treatment with standard of care therapies.

In some instances, the therapies, e.g., treatment with cytotoxic or anti-microbial drugs disrupt the composition or health of the GI tract's host cells and microbiota or that of non-GI sites. In one embodiment, the disruption by the drugs leads to the undesirable proliferation of harmful bacteria or pathogens. In some embodiments, the disruption of the host cells and/or microbiota by the drugs causes one or more of the symptoms described herein. In some embodiments, administration of the pharmaceutical glycan therapeutic compositions described herein is useful for alleviating those symptoms. In some embodiments, administration of the pharmaceutical glycan therapeutic composition improves the composition of the gastrointestinal or non-gut microbial community and host cells (e.g., modulates shifts in the composition or function of the microbiota that decrease the intensity or duration of the symptoms).

Provided herein are methods of treating an immune imbalance in a subject. Provided herein is a method of treating an immune imbalance in a human subject, comprising: administering to the subject a pharmaceutical composition, a medical food or a dietary supplement comprising a glycan therapeutic preparation, in an effective amount to treat the subject. Optionally, a second agent may be administered. The methods also include methods for reducing an infection and/or an inflammation in a subject having an immune imbalance. Also provided are methods of modulating the composition and/or metabolic activity of the intestinal bacterial community of a subject having an immune imbalance, and methods of modulating one or more functional pathways in a subject having an immune imbalance. Further, methods of treating a dysbiosis in a subject having an immune imbalance are provided. In some embodiments, the immune imbalance results in or is associated with a cancer.

In some embodiments, immune suppression and/or insufficient immune inflammatory activation is characterized by the overgrowth of pathogenic cells. Examples of pathogenic cells include intracellular pathogens, extracellular pathogens, viruses, and cancerous cells. Immune suppression and/or insufficient immune inflammatory activation, in some embodiments, is associated with tolerance, e.g., resulting from an imbalance in the ratio of tolerogenic cell subsets (e.g. regulatory T cells) or activities (e.g. tolerogenic cytokine secretion such IL-10, TGF-beta) to inflammatory cell subsets (e.g. Th1 cells) or activities (e.g. inflammatory cytokine secretion such as TNF-alpha, IL-17), with the tolerogenic functions displaying higher activity than the inflammatory functions. Immune suppression and/or insufficient immune inflammatory activation, in some embodiments, is associated with the immune system not recognizing the pathogenic cell as a pathogen, which frequently occurs in the case of cancerous cells.

Aberrant immune inflammatory activation, in some embodiments, is characterized by damage to or a decrease in the proliferation of non-pathogenic cells. Examples of non-pathogenic cells are any cells or cell-structures (including tissues and organs) that are not-targeted by the immune system for attack in a healthy individual. For example, the epithelium of the gastrointestinal tract is not substantially damaged by the immune system in healthy individuals but is damaged by the immune system in individuals with inflammatory diseases such as, e.g., inflammatory bowel disease. For example, the pancreas is not substantially targeted by the inflammatory arm of the immune system in patients who do not have autoimmune diabetes, but is targeted in patients with type-1 diabetes. Aberrant immune inflammatory activation, in some embodiments, is associated with an imbalance in the ratio of tolerogenic cell subsets (e.g. regulatory T cells) or activities (e.g. tolerogenic cytokine secretion such IL-10, TGF-beta) to inflammatory cell subsets (e.g. Th1 cells) or activities (e.g. inflammatory cytokine secretion such as TNF-alpha, IL-17), with the inflammatory functions displaying higher activity than the tolerogenic functions.

Examples of immune imbalances include: *Clostridium difficile* infection (CDI); Vancomycin-resistant enterococci (VRE) infection, infectious colitis, and *C. difficile* colitis; mycoses, such as, e.g., *Candida albicans* infection, *Campylobacter jejuni* infection, *Helicobacter pylori* infection; diarrhea, such as, e.g., *Clostridium difficile* associated diarrhea (CDAD), antibiotic-associated diarrhea (AAD), antibiotic-induced diarrhea, travelers' diarrhea (TD), pediatric diarrhea, (acute) infectious diarrhea, colon and liver cancers, ameboma; necrotizing enterocolitis (NEC), and small intestine bacterial overgrowth (SIBO); indigestion or non-ulcer dyspepsia; anal fissures, perianal abscess and anal fistula; diverticulosis or diverticulitis; peptic ulcers; and gastroenteritis. Cancers that are solid or liquid cancer and includes benign or malignant tumors, and hyperplasias, including gastrointestinal cancer (such as non-metastatic or metastatic colorectal cancer, pancreatic cancer, gastric cancer, oesophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g. head and neck squamous cell cancer); CNS cancer including malignant glioma, astrocytomas, retinoblastomas and brain metastases; malignant mesothelioma; non-metastatic or metastatic breast cancer (e.g. hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and haematologic neoplasias (such as multiple myeloma, acute myelogenous leukemia, chronic myelogenous leukemia, myelodysplastic syndrome, acute lymphoblastic leukemia, Hodgkin's lymphoma).

Other examples of immune imbalances include: Gastrointestinal inflammatory diseases including inflammatory bowel disease (IBD), ulcerative colitis (UC), Crohn's disease (CD), idiopathic inflammation of the small bowel, indeterminatal colitis, pouchitis; irritable bowel syndrome (IBS), colon and liver cancers, necrotizing enterocolitis (NEC), intestinal inflammation, constipation, microscopic colitis, diarrhea; graft versus host disease (GVHD); (food) allergies; pseudomembranous colitis; indigestion or non-ulcer dyspepsia; diverticulosis or diverticulitis, ischemic colitis; radiation colitis or enteritis; collagenous colitis; gastroenteritis; and polyps.atopic dermatitis, asthma, multiple sclerosis, immune-mediated or Type I diabetes mellitus, systemic lupus erythematosus, psoriasis, scleroderma, autoimmune thyroid disease, alopecia greata, Grave's disease, Guillain-Barré syndrome, celiac disease, Sjögren's syndrome, rheumatic fever, gastritis, autoimmune atrophic gastritis, autoimmune hepatitis, insulitis, oophoritis, orchitis, uveitis, phacogenic uveitis, myasthenia gravis, primary myxoedema, pernicious anemia, autoimmune haemolytic anemia, Addison's disease, scleroderma, Goodpasture's syndrome, nephritis, for example, glomerulonephritis, psoriasis, pemphigus vulgaris, pemphigoid, sympathetic opthalmia, idiopathic thrombocylopenic purpura, idiopathic feucopenia, Wegener's granulomatosis and poly/dermatomyositis.

Provided herein are methods of treating a nutritional imbalance in a subject. Provided herein is a method of treating a nutritional imbalance in a human subject, comprising: administering to the subject a pharmaceutical composition, a medical food or a dietary supplement comprising a glycan therapeutic preparation, in an effective amount to treat the subject. Optionally, a second agent may be administered. The methods also include methods for reducing an infection and/or an inflammation in a subject having a nutritional imbalance. Also provided are methods of modulating the composition and/or metabolic activity of the intestinal bacterial community of a subject having a nutritional imbalance, and methods of modulating one or more functional pathways in a subject having a nutritional imbalance. Further, methods of treating a dysbiosis in a subject having a nutritional imbalance are provided. In some embodiments, the nutritional imbalance results in or is associated with a cancer.

In some embodiments, the nutritional imbalances is associated with an aberrant inflammatory immune activation that alters metabolic homeostasis. In some embodiments, the nutritional imbalance is associated with an imbalance in the ratio of tolerogenic cell subsets (e.g. regulatory t cells) or activities (e.g. tolerogenic cytokine secretion such IL-10, TGF-beta) to inflammatory cell subsets (e.g. Th1 cells) or activities (e.g. inflammatory cytokine secretion such as TNF-alpha, IL-17), with the inflammatory functions displaying higher activity than the tolerogenic functions. In some embodiments, an increased immune in inflammatory activity affects the mechanisms that metabolic organs and systems utilize for communication. For example, cancer patients who have malnutrition often exhibit a high level of leptin, which is a hormone that induces satiety and thus decreases the patient's hunger. Other diseases that lead to cachexia include, e.g. chronic obstructive pulmonary disease (COPD), rheumatoid arthritis, chronic infection or sepsis, renal failure, heart failure and cancer. The condition is characterized by inflammation, anorexia, insulin resistance and increased muscle protein breakdown with or without a loss of fat mass.

Examples of nutritional imbalance include: Cachexia, anorexia nervosa, kwashiorkor and marasmus. Diseases that lead to cachexia include, e.g. chronic obstructive pulmonary disease (COPD), rheumatoid arthritis, chronic infection or sepsis, renal failure, heart failure and cancer. The condition is characterized by inflammation, anorexia, insulin resistance and increased muscle protein breakdown with or without a loss of fat mass.

Drug- or Treatment-Induced Toxicities

Provided herein are methods of reducing drug- or treatment-induced symptoms in a human subject, e.g. a subject undergoing anti-cancer treatment (being treated with an anti-cancer agent), and subjects in treatment for or having an immune imbalance or a nutritional imbalance. Such drug- or treatment-induced symptoms include any toxicity, digestive abnormalities or gastrointestinal distress. Provided herein are methods for preventing, treating or alleviating the symptoms of various gastrointestinal ailments by administering the glycan therapeutic compositions described herein. The method include administering to the human subject a pharmaceutical composition comprising a glycan therapeutic preparation in an amount effective to reduce one or more symptoms induced by a drug or treatment. In one embodiment, the treatment is radiation treatment, cryotherapy, hyperthermia or surgical excision of tumor tissue.

Exemplary toxicities or digestive abnormalities (gastrointestinal distress) include weight-gain, constipation, heartburn, upset stomach, gas, bloating, flatulence, diarrhea, abdominal pain, cramping, nausea, and vomiting. In some embodiments, the digestive abnormality is diarrhea. In some embodiments, the digestive abnormality is constipation.

Other examples include treatment (or toxicity) associated symptoms such as gas, heartburn, stomach upset, bloating, flatulence, diarrhea, abdominal pain, cramping, nausea, or vomiting.

Minor digestive problems related to the GI also include occasional bloating, diarrhea, constipation, gas, or stomach upset.

If desired, the glycan therapeutic compositions described herein can be administered in combination with various therapies that are associated with gastrointestinal distress. Such therapies include, without limitation, radiation and chemotherapy for cancers, and antibiotic therapy for various microbial maladies. In some embodiments, the therapies disrupt the composition and health of the intestine's normal microbiota. In some instances, the disruption leads to the undesirable proliferation of harmful bacteria and accompanying symptoms described herein. Administration of the glycan therapeutic compositions described herein is useful for treating those symptoms.

The glycan therapeutic compositions described herein are suitable for administration to humans in need thereof. In certain embodiments, the subject is a human who has one or more symptoms of a disturbed gut microbiota. In some embodiments, the disturbance can be rectified by the use of the glycan therapeutics described herein so that normal physiological growth and function of both the commensal microbiota and the host can be achieved.

In some embodiments, the glycan therapeutics described herein may be used in combination with one or more of: a pain-management drug (e.g., opioids) an antidepressant, an antiepileptic, a steroid, a drug for managing a GI tract motility disorder, an anti-inflammatory agent (e.g., NSAID), and an antimicrobial agent (e.g., antibiotic), described elsewhere herein, to treat any toxicity, digestive abnormalies and other gastrointestinal distress associated with administration of the drugs to a subject.

Other examples of drugs which often are associated with drug- or treatment-induced (toxicity) symptoms include, a cancer drug, an anti-diabetic, an immune-suppressive drug, an antimicrobial drug, a chemotherapeutic, an anti-psychotic, a proton pump inhibitor, and a non-steroid anti-inflammatory drug (NSAID).

In some embodiments, the glycan therapeutics described herein may be used in combination with one or more anti-cancer agents, including, checkpoint modulators, cell therapies, cancer vaccines, chemotherapeutic agents, and biologics, described elsewhere herein, to treat toxicities, digestive abnormalies and other gastrointestinal distress associated with administration of the drugs to a subject.

Provided herein are methods of lowering or reducing the number or intensity of an unwanted side effect of a treatment or therapy, such as, e.g., an anti-cancer treatment or therapy (and treatments or therapies relating to immune imbalances or nutritional imbalances), in a subject, comprising a) administering a pharmaceutical composition comprising a glycan therapeutic preparation described herein to a subject who has received the treatment or therapy; b) administering the treatment or therapy to a subject who has been treated with a pharmaceutical composition comprising a glycan therapeutic preparation; or c) administering a pharmaceutical composition comprising a glycan therapeutic preparation and administering the treatment or therapy, to a subject, thereby decreasing the side effect effect of the treatment or therapy in the subject. In some embodiments, the onset of the side effect is prior to administration of the glycan therapeutic preparation. In some embodiments, the glycan therapeutic preparation is administered after onset of the side effect. In some embodiments, the side effect of the treatment or therapy results in an unwanted symptom. In some embodiments, the unwanted side effect is a gastrointestinal side effect, such as a digestive abnormality. In some embodiments, the unwanted side effect is a non-gastrointestinal side effect, such as, e.g., anxiety, fear, depression, mental fog, dermatitis, chest pain, shortness of breath, weight gain, weight loss, etc.

In some embodiments, the unwanted side effect is one or more of: abdominal pain, cramping, nausea, or vomiting, upset stomach, gas, bloating, flatulence, diarrhea, constipation, heartburn, mucositis, weight loss, and weight-gain.

In some embodiments, the unwanted side effect is associated with anti-cancer treatment (or treatments for an immune imbalance or a nutritional imbalance). In some embodiments, the unwanted side effects related to anticancer treatment include one or more of: radiation injury pain, surgical pain, phantom pain, acute pain, chronic or persistent pain, breakthrough pain, peripheral neuropathy, stomatitis, mucositis, nausea, vomiting, diarrhea (acute, chronic), constipation (acute, chronic), urinary incontinence, fatigue (acute or chronic), anemia, lymphedema, infections, anxiety, fear, depression, fertility defects, and risk of developing a second cancer. In some embodiments, the unwanted side effects related to anti-cancer treatment include infections, such as bacterial infections, including: *Pseudomonas aeruginosa, Klebsiella pneumonia, Escherichia coli, Salmonella, Clostridium difficile, Staphylococcus aureus, Staphylococcus epidemidis, Streptococcus viridians, Pneumococcus, Enterococcus*; viral infections, including: Varicella zoster virus (VZV), Herpes simplex virus (HSV), Cytomegalovirus (CMV), hepatitis viruses, respiratory viruses (e.g., influenza, respiratory syncytial virus (RSV)); protozoal infections, including: *Toxoplasma gondii*, and *Cryptosporidium*; and fungal infections, including: *Pneumocystis jirovecii, Candida, Aspergillus, Cryptococcus, Histoplasma, Coccidioides*.

In some embodiments, the unwanted side effects related to anti-cancer treatment include malnutrition and cachexia (wasting syndrome).

In some embodiments, the unwanted side effect related to anti-cancer treatment is mucositis, including mucosal tissue ulceration and infection. In some embodiments, the unwanted side effect related to anti-cancer treatment (such as, e.g., chemotherapy and radiation) is oral mucositis.

In some embodiments, the one or more unwanted side effects are dose-limiting, e.g., they require a reduction in subsequent therapeutic doses (e.g. for chemotherapy). Dose limiting toxicity prevents subjects from being treated with the maximal efficacious dose of a drug.

In some embodiments, the methods further comprise administering a pharmaceutical composition comprising a glycan therapeutic preparation to a subject who has received a first treatment (e.g. an anti-cancer drug treatment or anti-cancer therapy), and optionally, providing a second treatment, e.g., wherein the second treatment comprises administration of the drug or therapy at a higher dosage, at more frequent intervals, at a higher total of individual administrations, providing a higher Cmax, providing a higher trough level, etc., than the prior treatment.

In some embodiments, the methods further comprise providing a subsequent treatment (e.g. an anti-cancer drug treatment or anti-cancer therapy) to a subject who has received a pharmaceutical composition comprising a glycan therapeutic preparation and received the first treatment, wherein the second treatment comprises administration of the drug or therapy at a higher dosage, at more frequent intervals, at a higher total of individual administrations, providing a higher Cmax, providing a higher trough level, etc., than the prior treatment.

In one embodiment, the subject being identified to be suitable for treatment with a glycan therapeutic has, is suspected of having or is suspected of developing drug-induced diarrhea (such as, e.g., 5-fluorouracil (5-FU), methotrexate, irinotecan, taxanes, monoclonal antibodies and hormonal agents). In one embodiment, the subject being identified to be suitable for treatment with a glycan therapeutic has, is suspected of having or is suspected of developing drug-induced constipation (such as, e.g., *vinca* alkaloids, platinums (e.g., cisplatin), thalidomide and hormonal agents). In one embodiment, the subject being identified to be suitable for treatment with a glycan therapeutic has, is suspected of having or is suspected of developing a drug-induced toxicity. In one embodiment, the subject being identified to be suitable for treatment with a glycan therapeutic has, is suspected of having or is suspected of developing chemotherapy-induced mucositis. In one embodiment, the subject being identified to be suitable for treatment with a glycan therapeutic has, is suspected of having or is suspected of developing a drug-induced intolerance (e.g. to chemotherapies). In one embodiment, the subject being identified to be suitable for treatment with a glycan therapeutic has, is suspected of having or is suspected of developing cachexia (wasting syndrome). In one embodiment, the subject being identified to be suitable for treatment with a glycan therapeutic has, is suspected of having or is suspected of developing drug-induced microbiome damage, drug-induced microbiome disease, drug-induced gastrointestinal disease, drug-induced enteritis or colitis or similar drug-induced disorder or condition.

In some embodiments, the pharmaceutical composition comprising a glycan therapeutic preparation is administered prior to, concomitant with or after administration of the (e.g. anti-cancer) drug or non-drug (e.g., anti-cancer) treatment, administration of which induces the symptoms.

In some embodiments, administration of a drug is associated with dysbioses that can, e.g., occur during the treatment regimen. In some embodiments, the dysbiosis causes or amplifies the drug- or treatment-induced symptoms, such as toxicities, including digestive abnormalities. In some embodiments, administration of the glycan therapeutic modulates the microbiome such that the drug- or treatment-induced symptoms are reduced. In some embodiments, the glycan therapeutic promotes the growth of commensal bacteria and/or supports the growth of beneficial microbial communities which would negatively be affected or lost in response to the drug treatment or which can complement commensal bacteria that have been negatively affected or lost in response to the drug treatment.

Provided herein are methods of treating a dysbiosis in a subject comprising administering to the subject a pharmaceutical composition comprising a glycan therapeutic preparation thereby treating the dysbiosis. The dysbiosis, in some embodiments, is concurrent with (or the result of) a disease, disorder or condition, such as, e.g., an immune imbalance, a nutritional imbalance and/or cancer. In some embodiments, the dysbiosis is concurrent with (or the result of) a treatment or therapy, e.g., anti-cancer therapy, pain management, etc.

In some embodiments, the unwanted side effects, including toxicities such as digestive abnormalities, are associated with treatment of the subject with a chemotherapeutic agent. In one embodiment, the digestive abnormality is diarrhea. In specific embodiments, the chemotherapeutic agent is Irinotecan, 5-fluorouracil, leucovorin, or combinations thereof. In specific embodiments, the chemotherapeutic agent is oxaliplatin, leucovorin, 5-fluorouracil, or combinations thereof. In specific embodiments the chemotherapeutic agent is bortezomib, imatinib, lenalidomide, imbruvica, ipilimumab, pertuzumab, capecitabine, docetaxel, lapatinib, erlotinib, or combinations thereof. In some embodiments, the chemotherapeutic agent is Carmustine, Etoposide, Aracytine, Melphalan, or combinations thereof. In specific embodiments the chemotherapeutic agent is cytarabine, daunorubicine, etoposide, or combinations thereof. In specific embodiments the chemotherapeutic agent is amsacrine, cytarabine, etoposide, or combinations thereof. In specific embodiments, the chemotherapeutic agent is mitoxantrone, cytarabine, or combinations thereof.

In some embodiments, the unwanted side effects, including toxicities such as digestive abnormalities, are associated with treatment of the subject with an antibiotic. In one embodiment, the digestive abnormality is diarrhea. In specific embodiments, the antibiotic is ciprofloxacin, clindamycin, amoxicillin-clavulanate, cefixime, ephalosporins, fluoroquinolones, azithromycin, clarithromycin, erythromycin, tetracycline, or azithromycin.

In some embodiments, the unwanted side effects, including toxicities such as digestive abnormalities, are associated with treatment of the subject with an anti-psychotic drug. In one embodiment, the digestive abnormality is weight gain. In one embodiment, the drug is olanzapine.

In some embodiments, the unwanted side effects, including toxicities such as digestive abnormalities, are associated with treatment of the subject with a proton-pump inhibitor drug. In one embodiment, the digestive abnormality is diarrhea. In specific embodiments, the drug is ranitidine, famotidine, cimetidine, omeprazole, sucralfate, or esomeprazole.

In some embodiments, the unwanted side effects, including toxicities such as digestive abnormalities, are associated with treatment of the subject with a non-steroidal anti-inflammatory drug (NSAID). In one embodiment, the digestive abnormality is diarrhea. In specific embodiments, the drug is naproxen, diclofenac, indomethacin, ibuprofen, ketoprofen, piroxicam, celecoxib, nimesulid, or aspirin.

In some embodiments, the unwanted side effects, including toxicities such as digestive abnormalities, are associated with treatment of the subject with metformin, paroxetine, valproic acid, or clozapine.

In one embodiment, reducing the one or more symptoms (e.g., of unwanted side effects) increases compliance by the subject to the treatment regimen. In one embodiment, reducing one or more symptom (e.g., of unwanted side effects) enables the physician to prescribe a higher-dose of the drug to be administered. In such embodiments, treatment of the underlying disease is more effective (e.g. increased reduction of disease symptoms, shorter period to achieve a disease or symptom-free state, or longer maintainance of a disease or symptom-free state, etc.).

In one embodiment, a method of lowering toxicity of a drug treatment (e.g., an anti-cancer drug treatment) in a subject is provided. The method includes: a) administering a pharmaceutical composition comprising a glycan therapeutic preparation to a subject who has received the drug treatment; b) administering the drug treatment to a subject who has been treated with a pharmaceutical composition comprising a glycan therapeutic preparation; or c) administering a pharmaceutical composition comprising a glycan therapeutic preparation and administering the drug treatment, to a subject, thereby treating the subject. In some embodiments, the toxicity is dose-limiting toxicity. In some embodiments, the method increases the tolerance of the subject to drug treatment, e.g. an anti-cancer drug treatment.

In some embodiments, dose limiting toxicity prevents subjects from being treated with the maximal efficacious dose of a drug. As one example of dose-limiting toxicity, diarrhea can be caused by the chemotherapy drugs irinotecan and 5-fluoruracil. Irinotecan and 5-fluorouracil may damage the intestinal epithelium of subjects. As a result nutrient and fluid absorption and secretion is modulated. In some instances, the digestive abnormality forces a clinician to reduce the dose of the drug to adjust it to the subject's tolerance level. In some instances, the lowering may lead to a treatment regimen with a less efficacious dose thereby limiting the treatment effect (or prolonging the treatment interval. In some embodiments, glycan therapeutic preparations are administered to treat dose limiting toxicity, e.g., to increase the dose that is tolerated by the subject. In some embodiments, tolerability is increased by limiting one or more digestive abnormalities associated with the respective efficacious drug dose.

Other Embodiments

In some embodiments, the subject experiences a reduction in at least one symptom of the gastrointestinal disease, disorder or condition following treatment. In some embodiments, a reduction in the severity of a symptom following treatment can be determined (e.g. by measuring a known biomarker) and is in the order of about 3%, 5%, 7%, 10%, 20%, 30%, 40%, 50%, 60%, 70%, 80%, 90%, 95%, or about 100%. In some embodiments, the symptoms, measured as described herein, are decreased by an average of about 10%, 20%, 30%, 40%, 50%, 60%, 70%, 80%, 90%, 95%, or about 100% when compared to symptoms prior to the administration of a pharmaceutical glycan therapeutic composition. In some embodiments, the reduction in the severity of the symptom persists for at least about a day, two days, three days, four days, five days, a week, two weeks, three weeks, a month, 3 months, 6 months, 9 months, a year, two years, five years, ten years after treatment or the reduction is permanent.

In one embodiment, a symptom of a gastrointestinal disease, disorder or condition remains partially, substantially, or completely eliminated or decreased in severity in a subject for at least about 1 day, 1 week, 1 month, 2 months, 3 months, 4 months, 5 months, 6 months, 9 months, one year, 18 months, two years, three years, four years, five years, ten years, or more than ten years after the termination of treatment. In another embodiment a symptom of a gastrointestinal disease, disorder or condition is permanently eliminated or decreased in severity in a subject after the termination of treatment.

Proteomic Analysis of Microbial Populations

Preparations of glycan therapeutics may be selected based on their ability to increase the expression of microbial proteins associated with healthy states or to decrease the expression of microbial proteins associated with diseased states. Proteomic analysis of microbial populations can be performed following protocols known to one skilled in the art (e.g., Cordwell, Exploring and exploiting bacterial proteomes, Methods in Molecular Biology, 2004, 266:115). To identify differentially expressed proteins (for example, to identify changes in protein expression upon treatment of microbial populations with glycan therapeutics), proteomic analysis can be performed as described, e.g., in Juste et al. (Bacterial protein signals are associated with Crohn's disease, Gut, 2014, 63:1566). For example, the protein is isolated from the microbial lysates of two samples (for example, an untreated microbial population and a population that has been treated with glycan therapeutics). Each protein sample is labeled (e.g., with a fluorescent dye, e.g., Cy3 or Cy5 CyDye DIGE Fluor minimal dye, GE Healthcare) and analyzed by two-dimensional differential gel electrophoresis (2D-DIGE). Gels are stained and protein spots identified as being significantly different between the two samples are excised, digested, and analyzed by liquid chromatography-tandem mass spectrometry (LC-MS/MS). X!TandemPipeline can be used to identify differentially expressed proteins.

Preparations of glycan therapeutics may also be selected for administration to a human subject based on their effect on the presence of microbial fermentation products. For example, preparations of glycan therapeutics can be selected for their ability to induce or promote growth of bacteria that produce short chain fatty acids such as propionate (propionic acid), acetate, and/or butyrate (butyric acid). Similarly, preparations of glycan therapeutics can be selected for their ability to induce or promote growth of bacteria that produce lactic acid, which can modulate the growth of other bacteria by producing an acidic environment. Such analysis may also be used to pair probiotic bacteria with glycan therapeutics such that the glycan therapeutic is a substrate for the production of the desired fermentation products.

The metabolites that are present in fresh or spent culture media or in biological samples collected from human subjects may be determined using methods known in the art and described herein. Unbiased methods that may be used to determine the relative concentration of metabolites in a sample and are known to one skilled in the art, such as gas or liquid chromatography combined with mass spectrometry or $^1$H-NMR. These measurements may be validated by running metabolite standards through the same analytical systems.

In the case of gas chromatography-mass spectrometry (GC-MS) or liquid-chromatography-mass spectrometry (LC-MS) analysis, polar metabolites and fatty acids can be extracted using monophasic or biphasic systems of organic solvents and an aqueous sample and derivatized (Fendt et al., Reductive glutamine metabolism is a function of the a-ketoglutarate to citrate ratio in cells, Nat Commun, 2013, 4:2236; Fendt et al., Metformin decreases glucose oxidation and increases the dependency of prostate cancer cells on reductive glutamine metabolism, Cancer Res, 2013, 73:4429; Metallo et al., Reductive glutamine metabolism by IDH1 mediates lipogenesis under hypoxia, Nature, 2011, 481:380). An exemplary protocol for derivatization of polar metabolites involves formation of methoxime-tBDMS derivatives through incubation of the metabolites with 2% methoxylamine hydrochloride in pyridine followed by addition of N-tert-butyldimethylsilyl-N-methyltrifluoroacetamide (MTBSTFA) with 1% tert-butyldimethylchlorosilane (t-BDMCS). Non-polar fractions, including triacylglycerides and phospholipids, may be saponified to free fatty acids and esterified to form fatty acid methyl esters, for example, either by incubation with 2% $H_2SO_4$ in methanol or by using Methyl-8 reagent (Thermo Scientific). Derivatized samples may then be analyzed by GC-MS using standard LC-MS methods, for example, a DB-35MS column (30 m×0.25 mm i.d.×0.25 µm, Agilent J&W Scientific) installed on a gas chromatograph (GC) interfaced with an mass spectrometer (MS). Mass isotopomer distributions may be determined by integrating metabolite ion fragments and corrected for natural abundance using standard algorithms, such as those adapted from Fernandez et al. (Fernandez et al., Correction of 13C mass isotopomer distributions for natural stable isotope abundance, J Mass Spectrom, 1996, 31:255). In the case of liquid chromatography-mass spectrometry (LC-MS), polar metabolites may be analyzed using a standard benchtop LC-MS/MS equipped with a column, such as a SeQuant ZIC-pHILIC Polymeric column (2.1×150 mm; EMD Millipore). Exemplary mobile phases used for separation could include buffers and organic solvents adjusted to a specific pH value. In combination or in the alternative, extracted samples may be analyzed by $^1$H-nuclear magnetic resonance ($^1$H-NMR). Samples may be combined with isotopically enriched solvents such as D20, optionally in the presence of a buffered solution (e.g., $Na_2HPO_4$, $NaH_2PO_4$ in $D_2O$, pH 7.4). Samples may also be supplemented with a reference standard for calibration and chemical shift determination (e.g., 5 mM 2,2-dimethyl-2-silapentane-5-sulfonate sodium salt (DSS-$d_6$, Isotec, USA)). Prior to analysis, the solution may be filtered or centrifuged to remove any sediment or precipitates, and then transferred to a suitable NMR tube or vessel for analysis (e.g., a 5 mm NMR tube). $^1$H-NMR spectra may be acquired on a standard NMR spectrometer, such as an Avance II+500 Bruker spectrometer (500 MHz) (Bruker, Del.), equipped with a 5 mm QXI-Z C/N/P probehead) and analyzed with spectra integration software (such as Chenomx NMR Suite 7.1; Chenomx Inc., Edmonton, AB). (Duarte et al., $^1$H-NMR protocol for exometabolome analysis of cultured mammalian cells, Methods Mol Biol, 2014:237-47). Alternatively, $^1$H-NMR may be performed following other published protocols known in the art (Chassaing et al., Lack of soluble fiber drives diet-induced adiposity in mice, Am J Physiol Gastrointest Liver Physiol, 2015; Bal et al., Comparison of Storage Conditions for Human Vaginal Microbiome Studies, PLoS ONE, 2012: e36934).

All publications, patents, and patent applications cited or referenced in this specification are herein incorporated by reference to the same extent as if each independent publication or patent publication was specifically and individually indicated to be incorporated by reference.

EXAMPLES

The invention is further illustrated by the following examples. The examples are provided for illustrative purposes only, and are not to be construed as limiting the scope or content of the invention in any way. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); Green K. Sambrook et al., Molecular Cloning: A Laboratory Manual, 4th Edition (Cold Spring Harbor Laboratory Press, 2012); Colowick & Kaplan, Methods In Enzymology (Academic Press); Remington: The Science and Practice of Pharmacy, 22nd Edition (Pharmaceutical Press, 2012); Sundberg & Carey, Advanced Organic Chemistry: Parts A and B. 5th Edition (Springer, 2007).

Example 1: Preparation of Glycan Therapeutics

To a round bottom flask equipped with an overhead stirrer and a jacketed short-path condenser was added one or more mono- or disaccharides along with 3-20% by dry weight of one or more of the catalysts described in U.S. Pat. No. 8,466,242 and WO 2014/031956, which are incorporated herein by reference in their entirety. Water or another compatible solvent (1.54 equiv) was added to the dry mixture and the slurry was combined at approximately 100 rpm using a paddle sized to match the contours of the selected round bottom flask as closely as possible. The mixture was then heated to 80-155° C. Once the solids achieved a molten state, the vessel was placed under 10-1000 mbar vacuum pressure. The reaction was stirred for 30 minutes to 8 hours, constantly removing water from the reaction. Reaction progress was monitored by HPLC. When sufficient oligomerization had occurred, the stirrer was shut off, the reaction was cooled to room temperature and vented to atmospheric pressure, and the solid mass was dissolved in a volume of water sufficient to create a solution of approximately 50 Brix (grams sugar per 100 g solution). Once dissolution was complete, solid catalyst was removed by filtration and the oligomer solution was concentrated to approximately 50-75 Brix by rotary evaporation. In cases in which an organic solvent has been used, water immiscible solvents can be removed by biphasic extraction and water miscible solvents can be removed by rotary evaporation concomitant to the concentration step.

Preparation of Man100

To a 1000 mL round bottom flask equipped with an overhead stirrer and a jacketed short-path condenser was added 100 grams D-mannose along with 7.14 g catalyst (5% by dry weight) and 50 mL water (50% by dry weight). The slurry was combined at approximately 100 rpm using a paddle sized to match the contours of the selected round bottom flask as closely as possible. The mixture was then heated to 155° C. until the slurry achieved a molten state. The reaction was then placed under 300 mbar vacuum and stirred at 100 RPM for 3 hours, constantly removing water from the reaction. After the pre-established time had elapsed, the stirrer was shut off, the reaction was vented to atmospheric pressure, and the slurry was cooled to room temperature. 100 mL of water (100% by dry weight) was added to the now solid mass and the material was allowed to dissolve over 16 hour to create a solution of approximately 50 Brix (grams sugar per 100 g solution). Once dissolution was complete, solid catalyst was removed by filtration through a coarse glass-fritted funnel. The catalyst was washed once with 25 mL water and the combined liquids were carried on to the purification step.

Preparation of xyl100

To a 1000 mL round bottom flask equipped with an overhead stirrer and a jacketed short-path condenser was added 100 grams D-xylose along with 7.11 g catalyst (5% by dry weight) and 50 mL water (50% by dry weight). The slurry was combined at approximately 100 rpm using a paddle sized to match the contours of the selected round bottom flask as closely as possible. The mixture was then heated to 155° C. until the slurry achieved a molten state. The reaction was then placed under 300 mbar vacuum and stirred at 100 RPM for 2 hours, constantly removing water from the reaction. After the pre-established time had elapsed, the stirrer was shut off, the reaction was vented to atmospheric pressure, and the slurry was cooled to room temperature. 100 mL of water (100% by dry weight) was added to the now solid mass and the material was allowed to dissolve over 16 hour to create a solution of approximately 50 Brix (grams sugar per 100 g solution). Once dissolution was complete, solid catalyst was removed by filtration through a coarse glass-fritted funnel. The catalyst was washed once with 25 mL water and the combined liquids were carried on to the purification step.

Among others, the following 25 glycans were made in multiple batches and tested in various assays described herein:

Single glycan unit (homo-glycans): xyl100, rha100, ara100, gal100, glu100, and man100.

Two glycan units (hetero-glycans): ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 and glu90gly10.

Three glycan units (hetero-glycans): xyl75glu12gal12, xyl33glu33gal33, glu33gal33fuc33, man52glu29gal19, and glu33gal33neu33.

Example 2: Purification of Glycan Therapeutics

Oligosaccharides synthesized as in Example 1 were dissolved in deionized water to a final concentration of 25-50 Brix. The material was then exposed to at least 2 mass equivalents of Dowex Monosphere 88 ion exchange resin. Exposure may occur by swirling in a flask at 120-170 rpm or by filtration through a wet slurry packed column as long as the residence time is sufficient for the solution to achieve a final pH between 3 and 5. The oligomer solution was isolated by filtration (as in the case of swirled reactions) or elution (as in the case of column filtration) and the process was repeated with Dowex Monosphere 77 ion exchange resin in an analogous fashion until the solution pH was above 5.5. Finally the solution was exposed to Dowex Optipore SD-2 Adsorbent decolorizing resin until the solution was sufficiently clarified and filtered through a 0.2 micron filter to remove residual resin and resin fines. The final solution was then concentrated to 50-85 Brix by rotary evaporation or to a solid by lyophilization.

Man100 and xyl100 were synthesized as in Example 1 and were purified by ion exchange. The material was purified by elution through three different ion-exchange chromatography columns using deionized water as an eluent at a speed of 2 bed volumes per hour. The columns were arranged serially in the following order: Dowex Monosphere 88 strong cation resin, Dowex Monosphere 77 weak base resin, and Dowex Optipore SD-2 adsorbent decolorizing resin. Each column was 220 mL in bed volume. After passage, the solution was filtered through a 0.20 micron filter to remove residual resin and resin fines. The final solution was then concentrated to a 65-75 Brix syrup by rotary evaporation or to a 92-98 Brix solid by lyophilization. Isolated yields of glycan varied by monomeric content and preparation but were consistently between 80-85% by recovered mass and 88-94% by molar equivalent.

Example 3: Modification of Glycan Therapeutics by Removal of Low Molecular Weight Species Oligomers prepared and purified as in Examples 1 and 2 were modified so as to remove low molecular weight species. The separation was achieved by osmotic separation. Approximately 45 cm of 1.0 kD MWCO Biotech CE dialysis tubing (31 mm flat width) from Spectrum Labs was placed into deionized water and soaked for 10 minutes, then one end was sealed with a dialysis tubing clip. A 25 Brix solution of 8 grams dry oligosaccharide was sterile filtered and sealed into the tube with a second clip along with a few mL of air to permit the tube to float. The filled tube was then placed in a 3 gallon tank of deionized water which was stirred with sufficient force to induce slow swirling of the sealed tubes. After 8 hours, the water in the tank was replaced and the tube was allowed to stir for an additional 16 hours. Once the dialysis was complete and the material had a DP2+yield greater than 95% and a DP3+yield greater than 90%, the dilute solution was sterile filtered and concentrated in vacuo to a final concentration of approximately 65 Brix or lyophilized to a solid with a residual moisture between 1 and 10%. Alternatively, the separation was achieved by tangential flow filtration (TFF). In this case, 100 mL of 25 Brix glycan sample dissolved in deionized water and sterile filtered was placed into the feed bottle of a Spectrum Labs KrosFlo Research IIi TFF system that was prepared according to the manufacturer's recommendation. The sample was then diafiltered through a 1 kD mPES MidiKros hollow-fiber filter at a transmembrane pressure of 25 psig. HPLC samples of the feed stock taken every 0.5 diafiltration volumes were used to determine when the material had a DP2+yield greater than 95% and a DP3+yield greater than 90% at which point the solution was sterile filtered and concentrated in vacuo to a 65 Brix syrup or lyophilized to a solid with residual water content of 1-10% by mass. Low molecular weight oligomers can also be removed by precipitation with 70% ethanol as in Gras, et al. Food Chem. 2001, 128, 773-777. Glycans can also be fractionated into pools with different average molecular weights by activated charcoal chromatography as in Sanz, et al. Chromatographia 2006, 64, 233-236.

Example 4: Methods for Analyzing Preparations of Glycan Therapeutics

Measurement of Glycan Content by Liquid Refractometry

This experiment was designed to quantitate the amount of glycan in any given aqueous solution. A Mettler-Toledo Refracto 30GS portable sugar refractometer was calibrated using high-purity reverse-osmosis deionized water. Several drops of the glycan solution were filtered through a 0.2 micron syringe filter directly onto the lens of the refractometer. The measurement was taken at room temperature and reported as Brix. The glycans were routinely concentrated to 75 Brix without obvious solidification or crystallization at 23° C. Brix can then be converted to solubility assuming a specific density of water equal to 1.0 g/mL. Thus, 75 Brix (100 grams of solution consisting of 75 grams of glycan and 25 grams of water) equals an aqueous solubility of 3.0 g/mL. As a comparison, the aqueous solubility of D-glucose is reported to be 0.909 g/mL (48 Brix) at 25° C. by Sigma-Aldrich.

Monomeric Composition by Hydrolysis and GC-MS

This experiment was designed to quantitate the ratio of monomer content within a given oligosaccharide. Glycosyl composition analysis was performed by combined gas chromatography/mass spectrometry (GC/MS) of the per-O-trimethylsilyl (TMS) derivatives of the monosaccharide methyl glycosides produced from the sample by acidic methanolysis as described previously by Santander et al. (2013) Microbiology 159:1471. Between 100 and 200 g of sample were lyophilized into a suitable test tube. Inositol (20 □g) was added to the sample as an internal standard, then the sample was heated to 80° C. in 1M HCl/methanol for 18 hours. The resulting monosaccharides were then re-acetylated using pyridine and acetic anhydride in MeOH, and per-O-trimethylsilylated with Tri-Sil (Pierce) at 80° C. for 30 minutes. GC/MS analysis of the TMS methyl glycosides was performed on an Agilent 7890A GC interfaced to a 5975C MSD, using a Supelco Equity-1 fused silica capillary column (30 m×0.25 mm ID). Each peak was assigned to a component sugar based upon comparison to known standards and integration of the respective peaks allowed clean calculation of the relative percentage of monomers within an exemplified glycan. In all tested cases, the monomer composition of a given oligosaccharide matched the input ratio within experimental error and the output composition matched the input composition within the precision of the measurement.

Molecular Weight Distribution by Size-Exclusion Chromatography (SEC)

This experiment was designed to quantitate the distribution of molecular weights within a given oligosaccharide. The measurement was made by HPLC using the method described in Monograph of United States Pharmacopeia, 38(6) In-Process Revision: Heparin Sodium (USP37-NF32). Separations were achieved on an Agilent 1100 HPLC system via dual Shodex OHpak SB-802.5 HQ columns using pure HPLC grade water as the eluent at 1.0 mL/min flow rate and an RI detector held at 40° C. The column temperature was set at 40° C. and glucose (180 g/mol), maltose (342 g/mol), pullulan 1300 (1080 g/mol; provided by Sigma-Aldrich), and pullulan 6000 (6100 g/mol; provided by Sigma-Aldrich) were used to draw a standard curve. A 1 mg/mL solution of the sample was prepared and passed through a 0.22 µm syringe filter, followed by 10 µl injections into the HPLC. A third-order polynomial curve was constructed based on the logarithmic molecular weights and elution volumes of the listed standards. The weight-average molecular weight (Mw), the number average molecular weight (Mn), and the polydispersity index (PDI) for the sample were calculated by comparison to the standard curve. Table 5 contains the SEC data for man100 and xyl100.

TABLE 5

SEC measurements for glycan preparations of man100 and xyl100.

| glycan | Mn (g/mol) | Mw (g/mol) | PDI (Mw/Mn) | Highest observed MW (g/mol) |
|---|---|---|---|---|
| Man100 | 371 | 1066 | 2.87 | 5941 |
| Xyl100 | 417 | 1710 | 4.10 | >10,000* |

*above the limit of exclusion under these conditions

FIG. 1 shows the curve generated during the SEC evaluation of a glu100 sample in which the average molecular weight was determined to be 1212 g/mol or approximately DP7. The upper end of molecular weight of the material as defined by the point of the curve at 10% of maximum absorption leading the curve was determined to be 4559 g/mol or approximately DP28. The lower end of molecular weight of the material as defined by 10% of the maximum absorption trailing the curve was determined to be 200 g/mol or approximately DP1. Similar analysis of a glu50gal50 sample showed a MW, high mass, and low mass of 1195 g/mol (~DP7), 4331 g/mol (~DP27), and 221 g/mol (~DP1) respectively.

Molecular Weight Distribution by Ion-Affinity Chromatography (IAC)

The proportion of glycan with DP greater than or equal to 2 (DP2+) and 3 (DP3+) may be measured by ion-affinity chromatography. A sample of glycan was diluted out to 50-100 mg/mL and 10 µL of this solution was injected onto an Agilent 1260 BioPure HPLC equipped with a 7.8×300 mm BioRad Aminex HPX-42A column and RI detector. Using pure HPLC-grade water as an eluent, the sample was eluted at 0.6 mL/min through an 80° C. column and an RI detector maintained at 50° C. The peaks representing DP1-6 are assigned by comparison to reference standards and integrated using the Agilent ChemStation software. Peaks are typically integrated as DP1, DP2, DP3, DP4-7, and DP8+. The DP that is achievable by the reaction described in Example 1 varies from monomer to monomer although it is consistent across batches if the procedure is followed correctly, e.g. glucose reliably achieves higher DP values than arabinose. For example, across 17 batches of glu100, DP2+values ranged from 85-93% and DP3+values ranged from 80-90%. Conversely, across 6 batches of ara100, DP2+values ranged from 63-78% and DP3+values ranged from 48-71%. Mixtures of monomers behaved as averages of the individual components. For man100 and xyl100 the DP2+yield was 91.9% and 89.6, respectively, and the DP3+ yield was 85.5 and 85.5, respectively.

Alpha-/Beta-Distribution by 2D NMR

Figure 2:
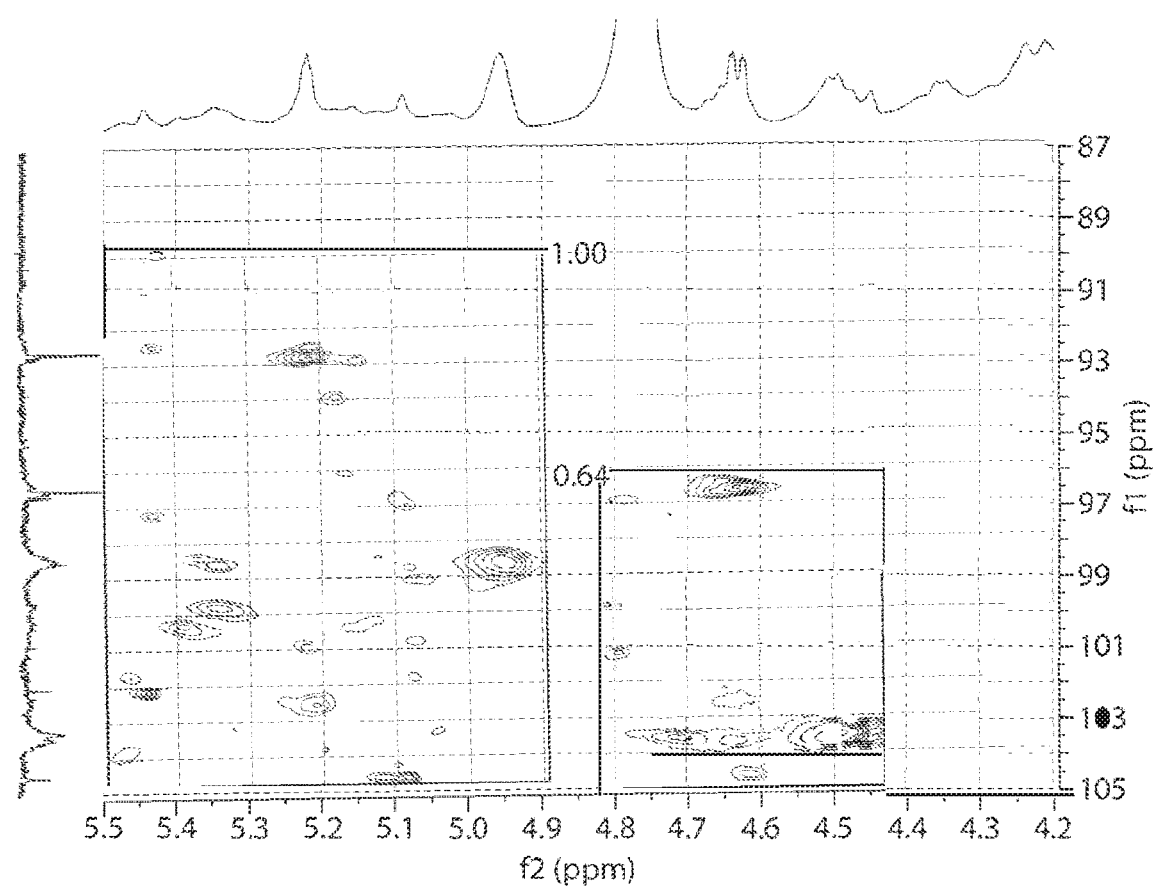
FIG. 2: A representative anomeric region of an $^1$H-$^{13}$C HSQC spectrum of a glu100 sample showing the signal distribution of alpha- and beta-glycosidic bonds FIGS. 3A-3C. A representative anomeric region of an $^1$H-$^{13}$C HSQC spectrum of glu100 (FIG. 3A), glu50gal50 (FIG. 3B), and gal100 (FIG. 3C) samples, demonstrating the additive effect of the fingerprint peaks.

This experiment was designed to quantitate the ratio of alpha- and beta-glycosidic bonds within a given sample by two-dimensional NMR. Approximately 150 mg of 65 Brix oligosaccharide solution was dried to stable mass in a vacuum oven at 45-95° C. under 400 mbar pressure. The sample was subjected to two cycles of dissolution in D20 and drying to remove residual H₂O. Once dried, the sample was dissolved in 750 µL D20 with 0.1% acetone, placed into a 3 mm NMR tube, and analyzed in a Bruker Avance-III operating at 500.13 MHz 1H (125.77 MHz 13C) equipped with a Bruker BBFO probe operating at 21.1° C. The sample was analyzed using a heteroatomic single quantum coherence pulse sequence (HSQC) using the standard Bruker pulse sequence. Anomeric protons between 4-6 ppm (1H) and 80-120 ppm (13C) were assigned by analogy to glucose as reported in Roslund, et al. (2008) *Carbohydrate Res.* 343:101-112. Spectra were referenced to the internal acetone signal: 1H—2.22 ppm; 13C—30.8 ppm. Isomers were quantitated by integration of their respective peaks using the MNova software package from Mestrelab Research (Santiago de Compostela, Spain). FIG. 2 shows the anomeric region of a representative spectrum. Table 6 lists the distribution across 13 distinct combinations of monomers showing the alpha-/beta-ratio to be as high as 4:1 as in the case of rha100 and as low as 1:1 as in the case of glu50gal50.

TABLE 6

Distribution of alpha- and beta-bonds across batches and types of glycans

| glycans | alpha-bonds (%) | beta-bonds (%) |
|---|---|---|
| Glu100 | 58 | 42 |
|  | 61 | 39 |
|  | 60 | 40 |
| Gal100 | 60 | 40 |
| Glu50gal50 | 50 | 50 |
|  | 56 | 44 |
| Glu33gal33fuc33 | 55 | 45 |
| Man100 | 57 | 43 |
| Man52glu29gal19 | 76 | 24 |
| Ara100 | 67 | 33 |
| Rha100 | 80 | 20 |
| Xyl100 | 57 | 43 |
|  | 59 | 41 |
| Xyl75gal25 | 56 | 44 |

Identification of Composition by NMR

Figure 7A:
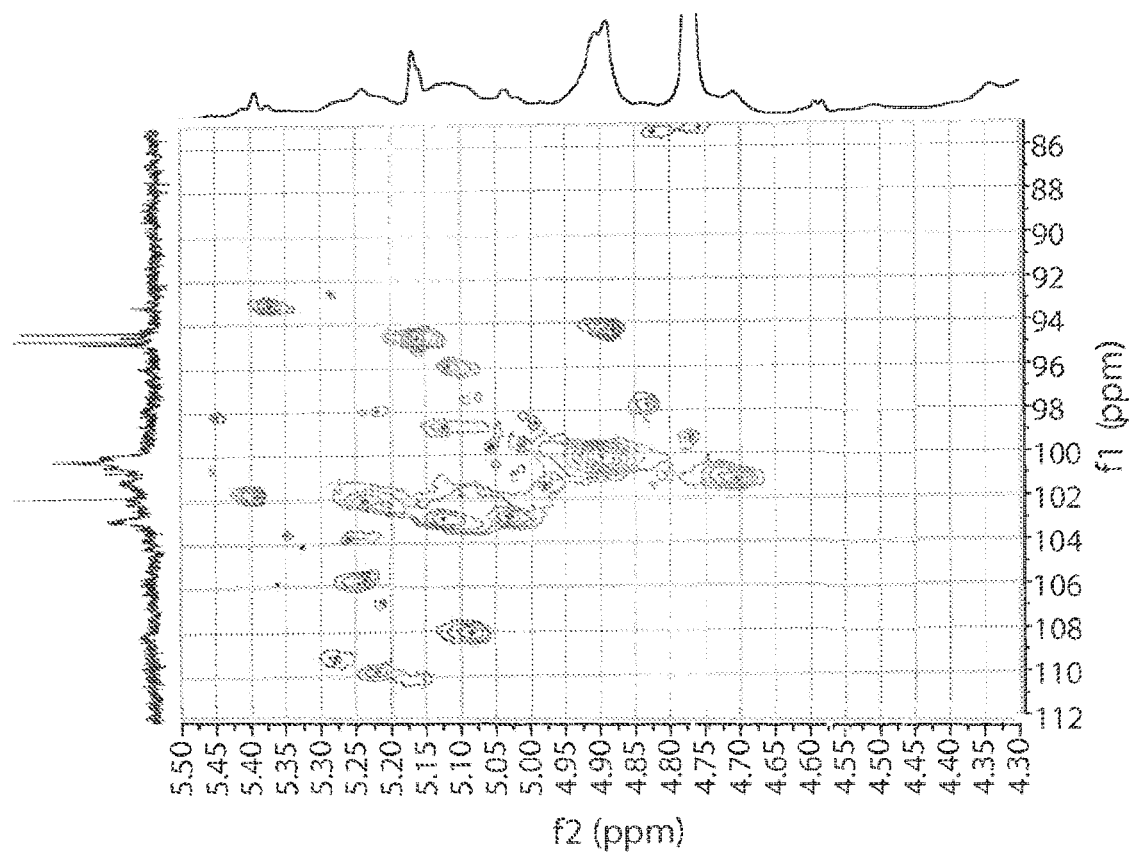
FIG. 7A. Anomeric region of the 1H-13C HSQC spectrum of man100.
Figure 7B:
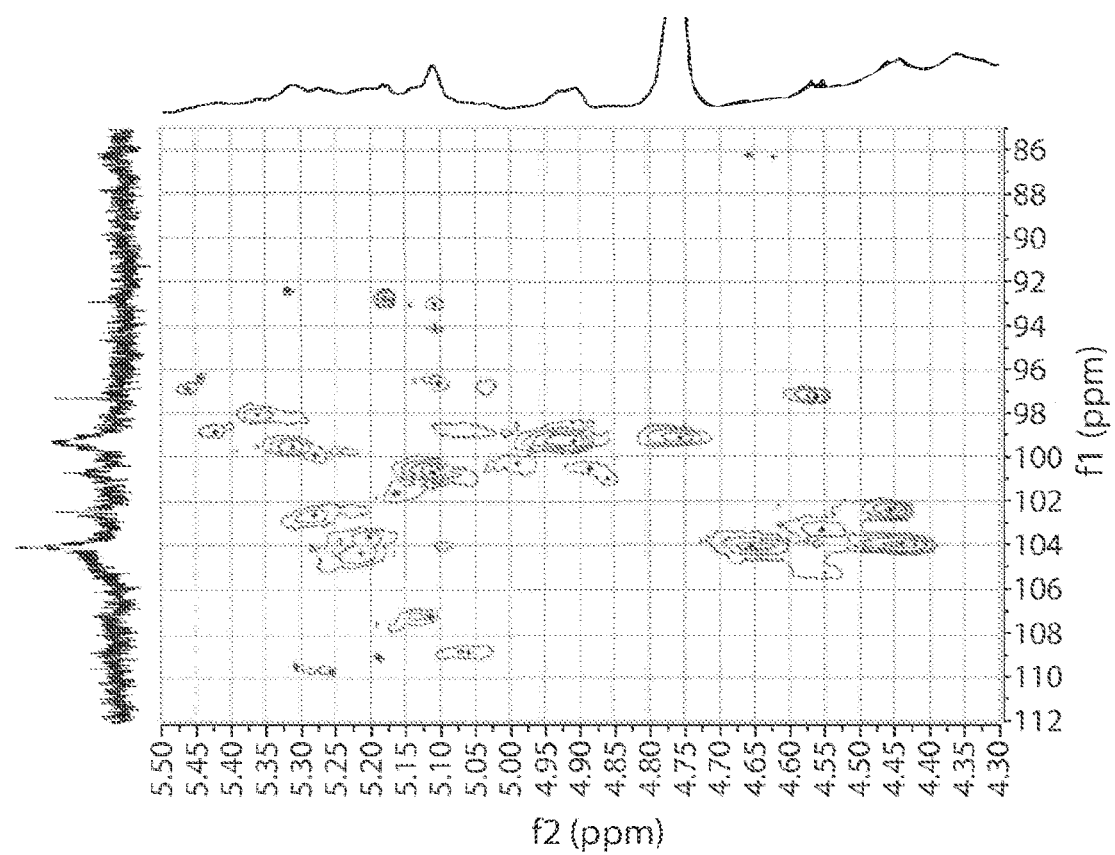
FIG. 7B. Anomeric region of the 1H-13C HSQC spectrum of xyl100.

This experiment was designed to identify the composition of a glycan by 2D-NMR identification of the constituent monomers. Approximately 150 mg of 65 Brix oligosaccharide solution was dried to stable mass in a vacuum oven at 45° C. under 300 mbar pressure, typically requiring 4-8 hours. Once dried, the sample was dissolved in 1.0 mL D₂O with 0.1% acetone, placed into a 3 mm NMR tube, and analyzed in a Bruker Avance-III using the spectral parameters listed in Table 7. The sample was analyzed using a 13C-1H heteroatomic single quantum coherence pulse sequence (HSQC) using the standard Bruker pulse sequence. Spectra were manually phased then referenced in both dimensions to the internal acetone signal: 1H—2.22 ppm; 13C—30.89 ppm. The anomeric region of each glycan spectra derived from a single sugar monomer was then examined for peaks representing specific glycosidic bonds characteristic to that monomer. Tables 7 and 8 list the diagnostic HSQC peaks for man100 and xyl100, respectively. FIGS. 7a and 7b show the HSQC spectra for man100 and xyl100, respectively.

TABLE 7

Spectral collection parameters used in HSQC fingerprint experiments

| Parameter | Value |
|---|---|
| Solvent | D2O |
| Temperature | 298.4 |
| Pulse Sequence | hsqcetgp |
| Experiment | HSQC |
| Probe | Z119470_0197 (PA BBO 500S1 BBF-H-D-05 Z SP) |
| Number of Scans | 8 |
| Receiver Gain | 123.5 |
| Relaxation Delay | 1.0000 |
| Pulse Width | 9.2000 |
| Spectrometer Frequency | (500.13, 125.77) |
| Spectral Width | (3001.2, 13850.4) |
| Lowest Frequency | (778.0, 3213.4) |
| Nucleus | (1H, 13C) |
| Acquired Size | (1024, 512) |
| Spectral Size | (1024, 1024) |

TABLE 8

Fingerprint peaks for man100 HSQC.

| F1: 13C (ppm) | f2: 1H (ppm) | f1: 13C (ppm) | f2: 1H (ppm) |
|---|---|---|---|
| 110.2 | 5.15 | 100.1 | 4.90 |
| 109.8 | 5.22 | 99.2 | 4.77 |
| 109.2 | 5.28 | 97.9 | 5.22 |
| 108.0 | 5.09 | 97.7 | 4.83 |
| 105.7 | 5.24 | 95.8 | 5.12 |
| 102.9 | 5.13 | 94.6 | 5.16 |
| 102.8 | 5.03 | 94.3 | 4.88 |
| 102.0 | 5.24 | 93.1 | 5.37 |
| 101.8 | 5.10 | 92.6 | 5.29 |
| 101.8 | 5.39 | 85.3 | 4.82 |
| 101.4 | 4.98 | 85.1 | 4.76 |
| 101.1 | 4.70 |  |  |

TABLE 9

Fingerprint peaks for xyl100 HSQC

| f1: 13C (ppm) | f2: 1H (ppm) |
|---|---|
| 108.8 | 5.06 |
| 107.1 | 5.12 |
| 104.3 | 5.21 |
| 104.0 | 4.66 |
| 103.9 | 4.44 |
| 103.6 | 5.20 |
| 103.2 | 4.55 |
| 102.6 | 5.28 |
| 102.4 | 4.46 |
| 101.6 | 5.16 |
| 100.6 | 5.11 |
| 99.5 | 5.31 |
| 99.2 | 4.91 |
| 99.0 | 4.76 |
| 98.0 | 5.36 |
| 97.2 | 4.56 |
| 92.7 | 5.18 |

Figure 3A:
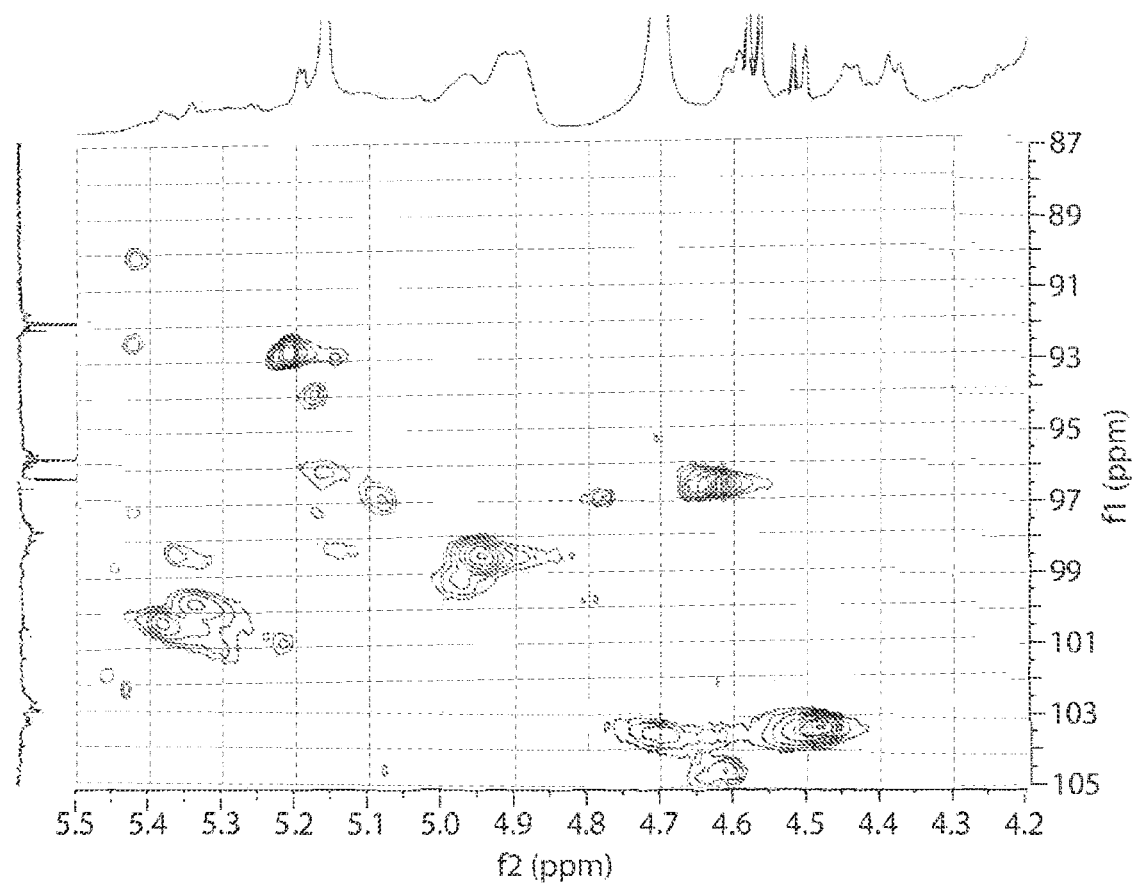
Figure 3B:
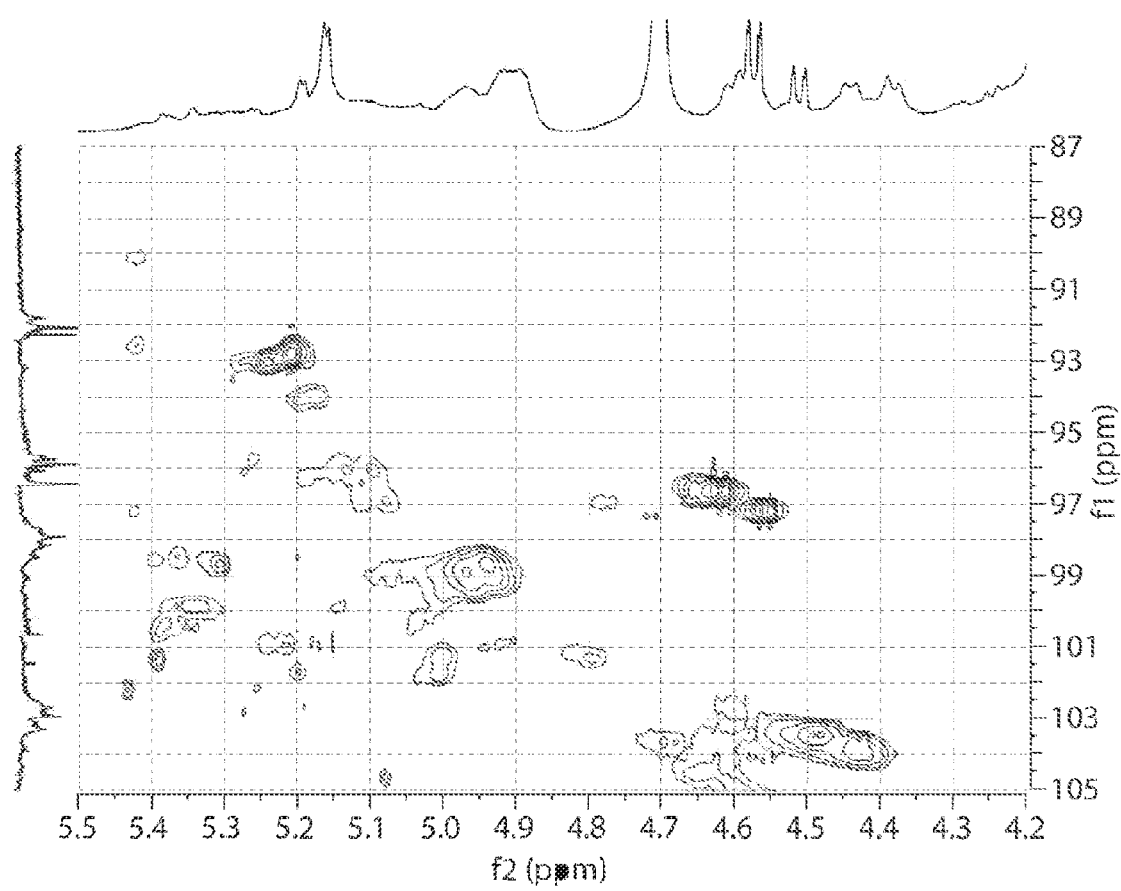
Figure 3C:
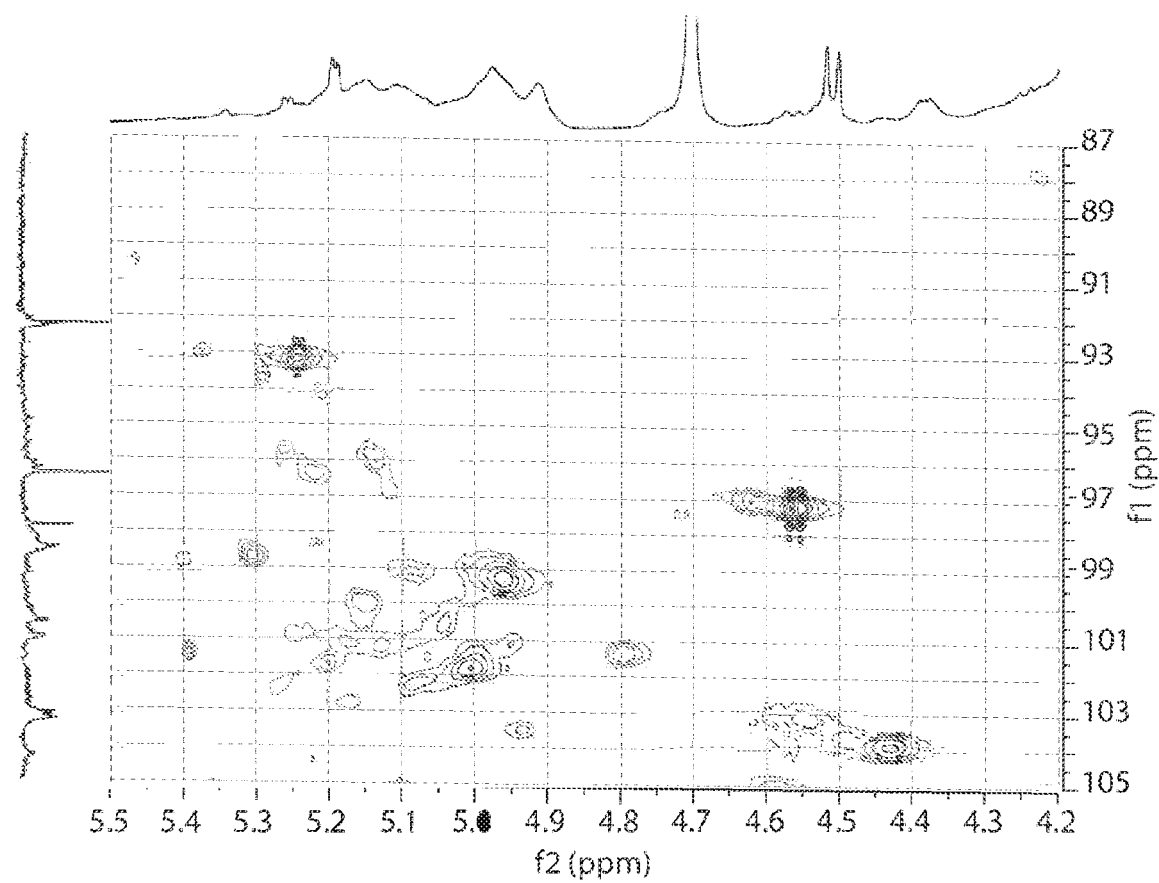

Due to the spin-isolated nature of single carbohydrate rings within polysaccharides, the HSQC spectrum of a glycan with more than one monomer is predicted to be represented by the sum of the HSQC peaks of each of its constituent sugars. Therefore, each constituent monomer has unique HSQC peaks that will appear in any glycan that contains that monomer irrespective of other constituent monomers and furthermore, the monomers used to synthesize a glycan can be determined by identifying the fingerprint peaks unique to each constituent monomer. For example, FIG. 3 shows that the HSQC spectra of glu50gal50 is a hybrid of the spectra of glu100 and gal100. Table 10 lists the fingerprint peaks for selected glycan units.

TABLE 10

Diagnostic HSQC peaks for each component sugar.

| Monomer | 1H shift | 13C shift | Monomer | 1H shift | 13C shift |
|---|---|---|---|---|---|
| Glucose | 5.42 | 92.5 | Xylose | 5.18 | 93.0 |
|  | 5.21 | 92.8 |  | 5.10 | 94.3 |
|  | 5.18 | 93.9 |  | 5.34 | 98.2 |
|  | 5.08 | 97.0 |  | 5.31 | 99.6 |
|  | 5.36 | 98.4 |  | 5.11 | 100.8 |
|  | 5.34 | 99.8 |  | 4.91 | 99.4 |
|  | 5.38 | 100.3 |  | 4.56 | 97.3 |
|  | 4.95 | 98.6 |  | 4.64 | 104.2 |
|  | 4.62 | 96.6 |  | 4.54 | 103.4 |
|  | 4.70 | 103.6 |  | 4.44 | 102.6 |
|  | 4.49 | 103.4 |  | 4.44 | 104.1 |
| Galactose | 5.37 | 92.9 | Arabinose | 5.22 | 93.2 |
|  | 5.24 | 93.1 |  | 5.13 | 93.2 |
|  | 5.14 | 96.0 |  | 5.29 | 96.0 |
|  | 4.96 | 99.3 |  | 5.26 | 97.2 |
|  | 5.31 | 98.7 |  | 5.12 | 96.6 |
|  | 5.39 | 101.4 |  | 5.18 | 99.6 |
|  | 5.00 | 101.8 |  | 5.06 | 99.2 |
|  | 4.80 | 101.3 |  | 4.99 | 100.0 |
|  | 4.63 | 97.0 |  | 5.26 | 101.9 |
|  | 4.56 | 97.2 |  | 5.06 | 102.1 |
|  | 4.53 | 103.1 |  | 4.55 | 97.4 |
|  | 4.43 | 104.1 |  | 4.54 | 105.2 |
| Fucose | 5.18 | 92.9 |  | 4.50 | 105.5 |
|  | 5.33 | 92.4 |  | 4.38 | 103.9 |
|  | 5.04 | 96.3 | Rhamnose | 5.21 | 93.2 |
|  | 4.90 | 99.7 |  | 5.10 | 94.5 |
|  | 4.52 | 97.0 |  | 4.85 | 94.1 |
|  | 4.39 | 103.6 |  | 5.01 | 95.8 |
| Mannose | 5.37 | 93.0 |  | 5.35 | 100.5 |
|  | 5.16 | 94.6 |  | 5.15 | 102.2 |
|  | 4.88 | 94.2 |  | 5.04 | 102.9 |
|  | 5.39 | 101.7 |  | 4.78 | 97.9 |
|  | 5.24 | 101.9 |  | 4.71 | 99.0 |
|  | 5.13 | 102.8 |  | 4.72 | 101.0 |
|  | 5.03 | 102.7 |  |  |  |
|  | 5.24 | 105.6 |  |  |  |
|  | 5.09 | 108.0 |  |  |  |
|  | 4.88 | 94.2 |  |  |  |
|  | 4.89 | 100.0 |  |  |  |
|  | 4.70 | 101.1 |  |  |  |

At least 5 peaks appeared for each glycan unit used as a starting material in the synthesis of a glycan therapeutic containing 3 or fewer distinct glycan units. The HSQC spectra of glycan therapeutics containing 4 or more distinct glycan units have at least 4 peaks for each constituent glycan unit.

Branching Analysis

Figure 4:
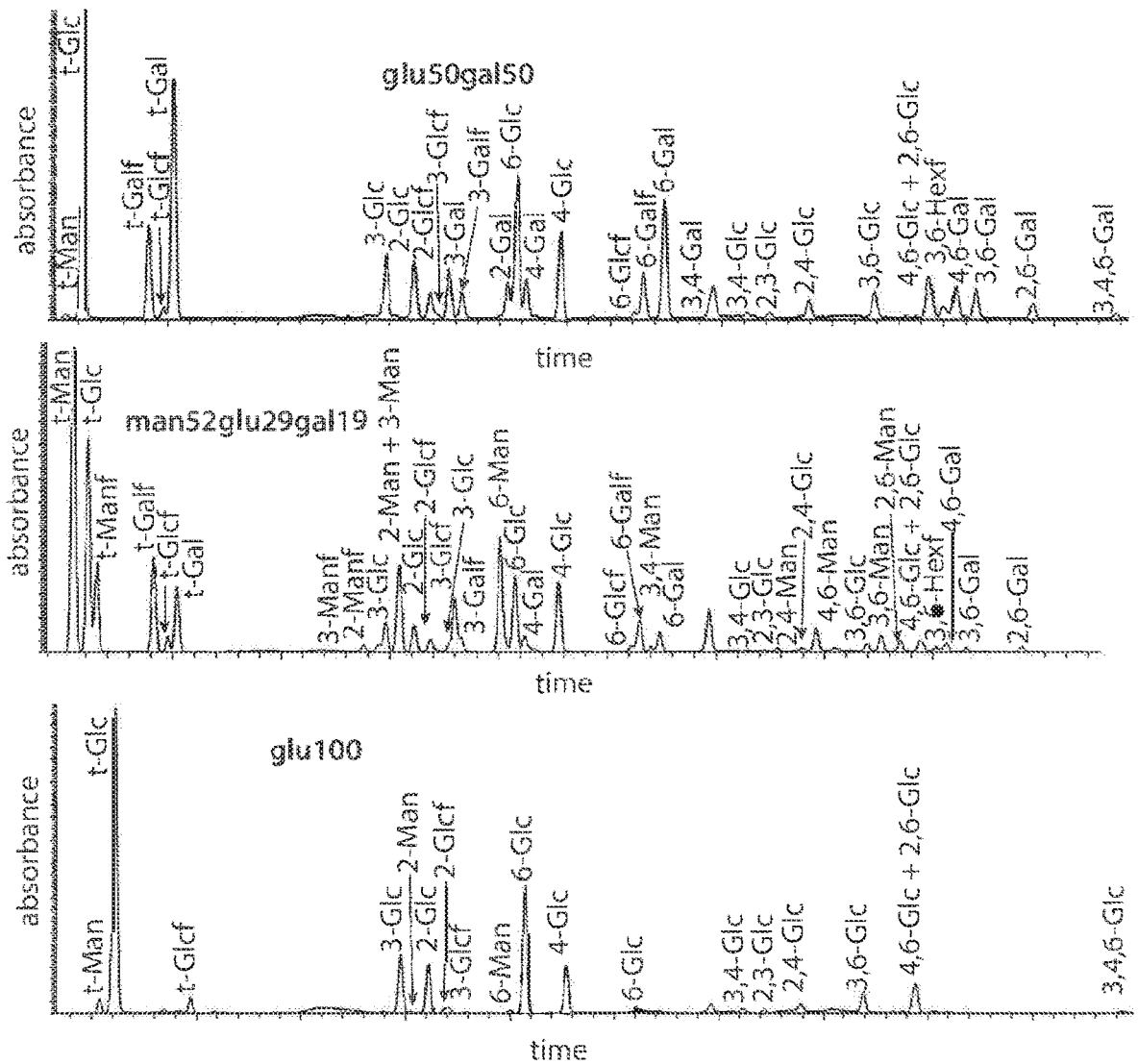
FIG. 4: Representative GC chromatograms of three representative permethylated and hydrolyzed glycans showing distribution of regiochemistry as assigned by comparison to known standards.

This experiment was designed to quantitate the distribution of glycosidic regioisomers (branching) within a given oligosaccharide. For glycosyl linkage analysis, the samples were permethylated, depolymerized, reduced, and acetylated; and the resultant partially methylated alditol acetates (PMAAs) analyzed by gas chromatography-mass spectrometry (GC-MS) as described by Heiss et al (2009) Carbohydr. Res. 344:915. The samples were suspended in 200 μl of dimethyl sulfoxide and left to stir for 1 day. Permethylation was effected by two rounds of treatment with sodium hydroxide (15 min) and methyl iodide (45 min). The aqueous solution was hydrolyzed by addition of 2M trifluoroacetic acid and heating to 121° C. for 2 hours. Solids were isolated in vacuo and acetylated in acetic acid/trifluoroacetic acid. The resulting PMAAs were analyzed on an Agilent 7890A GC interfaced to a 5975C MSD (mass selective detector, electron impact ionization mode); separation was performed on a 30 m Supelco SP-2331 bonded phase fused silica capillary column. FIG. 4 shows three representative GC spectra from this analysis. These analyses show that the glycans had at least 0.1-10% of each of the 1,2-; 1,3-; 1,4-, and 1,6-glycoside bond types. The materials also contained at least 5% of the branched bond types (including but not limited to 1,3,6-; 1,4,6-; or 1,2,4-glycosides) and at least 3% of the monomeric units existed in the furanose form. A glycan originating from a single monomer consisted of at least 12 distinct non-terminal substitution patterns. A glycan originating from two monomers consisted of at least 18 distinct non-terminal substitution patterns. A glycan originating from three or more monomers consisted of at least 24 distinct non-terminal substitution patterns.

Example 5: Effect of Glycans on Microbial Populations Ex Vivo

To determine the desired composition of glycans, bacterial cultures are grown in the presence of candidate glycans and assayed for their growth, community composition (e.g., by 16S rRNA gene sequencing), production of metabolites, and phenotypic or transcriptomic properties. Desired glycans are selected based on their ability to elicit desired properties within the bacterial culture. Bacterial cultures include monocultures, mixed cultures, cultures isolated from humans or laboratory animal models, cultures isolated from a human or laboratory animal model and spiked with an isolate or collection of isolates, or cultures isolated from a human or laboratory animal model and depleted of a collection of species (for example, by application of an antibiotic). This assay can be performed in the presence of antibiotics or other test compounds. The results obtained from the in vitro assays are compared with those obtained after treating humans with glycans or administering the glycans to a laboratory animal establishing the in vitro-in vivo correlation of results.

Example 6: Effect of Glycans on Commensal Bacteria In Vitro

An in vitro assay was performed to assess the ability of various bacterial strains, including commensals of the gastrointestinal tract, to utilize different glycans as growth substrates. This assay was designed to assess the ability of selected glycans to promote the growth of microbiota associated with effects on cancer progression, including protective effects. Bacterial strains were handled at all steps in an anaerobic chamber (AS-580, Anaerobe Systems) featuring a palladium catalyst. The chamber was initially made anaerobic by purging with an anaerobic gas mixture of 5% hydrogen, 5% carbon dioxide and 90% nitrogen and subsequently maintained in an anaerobic state using this same anaerobic gas mixture. Anaerobicity of the chamber was confirmed daily using Oxoid anaerobic indicator strips that change color in the presence of oxygen. All culture media, assay plates, other reagents and plastic consumables were pre-reduced in the anaerobic chamber for 24-48 hours prior to contact with bacteria. Glycans ara50gal50, glu33gal33fuc33, glu50gal50, gal100, glu100, xyl100, ara100, ara60xyl40, glu80man20, glu60man40, man52glu29gal19, man100, xyl75ara25, and a commercially available control, FOS (Nutraflora FOS; NOW Foods, Bloomingdale Ill.), were prepared at 5% w/v in water, filter-sterilized and added to Costar 3370 assay plates for a final concentration of 0.5% w/v in the assay, with each glycan assayed in two non-adjacent wells and dextrose and water supplied as positive and negative controls.

Bacterial isolates were obtained from the American Type Culture Collection (ATCC) and Leibniz Institute DSMZ-German Institute of Microorganisms and Cell Cultures (DSMZ). Cultures of the Bacteroidetes *Bacteroides caccae* ATCC 43185 "BCA.26", *Bacteroides thetaiotaomicron* ATCC 29741 "BTH.8", *Bacteroides cellulosilyticus* DSM 14838 "BCE.71", *Parabacteroides distasonis* ATCC 8503 "PDI.6", *Bacteroides vulgatus* ATCC 8482 "BVU.10" and *Prevotella copri* DSM 18205 "PCO.72"; the Clostridiales *Clostridium scindens* ATCC 35704 "CSC.32", *Dorea formicigenerans* ATCC 27755 "DFO.36", *Dorea longicatena* DSM 13814 "DLO.76", *Ruminococcus obeum* ATCC 29714 "ROB.74" and *Blautia hansenii* ATCC 27752 "BHA.20"; and the Bifidobacteria *Bifidobacterium longum* ATCC 15707 "BLO.16" and *Bifidobacterium longum* DSM 20088 "BLO.83", were grown anaerobically in Chopped Meat Glucose broth (CMG, Anaerobe Systems), a pre-reduced enriched medium including lean ground beef, enzymatic digest of casein, yeast extract, potassium phosphate, dextrose, cysteine, hemin and Vitamin K1, for 18-48 hours at 37° C. Inocula were prepared by determining the optical density of each culture at 600 nM (0D600) in a Costar 3370 polystyrene 96-well flat-bottom assay plate using a Biotek Synergy 2 plate reader with Gen5 2.0 All-In-One Microplate Reader Software according to manufacturer's protocol, and diluting the cells to $OD_{600}$ 0.01 final in defined and semi-defined media that were prepared without sugars. *B. vulgatus, D. formicigenerans, P. distasonis, B. longum, B. hansenii* and *D. longicatena* isolates were tested in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114), supplemented with 0-10% (v/v) CMG. *B. thetaiotaomicron, B. caccae* and *B. cellulosyliticus* were tested in 100 mM potassium phosphate buffer (pH 7.2), 15 mM sodium chloride, 8.5 mM ammonium sulfate, 4 mM L-cysteine, 1.9 μM hematin, 200 μM L-histidine, 100 μM magnesium chloride, 1.4 μM iron sulfate heptahydrate, 50 μM calcium chloride, 1 μg/mL vitamin K3 and 5 ng/mL vitamin B12 (Martens E C et al. Cell Host & Microbe 2008; 4, 447-457). *C. scindens, P. copri* and *R. obeum* were tested in 10 g/L tryptone peptone, 5 g/L yeast extract, 0.5 g/L L-cysteine hydrochloride, 0.1 M potassium phosphate buffer pH 7.2, 1 μg/mL vitamin K3, 0.08% w/v calcium chloride, 0.4 μg/mL iron sulfate heptahydrate, 1 μg/mL resazurin, 1.2 μg/mL hematin, 0.2 mM histidine, 0.05% Tween 80, 0.5% meat extract (Sigma), 1% trace mineral supplement (ATCC), 1% vitamin supplement (ATCC), 0.017% v/v acetic acid, 0.001% v/v isovaleric acid, 0.2% v/v propionic acid and 0.2% v/v N-butyric acid (Romano K A et al. mBio 2015; 6(2):e02481-14). Bacteria were exposed to glycans ara50gal50, glu33gal33fuc33, glu50gal50, gal100, glu100, xyl100, ara100, ara60xyl40, glu80man20, glu60man40, man52glu29gal19, man100, xyl75ara25, commercial FOS and dextrose at a final concentration of 0.5% w/v in 96-well microplates, 200 μL final volume per well, at 37° C. for 18-48 hours, anaerobically. OD600 measurements for each isolate at the end of the incubation period were obtained using a Biotek Synergy2 reader with Gen5 2.0 software according to manufacturer's specifications. Measurements were normalized by dividing the OD600 readings of the isolate on test glycans by the average OD600 of the isolate in medium supplemented with 0.5% w/v dextrose to facilitate comparison of glycan utilization by strains that grow within significantly different OD600 ranges. Table 11 provides a key to Tables 12-14.

TABLE 11

| Key |  |
| --- | --- |
| Key to Glycans | |
| glycan # | glycan identity |
| 1 | glu50gal50 |
| 2 | ara50gal50 |
| 3 | glu100 |
| 4 | gal100 |
| 5 | glu80man20 |
| 6 | glu60man40 |
| 7 | glu33gal33fuc33 |
| 8 | ara100 |
| 9 | man52glu29gal19 |
| 10 | ara60xyl40 |
| 11 | man80glu20 |
| 12 | xyl100 |
| 13 | man100 |
| 14 | xyl75ara25 |
| 15 | FOS |

Most glycans supported growth of most of the commensal strains tested in the assay, with Average Normalized Growth values of at least 0.2. Glycans varied in the number and diversity of strains they supported (see Table 12) in the assay. In the assay, glu50gal50, ara50gal50, glu100, gal100, glu80man20, glu60man40, glu33gal33fuc33 and ara100 supported growth of a combination of Bacteroidales; Clostridiales, including the Lachnospiraceae DFO.36, DLO.76, CSC.32 and BHA.20; and Bifidobacteria. In the assay, man52glu29gal19, ara60xyl40 and man80glu20 supported growth of a combination of Bacteroidales and Lachnospiraceae, and xyl100 and man100 supported growth of members of Bacteroidales.

TABLE 12

Glycan-supported growth of commensal bacteria.

| | Commensals, Average Normalized Growth | | | | | | | | | |
| --- | --- | --- | --- | --- | --- | --- | --- | --- | --- | --- |
| glycan # | PDI.6 | BVU.10 | BTH.8 | PCO.72 | DFO.36 | DLO.76 | CSC.32 | BHA.20 | BLO.16 | BLO.83 |
| 1 | ++ | + | + | ++ | ++ | + | + | + | − | + |
| 2 | ++ | ++ | + | ++ | + | + | + | + | − | − |
| 3 | ++ | + | + | ++ | + | + | − | + | + | − |
| 4 | + | + | + | + | ++ | + | + | + | − | − |

TABLE 12-continued

Glycan-supported growth of commensal bacteria.

| | | | | | | | | | | |
|---|---|---|---|---|---|---|---|---|---|---|
| 5 | ++ | + | + | + | ND | + | + | − | + | − |
| 6 | ++ | + | + | − | ND | + | + | − | + | − |
| 7 | + | + | + | − | ++ | + | + | − | − | − |
| 8 | − | + | + | ++ | + | + | − | − | + | − |
| 9 | ++ | + | + | − | + | − | + | − | − | − |
| 10 | + | + | + | + | + | − | − | − | − | − |
| 11 | ++ | + | + | − | ND | ND | + | − | − | − |
| 12 | + | + | + | + | − | − | − | − | − | − |
| 13 | ++ | + | + | − | ND | − | − | − | − | − |
| 14 | − | − | − | − | − | − | − | − | − | ND |
| 15 | ++ | ++ | + | + | + | ++ | + | ++ | ++ | ++ |

Key

| symbol | NGV |
|---|---|
| − | <0.2 |
| + | 0.2-0.6 |
| ++ | >0.6 |
| ND | Not Determined |

Glycans may increase the concentration of microbial proteins that are sufficiently similar to tumor antigens to elicit immune cell activity via antigenic mimicry or cross-reactivity. Antigen mimicry may drive anti-tumor effects via two mechanisms. First, if microbes remain confined in the intestinal lumen, microbes or microbial antigens are locally captured by CD103+CD11b+dendritic cells that migrate to the draining lymph node to present relevant antigen to T cells.

Subsequently, these T cells can traffic to the tumor to drive an anti-tumor immune response. A second mechanism is that microbial antigens, rather than T cells, can travel through the body to a tumor site. Translocation of microbial proteins and even entire microorganisms from the intestine to mesenteric lymph nodes, the spleen, and other sites has been documented (Abt et al. (2012). Commensal bacteria calibrate the activation threshold of innate antiviral immunity. Immunity 37, 158-170; Wheeler et al. (2014). The biology of bacterial peptidoglycans and their impact on host immunity and physiology. Cell. Microbiol. 16, 1014-1023), and this breach of the mucosal barrier may prove essential for instances in which antigenic mimicry determines the long-range effects of the microbiome on immunosurveillance. Additionally, such antigenic mimicry may aid the immune systems recognition of pathogenic microorganisms that share antigens with microbial molecules that are exposed to the immune system.

In mouse models, the efficacy of such immune checkpoint blockade is strongly dependent on the gut microbiome. CTLA4 blockade lost its therapeutic activity against fibrosarcomas in mice that were either raised in a germ-free environment or that had been raised in specific pathogen-free conditions and then treated with multiple broad-spectrum antibiotics to sterilize the gut (Vetizou, et al. (2015). Anticancer immunotherapy by CTLA-4 blockade relies on the gut microbiota. Science 350, 1079-1084). This defect was overcome by gavage with *Bacteroides fragilis*, by immunization with *B. fragilis* polysaccharides, or by adoptive transfer of *B. fragilis*-specific T cells, suggesting a therapy-relevant crossreactivity between microbial and tumor antigens recognized by the same T cell receptor (TCR). Accordingly, both in mice and in patients, T cell responses specific for distinct *Bacteroides* species (*B. fragilis* and *B. thetaiotaomicron*) were associated with the administration (in humans) and efficacy (in mice) of CTLA-4 blockade. The microbiome also affects the therapeutic efficacy of PD-L1 blockade. Injection of a blocking antibody against PD-L1 was much more efficient in reducing the growth of melanomas in mice containing a high abundance of *Bifidobacterium* in their gut than in mice lacking this genus. *Bifidobacterium*-treated mice exhibited significantly improved tumor control compared with their untreated littermates, and this effect was mediated by CD8+ T cells. DCs purified from mice that had been treated with *Bifidobacterium* were particularly active in presenting a melanoma-derived peptide antigen to T cells for stimulation of their proliferation and IFN-g production, suggesting that *Bifidobacterium* improves the anticancer immune response through an effect on DCs (Sivan et al. (2015) Commensal *Bifidobacterium* promotes antitumor immunity and facilitates anti-PD-L1 efficacy. Science 350, 1084-9), which may increase the presentation of a microbiome-derived antigen. By shifting the concentration of microbes present in the microbiome, the antigens may also be shifted and the prevalence of antigens that mimic tumor-associated antigens may be increased.

As shown in Table 13, most glycans supported growth of Parabacteroides PDI.6 and *Bacteroides* isolates BVU.10, BTH.8, BCA.26 and/or BCE.71 with Average Normalized Growth values of at least 0.2 in the assay. In the assay, glu80man20, glu100, glu60man40, glu50gal50 and ara100 supported growth of *Bifidobacterium longum*, in addition to the Bacteroidetes PDI.6, BVU.10, BTH.8, BCA.26 and/or BCE.71.

TABLE 13

Glycan-supported growth of Parabacteroides, Bacteroides and Bifidobacteria

| glycan # | Parabacteroides, Bacteroides and Bifidobacteria, Average Normalized Growth | | | | | | |
|---|---|---|---|---|---|---|---|
| | PDI.6 | BVU.10 | BTH.8 | BCA.26 | BCE.71 | BLO.16 | BLO.83 |
| 5 | ++ | + | + | ++ | ++ | + | − |
| 3 | ++ | + | + | ++ | + | + | − |
| 6 | ++ | + | + | + | + | + | − |
| 13 | ++ | + | + | + | + | − | − |
| 11 | ++ | + | + | + | + | − | − |
| 9 | ++ | + | + | + | + | − | − |
| 4 | + | + | + | ++ | + | − | − |
| 1 | ++ | + | + | + | − | − | + |
| 2 | ++ | ++ | + | ND | ND | − | − |
| 7 | + | + | + | + | + | − | − |
| 12 | + | + | + | − | + | − | − |
| 10 | + | + | + | ND | ND | − | − |
| 8 | − | + | + | ND | ND | + | − |

TABLE 13-continued

Glycan-supported growth of Parabacteroides, Bacteroides and Bifidobacteria

| glycan # | Parabacteroides, Bacteroides and Bifidobacteria, Average Normalized Growth | | | | | | |
|---|---|---|---|---|---|---|---|
| | PDI.6 | BVU.10 | BTH.8 | BCA.26 | BCE.71 | BLO.16 | BLO.83 |
| 14 | – | – | – | – | – | – | ND |
| 15 | ++ | ++ | + | ++ | ++ | ++ | ++ |

As shown in Table 14, most glycans support the growth of at least one strain of Clostridiales in the assay. The Clostridiales include the Lachnospiraceae DFO.36, DLO.76, CSC.32 and BHA.20.

TABLE 14

Glycan-supported growth of Clostridiales

| glycan # | Clostridiales, Average Normalized Growth | | | | |
|---|---|---|---|---|---|
| | DFO.36 | DLO.76 | CSC.32 | ROB.74 | BHA.20 |
| 4 | ++ | + | + | + | + |
| 1 | ++ | + | + | – | + |
| 7 | ++ | + | + | + | – |
| 2 | + | + | + | ND | + |
| 5 | ND | + | + | + | – |
| 3 | + | + | – | – | + |
| 9 | + | – | + | + | – |
| 8 | + | + | – | ND | – |
| 6 | ND | + | + | – | – |
| 10 | + | – | – | ND | – |
| 11 | ND | ND | + | – | – |
| 13 | ND | – | – | – | – |
| 14 | – | – | – | – | – |
| 12 | – | – | – | – | – |
| 15 | + | ++ | + | ++ | ++ |

These data suggest that glycan therapeutics support growth of commensal bacteria.

Example 7: Collection of Fecal Samples

Fecal samples were collected by providing subjects with the Fisherbrand Commode Specimen Collection System (Fisher Scientific) and associated instructions for use. Collected samples were stored with ice packs or at −80° C. until processing (McInnes & Cutting, Manual of Procedures for Human Microbiome Project: Core Microbiome Sampling Protocol A, v12.0, 2010, hmpdacc.org/doc/HMP_MOP_Version12_0_072910.pdf). Alternative collection devices may also be used. For example, samples may be collected into the Globe Scientific Screw Cap Container with Spoon (Fisher Scientific) or the OMNIgene-GUT collection system (DNA Genotek, Inc.), which stabilizes microbial DNA for downstream nucleic acid extraction and analysis. Aliquots of fecal samples were stored at −20° C. and −80° C. following standard protocols known to one skilled in the art.

Example 8: Determining the Titer of Microbial Samples Collected from Feces and Culturing Samples To determine the titer of common bacteria of the gastrointestinal tract, fecal samples were collected as described in Example 7 and prepared as a 10% weight/volume suspensions in sterile phosphate buffered saline (PBS). Ten-fold serial dilutions were prepared in sterile PBS and plated (100 μL per dilution) to Brucella Blood Agar (Anaerobe Systems; incubated anaerobically to non-selectively titer common member of the gut microbiota, including Bacteroides, or incubated aerobically to non-selectively titer facultative anaerobes such as Proteobacteria). Bacteroides Bile Esculin Agar (Anaerobe Systems; cultured anaerobically to titer Bacteroides fragilis group), Cycloserine-Cefoxitin Fructose Agar (Anaerobe Systems; cultured anaerobically to titer Clostridium difficile), Lactobacillus-MRS Agar (Anaerobe Systems; cultured anaerobically to titer Lactobacillus), Eosin Methylene Blue Agar (Teknova; cultured aerobically to titer Escherichia coli and other Gram-negative enteric bacteria), Bile Esculin Agar (BD; cultured aerobically to titer Enterococcus species), Bifidobacterium Selective Agar (Anaerobe Systems; to titer Bifidobacterium species), or MacConkey Agar (Fisher Scientific; to titer E. coli and other Gram-negative enteric bacteria) may also be used. Plates were incubated at 37° C. under aerobic or anaerobic conditions as appropriate for the target species. After 24-48 hours, colonies were counted and used to back-calculate the concentration of viable cells in the original sample.

To non-selectively culture samples containing bacteria collected from a human or laboratory animal model, rich media or agar such as Brucella Blood Agar (Anaerobe Systems), Brain Heart Infusion Broth (Teknova), or Chopped Meat Glucose Broth (Anaerobe Systems) were used. A minimal media formulation such as M9 (Life Technologies) supplemented with amino acids, carbon sources, or other nutrients as needed were used to non-selectively culture bacteria during in vitro assays testing the effects of glycans or other compounds on bacterial populations. Alternatively, other minimal media formulations known to one skilled in the art were used, for example, as reported in Martens et al. (Mucosal Glycan Foraging Enhances Fitness and Transmission of a Saccharolytic Human Gut Bacterial Symbiont, 2008, Cell Host & Microbe, 4:447-457). Alternatively, fecal slurries at a concentration of 0.1%-10% weight/volume in PBS were used in the presence or absence of additional media elements for in vitro assays testing the effects of glycans or other compounds on bacterial populations.

Example 9: Effects of Glycans on Ex Vivo Human Fecal Microbial Communities

The ex vivo assay was designed to determine if glycans can modulate a complex human fecal microbial community. Modulation of the community may induce functional and/or taxa shifts that may affect various host responses that may relate to the protection against or treatment of diseases, including cancer. Fecal samples and slurries were handled in an anaerobic chamber (AS-580, Anaerobe Systems) featuring a palladium catalyst. Glycans glu100, xyl100, man52glu29gal19, and a commercially available control, FOS (Nutraflora FOS; NOW Foods, Bloomingdale Ill.), were prepared at 5% w/v in water, filter-sterilized and added to 96-deep well assay plates for a final concentration of 0.5% w/v, with each glycan assayed in two non-adjacent wells and dextrose and water supplied as positive and negative controls.

A human fecal sample donation was stored at −80° C. To prepare working stocks the fecal sample was transferred into the anaerobic chamber and allowed to thaw. The fecal sample was prepared to 20% w/v in phosphate buffered saline (PBS) pH 7.4 (P0261, Teknova Inc., Hollister, CA), 15% glycerol, centrifuged at 2,000×g, the supernatant was removed, and the pellet was suspended in PBS pH 7.4 to 1% w/v fecal slurry. Prepared 1% w/v fecal slurry were contacted with glycans to 500 µL final volume per well, at 37° C. for 18 hours, anaerobically. Genomic DNA was extracted from the fecal samples and variable region 4 of the 16S rRNA gene was amplified and sequenced (Earth Microbiome Project protocolwww.earthmicrobiome.org/emp-standard-protocols/16s/ and Caporaso J G et al. 2012. Ultra-high-throughput microbial community analysis on the Illumina HiSeq and MiSeq platforms. ISME J.). Operational Taxonomic Units (OTUs) were generated by aligning 16S rRNA sequences at 97% identity. Microbial communities were compared to each other using UniFrac distance metric (Lozupone C. et al., Appl. Environ. Microbiol. December 2005 vol. 71 no. 12 8228-8235).

Figure 8A:
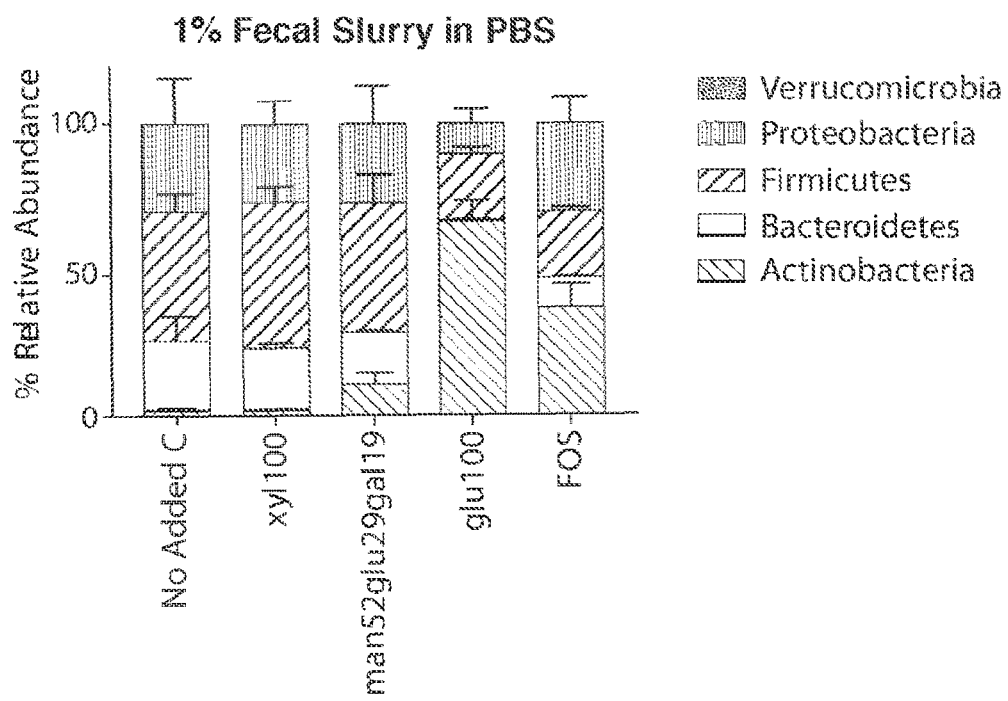
FIGS. 8A-8E. Taxa shifts in human fecal slurry grown with selected glycan therapeutics.
Figure 8B:
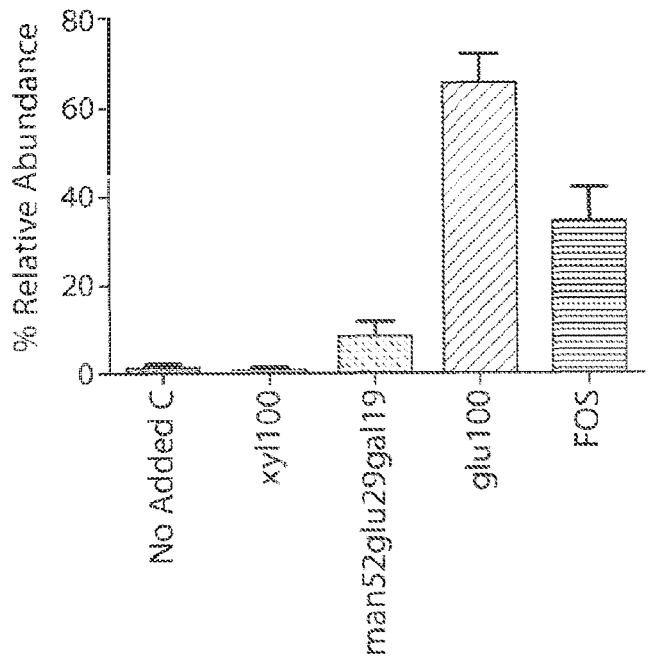
Figure 8C:
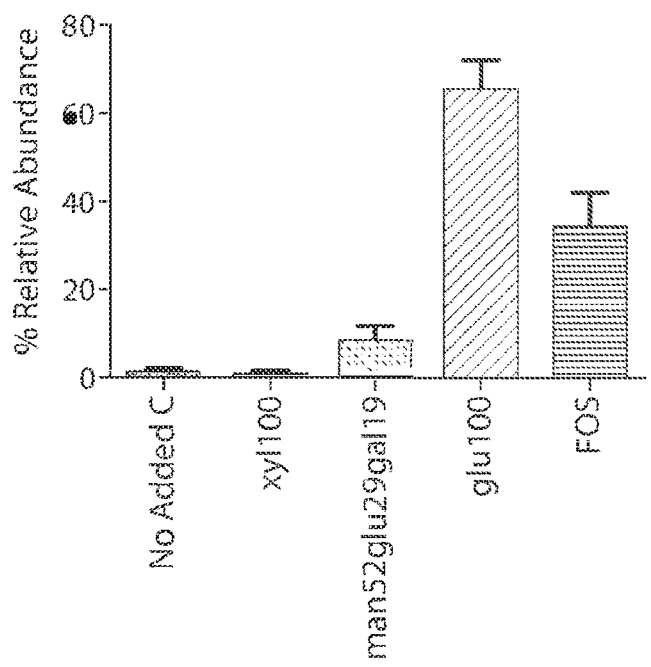
Figure 8D:
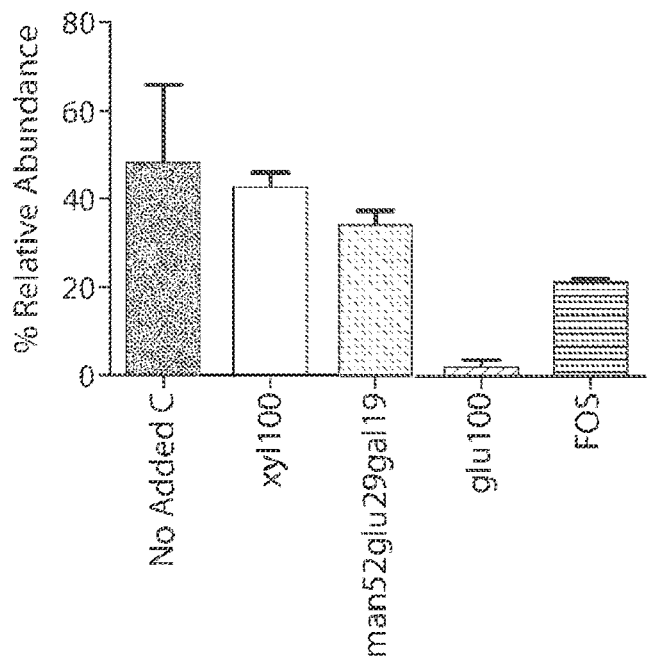
Figure 8E:
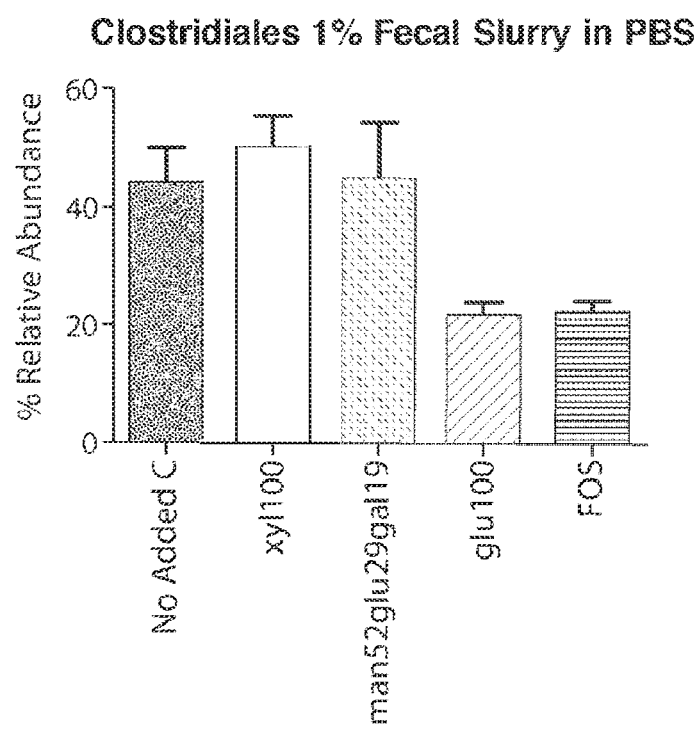

As shown in FIG. 8a, Actinobacteria relative abundance is increased while Bacteroidetes and Firmicutes relative abundance is decreased in 1% w/v fecal slurry in FOS control and glu100, compared to control fecal slurry lacking added carbon source. As shown in FIG. 8b-e glu100 and FOS control significantly increased the relative abundance of Bifidobacteriales (FIG. 8b) and Bifidobacteria (FIG. 8e) compared to control fecal slurry lacking added carbon source. Glu100 and FOS also significantly reduced the relative abundance of Bacteroidales (FIG. 8c) and Clostridiales (FIG. 8d). Xyl100 and man52glu29gal19 did not have a statistically significant effect in this assay. Modulation of *Bifidobacterium* and *Bacteroides* species is thought to play a role in controlling and treating tumors (see Example 6).

Example 10: Effects of Glycans on Microbial Communities In Vivo in Healthy Human Volunteers A Randomized, single-blind, cross-over, controlled study was conducted to analyze the effects of glycans on the microbiota of the human GI tract. 45 healthy human volunteers were enrolled in the 35-day study which included a 7 day run-in period prior to randomization. All volunteers were between 18 and 40 years of age and had a BMI between 20 and 27 kg/m². Following the 7 day run-in period, subjects that met eligibility criteria were randomized to one of three treatment groups of 15 subjects each: glu50gal50, glu100 as a syrup, and a commercial FOS control in powder form. Subjects consumed the equivalent of 8 grams dry weight of glycan and FOS once a da-y for 7 days followed by a 7 day washout period. They then consumed the equivalent of 16 grams dry weight of glycan and FOS once a day for 7 days followed by a 7 day washout period. Subjects were instructed to mix the glycan and FOS with 200 ml of tap water prior to consumption.

The study identified two classes of taxa responding to glycan treatment (see, Table 15): (1) taxa that are in all or a large percentage of individuals, but respond robustly only in a subset of individuals (e.g. OTU 11 in individuals treated with glu50gal50) and (2) taxa that are found in a small subset of individuals, but robustly respond in all subjects (e.g. OTU 51 in glu100 and glu50gal50). Therapeutic glycans modulated a larger number of OTU than the commercial FOS control: two in FOS and four each in glu100 and glu50gal50. The glycans showed overlapping (OTU 11 and OTU 51) and differential modulation of OTUs (see, Table 15).

TABLE 15

OTUs that respond to glycan treatments in humans. Percentages represent the approximate number of individuals in which the indicated taxa responded to the treatment. Percentages in the parentheses represent the number of individuals

| | Taxa | FOS | glu100 | glu50gal50 |
|---|---|---|---|---|
| OTU 11 | *Blautia* species | | 64% (79%) | 29% (100%) |
| OTU 10 | *Bifidobacterium* species | 57% (93%) | | |
| OTU 2 | *Roseburia* species | | 45% (93%) | |
| OTU 14 | *Coprococcus* species | 64% (100%) | | |
| OTU 5 | Lachnospiraceae (family) | | 50% (93%) | |
| OTU 50 | *Faecalibacterium prausnitzii* | | | 36% (93%) |
| OTU 20 | *Parabacteroides* species | | | 62% (69%) |
| OTU 51 | *Ruminococcaceae* species | | 43% (43%) | 38% (38%) |

Figure 9:
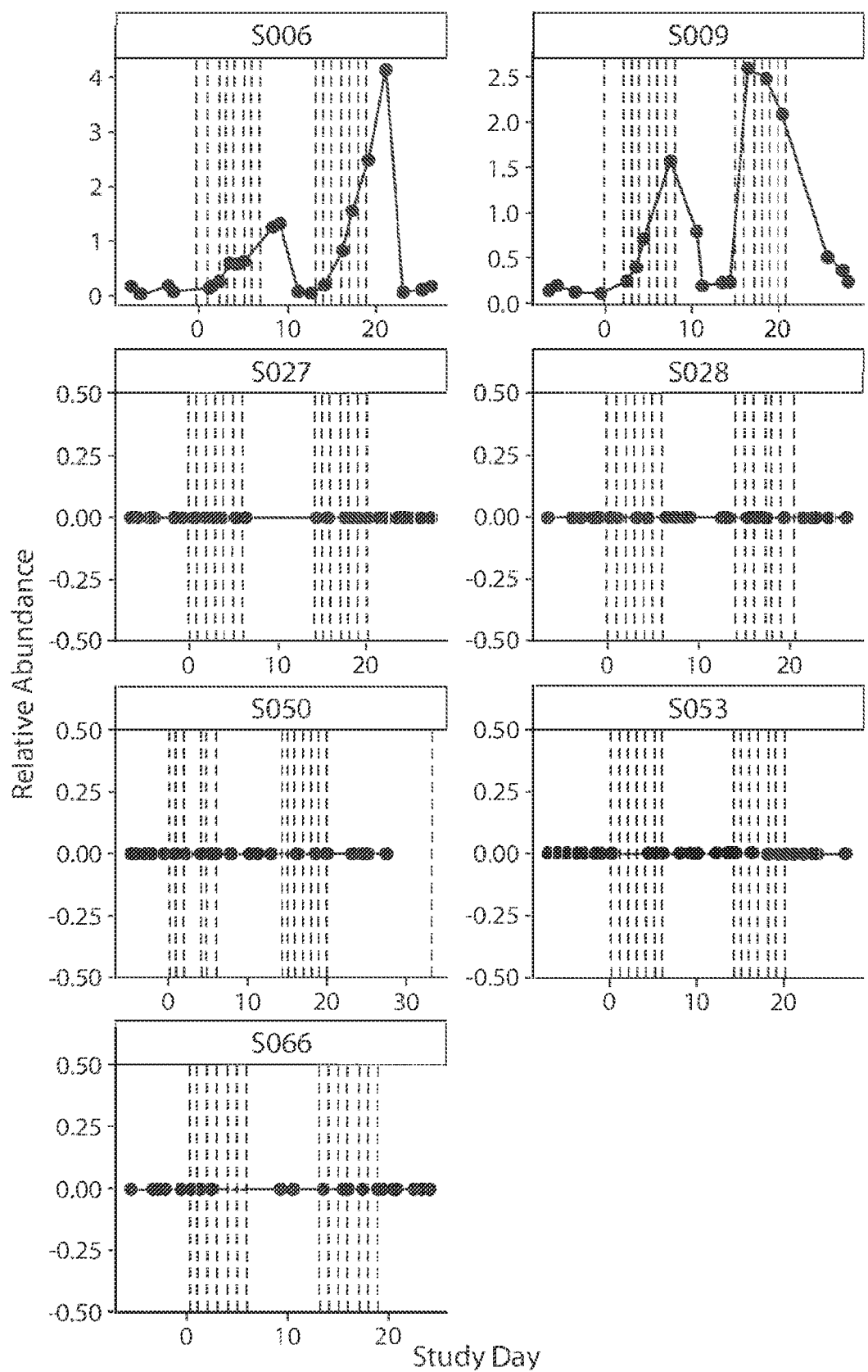
FIG. 9. Relative abundance of OTU 51 in individuals treated with glu50gal50. Dashed vertical lines represent treatment doses. 62% of individuals did not have this OTU in their gut microbiota prior to treatment.
Figure 9:
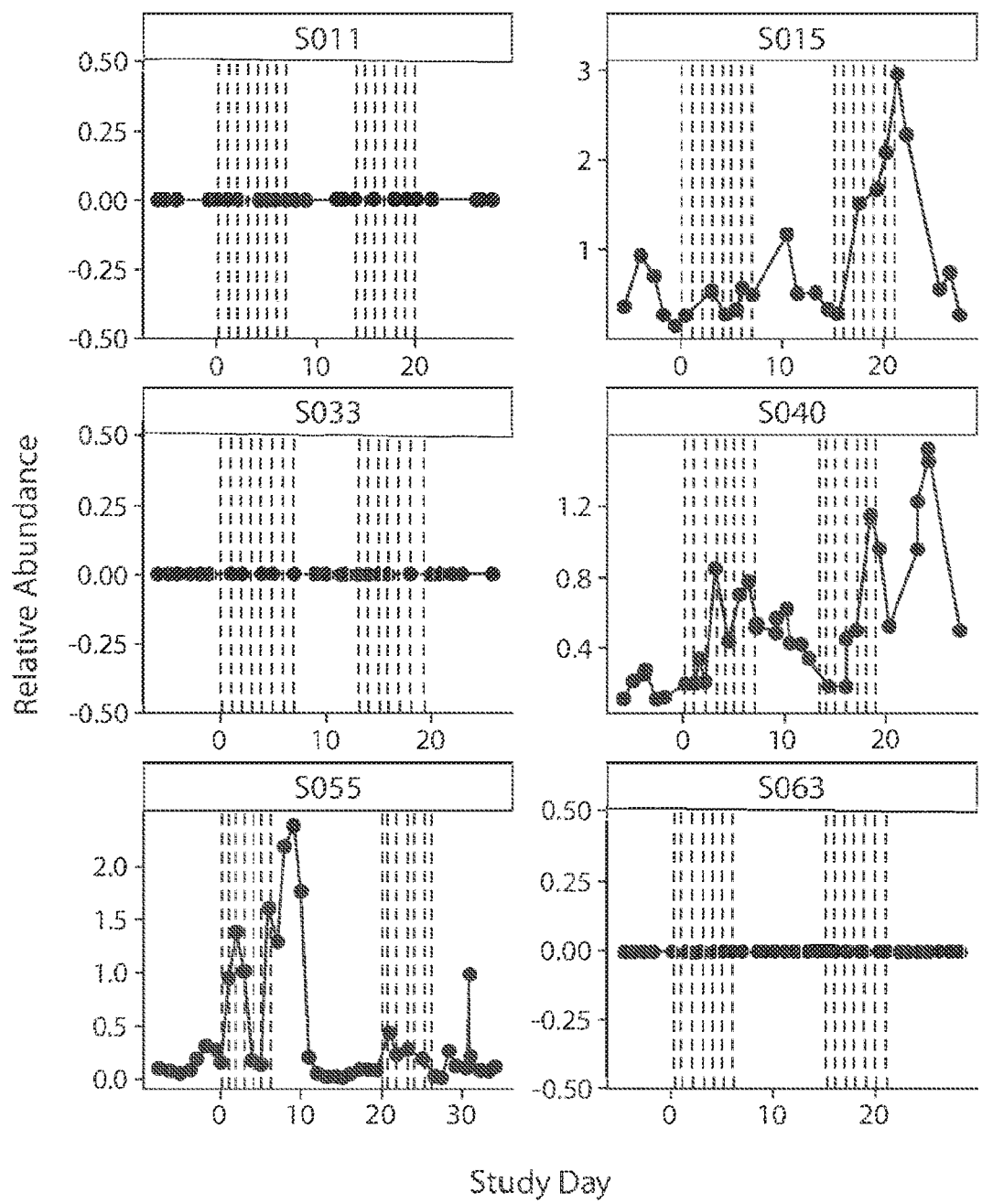

As can be seen from Table 15 not all subjects host all OTUs but OTUs 11, 10, 2, 14, 5, 50, and 20 are present in most subjects tested (in about 70% or more of subjects). For most OTUs growth modulation varies between subjects, some of which show modulation while others don't exhibit a shift in the taxa. For at least one OTU (OTU 51) all subjects hosting the OTU showed a modulation. The microbial community in the subjects was stable during the course of the study. Bacteria that were absent at the beginning of the study did not appear during the course of the study (see FIG. 9). As shown in FIG. 9 for OTU 51, subjects that host the OTU show growth of the OTU in the GI tract in response to the glycan treatment, often shortly after the begin of consumption of the glycan. Others that do not host the OTU do not show any changes in abundance for OTU upon administration of the glycan. Subjects may be classified as responders and non-responders to glycans and may further be selected for glycan treatment, e.g. on the basis of the presence or absence of particular taxa.

Modulation of *Bifidobacterium* and *Bacteroides* species is thought to play a role in controlling and treating tumors (see Example 6). As shown in Table 16 the therapeutic glycan glu50gal50 modulated growth of Parabacteroides in 85% of the healthy human subjects in this study and FOS modulated *Bifidobacterium* in 57% of subjects.

TABLE 16

Genus that respond to glycan treatments in humans. Percentages represent the approximate number of individuals in which the indicated genera responded to the treatment.

| Genus | FOS | glu50gal50 |
|---|---|---|
| *Bifidobacterium* | 57% (100%) | |
| *Parabacteroides* | | 85% (100%) |

These data suggest that the abundance of specific taxa, including taxa potentially involved in anti-cancer responses can be modulated in human subjects by administering glycans.

Example 11: Effect of Glycans on Gene Expression in a Mouse Model

In a study two groups of mice are used. The control group of mice are fed with standard chow, and the different treatment groups of mice are fed with standard chow supplemented with glycans. After 1-30 days, blood samples are drawn from the mice, the mice are sacrificed, and tissues from the intestine, liver, skin, and other sites of interest are collected and stored at −80° C. RNA is isolated from the tissues and converted to cDNA. The GeneChip Mouse Genome 430 2.0 Array (Affymetrix) is used to analyze the differential expression between the untreated and glycan-treated animals of approximately 14,000 murine genes. The experimental protocol and raw data analysis are performed according to the manufacturer's instructions and standard protocols. The biological function of the differentially expressed genes and their involvement in various processes are obtained from the following databases: RefGene (Reference for genes, proteins and antibodies: refgene.com/), CTD (Comparative Toxicogenomics Database: ctd.mdibl.org/), MGI (Mouse Genomics Informatics: www.informatics.jax.org/), KEGG (Kyoto Encyclopedia of Genes and Genomes: www.genome.jp/kegg/genes.html). This procedure is used to identify the differential expression of genes encoding inflammatory cytokines, immunomodulatory cytokines, antimicrobial peptides, and other relevant effector molecules.

Example 12: Effect of Glycans on the Intestinal Microbiota of Naïve Mice

This study was carried out to assess the effect of glycan therapeutics on the gut microbiota of naïve mice. In this model, normal mice are administered glycans in their drinking water over a period of 6 days with fecal samples taken from each mouse for 16S rRNA analysis.

Mice, C57Bl/6 (B6N Tac), mouse pathogen free (MPF; Taconic Biosciences, Germantown, N.Y.) aged 8-10 weeks were housed singly in cages, with 6 animals per dose group. Animals were fed PicoLab Rodent Diet 20 ("5053"; Lab-Diet, St. Louis, Mo.) or zero fiber diet ("ZFD"; Modified rodent diet AIN-93G: D15091701, Research Diets, New Brunswick, N.J.) ad libitum throughout the course of the study and had free access to water. Mice were maintained on a 12 h light/dark cycle. Mice were acclimated for 7 days (days −7 to −1) prior to glycan administration.

Glycans were administered to the mice by inclusion in their drinking water at 1% weight/volume (w/v) from day 0 through day 5. Control mice received water containing no glycan. Fresh fecal collections were performed for each mouse from days −2 to 5. Mouse weights were monitored on days −1, 1, 3 and 4. Body weights of the mice did not change significantly throughout the course of the study.

Genomic DNA was extracted from the fecal samples and variable region 4 of the 16S rRNA gene was amplified and sequenced (Earth Microbiome Project protocol www.earth-microbiome.org/emp-standard-protocol/16s/ and Caporaso J G et al. 2012. Ultra-high-throughput microbial community analysis on the Illumina HiSeq and MiSeq platforms. ISME J.). Operational Taxonomic Units (OTUs) were generated by aligning 16S rRNA sequences at 97% identity. Microbial communities were compared to each other using UniFrac distance metric (Lozupone C. et al., Appl. Environ. Microbiol. December 2005 vol. 71 no. 12 8228-8235).

Figure 10:
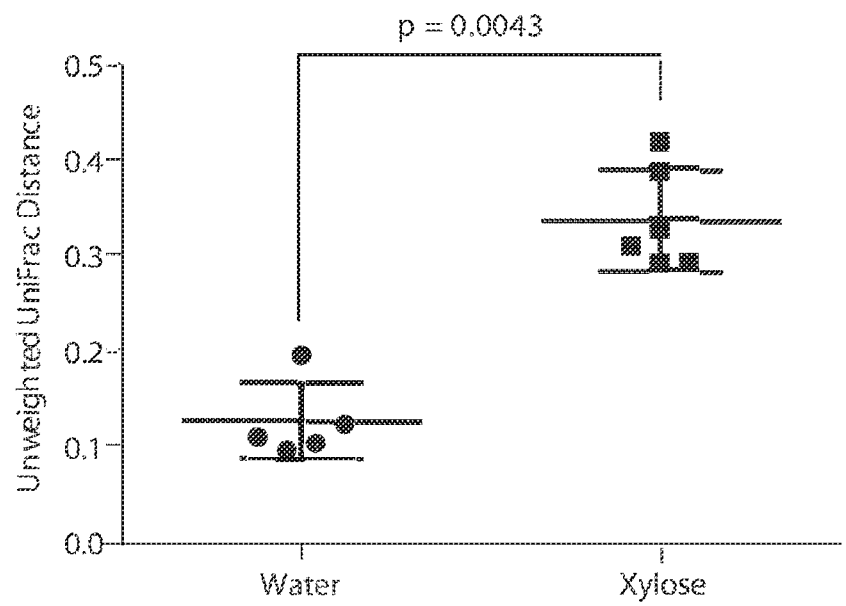
FIG. 10. Distances were calculated for each mouse between microbiota sampled at 1 day before and 5 days after glycan or water administrated. The larger the distance, the bigger change in microbial composition is observed.
Figure 11:
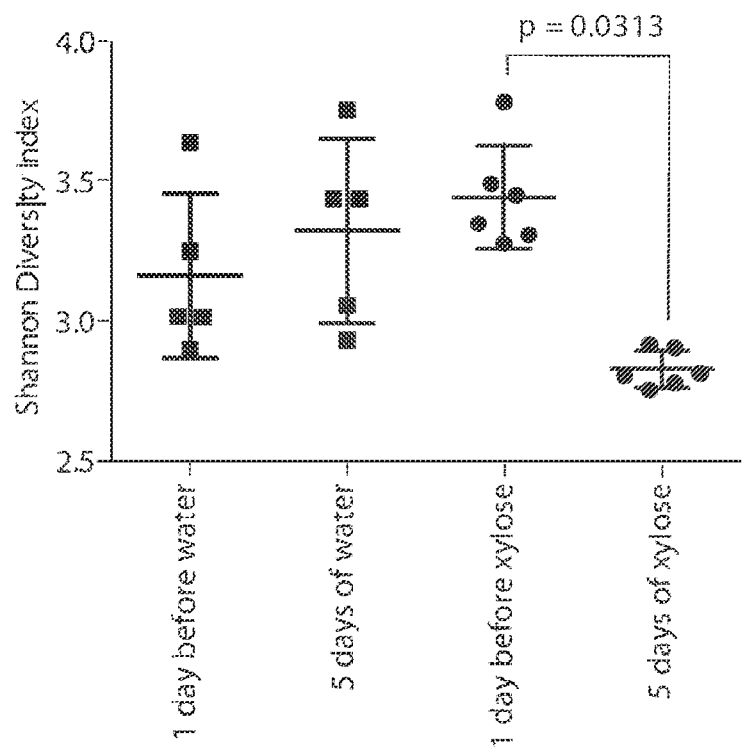
FIG. 11. Shannon diversity index. Paired Wilcoxon test was used to calculate the significance of observed differences.

Significant changes were observed when mice were administered a xyl 100 preparation. UniFrac distances between microbiota sampled at one day before and 5 days after glycan administration were significantly larger in mice treated with xylose compared to mice who did not receive any glycan (p=0.0043, Mann-Whitney test, FIG. 10). Alpha diversity was measured by calculated Shannon Index in microbiota before and after glycan or water administration. Shannon index significantly decreased after 5 days of xylose administration (p=0.0313, Wilcoxon paired test, FIG. 11).

Figure 12A:
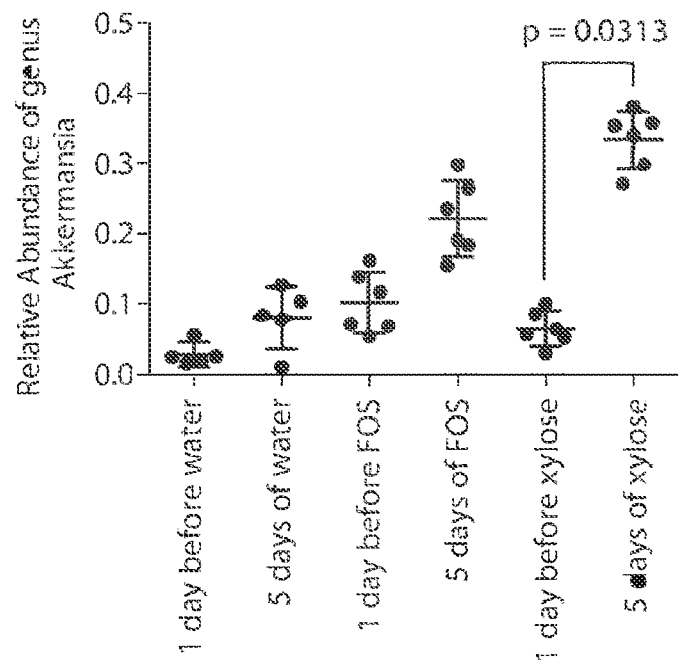
FIGS. 12A-12B. Relative abundance of sequences assigned to genus *Akkermansia*, phylum Verrucomicrobia is shown in FIG. 12A Relative abundance of sequences assigned to genus Blautia, phylum Firmicutes is shown in FIG. 12B.
Figure 12B:
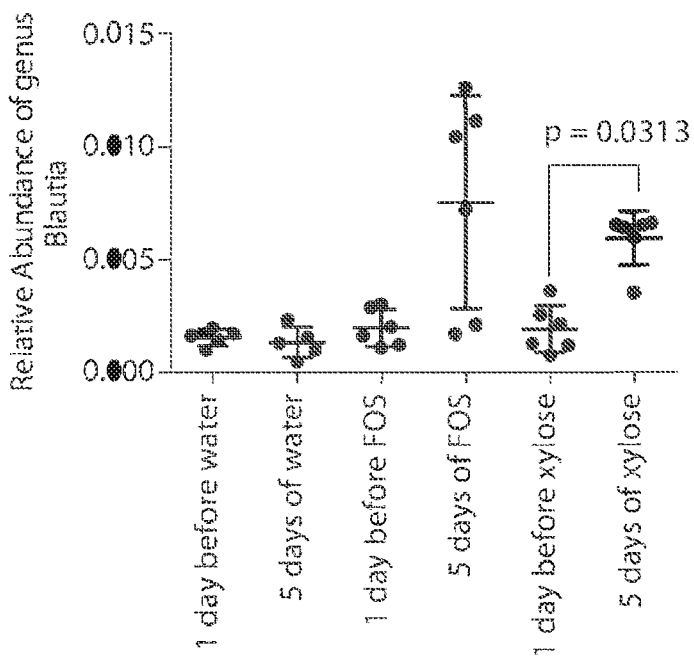

The changes in observed shifts with administration of xylose were attributed to an increase in relative abundance of sequences assigned to genus *Akkermansia* (phylum Verrucomicrobia, p=0.0313, Wilcoxon paired test, FIG. 12a), and genus *Blautia* (phylum Firmicutes, family Lachnospiraceae, p=0.0313, Wilcoxon paired test, FIG. 12b).

The most prominent *Akkermansia* species in the mammalian gut is *Akkermansia muciniphila*. Its preferred energy source is host intestinal mucin. Consumption of a low fiber diet and high intake of simple sugars and fat results in decreased mucus production (British Journal of Nutrition/Volume 102/Issue 01/July 2009, pp 117-125, Quantitative Imaging of Gut Microbiota Spatial Organization, Earle K A et al, Cell Host Microbe. 2015 Oct. 14; 18(4):478-88). Thinning of intestinal mucus may result in increased gut permeability and translocation of microorganisms or their components, such as lipopolysaccharide (LPS), which induce inflammation. LPS levels are increased upon consumption of high fat diet in rodents which then develop metabolic syndrome (Metabolic endotoxemia initiates obesity and insulin resistance, Cani P D et al, Diabetes. 2007 July; 56(7):1761-72).

Bacteroidetes, may induce the growth of *Akkermansia*. For example, colonization of germ free mice with *Bacteroides* thetaiotaomicron induces mucus production by intestinal goblet cells (Wrzosek et al. BMC Biology 2013 11:). This may create a favorable environment for *Akkermansia* growth. Consumption of mucus by *Akkermansia* may stimulate increased mucus production and play a role in the restoration of the gut barrier that prevents leaking of microbial endotoxin LPS. Decreased endotoxemia reduces inflammation Inflammation precedes most cancers. Bronchitis, colitis, cervicitis, gastritis, and hepatitis, for example, reflect inflammation of the bronchus, colon, cervix, stomach, and liver, respectively. Many cancers, especially solid tumors, appear to be preceded by inflammation of a given organ. For instance, people who smoke cigarette develop bronchitis, and 15% to 20% of these people develop lung cancer (Wingo et al. Annual report to the nation on the status of cancer, 1973-1996, with a special section on lung cancer and tobacco smoking. J Natl Cancer Inst 1999; 91:675-90). Similarly, people who have colitis are at high risk of developing colon cancer (Itzkowitz, Inflammation and cancer IV. Colorectal cancer in inflammatory bowel disease: the role of inflammation. Am J Physiol Gastrointest Liver Physiol 2004; 287:G7-1734). Infection with *Helicobacter pylori* can induce gastritis, which in its chronic form can lead to gastric cancer (Peter, *Helicobacter pylori* and gastric cancer: the causal relationship. Digestion 2007; 75:25-35).

*Akkermansia muciniphila* metabolites include the SCFA propionate which is also thought to modulate inflammation (see, Example 15). Glycan therapeutics when administered in an effective amount may modulate bacterial species, such as, e.g., *Akkermansia* that play a role in the reduction of inflammation.

Example 13: Effect of Glycans on the Colonic Epithelium of Mice Challenged with an Inflammatory Agent This study was carried out to assess the effect of glycan therapeutics on the host gene expression in the large intestine. Glycan treatment may alter inflammatory pathways in the gastrointestinal tract and decrease inflammation in the gastrointestinal tract, which may prevent the development of cancer.

In this model, normal mice were administered glycans (non-fermentable Acacia fiber, Glu100 or Man52glu29gal19) in their drinking water over a period of 21 days. On days 8-13 all mice were treated with 2.5% Dextran sulfate sodium (DSS) to induce intestinal inflammation. Dextran sulfate sodium is a chemical that drives inflammation in the intestine of animals. On day 21 mice were sacrificed by $CO_2$ asphyxiation. Two 3-5 mm adjacent sections of flushed colon were placed in 2 separate freezer vials and snap frozen. Messenger RNA was extracted and sequenced on Illumina HiSeq sequencer.

Animals treated with non-fermentable Acacia fiber, lost significantly more weight and had higher endoscopy score than those who received either Glu100 or Man52glu29gal19 ($p<0.05$, Kruskal-Wallis test with Dunn's multiple comparisons), suggesting that the glycans reduced inflammation in the animals.

Sequences from each animal were mapped to mouse genome and number of sequences mapped to each gene were quantified using htseq-count software (HTSeq—a Python framework to work with high-throughput sequencing data. Anders S, Pyl PT, Huber W. Bioinformatics. 2015 Jan. 15; 31(2):166-9. doi: 10.1093/bioinformatics/btu638. Epub 2014 Sep. 25). Genes differentially expressed between groups were determined using DeSeq2 package in R (Michael I Love, Wolfgang Huber, Simon Anders: Moderated estimation of fold change and dispersion for RNA-seq data with DESeq2. Genome Biology 2014, 15:550).

There were 182 genes differentially expressed (p value adjusted for multiple comparison <0.05) between animals treated with Glu100 and control animals who did not receive any treatment. Of those, 92 genes were also differentially expressed between animals treated with Man52glu29gal19 compared to control animals. The latter comparison revealed additional 531 genes that were significantly different in their expression between 2 groups. A majority of genes that were down-regulated in mouse host treated with glycans are involved in inflammatory responses: complement pathway, apoptosis, antigen presentation, oxidative stress, cell adhesion and cytoskeleton remodeling. The data suggest that altered genetic regulation in response to glycan treatment decreased the inflammation which can be a requisite for the development of cancer.

Genes that were upregulated in mice treated with glycans were involved in Notch signaling and Wnt signaling pathways, which control cell proliferation, migration and tissue regeneration. This could be a sign of more active epithelial regeneration induced by functional shifts of the microbiota as a result of the glycan treatment.

Example 14: In Vitro Co-Culture Models to Test the Effect of Glycans on Host Responses to Bacterial Communities at Intestinal Sites Bacteria can elicit both pro- and anti-inflammatory responses from host (mammalian) cells, and different bacterial species can elicit different host responses. The immune system and pro- and anti-inflammatory responses are linked to diseases, disorders or pathological conditions related to, e.g., immune imbalances, nutritional imbalances which can lead to and may be associated with cancers. Preparations of glycans are used to alter the bacterial population to elicit a desired host response. An in vitro co-culture model is used to measure the host responses elicited by bacterial populations grown in the presence of glycans. Glycans that promote bacterial populations that elicit beneficial host responses or minimize detrimental host responses are selected using this assay.

Epithelial cell lines or tissues from the intestine are used in a co-culture model (Haller D, Bode C, Hammes W P, Pfeifer A M A, Schiffrin E J, Blum S, 2000. Non-pathogenic bacteria elicit a differential cytokine response by intestinal epithelial cell/leucocyte co-cultures. Gut. 47:79-97) (Borruel et al., 2003. Effects of nonpathogenic bacteria on cytokine secretion by human intestinal mucosa. Am J Gastroenterology. 98:865-870). Human enterocyte-like CaCO-2 cells are seeded at a density of $2.5 \times 10^5$ cells/ml on 25 mm cell culture inserts (0.4 µm nucleopore size; Becton Dickinson). The inserts are placed into 6-well tissue culture plates (Nunc) and cultured 18-22 days at 37° C./10% $CO_2$ in DMEM (glutamine, high glucose; Amimed) supplemented with 20% heat-inactivated fetal calf serum (56° C., 30 minutes; Amimed), 1% MEM non-essential amino acids (Gibco BRL), 10 µg/ml gentamycin (Gibco BRL), and 0.1% penicillin/streptomycin (10 000 IU/ml/10 000 UG/ml; Gibco BRL). The cell culture medium is changed every second day until the cells are fully differentiated. Alternatively, a 3D reconstructed tissue model produced from normal, human cell-derived small intestine epithelial and endothelial cells and fibrobasts (EpiIntestinal model; MatTek Corporation, Ashland, Mass.) is used. Transepithelial electrical resistance (TEER) is determined using a MultiCell-ERS voltmeter/ohmmeter. Tissue culture inserts are washed twice with prewarmed antibiotic-free medium prior to challenge with bacterial cultures. Separately, bacterial cultures are grown in the presence of preparations of glycan. After 16-24 hours of growth in the presence of glycans, the bacterial suspensions are prepared in antibiotic-free medium and $10^6$-$10^8$ CFU are added to confluent cell or tissue cultures. The co-cultures are incubated at 37° C. for 4-24 hours.

At the conclusion of the co-incubation period, the supernatant is collected and analyzed for inflammatory and immunomodulatory cytokines including IL-1α, IL-1β, TNF, IL-8, RANTES, IL-10, TGF-β, IFN-γ, IL-4, IL-6, IL-12, IL-17, and IL-23. This analysis is performed by enzyme linked immunosorbent assay (ELISA) or other comparable quantification technique (e.g., Luminex Assay; Life Technologies, Carlsbad, Calif.) following standard protocols. To analyze a broader range of responses, gene expression (e.g., by microarray) or transcriptomic (e.g., by RNA-Seq) analysis is performed by lysing the cells, purifying RNA, and following standard protocols. This procedure is used to analyze the expression of genes encoding inflammatory cytokines, immunomodulatory cytokines, antimicrobial peptides, and other relevant host responses.

Figure 13:
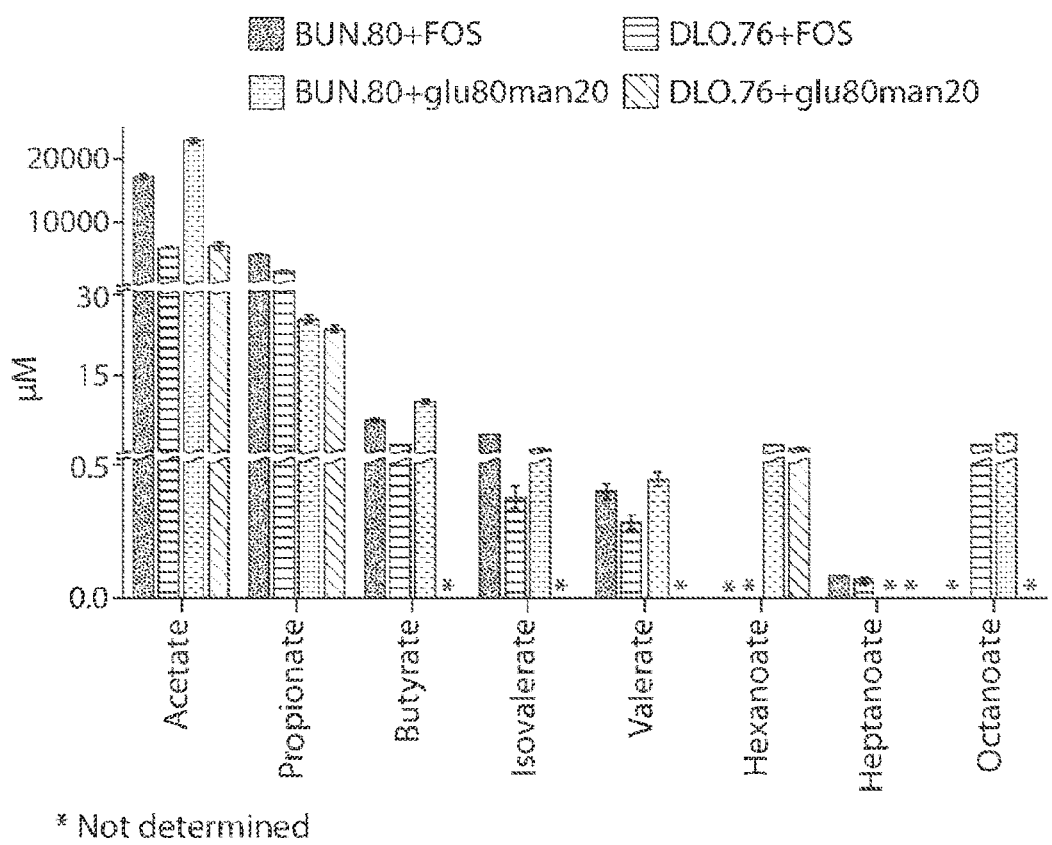
FIG. 13. SCFA concentrations in supernatants of BUN.80 and DLO.76 grown with either FOS or glycan glu80man20

Example 15: Effect of Glycans on Microbial SCFA Metabolite Production In Vitro An in vitro assay was performed to assess the production of short chain fatty acids by gut commensal bacteria cultured with the glycan glu80man20 or commercially available FOS as a carbon source. Strains were handled under strictly anaerobic conditions in an AS-580 anaerobic chamber (Anaerobe Systems) using pre-reduced reagents and materials. The Bacteroidete *Bacteroides uniformis* (ATCC 8492) "BUN.80" was tested in 100 mM potassium phosphate buffer (pH 7.2), 15 mM sodium chloride, 8.5 mM ammonium sulfate, 4 mM L-cysteine, 1.9 µM hematin, 200 µM L-histidine, 100 µM magnesium chloride, 1.4 µM iron sulfate heptahydrate, 50 µM calcium chloride, 1 µg/mL vitamin K3 and 5 ng/mL vitamin B12 (Martens E C et al. Cell Host & Microbe 2008; 4, 447-457). The Lachnospiracea *Dorea longicatena* (DSM 13814) "DLO.76" was tested in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114), supplemented with 10% (v/v) Chopped Meat Glucose broth (Anaerobe Systems). Bacteria were exposed to either glycan glu80man20 or FOS at 0.5% (w/v) final and incubated at 37° C. for 39-50 hours. Following incubation, cells were pelleted from 1.5 mL aliquots of cultures in duplicate by centrifugation at 18,000×g for five minutes, the supernatant was sterilized through a 0.22 um polyethersulfone filter, and the supernatant was stored at −80° C. or on dry ice until it was analyzed. Short chain fatty acid (SCFA) analysis was performed on the filtered culture supernatants using a cold extraction of short chain fatty acids, measured by EI-CGMS without derivatization. FIG. 13 summarizes the results obtained. In the assay, cultures of Bacteroidete BUN.80 and Lachnospiracea DLO.76 grown with either glycan glu80man20 or FOS produced supernatants with total SCFA concentrations in excess of 5,000 µM. Acetate was the SCFA produced in the highest concentrations in the assay, and propionate was produced at the second-highest levels. Butyrate, isovalerate, valerate, hexanoate and octanoate were also detected in the assay.

Example 16: Effect of Glycans on Microbial SCFA Metabolite Production In Vivo

Figure 14:
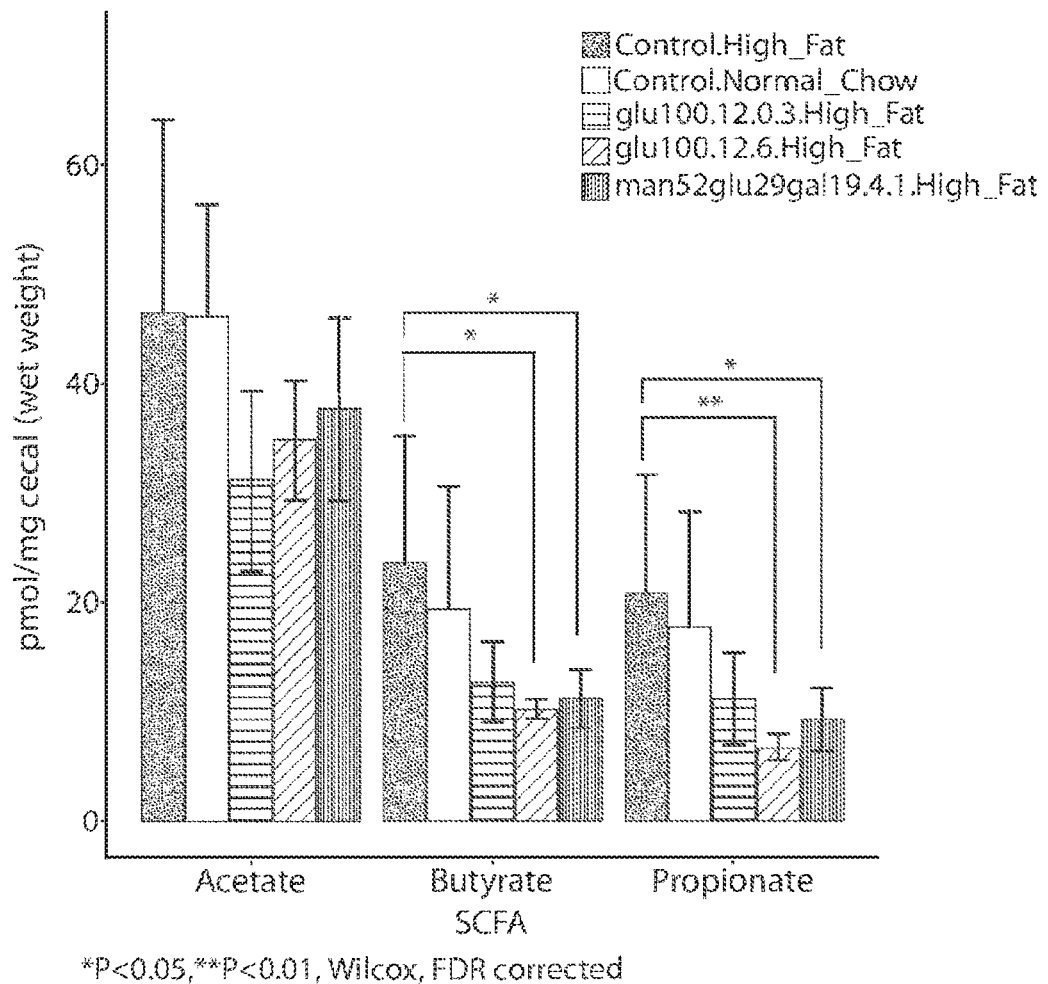
FIG. 14. Most abundant SCFA in the cecal contents of mice fed either a normal mouse chow, high fat diet, or high fat diet+glycans. (*$P<0.05$,**$P<0.01$, Wilcox, FDR corrected).

To assess the production of short chain fatty acids by gut commensal bacteria upon glycan administration in vivo, short chain fatty acid analysis was performed on 30-50 mg of cecal contents from mice fed either a High Fat diet (Research Diets D12492), Normal Mouse chow (Research Diets D12450), or High Fat diet+glycan using a GC-based method. High fat diets are associated with pro-inflammatory states and the development of colonic cancers. Treatment with glycans (glu100 at 6% or man52glu29gal19 at 1%) reduced the abundance of both butyrate and propionate in the cecal contents of mice compared to high fat diet alone (FIG. 14). As shown in Table 17, glycans reduced the levels of certain SCFAs in this study.

TABLE 17

Glycans reduce SCFAs.

|  | glu100 | man52glu29gal19 |
|---|---|---|
| Acetate |  |  |
| Propionate | − | − |
| Butyrate | − | − |
| Isovalerate | − | − |

TABLE 17-continued

Glycans reduce SCFAs.

|  | glu100 | man52glu29gal19 |
|---|---|---|
| Valerate | − | − |
| Hexanoate | − | − |
| Heptanoate | − | − |
| Octanoate | − | − |

(− indiciates $P < 0.05$, Wilcox, FDR corrected)

The decrease in short chain fatty acids due to glycan treatment (FIG. 14 and Table 17) may increase the propensity of T cells that differentiate in the gastrointestinal tract to become inflammatory T cells (e.g. Th17) that can traffic to tumor sites and drive inflammatory responses against the tumor. SCFAs constitute an important energy source for colonocytes and also function as signaling molecules, modulating intestinal inflammation, and metabolism. SCFAs, in particular acetate, propionate, and butyrate, favor histone H3K27 acetylation and increased expression of the Treg-specific transcription factor gene, Foxp3, thereby boosting Treg development in the gastrointestinal tract (Furusawa et al., 2013. Commensal microbe-derived butyrate induces the differentiation of colonic regulatory T cells. Nature 504, 446-450). These Tregs are absent in germfree mice that lack both commensal bacteria and their metabolites, such as the short-chain fatty acid (SCFA) butyrate, and are necessary for their development (Arpaia et al., 2013 Metabolites produced by commensal bacteria promote peripheral regulatory T-cell generation. Nature 504, 451-455; Atarashi et al., 2011 Induction of colonic regulatory T cells by indigenous *Clostridium* species. Science 331, 337-341; Furusawa et al., 2013). The modulation of T cell function by the microbiota, through SCFAs, toward tolerance (IL-10 secretion) rather than inflammation (IL-17 secretion) has also been proposed for IL-10/IL-17 double-secreting T cells. Thus, T cells can switch from a tolerance to inflammatory phenotype and vice versa based on the presence or absence of SCFAs (Ruff and Kriegel, 2015, Autoimmune host-microbiota interaction at barrier sites and beyond. Trends Mol. Med. 21, 233-244), and the decrease of SCFAs driven by glycans likely leads to an increase in inflammatory T cells. It is also well-appreciated in the art that Th17 cells primed in the intestine could traffic to peripheral sites, undergo functional plasticity, and mediate inflammation: A number of mouse models of chronic inflammation residing in distant, non-mucosal tissues, where an impact of the gut microbiota was demonstrated, outlined the pro-inflammatory role of intestinal Th17 cells (Lee et al., 2011, Proinflammatory T-cell responses to gut microbiota promote experimental autoimmune encephalomyelitis. Proc. Natl. Acad. Sci. USA 108 (Suppl 1), 4615-4622; Wu et al., 2010, Gut-residing segmented filamentous bacteria drive autoimmune arthritis via T helper 17 cells. Immunity 32, 815-827; Yang et al., 2014, Focused specificity of intestinal TH17 cells towards commensal bacterial antigens. Nature 510, 152-156). It has been shown in the art that an increase in inflammatory T cells or increase in activity of inflammatory T cells in a tumor can drive improved control over cancer (Sharma and Alison, 2015, Immune checkpoint targeting in cancer therapy: toward combination strategies with curative potential. Cell 161, 205-214).). The decreased generation of tolerogenic T cells may also lead to an activation of inflammatory functions against pathogens or infections resulting from decreased inflammatory immune function. Both pro- and anti-inflammatory responses are linked to diseases, disorders or pathological conditions related to, e.g., immune imbalances, nutritional imbalances and cancers.

Example 17: Effect of Glycans on Total Microbial Metabolite Production In Vivo

Figure 15:
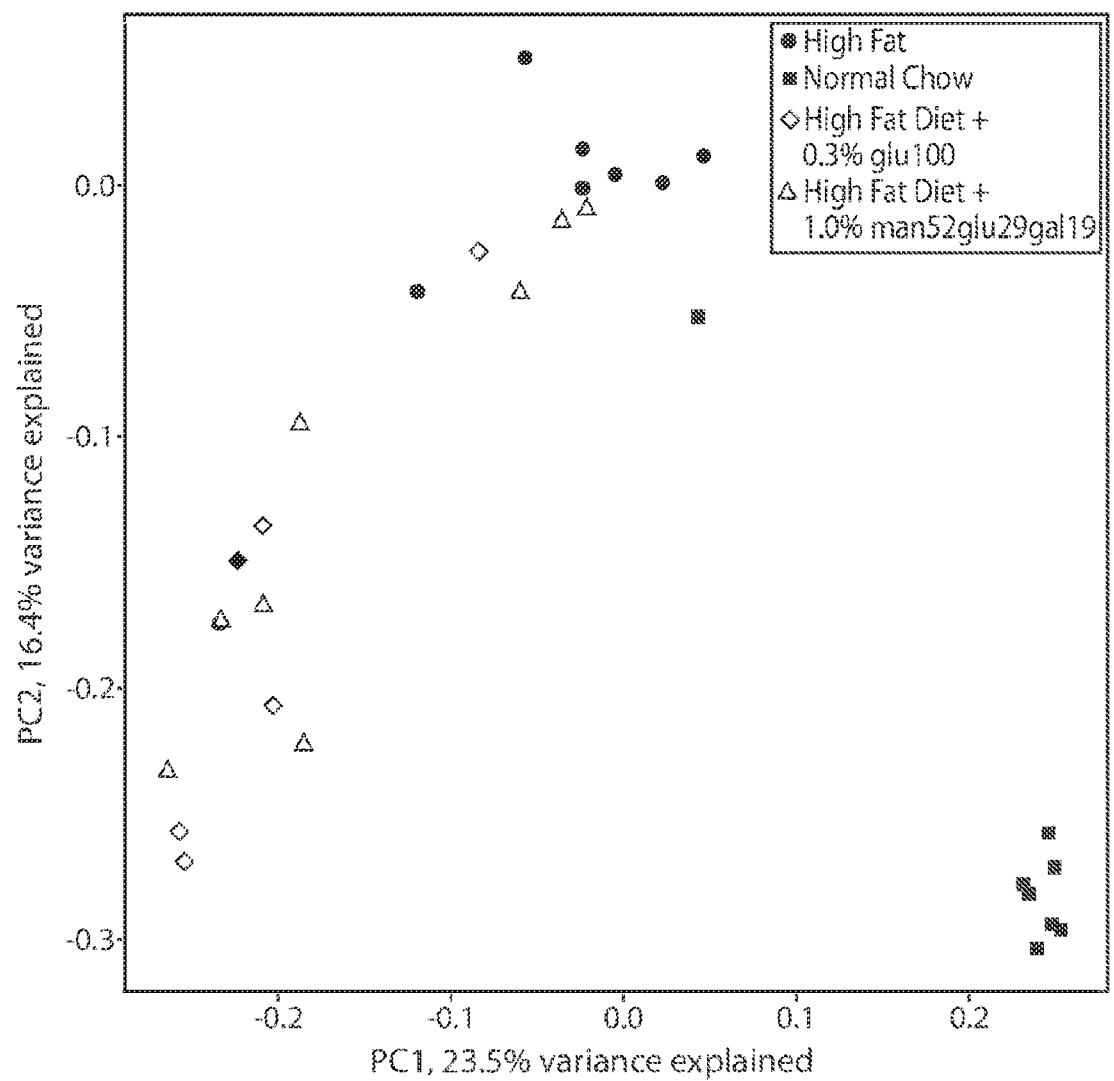
FIG. 15. PCoA of metabolomic profile.

Untargeted metabolomics was performed on 30-50 mg of cecal contents from mice fed either a High Fat diet (Research Diets D12492), Normal Mouse chow (Research Diets D12450), or High Fat diet+glycan using Metabolon's LC-MS based DiscoveryHD4 platform. A total of 538 metabolites were identified and 149 were differentially abundant in High Fat vs. Normal Chow, 26 with treatment with glu100 0.3%, and 36 with treatment with man52glu29gal19 1% (Tables 18 and 19). Treatment with glycans significantly shifted the composition of the mouse cecal metabolome ($P<0.01$, adonis, FIG. 15).

TABLE 18

Total differentially abundant metabolites between diets and with glycan treatments.

| | High Fat vs. Normal Chow | High Fat vs. High Fat + glu100 0.3% | High Fat vs. High Fat + man52glu29gal19 1% |
|---|---|---|---|
| Number of metabolites significantly different ($p < 0.05$) | 149 | 26 | 36 |
| INCREASE | 81 | 19 | 19 |
| DECREASE | 68 | 7 | 17 |

$P < 0.05$, Welch's T-test.

TABLE 19

Differentially abundance metabolites between High Fat diet control vs. High Fat diet with the addition of glycan treatment.

| SUPER PATHWAY | SUB PATHWAY | BIOCHEMICAL |
|---|---|---|
| Amino Acid | Alanine and Aspartate Metabolism | N-acetylasparagine |
| | | N-acetylaspartate.(NAA) |
| | Creatine Metabolism | guanidinoacetate |
| | Glutamate Metabolism | N-acetylglutamine |
| | Methionine, Cysteine, SAM and Taurine Metabolism | cysteine |
| | | cysteine.sulfinic.acid |
| | | N-acetylmethionine.sulfoxide |
| | Phenylalanine and Tyrosine Metabolism | N-formylphenylalanine |
| | | phenol.sulfate |
| | Polyamine Metabolism | N1,N12-diacetylspermine |
| | Tryptophan Metabolism | indoleacetate |
| | | kynurenate |
| Carbohydrate | Aminosugar Metabolism | diacetylchitobiose |
| | Disaccharides and Oligosaccharides | sucrose |
| | Fructose, Mannose and Galactose Metabolism | galactonate |
| | | mannitol/sorbitol |
| | | mannose |
| | Glycolysis, Gluconeogenesis, and Pyruvate Metabolism | glucose |
| | Pentose Metabolism | xylose |
| Cofactors and Vitamins | Pantothenate and CoA Metabolism | pantethine |
| Lipid | Carnitine Metabolism | carnitine |
| | Fatty Acid Synthesis | malonate |
| | Fatty Acid, Dicarboxylate | octadecanedioate.(C18) |
| | Fatty Acid, Monohydroxy | 2-hydroxypalmitate |
| | Long Chain Fatty Acid | pentadecanoate.(15:0) |
| | Lysolipid | 1-oleoyl-GPG.(18:1)* |
| | | 1-palmitoyl-GPE.(16:0) |

TABLE 19-continued

Differentially abundance metabolites between High Fat diet control vs. High Fat diet with the addition of glycan treatment.

| SUPER PATHWAY | SUB PATHWAY | BIOCHEMICAL |
|---|---|---|
| | Primary Bile Acid Metabolism | cholate |
| | | tauro-beta-muricholate |
| | Secondary Bile Acid Metabolism | taurodeoxycholate |
| | | taurohyodeoxycholic.acid |
| | | taurolithocholate |
| | | tauroursodeoxycholate |
| | | ursodeoxycholate |
| | Sphingolipid Metabolism | 3-ketosphinganine |
| Nucleotide | Purine Metabolism, (Hypo)Xanthine/Inosine containing | inosine |
| | Purine Metabolism, Guanine containing | guanosine |
| | Pyrimidine Metabolism, Uracil containing | uridine |
| Peptide | Dipeptide | valylleucine |
| Unknown | Unknown | X.-.12101 |
| | | X.-.14254 |
| | | X.-.14302 |
| | | X.-.15806 |
| | | X.-.15843 |
| | | X.-.17438 |
| | | X.-.17852 |
| | | X.-.21365 |
| | | X.-.21788 |
| | | X.-.22035 |
| | | X.-.22062 |
| | | X.-.24664 |
| | | X.-.24670 |
| | | X.-.24721 |
| | | X.-.24831 |
| Xenobiotics | Food Component/Plant | enterolactone |
| | | stachydrine |

$P < 0.05$, Welch's T-test.

The data suggest that glycan treatment modulates the total metabolite output of the GI tract microbiota in the animal including SCFAs (see Example 16) and bile acids (see Example 18). Metabolic changes and potential links to the immune system and inflammatory responses are thought to play a role in diseases, disorders or pathological conditions related to, e.g., immune imbalances, nutritional imbalances and cancers.

Example 18: Effect of Glycans on Bile Acid Production In Vivo

The production of certain bile acids, such as deoxycholic acid (DOC) and Lithocholic acid (LCA) which are associated with a high fat diet have been linked to cancer development. Deoxycholic acid (DOC) is secondary bile acid produced solely by the 7a-dehydroxylation of primary bile acids carried out by anaerobic gut bacteria from the genus *Clostridium*. DOC can be considered as a microbial co-carcinogen that not only contributes to colon carcinogenesis, but that also participates to the development of liver cancer, presumably by inducing the senescence-associated secretory phenotype of hepatic stellate cells, thereby stimulating pro-inflammatory and tumor-promoting reactions in a mouse model of obesity-associated hepatocellular carcinoma (Yoshimoto et al., 2013, Obesity-induced gut microbial metabolite promotes liver cancer through senescence secretome. Nature 499, 97-101). DOC may well cooperate with other bacterial products, including LPS, in promoting hepatocellular carcinoma (Dapito et al., 2012, Promotion of hepatocellular carcinoma by the intestinal microbiota and TLR4. Cancer Cell 21, 504-516). Numerous other studies have shown that DOC induces apoptosis in colon cells in short-term cultures.

Figure 16:
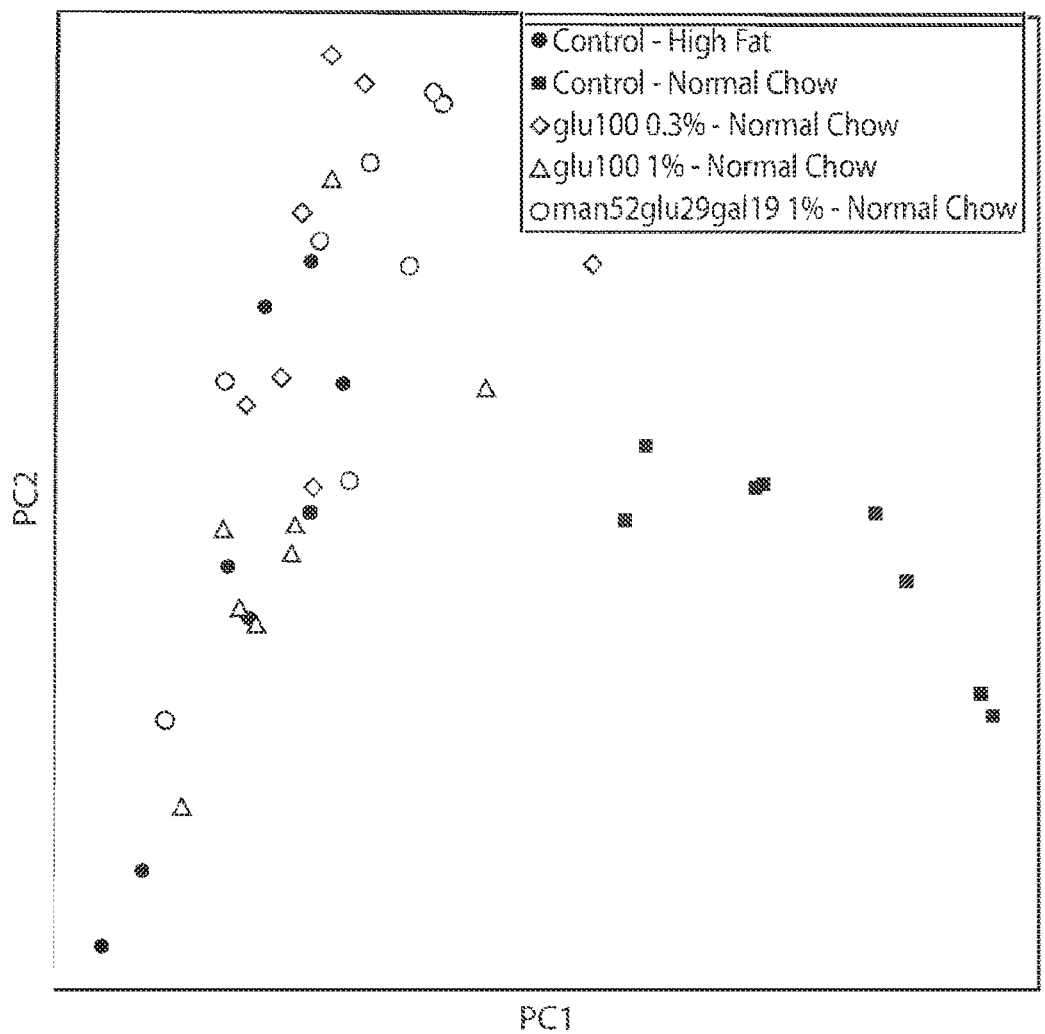
FIG. 16. PCoA of bile acid composition of mouse cecal contents on Normal Chow and High Fat Diet+/−glycan treatment.

Bile acid analysis was performed on 30-50 mg of cecal contents from mice fed either a High Fat diet (Research Diets D12492), Normal Mouse chow (Research Diets D12450), or High Fat diet+glycan using Biocrates LC-MS based Bile Acid Kit. Glycan treatment significantly altered the bile acid composition of the mouse cecum (FIG. 16, Table 20), while total bile acid pool size did not change.

TABLE 20

Bile acid species that are significantly different with glycan treatment

| Bile Acid | Type |
|---|---|
| Glycodeoxycholic acid | Secondary |
| Glycolithocholic acid | Secondary |
| Alpha-Muricholic acid | Primary |
| Beta-Muricholic acid | Primary |
| Taurocholic acid | Primary |
| Taurochenodeoxycholic acid | Primary |

(P < 0.05, Wilcoxon Rank Sum with FDR correction for multiple hypotheses)

Figure 17:
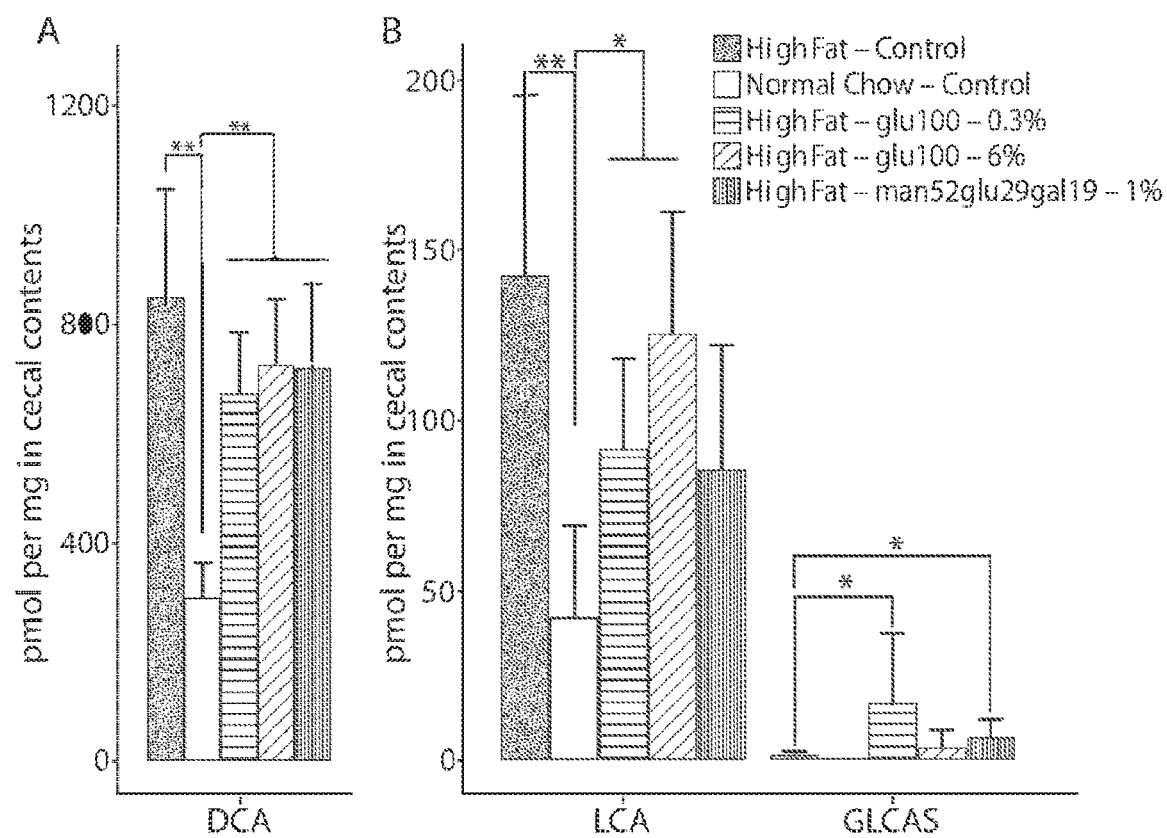
FIG. 17. Glycan treatment resulting in a reduction of (A) DCA (deoxycholic acid) and (B) LCA (lithocholic acid) compared to high fat control.

As shown in FIG. 17, glycan treatment resulted in a reduction of (A) DCA (deoxycholic acid) and (B) LCA (lithocholic acid) compared to high fat control. The reduction in bile acids resulting from glycan treatment may prevent the development of cancer.

Many undiscovered links between other bile acids and the development of cancer may exist. For example, the concentration of Glycodeoxycholic acid, Glycolithocholic acid, Alpha-Muricholic acid, Beta-Muricholic acid, Taurocholic acid, and Taurochenodeoxycholic acid, which are all significantly altered by glycan treatment (Table 20) may affect cancer development. Furthermore, population-based studies have shown that subjects who consume high-fat and high-beef foods display elevated levels of fecal secondary BAs, mostly DOC and LCA, as do patients diagnosed with colonic carcinomas. Glycan treatment may modulate the bile acids present in the gastrointestinal tract of subjects consuming a high fat diet to prevent cancer development. Furthermore, the decrease in inflammation resulting from alterations of bile acids may systemically decrease inflammatory cell numbers across the body and thereby may influence diseases that are related to aberrant immune inflammatory activation, e.g., auto-immune diseases and other diseases related to immune imbalances and nutritional imbalances.

Example 19: Effect of Glycans on Chemotherapy-Induced Toxicity and Immune Responses In Vivo This study was conducted to elucidate the effects of glycan therapeutics on chemotherapy-induced toxicity in a modified rat model (Fukudome et al., Diamine oxidase as a marker of intestinal mucosal injury and the effect of soluble dietary fiber on gastrointestinal tract toxicity after intravenous 5-fluorouracil treatment in rats, Med Mol Morphol. 2014 June; 47(2):100-7). Off-target toxicity of chemotherapeutics including diarrhea, oral and gastrointestinal mucositis, and leukopenia and neutropenia, can limit dose and frequency of treatment, and can cause significant suffering and decreased quality of life in affected patients. In these studies, normal rats were treated with glycans and the chemotherapeutic drug 5-fluorouracil (5-FU), then monitored for manifestations of toxicity including weight loss, diarrhea, and hematological effects.

In this study, 75 male Sprague-Dawley rats (Charles River Laboratories) were randomized into five groups of fifteen animals each, and each animal was individually housed. The rats were allowed to acclimate for four days following arrival, and starting on Day −7, animals in four glycan-treated groups began treatment with novel glycan compositions (glu100, glu50/gal50, glu33/gal33/fuc33, or man100) at 2.5% wt/wt ad libitum in drinking water; treatment with glycans continued through Day 9. During this same period, animals in the control group received plain water. Beginning on Day 0, all rats were dosed with 5-FU (100 mg/kg in 0.2 mL/100 g) via intraperitoneal injection once daily through Day 3. Daily, rats were weighed, monitored for survival, and assessed visually for the presence of diarrhea. Animals exhibiting weight loss greater than 30% were euthanized. Diarrhea severity was scored on a scale of 0-4 as follows: a score of 0 indicates a normal, well-formed pellet; a score of 1 indicates a loose stool that is soft but stays in shape; a score of 2 indicates a loose stool of abnormal form with excess moisture; a score of 3 indicates watery stool or diarrhea; and a score of 4 indicates bloody diarrhea. On Day 5, non-terminal blood samples were collected via retro-orbital bleed from 7-10 rats/group and a complete blood count was performed.

Figure 18:
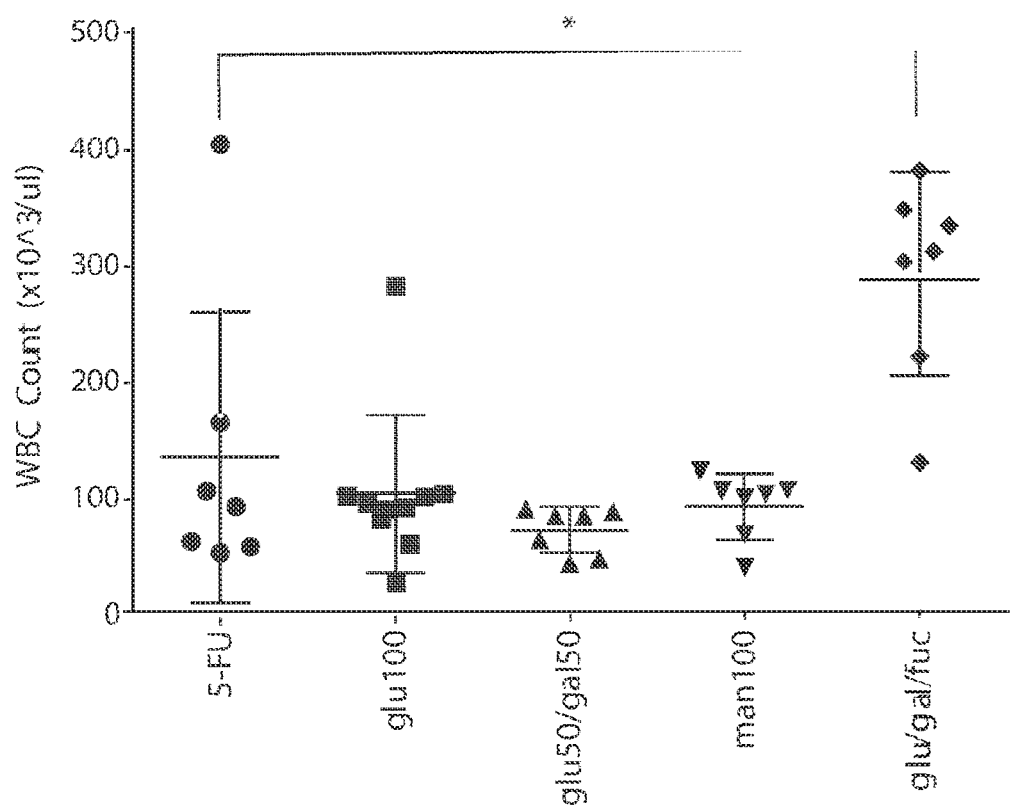
FIG. 18. White blood cell count on Day 5; bars represent mean and standard deviation. Significance was determined by using one-way ANOVA with Dunnett's multiple comparisons test. *$p<0.05$.

While there were no significant differences in body weight or diarrhea score between control and glycan-treated rats in this study, administration of glu/gal/fuc significantly increased white blood cell count on Day 5 ($p<0.05$) compared to 5-FU treatment alone (FIG. 18).

Treatment with 5-FU elicits a number of off-target toxicities, including neutropenia and leukopenia. In this study, treatment of rats with glu/gal/fuc increased the white blood cell count compared to 5-FU treatment alone. In an inflammatory response, white blood cells (leukocytes, neutrophils, macrophages, or monocytes) are recruited to the site of injury in response to damage, e.g. to the intestinal mucosa, caused by the 5-FU insult. A potential mechanism for the increase in WBCs by glu/gal/fuc may be through direct or indirect action upon the production of short chain fatty acids (SCFAs) via the gut microbiota. Bacterially-derived SCFAs have demonstrated both pro- and anti-inflammatory actions, depending upon the cell type affected; SCFAs may inhibit leukocyte function and migration, but may also increase accumulation of neutrophils (Vinolo et al., Regulation of inflammation by short chain fatty acids, Nutrients. 2011 October; 3(10)). While further analysis is required to determine the subpopulation(s) of white blood cells affected by glu/gal/fuc, the increase in WBCs seen with glu/gal/fuc may confer an increased ability to react to bacterial infiltration across the gut membrane and thus ameliorate some of the toxic effects of 5-FU treatment. In this way, glu/gal/fuc or similar glycans may decrease the presentation or severity of side effects and possibly prevent the need to decrease 5-FU dose or frequency. Several drug toxicities are also related to or associated with immune imbalances and nutritional imbalances apart from cancer.

Example 20: Effect of Glycans on Drug Toxicity and GI Tract Motility In Vivo

This study was conducted to analyze the effects of glycan therapeutics in a mouse model of opioid-induced constipation. In this model, normal mice are dosed with glycan or control for several days and then administered a dose of morphine sufficient to produce decreased gastrointestinal (GI) transit and colonic propulsion (Coates et al. 2006 Neurogastroenterol Motil 18:464-471). In humans, morphine and related opiate drugs are known to cause constipation. They act on neurons in the myenteric plexus as mu-opioid receptor agonists, leading to decreased GI motility and propulsion. The proportion of the US adult population who take opiates chronically (non-cancer patients), is roughly 4%. In an observational study of patients on opiates for chronic pain, 47% experienced constipation (Tuteja et al. 2015 Neurogastroenterol Motil 22: 424-430). There is evidence that chronic constipation can predispose individuals to benign GI neoplasms and colorectal cancer. The hypothesis for this is that increased transit times allow for greater exposure of the GI mucosa to carcinogenic agents such as some bile acids.

Approximately 30% of cancer patients undergoing treatment/surgery and 90% of advanced stage patients experience significant cancer pain and are most often treated with opioids (Levy M H, Samuel T A. 2005. Semin Oncol. 32:179-93), which in turn cause constipation in up to 90% of patients (Ahmedzai et al. 2015. Supp Care Cancer 23:823-830). Despite this side effect, opioids are the most efficacious analgesics in this setting. Dose limitation of opioids in cancer patients due to side-effects may result in a lack of adequate pain management.

Chemotherapeutic agents themselves can cause constipation. *Vinca* alkaloids, platinum agents, thalidomide and hormonal agents result in a high incidence of constipation (Gibson, Rachel J., and Dorothy M K Keefe. "Cancer chemotherapy-induced diarrhoea and constipation: mechanisms of damage and prevention strategies." Supportive Care in Cancer 14.9 (2006): 890-900).

Several drug toxicities affecting GI motility (e.g. causing constipation or diarrhea) in cancer are also related to or associated with other immune imbalances and nutritional imbalances. In this study, mice (male ICR; CD-1, 6-7 weeks old, 25-30 grams; Charles River Laboratories, Wilmington, Mass.) were individually housed. Mice were treated with either commercially-available fiber polydextrose (PDX; "Litesse", Dupont Danisco, Surrey, United Kingdom) or xylo-oligosaccharide (XOS; "Llife-Oligo XOS", Bio Nutrition, Inc., Island Park, N.Y.) or novel glycan compositions (xyl100, ara100, glu100); all administered at 1% ad libitum in drinking water for 11 days. A control group received plain drinking water. On day 12, all mice were administered morphine at a dose of 3 mg/kg subcutaneously to reduce colonic propulsion. One control group of mice were treated with naloxone, a mu-receptor inverse agonist 30 minutes prior to morphine administration. Naloxone is known to counteract the action of morphine at the mu-receptor. Colonic propulsion was assessed as follows: thirty minutes post morphine dosing, a 3 mm glass bead was inserted at a depth of 2 cm into the distal colon through each mouse's anus. Mice were observed for 30 minutes for expulsion of the bead, and the time in seconds to expulsion was noted. A cutoff of 30 minutes was used as a maximum time.

Figure 19:
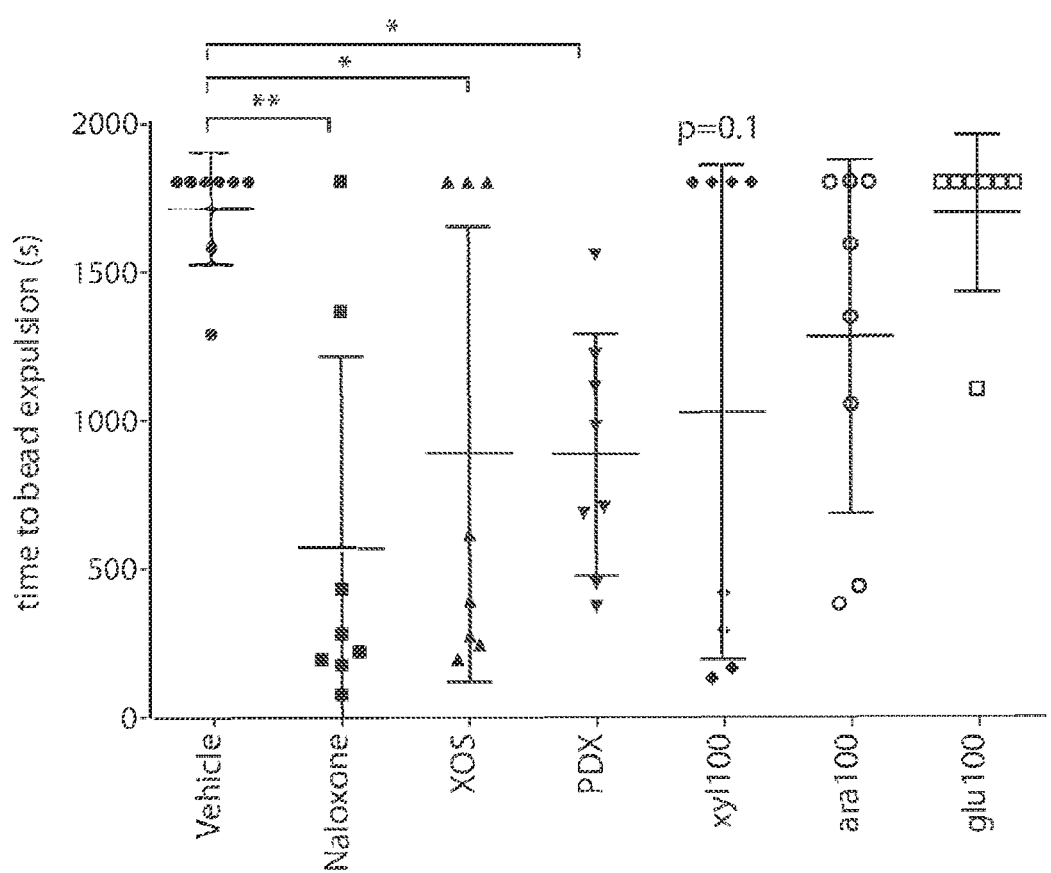
FIG. 19. Effect of commercial fibers and novel glycans on colonic propulsion in morphine-treated mice. Significance was determined by using one-way ANOVA with Dunnett's multiple comparisons test. *$p<0.05$, **$p<0.01$.

Administration of naloxone, XOS and PDX had significant effects on the time to bead expulsion, with overall latency decreased (FIG. 19). Xyl100-treated animals had an overall average decrease in expulsion time, but this did not reach significance. Naloxone, XOS and xyl100-treated groups, fell into two groups, those mice that responded and ones that responded significantly less to the treatments. This effect was seen less in the PDX-treated animals. Seventy-five percent of mice in the vehicle-treated group reached the maximal cutoff time. Ara100 and glu100 had a non-statistically significant effect on bead expulsion.

A second analysis was performed using a reduction in expulsion of >25% of maximum expulsion time as a cutoff to define a "responder" (1350 seconds)). Using this arbitrary cutoff, naloxone had 6/8 mice respond to treatment, PDX, 7 had responders, XOS had 5 responders, and xyl100 and ara100 had 4 responders each, and glu100 and vehicle had 1 responder.

Figure 20A:
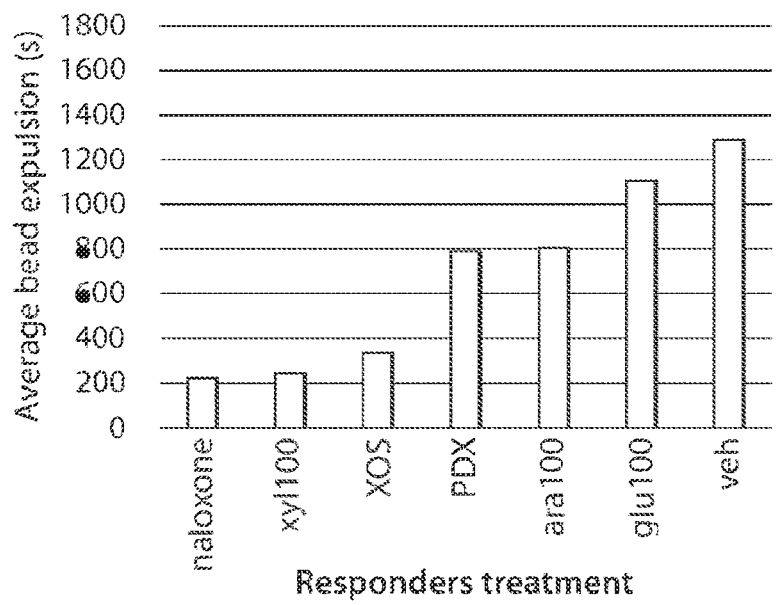
FIGS. 20A-20B. Colonic propulsion in treatment responder (FIG. 20A) and treatment non-responder (FIG. 20B) groups. Average time to bead expulsion, an indicator of colonic propulsion, was similar in animals that responded to naloxone, xyl100 and XOS Likewise, average time to bead expulsion in responders was similar in PDX and ara100. Time to bead expulsion was similar across all non-responder groups regardless of treatment.
Figure 20B:
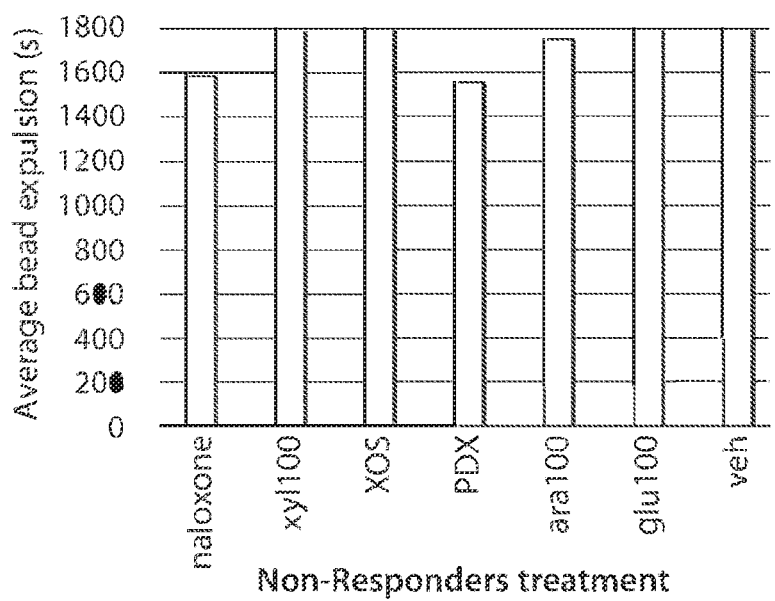

A third analysis was performed to determine the average time to bead expulsion in the responder versus non-responder animals in each treatment group (FIGS. 20*a* and 20*b*). A cutoff time for bead expulsion was set at 1800 seconds. In this mouse model of colonic propulsion, naloxone had the expected effect of reversing the effects of morphine, as it is a direct inverse agonist, competing with morphine for mu-receptor occupancy and blocking its known effects on gastrointestinal motility. XOS and PDX have been shown to have efficacy in clinical constipation settings (Shimada et al, 2015 J. Nutr Sci Vitaminol 61:345-353; Tateyama et al., 2005 J Nutr Sci Vitaminol 51:445-448), and had positive effects in this mouse study. Xyl100, XOS and naloxone had an effects in this model and PDX and ara100 had similar effects as well, especially when the group of responders was assessed (FIG. 20*b*).

These results, obtained in a widely used animal model for colonic propulsion suggest that glycan therapeutics reduced morphine's effect of decreased colonic motility, as measured by colonic propulsion. Selected glycans appear to increase colonic propulsion in animals responsive to treatment, whereas some animals were not responsive.

Example 21: Effect of Glycans on Cancer Development in a Mouse Melanoma Model

To study efficacy of the therapeutic glycans described herein in the treatment of cancer, an animal model of melanoma was chosen. In this model, mice usually develop tumors within 7-21 days and a treatment effect can be observed by measuring the kinetics of tumor growth. For example, a treatment effect can be in the form of delaying tumor growth.

Melanoma is a cancer of the skin, but is mostly observed in skin exposed to sunlight. Melanoma is most commonly diagnosed in non-Hispanic whites; 1 per 100,000 in African Americans, 4 per 100,000 in Hispanics, and 25 per 100,000 in non-Hispanic whites. The number of deaths in 2015 was 2.7 per 100,000 men and women per year. The rates of melanoma have been rising for at least 30 years. The estimated 5-year survival rate for patients whose melanoma is detected early is about 98 percent in the U.S. The survival rate falls to 63 percent when the disease reaches the lymph nodes, and 17 percent when the disease metastasizes to distant organs.

New checkpoint inhibitor therapies have improved the outlook for patients with metastatic melanoma. Anti-PD-1 therapies (e.g. nivolumab and pembrolizumab) have been shown to produce overall response rates on the order of 30% in metastatic melanoma patients (nivolumab FDA label and pembrolizumab FDA label). Combination studies of anti-PD-1 therapy with anti-CTLA4 therapy have shown 60% overall response rate (compared to 11% with anti-CTLA4 therapy alone) and a median progression-free survival of 8.9 months (nivolumab FDA label). Larkin et al. showed median progression-free survival among stage III and IV metastatic melanoma patients of 11.5 months for combination therapy of nivolumab (anti-PD-1) and ipilimumab (anti-CTLA4)

compared to 6.9 months for nivolumab alone, and 2.9 months for ipilimumab alone (DOI: 10.1056/NEJ-Moa1504030).

Some commensal bacterial species may be implicated in regulating gut immunity and responses to immunotherapies in physically distant tumors (Vétizou M et al. Anticancer immunotherapy by CTLA-4 blockade relies on the gut microbiota. Science 2015 Nov. 27; 350:1079). Sivan et al. showed decreased tumor growth kinetics of B16 melanoma cells in mice by combining bifidobacteria species with anti-PD-L1 therapy (Sivan A et al. Commensal *Bifidobacterium* promotes antitumor immunity and facilitates anti-PD-L1 efficacy. Science 2015 Nov. 27; 350:1084). Therapeutic glycans capable of modulating the microbiota (such as, e.g., *Bifidobacterium*, Bacteroidales, Clostridiales) may be useful in cancer therapy, in some cases by promoting anti-tumor immunity, in some cases by increased melanoma-specific effector T-cell responses. Therapeutic glycans combined with existing immunotherapies may produce an additive or synergistic effect. Cancer models, such as the animal melanoma model are informative with respect to efficacy of agents for the treatment of immune imbalances and/or nutritional imbalances.

Melanoma Cell Line

B16.F10.SIY cells were cultured at subconfluence in Dulbecco's Modified Eagle's Medium with (DMEM) supplemented with 10% fetal bovine serum (FBS) and standard Pen/Step supplement (Life Technologies). Cell expression of GFP-SIY fusion was ascertained via flow cytometry and cells were only injected if >90% of cells were positive for SIY peptide expression. Cells were trypsinized and counted, and cell viability determined via trypan blue exclusion assay prior to injection.

Mouse Model of Melanoma

Six to eight week old female C57BL/6 mice were acquired from Taconic, housed under SPF conditions, and fed a chow of Harlan Teklan 2018 ad libitum. At the beginning of the study, a total of $1\times10^6$ cells of the syngeneic melanoma cell line B16.F10.SIY were injected subcutaneously into each of the mice. Tumor size was measured twice per week by multiplying length times the square of the width times 0.5.

Glycans were dissolved in the drinking water of the mice at a concentration of 1%. Mice were divided into five treatment groups: (1) no treatment (n=15); (2) man100 administered from 5 days prior to the subcutaneous injection of the tumor cell line through to when tumor size exceeded 1500 $mm^3$ (n=10); (3) no glycan and subcutaneous injection of 100 ug an anti-mouse anti-PD-L1 antibody (e.g. clone 10f.9 g2 from BioXCell) at days 7, 10, 13, 16, 19, 22, 25, 28 post-tumor implantation (n=15); (4) 1e9 CFU of *Bifidobacterium* mixture (e.g. *B. bifidum, B. longum, B. lactis*, and *B. breve* probiotic mixture from Seeking Health) administered by oral gavage on days 7 and 14 post-tumor implantation (n=10); and (5) no treatment, but the normal Harlan Teklan 2018 diet was replaced with a modified AIN-93G diet that had dietary fiber replaced with free glucose (n=10). The anti-PD-L1 group was included as a control group, as anti-PD-L1 has been previously shown to delay tumor growth kinetics in this mouse model of melanoma (Sivan A et al.).

Figure 21:
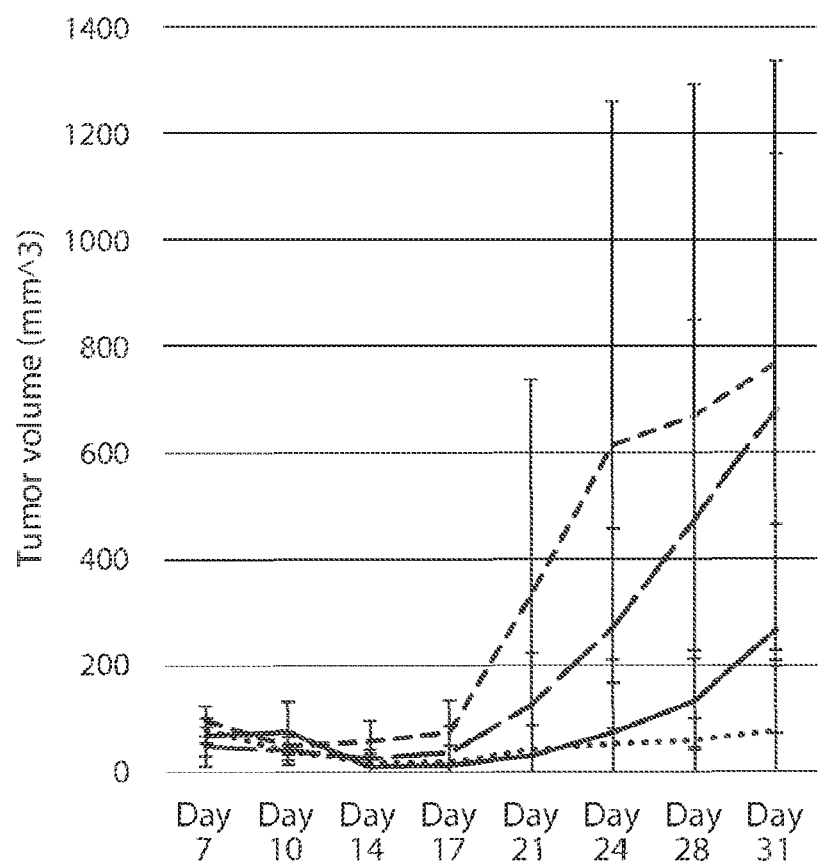
FIG. 21. Tumor growth curves: Group 1 received vehicle treatment (gray long-dashed line), Group 2 mice received man100 (black solid line), Group 3 mice received anti-PD-L1 (gray shortest-dashed line), and Group 4 mice received the bifidobacteria mix (gray medium-dashed line). Based on one-way ANOVA, the difference between Group 1 and Group 2 was significant with a $p<0.05$ on days 21, 24, 28, and 31. Values shown are mean+/−standard deviation across the groups.

FIG. 21 shows tumor growth curves for Group 1 mice that received vehicle treatment (gray long-dashed line) and Group 2 mice that received Man100 in the drinking water at 1% from 5 days prior to tumor inoculation through the duration of the study (black solid line). As can be seen in FIG. 21, the tumor growth curves were suppressed in mice that received man100 in the drinking water (Group 2) compared to the vehicle control (Group 1). Additionally, mice receiving anti-PD-L1 (Group 3) showed superior tumor growth suppression (gray shortest-dashed line), and addition of the bifidobacteria mix (Group 4, gray medium-dashed line) did not show significant tumor growth changes compared to Group 1. This effect was determined to be statistically significant (p<0.05) on days 21, 24, 28, and 31 based on one-way ANOVA comparing Group 2 to Group 1. Man100 inducing a delay in tumor growth in this model suggests enhanced immune control of the tumors throughout the duration of treatment.

Figure 22:
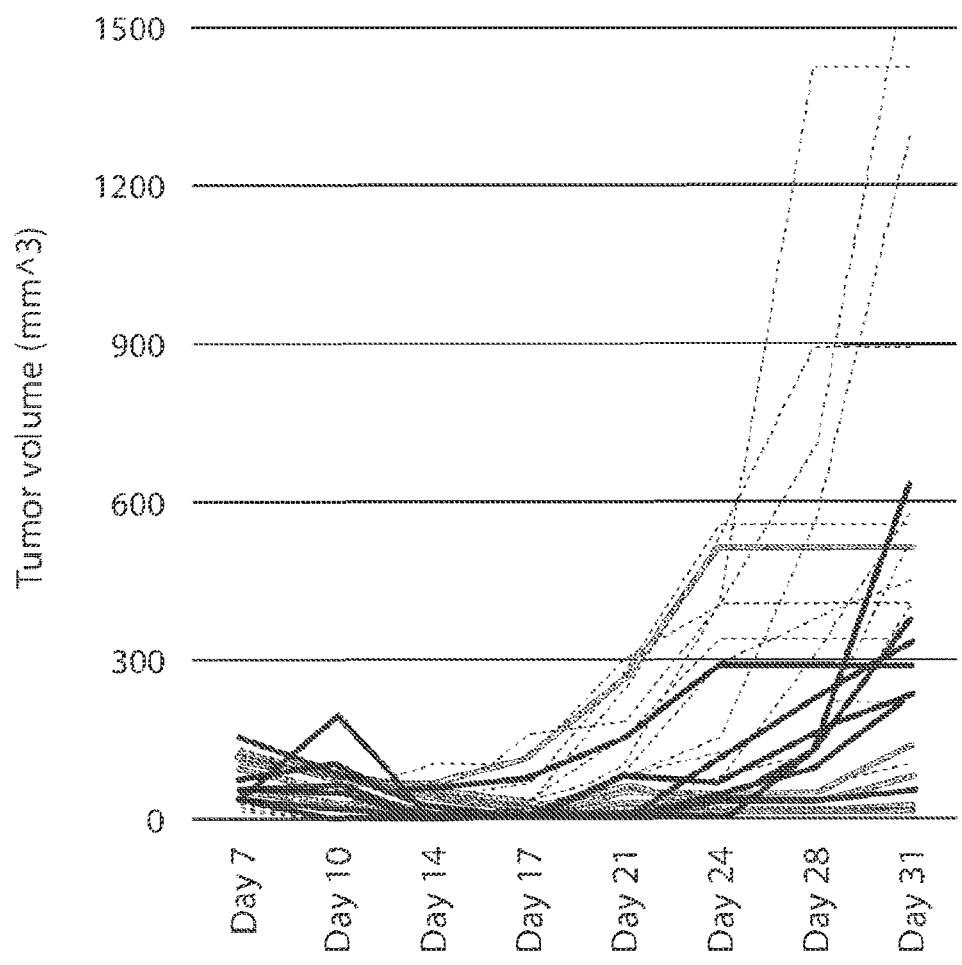
FIG. 22. Spider plots of vehicle control (Group 1, thin gray dotted lines), anti-PD-L1 (Group 3, thick gray solid lines), and man100 (Group 2, thick black solid lines) show tumor growth curves for each mouse from days 7-31.

FIG. 22 shows the spider plots of the individual tumor growth curves for Group 1 (vehicle control, thin gray dotted lines), Group 2 (Man100, thick black solid lines), and Group 3 ( ), anti-PD-L1, thick gray solid lines). By day 24, the tumor growth in most of the animals in Group 1 became exponential, whereas in Group 2 and Group 3, the exponential phase was delayed until days 28 or 31 for almost all of the animals. Since delay of tumor growth was achieved with both man100 and anti-PD-L1, but both groups relapsed, it suggests the possibility of additive or synergistic effects of combining man100 with anti-PD-L1 to suppress tumor growth or induce robust tumor rejection. Man100 could also be combined with other therapies to produce an additive or synergistic effect.

Example 22: Glycan Treatment in Patients with Melanoma

Patients diagnosed with metastatic melanoma are randomized to receive either 12 g per day of a glycan (dissolved in water and administered orally) or placebo for the full duration of standard-of-care therapy. Every month, tumor size is determined by CT scan, or where not available, by caliper measurement or X-ray. Every month, fecal samples are collected for analysis. Every 8 weeks, tumor biopsies are taken for analysis, including histology and microscopy to quantify tumor-infiltrating lymphocytes (TIL). Tumor size measurements, fecal samples, and tumor biopsies are taken at baseline prior to any therapy.

Fecal samples are expected to reveal that treatment with glycan increases the absolute and relative proportion of *Bifidobacterium* species in the feces.

Tumor biopsies are expected to reveal that treatment with glycan increases the proportion of TIL from baseline, and the magnitude of increase is larger than the placebo group.

On average, the glycan-treated patients are expected to experience less tumor growth over the period of treatment than the placebo controls.

Example 23: Glycan Treatment in Patients with Prostate Cancer

Patients diagnosed with prostate cancer are randomized to receive either 12 g per day of a glycan, dissolved in water and administered orally, or placebo for the full duration of standard-of-care therapy. Every month, fecal samples are collected for analysis. Every 8 weeks, tumor biopsies are taken for analysis, including histology and microscopy to quantify tumor-infiltrating lymphocytes (TIL). Tumor biopsies are taken at baseline prior to any therapy.

Fecal samples are expected to reveal that treatment with glycan increases the absolute and relative proportion of *Bifidobacterium* species in the feces.

Tumor biopsies are expected to reveal that treatment with glycan increases the proportion of TIL from baseline, and the magnitude of increase is larger than the placebo group.

Patients that experience an increase in TIL from baseline then receive 3 mg/kg of anti-CTLA4 therapy intravenously every 3 weeks for a total of four doses. Every month, tumor size is determined by CT scan, or where not available, by caliper measurement or X-ray. Every month, fecal samples are collected for analysis. Every 8 weeks, tumor biopsies are taken for analysis, including histology and microscopy to quantify tumor-infiltrating lymphocytes (TIL). Tumor size measurements, fecal samples, and tumor biopsies are taken at baseline prior to any therapy.

Fecal samples are expected to reveal that treatment with glycan increases the absolute and relative proportion of *Bifidobacterium* species in the feces.

Tumor biopsies are expected to reveal that treatment with glycan increases the proportion of TIL from baseline, and the magnitude of increase is larger than the placebo group.

On average, the glycan-treated patients experience less tumor growth over the period of treatment than the placebo controls.

Example 24: Properties of the Glycan Therapeutic in the Treatment, Co-Treatment and Prevention of Different Oncological Processes/Diseases In a group of mice that take a selected test glycan therapeutic a repression of the expression of oncogenes jun, myc and fos may be detected with respect to the control group. The jun and fos products are transcription factors that dimerize to form the transcription complex called AP-1 (Activating Protein-1). AP-1 is a transcription factor that regulates expression of genes induced by growth factors and tumor promoters. Overexpression of oncogenes Jun and/or fos is associated with several cancers such as breast, ovarian, colon, osteosarcoma, cervical, lung and bladder cancer. Therefore, AP-1 is used as a target for chemotherapeutic treatment of cancer. Myc oncogene product is a protein that regulates the expression of the transcription factor E2F and phosphatase responsible for activation of Cdc cyclins, which are involved in cell cycle regulation. The myc oncogene is overexpressed in many human cancers, including pancreatic, cervical, breast and colon cancer. Myc oncogene product is also used as target for cancer treatment. A study in humans showed that in the intestinal mucosa there is a repression in the expression of oncogenes jun, fos and myc after infusion of the membrane with a strain of *Lactobacillus*. In a group of mice that take a selected test glycan therapeutic a repression on the expression of the gene Adamts1 (a disintegrin-like and metalloproteinase (reprolysin type) with thrombospondin type 1 motif) may be detected with respect to the control group. Adamts1 gene product is a protein that has a metalloproteinase domain and disintegrin domain. This protein is involved in inflammatory processes and the development of cancer cachexia as tested in animal models of colon cancer. It has been demonstrated overexpression of Adamts1 gene in breast cancer with high metastatic activity. It has been speculated that overexpression of this gene might promote tumor growth by recruiting fibroblasts. In a group of mice that take a selected test glycan therapeutic a repression on the expression of the gene ATF3 (activating transcription factor 3) may be detected with respect to the control group. ATF3 gene product is a transcription factor expressed in conditions of stress and DNA damage in various tissues. In many breast tumors has been reported overexpression of ATF3. This protein is used as a marker of prostate cancer since its involvement has been shown in developing this type of cancer and is therefore a potential therapeutic target. In a group of mice that take a selected test glycan therapeutic an activation on the expression of Ddit4 gene (DNA-damage-inducible transcript 4) may be detected with respect to the control group. Ddit4 gene product is a protein called RTP801 or REDD1, which inhibits the pathway mTOR/S6K1, involved in cell proliferation. Inhibitors of this route are being evaluated as cancer therapy. In mice has been described that the gene Ddti4 deficiency promotes tumor growth, while in humans has been described repression of the gene in various cancers. In a group of mice that take a selected test glycan therapeutic a repression on the expression of Egr1 gene (early growth response 1) may be detected with respect to the control group. The Egr1 gene product is a transcription factor involved in various cellular processes and its involvement has been demonstrated in cell growth and survival of prostate cancer. In animal models of prostate cancer has shown that lack of Egr1 gene retards tumor growth. In a group of mice that take a selected test glycan therapeutic a repression on the expression of Sox9 gene (SRY (sex Determining Region Y)-box 9) may be detected with respect to the control group. The Sox9 gene produces a protein that acts as a transcription factor with DNA-binding domain type HMG (High Mobility Group). It has been shown an implication of Sox9 gene product in the proliferation of pancreatic cancer and overexpression of the same in different cell lines of colon cancer. In a group of mice that take a selected test glycan therapeutic a repression of the expression of interleukin 1 alpha gene (IL1a) may be detected with respect to the control group. The IL1a is a cytokine involved in inflammatory processes. The IL1a gene is overexpressed in various cancers, including lung cancer, colon and melanoma. In colon cancer IL1a stimulates the cell migration and angiogenesis and its expression is induced by prostaglandin E2. In a study in humans showed that in the intestinal mucosa occurs a repression in the IL1a gene expression after the infusion of the membrane with a strain of *Lactobacillus*. In a group of mice that take a selected test glycan therapeutic an activation of the expression of Gadd45b gene (growth arrest and DNA-damage-inducible 45 beta) and Gadd45q gene (growth arrest and DNA-damage-inducible 45 gamma) may be detected with respect to the control group. The products of Gadd45 g and Gadd45b genes are proteins related with cell cycle control. In mice models of melanoma have been shown that a lack of function of Gadd45b produces higher tumor growth. The product of this gene is required for activation of p38 kinase. The p38 protein is involved in tumor suppression. The expression of Gadd45 g and Gadd45b genes is repressed in various cancers.

TABLE 1

| Genus level Microbial Constituents of the GI tract. | | |
|---|---|---|
| Phylum | Class | Genus |
| Actinobacteria | Actinobacteria | *Actinomyces, Adlercreutzia, Atopobium, Bifidobacterium, Collinsella, Corynebacterium, Eggerthella, Mobiluncus, Propionibacterium, Rothia, Slackia* |

TABLE 1-continued

Genus level Microbial Constituents of the GI tract.

| Phylum | Class | Genus |
|---|---|---|
| Bacteroidetes | Bacteroidia | *Alistipes, Bacteroides, Dysgonomonas, Odoribacter, Parabacteroides, Porphyromonas, Prevotella, Tannerella* |
| | Flavobacteria | *Capnocytophaga* |
| Firmicutes | Bacilli | *Bacillus, Enterococcus, Gemella, Granulicatella, Lactobacillus, Lactococcus, Staphylococcus, Streptococcus, Turicibacter, Weissella* |
| | Clostridia | *Acidaminococcus, Anaerococcus, Anaerofilum, Anaerofustis, Anaerostipes, Anaerotruncus, Anaerovorax, Bacteroides, Bacteroides, Blautia, Clostridium, Coprococcus, Dehalobacterium, Dialister, Dorea, Eubacterium, Faecalibacterium, Finegoldia, Lachnobacterium, Lachnospira, Megamonas, Megasphaera, Mitsuokella, Moryella, Oribacterium, Oscillospira, Peptococcus, Peptoniphilus, Peptostreptococcus, Phascolarctobacterium, Pseudobutyrivibrio, Roseburia, Ruminococcus, Ruminococcus, Selenomonas, Subdoligranulum, Veillonella* |
| Fusobacteria | Fusobacteria | *Fusobacterium, Leptotrichia* |
| | Betaproteobacteria | *Comamonas, Herbaspirillum, Lautropia, Neisseria, Oxalobacter, Sutterella* |
| | Deltaproteobacteria | *Bilophila, Desulfovibrio,* LE30 |
| | Epsilonproteobacteria | *Campylobacter, Helicobacter* |
| | Gammaproteobacteria | *Actinobacillus, Aggregatibacter, Citrobacter, Escherichia, Haemophilus, Klebsiella, Moraxella, Pseudomonas, Raoultella* |
| Spirochaetes | Spirochaetes | *Treponema* |
| Synergistetes | Synergistetia | *Cloacibacillus, Synergistes* |
| Tenericutes | Erysipelotrichi | *Bulleidia, Catenibacterium, Clostridium, Coprobacillus, Holdemania,* RFN20 |
| | Mollicutes | *Asteroleplasma, Mycoplasma* |
| Verrucomicrobia | Verrucomicrobiae | *Akkermansia* |
| Euryarchaeota | Methanobacteria | *Methanobrevibacter* |

TABLE 2

Microbial Metabolites 2-hydroxyisobutyrate, 3-hydroxyisovalerate, 3-methyl-crotonylglycine, 3-methylcrotonylglycine, allantoin, betaine, formate, mannitol, p-cresol glucuronide, phenylacetylglycine, sarcosine, taurine, acetic acid, acetylaldehyde, ascorbic acid, butanedione, butyric acid, deoxycholic acid, ethylphenyl sulfate, formic acid/formate, indole, isobutyric acid, isovaleric acid, propionic acid, serotonin, succinic acid/succinate, TMAO, tryptophan, valeric acid, ursodeoxycholic acid, lactate, lactic acid, hydrogen peroxide

TABLE 3

Genus level microbial constituents predominant in the large intestine (compared to small intestine) in healthy humans.

| Phylum | Class | Genus |
|---|---|---|
| Bacteroidetes | Bacteroidia | *Bacteroides, Butyricimonas, Odoribacter, Parabacteroides, Prevotella* |
| Firmicutes | Clostridia | *Anaerotruncus, Phascolarctobacterium, Ruminococcus,* |
| Proteobacteria | Deltaproteobacteria | *Bilophila* |
| Verrucomicrobia | Verrucomicrobiae | *Akkermansia* |

TABLE 4

Genus level microbial constituents predominant in the small intestine (compared to large intestine) in healthy humans.

| Phylum | Class | Genus |
|---|---|---|
| Actinobacteria | Actinobacteria | *Cryocola, Mycobacterium* |
| Firmicutes | Bacilli | *Enterococcus, Lactococcus, Streptococcus, Turicibacter* |
| | Clostridia | *Blautia, Coprococcus, Holdemania, Pseudoramibacter Eubacterium* |
| Proteobacteria | Alphaproteobacteria | *Agrobacterium, Sphingomonas* |
| | Betaproteobacteria | *Achromobacter, Burkholderia, Ralstonia* |

EQUIVALENTS AND SCOPE

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present invention, as defined in the following claims.

The invention claimed is:

1. A method of treating cancer in a subject, comprising administering to the subject an effective amount of a composition comprising a glycan therapeutic preparation, wherein
    i) the glycan therapeutic preparation comprises branched glycans comprising glucose, galactose, arabinose, mannose, fructose, xylose, fucose, or rhamnose glycan units;
    ii) the average degree of branching (DB) of the branched glycans in the glycan therapeutic preparation is at least 0.01;
    iii) at least 50% of the glycans in the glycan therapeutic preparation have a degree of polymerization (DP) of at least 3 and less than 30 glycan units; and
    iv) the ratio of alpha- to beta-glycosidic bonds present in the glycans of the glycan therapeutic preparation is between about 1:1 to about 5:1; and
    wherein the composition is administered in combination with an anti-cancer drug or anti-cancer therapy.

2. The method of claim 1, wherein the composition is a pharmaceutical composition.

3. The method of claim 1, wherein the composition is a medical food.

4. The method of claim 1, wherein the composition is a dietary supplement.

5. The method of claim 1, wherein:
    (a) the subject has previously received an anti-cancer drug or anti-cancer therapy, or
    (b) the subject has previously received a composition comprising a glycan therapeutic preparation.

6. The method of claim 1, wherein the composition is administered simultaneously with the anti-cancer drug or anti-cancer therapy.

7. The method according to claim 1, further comprising administering to the subject a dietary fiber or probiotic bacterium.

8. The method of claim 1, wherein the combination is administered to a subject that has been previously treated for cancer.

9. The method of claim 1, wherein the combination is administered to a subject that has been previously not been treated for cancer.

10. The method according to claim 1, wherein the composition comprising the glycan therapeutic preparation has a final solubility limit in water of at least about 60 Brix at 23° C.

11. The method according to claim 1, wherein
    i) the branched glycans of the glycan therapeutic preparation comprise a mixture of beta and alpha linkages of one or more of (1-2), (1-3), (1-4), (1-6), (2-3), and (2-6);
    ii) the glycan therapeutic preparation comprises a mixture of branched glycans and unbranched glycans;
    iii) the glycan therapeutic preparation comprises a mixture of digestible and non-digestible glycans; or
    iv) any combination of one, two, or three of i), ii), and iii).

12. The method of claim 1, wherein the anti-cancer drug comprises a checkpoint inhibitor, a cancer vaccine, an anti-cancer biologic, or a chemotherapeutic agent.

13. The method of claim 12, wherein the checkpoint inhibitor comprises a targeted kinase inhibitor, a chemotherapeutic, an antibody, an antibody-drug conjugate, a fusion protein, or a small molecule.

14. The method of claim 12, wherein the cancer vaccine comprises a tumor cell vaccine, an antigen vaccine, a dendritic cell vaccine, a DNA vaccine, or a vector-based vaccine.

15. The method for use according to claim 12, wherein the checkpoint inhibitor is anti-PD-1, anti-PD-L1, anti-CTLA4, anti-TIM-3 or anti-LAG-3.

16. The method according to claim 13, wherein the targeted kinase inhibitor is Imatinib mesylate, Ibrutinib, Neratinib, Palpociclib, Erlotinib or Lapatinib.

17. The method according to claim 13, wherein the antibody is Bevacizumab, Trastuzumab, Rituximab or Cetuximab.

18. The method according to claim 12, wherein the chemotherapeutic is irinotecan, 5-flurouracil, lenalidomide, capecitabine or docetaxel.

19. The method according to claim 1, wherein the anti-cancer second therapy is surgery, radiotherapy, cryotherapy or immunotherapy.

20. The method according to claim 19, wherein the immunotherapy includes a checkpoint inhibitor, a T cell therapy, a natural killer (NK) cell immunomodulation or a cancer vaccine.

21. The method of claim 1, wherein the cancer comprises one or more of the following characteristics:
    (i) the cancer comprises a solid cancer or a liquid cancer;
    (ii) the cancer comprises a metastatic or metastasized tumor; or
    (iii) the cancer is an immunogenic cancer and comprises one or more of the following characteristics:
        (a) tumor infiltrating lymphocytes (TIL);
        (b) somatic mutations;
        (c) neoantigens;
        (d) tertiary lymphoid structures;
        (e) high expression of inflammatory gene expression; or
        (f) immune cells exhibiting immunosuppressive phenotype.

22. The method of claim 1, wherein the subject has neutropenia.

23. The method of claim 1, wherein, following administration of the composition, the subject has an increased white blood cell count relative to a control subject.

* * * * *